(12) United States Patent
Bihain et al.

(10) Patent No.: US 6,635,431 B1
(45) Date of Patent: Oct. 21, 2003

(54) LSR RECEPTOR, ACTIVITY, CLONING, AND USES FOR DIAGNOSING, PREVENTING AND/OR TREATING OBESITY AND RELATED RISKS OR COMPLICATIONS

(75) Inventors: Bernard Bihain, Encinitas, CA (US); Lydie Bougueleret, Vanves (FR); Frances Yen-Potin, San Diego, CA (US)

(73) Assignees: Genset, S.A. (FR); Institute National de la Sante et de la Recherche Medicale (INSERM) (FR)

( * ) Notice: Subject to any disclaimer, the term of this patent is extended or adjusted under 35 U.S.C. 154(b) by 0 days.

(21) Appl. No.: 09/269,939

(22) PCT Filed: Aug. 6, 1998

(86) PCT No.: PCT/IB98/01257
§ 371 (c)(1),
(2), (4) Date: May 28, 1999

(87) PCT Pub. No.: WO99/07737
PCT Pub. Date: Feb. 18, 1999

(30) Foreign Application Priority Data

Aug. 6, 1997 (FR) ............................................ 97 10088
Apr. 22, 1998 (FR) ............................................ 98 05032

(51) Int. Cl.⁷ ........................ C12N 15/12; G01N 33/567
(52) U.S. Cl. ...................... 435/7.21; 530/350; 536/23.5; 435/320.1; 435/325; 435/252.3; 435/69.1; 435/370
(58) Field of Search ........................ 530/350; 536/23.5; 435/252.3, 325, 69.1, 7.21

(56) References Cited

U.S. PATENT DOCUMENTS

| | | | |
|---|---|---|---|
| 5,270,170 A | | 12/1993 | Schatz et al. |
| 5,635,373 A | * | 6/1997 | Wozney et al. .......... 435/252.3 |
| 6,126,939 A | * | 10/2000 | Eisenbach-Schwartz et al. 424/185.1 |

FOREIGN PATENT DOCUMENTS

| | | |
|---|---|---|
| WO | WO 96 30400 | 10/1996 |
| WO | WO 96/34981 | 11/1996 |
| WO | WO 96/39429 | 12/1996 |
| WO | WO 97 27286 | 7/1997 |
| WO | WO 98/01257 | 1/1998 |
| WO | WO 98/20165 | 5/1998 |

OTHER PUBLICATIONS

Database SPTREMBL_17, Accession No. Q61148, Nov. 1, 1996.*
Database SPTREMBL_17, Accession No. O00112, Jul. 1, 1997.*
Database SPTREMBL_17, Accession No. O00426, Jul. 1, 1997.*
Alexeev and Yoon, "Stable and inheritable changes in genotype and phenotype of albino melanocytes induced by an RNA–DNA oligonucleotide," *Nature Biotech.*, 16:1343–1346, 1998.
Austin, et al., "Hypertriglyceridemia as a Cardiovascular Risk Factor," *Am. J. Cardiol.*, 81:7B–12B, 1998.
Baldo, et al., "The Adipsin–Acylation Stimulating Protein System and Regulation of Intracellular Triglyceride Synthesis," *J. Clin. Invest.*, 92:1543–1547 (1993).
Bartles, J.R., et al., "Biogenesis of the Rate Hepatocyte Plasma Membrane," *Methods Enzymol.*, 191:825–841 (1990).
Bihain, et al. (1995) Characterization and purification of the lipolysis–stimulated receptor. INSERM U391, Universite de Rennes.
Bihain, et al. (1992) Free Fatty Acids Activate a High Affinity Saturable Pathway for Degradation of Low–Density Lipoproteins in Fibroblasts from a Subject Homozygous for Familial Hypercholesterolemia. American Chemical Society 0006–2960/92/0431–4628.
Brendel, V., et al., "Methods and algorithms for statistical analysis of protein sequences," *Proc. Natl. Acad. Sci. USA*, 89:2002–2006, 1992.
Chen, W.J., et al., "NPXY, a Sequence Often Found in Cytoplasmic Tails, Is Required for Coated Pit–mediated Internalization of the Low Density Lipoprotein Receptor," *J. Biol. Chem.*, 265:3116–3123, 1990.
Cole–Strauss, et al., "Correction of the Mutation Responsible for Sickle Cell Anemia by an RNA–DNA Oligonucleotide," *Science*, 273:1386–1389, 1996.
Davis, C.G., et al., "The J.D. Mutation in Familial Hypercholesterolemia: Amino Acid Substitution in Cytoplasmic Domain Impedes Internalization of LDL Receptors," *Cell*, 45:15–24, 1986.
Everhart, J.E., "Weight Change and Obesity After Liver Transplantation: Incidence and Risk Factors," *Liver Transpl. Surg.*, 4:285–296, 1998.
Feeman, Jr., W.E., "Hypertriglyceridemia and Atherosclerosis," *Annals of Internal Medicine*, vol. 128, No. 1, pp. 73–74, 1998.

(List continued on next page.)

*Primary Examiner*—Lorraine Spector
*Assistant Examiner*—Eileen B. O'Hara
(74) *Attorney, Agent, or Firm*—Saliwanchik, Lloyd & Saliwanchik

(57) ABSTRACT

The present invention relates to a new complex receptor polypeptide LSR (Lipolysis Stimulated Receptor), characterized by its functional activities, the cloning of the cDNAs complementary to the messenger RNAs encoding each of the subunits of the multimeric complex, vectors and transformed cells, methods of diagnosis and of selection of compounds which can be used as medicament for the prevention and/or treatment of pathologies and/or of pathogeneses such as obesity and anorexia, hyperlipidemias, atherosclerosis, diabetes, hypertension, and more generally the various pathologies associated with abnormalities in the metabolism of cytokines.

57 Claims, 45 Drawing Sheets

OTHER PUBLICATIONS

Ghebrehiewet, et al. (1994) Isolation, cDNA Cloning, and Overexpression of a 33–kD Cell Surface Glysoprotein that Binds to the Globular "Heads" of C1q. The Rockfeller Univ. Press vol. 179, 1809–1821.

Goldstein, J.L., et al., "Familial Hypercholesterolemia," The Metabolic and Molecular Bases of Inherited Disease, vol. II, 7th Edition (Scriver, C.R., et al., ed). McGraw–Hill, New York, pp. 1981–2030, 1995.

Goldstein, et al., "Hyperlipidemia in Coronary Heart Disease," J. Clin. Invest., 52:1533–1543, 1973.

Gura, et al., "Obesity Sheds Its Secrets," Science, 275:751–753, Feb. 7, 1997.

Hayward, et al., "The cDNA Sequence of Human Endothelial Cell Multimerin," J. Biol. Chem., 270:18246–18251, 1995.

Henrion, et al. (1995) Structure, Sequence and Chromosomal Location of the Gene for USF2 Transcription Factors in Mouse. GENOMICS 25, 36–43.

Herz, J., et al., "Surface location and high affinity for calcium of a 500–kd liver membrane protein closely related to the LDL–receptor suggest a physiolocial role as lipoprotein receptor," European Molecular Biology Laboratory, 7:4119–4127(1988).

Honoré, B., et al., "Cloning and expression of a CDNA covering the complete coding region of the P32 subunit of human pre–mRNA splicing factor SF2," Gene, 134:283–287 (1993).

Huettinger, M., et al., "Characteristics of Chylomicron Remnant Uptake into Rat Liver," Clin. Biochem., 21:87–92 (1988).

Hu, et al., "AdiopQ is a Novel Adipose–specific Gene Dysregulated in Obesity*," J. Biol. Chem., 271, 18:10697–10703 (1996).

Karpe, F., et al., "Clearance of lipoprotein remnant particles in adipose tissue and muscle in humans," J. Lipid Res. 38:2335–2343 (1997).

Karpe, F., et al., "Magnitude of alimentary lipemia is related to intima–media thickness of the common carotid artery in middle–aged men," Elsevier Science Ireland, 141:307–314, 1998.

Krainer, A.R., et al., "Functional Expression of Cloned Human Splicing Factor SF2: Homology to RNA–Binding Proteins, U1 70K, and Drosophila Splicing Regulators," Cell, 66:383–394, 1991.

Lee, et al., "Characterization of cDNA Encoding a Cysteine–Rich Cell Surface Protein Located in the Flagellar Pocket of the Protozoan Trypanosoma brucei," Molec. Cell. Biol., 10:4506–4517 (1990).

Letourneur, F., et al., "A Novel Di–Leucine Motif and a Tyrosine–Based Motif Independently Mediate Lysosomal Targeting and Endocytosis of CD3 Chains," Cell, 69:1143–1157 (1992).

Lewis, G.F., et al., "Postprandial Lipoprotein Metabolism in normal and Obese Subjects: Comparison after the Vitamin A Fat–Loading Test," Jr. of Clinic. Endo., 71:1041–1050, (1990).

Lin, et al. (1994) Archaic Structure of the Gene Encoding Transcription Factor USF. Journal of Biological Chemistry vol. 269:19:23894–28903.

Liu, Q., et al., "Design of polydactyl zinc–finger proteins for unique addressing within complex genomes." Proc. Natl. Acad. Sci. USA, 94:5525–5530, 1997.

Maeda, et al., "cDNA Cloning and Expression of a Novel Adipose Specific Collagen–like Factor, apM1 (Adipose Most Abundant Gene Transcript 1)," Biochem. and Biophys. Research Comm., 221:286–289, 1996.

Mahley, R.W., et al., "Type III Hyperlipoproteinemia (Dysbetalipoproteinemia): The Role of Apolipoprotein E in Normal and Abnormal Lipoprotein Metabolism," The Molecular Basis of Inherited Disease, eds., Scriver, et al., McGraw Hill Inc., New York, pp. 1953–1980, 1995.

Mann, et al. (1995) Mechanism of Activation and Functional Significance of the Lipolysis–Stimulated Receptor. Evidence for a Role as Chylomiscron Remnant Receptor. American Chemical Society 0006–2960/95/0434–10421.

Mann, et al. Abstract; ApoC111 Inhibits the Binding of Triglyceride–Rich Lipoproteins to the Lipolysis Stimulated Receptor, Circulation 94(8) Supp. I–698. Oct. 1996.

Massie, et al., "Inducible Overexpression of a Toxic Protein by an Adenovirus Vector with a Tetracycline–Regulatable Expression Cassette," Journal of Virology, 72:2289–2296, 1998.

Montague, et all., "Congenital leptin deficiency is associated with severe early–onset obesity in humans," Nature, 387:903–908, 1997.

Parra–Lopez, C.A., et al., "Presentation on Class II MHC Molecules of Endogenous Lysozyme Targeted to the Endocytic Pathway[1]," J. Immunol., 158:2670–2679, 1997.

Pengue, G., et al., "Repression of transcriptional activity at a distance by the evolutionarily conserved KRAB domain present in a subfamily of zinc finger proteins," Nucleic Acids Research, vol. 22, No. 15, 2908–2914 (1994).

Rajput–Williams, J., et al., "Variation of Apolipoprotein–B gene is associated with obesity, high blood cholesterol levels, and increased risk of coronary heart disease," The Lancet, pp. 1442–1446 (1988).

Rutherford, S., et al., "Association of a low density lipoprotein receptor micro–satellite variant with obesity," Intl. Jr. of Obesity, 21:1032–1037 (1997).

Schäffler, et al., "Identification and characterization of the human adipocyte apM–1 promoter," Biochem. and Biophys. Res. Comm., 1399:187–197 (1998).

Scherer, et al., "A Novel Serum Protein Similar to C1q, Produced Exclusively in Adipocytes," J. Biol. Chem., 270:26746–26749 (1995).

Sellar, et al., "Characterization and organization of the genes encoding the A–, B–and C– chains of human complement subcomponent C1q," Biochemical Journal, 274:481–490, (1991).

Shimabukuro, M., et al., "Direct antidiabetic effect of leptin through triglyceride depletion of tissues," Proc. Natl. Acad. Sci. USA, 94:4637–4641, 1997.

Shimano, H., et al., "Overproduction of Cholesterol and Fatty Acids Causes Massive–Liver Enlargement in Transgenic Mice Expressing Truncated SREBP–1a," J. Clin. Invest., 98:1575–1584, 1996.

Shin, J., et al., "Phosphorylation–dependent Down–modulation of CD4 Requires a Specific Structure within the Cytoplasmic Domain of CD4," Jr. of Biol. Chem., vol. 266:10658–10665, 1991.

Simos, G., et al., "The lamin B receptor–associated protein p34 shares sequence homology and antigenic determinants with the splicing factor 2–associated protein p32," FEBS Letters, 346:225–228, 1994.

Steingrimsson, et al. (1995) Murine Chromosomal Location of Five bHLH–Zip Transcription Factor Genes. GENOMICS vol. 28:179–183.

Troussard, et al. (1995) Inhibitory Effect on the Lipolysis–stimulated Receptor of the 39–kDa Receptor–associated Protein, *Journal of Biological Chemistry* vol. 270:29:17068–17071.

Urade, Y., et al., "Precerebellin is a cerebellum–specific protein with similarity to the globular domain of complement C1q B chain," *Proc. Natl. Sci. USA*, 88:1069–1073, 1991.

Verhey, K. J., et al., "A leu–Leu Sequence is Essential for COOH–terminal Targeting Signal of GLUT4 Glucose Transporter in Fibroblasts," *J. Biol. Chem.*, 269:2353–2356, 1994.

Wang, et al., "Upstream Stimulatory Factor Binding to the E–box at–65 is required for Insulin Regulation of the Fatty Acid Synthase Promoter," *J. Biol. Chem.*, 272:26367–26374, 1997.

Yen, et al. (1994) Identification of Lipolysis–Stimulated Receptor That is Distinct from the LDL Receptor and the LDL Receptor Related Protein. American Chemical Society 0006–2960/94/0433–1172.

Zhang, et al., "tumor Necrosis Factor," *The Cytokine Handbook*, Third Ed., pp. 517–548, 1998.

Zhong, G., et al., "Related Leucine–based Cytoplasmic Targeting Signals in Invariant Chain and Major Histocompatibility Complex Class II Molecules Control Endocytic Presentation of Distinct Determinants in a Single Protein," *J. Exp. Med.*, 185:429–438, 1997.

Database, EMBL Entry MM49507, U49507. May 20, 1996.

Database, EMBL Entry 000112, 0001127. Jul. 1, 1997.

Database, EMBL Entry HSAC2128, AC002128. May 28, 1997.

Database, EMBL Entry 000426, 000426 Jul. 1, 1997.

Database EMBL, Entry HSAD684, AD000684. Mar. 26, 1997.

Database EMBL, Entry Q61127, Q61148, Nov. 1, 1996.

Database EMBL, Entry HSUSF2, Y07661. Jan. 24, 1997.

Abstract, Supplemental to Circulation, American Heart Assoc., vol. 94:8 (1996).

Van den Berg, R. H., et al., "Intracellular Localization of the Human Receptor for the Globular Domains of C1q[1]," American Association of Immunologists, 158: 3909–3916, 1997.

Dietrich, J., et al., "CD3γ Contains a Phosphoserine–Dependent Di–Leucine Motif Involved in Down–Regulation of the T Cell Receptor", EMBO Journal 13:2156–2166 1994.

* cited by examiner

```
LSR1.Hs (SEQ ID NO:8)    MQQDGLGVGTRNGSGKGRSVHPSWPWCAPRPLRYFGRDARARRAQTAAMALLAGGLSRGL
LSR1.Rn (SEQ ID NO:2)    ---------------------------------------------------MAPAAGACAGAP
LSR1.Mm (SEQ ID NO:16)   ---------------------------------------------------MAPAASACAGAP
                                                                            **  *

FFA
LSR1.Hs (SEQ ID NO:8)    GSHPAAAGRDAVVFVWLLLSTWCTAPARAIQVTVSNPYHVVILFQPVTLPCTYQMTSTPT
LSR1.Rn (SEQ ID NO:2)    DSHPAT-----VVFVCLFLIIFCPDPASAIQVTVSDPYHVVILFQPVTLPCTYQMSNTLT
LSR1.Mm (SEQ ID NO:16)   GSHPAT-----TIFVCLFLIIYCPDRASAIQVTVPDPYHVVILFQPVTLHCTYQMSNTLT
                          ****.      .** * *    * ****** .************** ******* . * *

LSR1.Hs (SEQ ID NO:8)    QPIVIWKYKSFCRDRIADAFSPASVDNQLNAQLAAGNPGYNPYVECQDSVRTVRVVATKQ
LSR1.Rn (SEQ ID NO:2)    VPIVIWKYKSFCRDRIADAFSPASVDNQLNAQLAAGNPGYNPYVECQDSVRTVRVVATKQ
LSR1.Mm (SEQ ID NO:16)   APIVIWKYKSFCRDRVADAFSPASVDNQLNAQLAAGNPGYNPYVECQDSVRTVRVVATKQ
                          *************.********************************************

LSR1.Hs (SEQ ID NO:8)    GNAVTLGDYYQGRRITITGNADLTFDQTAWGDSGVYYCSVVSAQDLQGNNEAYARIVLG
LSR1.Rn (SEQ ID NO:2)    GNAVTLGDYYQGRRITITGNADLTFEQTAWGDSGVYYCSVVSAQDLDGNNEAYARIVLG
LSR1.Mm (SEQ ID NO:16)   GNAVTLGDYYQGRRITITGNAGLTFEQTAWGDSGVYYCSVVSAQDLDGNNEAYARIVLG
                         ********************. ***.******************** ************

TM    ↓      ↓  ↓  ↓  ↓  ↓ ↓
LSR1.Hs (SEQ ID NO:8)    RTSGVAEILPGFQAGPIEDWLFVVVVCLAAFLIFLLLGICWCQCCPHTCCCYVRCPCCPD
LSR1.Rn (SEQ ID NO:2)    RTSEAPEILPGFRAGPLEDWLFVVVVCLASLLLFLLLGICWCQCCPHTCCCYVRCPCCPD
LSR1.Mm (SEQ ID NO:16)   RTSEAPEILPGFRAGPLEDWLFVVVVCLASLLFFLLLGICWCQCCPHTCCCYVRCPCCPD
                         ***    *****.***.************.    **************************

↓
LSR1.Hs (SEQ ID NO:8)    KCCCPEALYAAGKAATSGVPSIYAPSTYAHLSPAKTPPPP-AMIPMGPAYNGYPGGYPGD
LSR1.Rn (SEQ ID NO:2)    KCCCPEALYAAGKAATSGVPSIYAPSIYTHLSPAKTPPPPPAMIPMGPPY-----GYPGD
LSR1.Mm (SEQ ID NO:16)   KCCCPEALYAAGKAATSGVPSIYAPSIYTHLSPAKTPPPPPAMIPMRPPY-----GYPGD
                         ************************** * ****** ***** **** *       *****

LSR1.Hs (SEQ ID NO:8)    VDRSSSAGGQGSYVPLLRDTDSSVASEVRSGYRIQASQQDDSMRVLYYMEKELANFDPSR
LSR1.Rn (SEQ ID NO:2)    FDRHSSVGGHSSQVPLLRDVDGSVSSEVRSGYRIQANQQDDSMRVLYYMEKELANFDPSR
LSR1.Mm (SEQ ID NO:16)   FDRTSSVGGHSSQVPLLREVDGSVSSEVRSGYRIQANQQDDSMRVLYYMEKELANFDPSR
                          ** ** **  * ****** * ** ************ **********************

LSR1.Hs (SEQ ID NO:8)    PGPPSGRVERAMSEVTSLHEDDWRSRPSRGPALTPIRDEEWGGHSPRSPRGWDQEPAREQ
LSR1.Rn (SEQ ID NO:2)    PGPPNGRVERAMSEVTSLHEDDWRSRPSRAPALTPIRDEEWNRHSPQSPRTWEQEPLQEQ
LSR1.Mm (SEQ ID NO:16)   PGPPNGRVERAMSEVTSLHEDDWRSRPSRAPALTPIRDEEWNRHSPRSPRTWEQEPLQEQ
                         **** ************************ ********** * **. ***. * *** **

LSR1.Hs (SEQ ID NO:8)    AGGGWRARRPRARSVDALDDLTPPSTAESGSRSPTSNGGRSRAYMPPRSIRDDLYDQDD
LSR1.Rn (SEQ ID NO:2)    PRGGWGSGRPRARSVDALDDINRPGSTESGRSSPPSSGRRGRAYAPPRGRRDDLYDPDD
LSR1.Mm (SEQ ID NO:16)   PRGGWGSGRPRARSVDALDDINRPGSTESGRSSPPSSGRRGRAYAPPRGRRDDLYDPDD
                          *** .***********  *. ** ** .** ** *** ***  **  ******* **
```

FIG. 2A

```
LSR1.Hs (SEQ ID NO:8)   SRDFPRSRDPHY-DDFRSRERPPADPRSHHHRTRDPRDNGSRSGDLPYDGRLLEEAVRKK
LSR1.Rn (SEQ ID NO:2)   PRDLPHSRDPHYYDDIRSRD-PRADPR-SRQRSRDPRDAGFRSRDPQYDGRLLEEALKKK
LSR1.Mm (SEQ ID NO:16)  PRDLPHSRDPHYYDDLRSRD-PRADPR-SRQRSHDPRDAGFRSRDPQYDGRLLEEALKKK
                        ** *.****** ** ***. * ****   ..*..**** * ** *  *********..**
                                     +-+-
LSR1.Hs (SEQ ID NO:8)   GSEERRRPHKEEEEE---AYYPPAPPPYSETDSQASRERRLKKNLALSRESLVV
LSR1.Rn (SEQ ID NO:2)   GSGERRRVYREEEEEEE-GQYPPAPPPYSETDSQASRERRLKKNLALSRESLVV
LSR1.Mm (SEQ ID NO:16)  GAGERRRVYREEEEEEEGHYPPAPPPYSETDSQASRERRMKKNLALSRESLVV
                        *. ****  .*****   ********************.*************
```

FIG. 2B

```
                                                             FFA
LSR1.Hs (SEQ ID NO:8)   MQQDGLGVGTRNGSGKGRSVHPSWPWCAPRPLRYFGRDARARRAQTAAMALLAGGLSRGL
LSR2.Hs (SEQ ID NO:10)  MQQDGLGVGTRNGSGKGRSVHPSWPWCAPRPLRYFGRDARARRAQTAAMALLAGGLSRGL
LSR3.Hs (SEQ ID NO:12)  MQQDGLGVGTRNGSGKGRSVHPSWPWCAPRPLRYFGRDARARRAQTAAMALLAGGLSRGL
                        ************************************************************

LSR1.Hs (SEQ ID NO:8)   GSHPAAAGRDAVVFVWLLLSTWCTAPARAIQVTVSNPYHVVILFQPVTLPCTYQMTSTPT
LSR2.Hs (SEQ ID NO:10)  GSHPAAAGRDAVVFVWLLLSTWCTAPARAIQVTVSNPYHVVILFQPVTLPCTYQMTSTPT
LSR3.Hs (SEQ ID NO:12)  GSHPAAAGRDAVVFVWLLLSTWCTAPARAIQVTVSNPYHVVILFQPVTLPCTYQMTSTPT
                        ************************************************************

LSR1.Hs (SEQ ID NO:8)   QPIVIWKYKSFCRDRIADAFSPASVDNQLNAQLAAGNPGYNPYVECQDSVRTVRVVATKQ
LSR2.Hs (SEQ ID NO:10)  QPIVIWKYKSFCRDRIADAFSPASVDNQLNAQLAAGNPGYNPYVECQDSVRTVRVVATKQ
LSR3.Hs (SEQ ID NO:12)  QPIVIWKYKSFCRDRIADAFSPASVDNQLNAQLAAGNPGYNPYVECQDSVRTVRVVATKQ
                        ************************************************************

LSR1.Hs (SEQ ID NO:8)   GNAVTLGDYYQGRRITITGNADLTFDQTAWGDSGVYYCSVVSAQDLQGNNEAYAELVLG
LSR2.Hs (SEQ ID NO:10)  GNAVTLGDYYQGRRITITGNADLTFDQTAWGDSGVYYCSVVSAQDLQGNNEAYAELVL-
LSR3.Hs (SEQ ID NO:12)  GNAVTLGDYYQGRRITITGNADLTFDQTAWGDSGVYYCSVVSAQDLQGNNEAYAELVL-
                        ************************************************************

TM
LSR1.Hs (SEQ ID NO:8)   RTSGVAELPGFQAGPIEDWLFVVVVCLAAFLIFLLLGICWCQCCPHTCCCYVRCPCCPD
LSR2.Hs (SEQ ID NO:10)  -------E--------DWLFVVVVCLAAFLIFLLLGICWCQCCPHTCCCYVRCPCCPD
LSR3.Hs (SEQ ID NO:12)  -------E-------------------------------------------------

LSR1.Hs (SEQ ID NO:8)   KCCCPEALYAAGKAATSGVPSIYAPSTYAHLSPAKTPPPPAMIPMGPAYNGYPGGYPGDV
LSR2.Hs (SEQ ID NO:10)  KCCCPEALYAAGKAATSGVPSIYAPSTYAHLSPAKTPPPPAMIPMGPAYNGYPGGYPGDV
LSR3.Hs (SEQ ID NO:12)  -------VYAAGKAATSGVPSIYAPSTYAHLSPAKTPPPPAMIPMGPAYNGYPGGYPGDV
                        . ***********************************************

LSR1.Hs (SEQ ID NO:8)   DRSSSAGGQGSYVPLLRDTDSSVASEVRSGYRIQASQQDDSMRVLYYMEKELANFDPSRP
LSR2.Hs (SEQ ID NO:10)  DRSSSAGGQGSYVPLLRDTDSSVASEVRSGYRIQASQQDDSMRVLYYMEKELANFDPSRP
LSR3.Hs (SEQ ID NO:12)  DRSSSAGGQGSYVPLLRDTDSSVASEVRSGYRIQASQQDDSMRVLYYMEKELANFDPSRP
                        ************************************************************

LSR1.Hs (SEQ ID NO:8)   GPPSGRVERAMSEVTSLHEDDWRSRPSRGPALTPIRDEEWGGHSPRSPRGWDQEPAREQA
LSR2.Hs (SEQ ID NO:10)  GPPSGRVERAMSEVTSLHEDDWRSRPSRGPALTPIRDEEWGGHSPRSPRGWDQEPAREQA
LSR3.Hs (SEQ ID NO:12)  GPPSGRVERAMSEVTSLHEDDWRSRPSRGPALTPIRDEEWGGHSPRSPRGWDQEPAREQA
                        ************************************************************

LSR1.Hs (SEQ ID NO:8)   GGGWRARRPRARSVDALDDLTPPSTAESGSRSPTSNGGRSRAYMPDLGKRDDLYDQDDS
LSR2.Hs (SEQ ID NO:10)  GGGWRARRPRARSVDALDDLTPPSTAESGSRSPTSNGGRSRAYMPDLGKRDDLYDQDDS
LSR3.Hs (SEQ ID NO:12)  GGGWRARRPRARSVDALDDLTPPSTAESGSRSPTSNGGRSRAYMPDLGKRDDLYDQDDS
                        ************************************************************
```

FIG. 3A

```
LSR1.Hs (SEQ ID NO:8)    RDFPRSRDPHYDDFRSRERPPADPRSHHHRTRDPRDNGSRSGDLPYDGRLLEEAVRKKGS
LSR2.Hs (SEQ ID NO:10)   RDFPRSRDPHYDDFRSRERPPADPRSHHHRTRDPRDNGSRSGDLPYDGRLLEEAVRKKGS
LSR3.Hs (SEQ ID NO:12)   RDFPRSRDPHYDDFRSRERPPADPRSHHHRTRDPRDNGSRSGDLPYDGRLLEEAVRKKGS
                         ************************************************************
                              +-+-
LSR1.Hs (SEQ ID NO:8)    EERRRPHKEEEEEAYYPPAPPPYSETDSQASRERRLKKNLALSRESLVV
LSR2.Hs (SEQ ID NO:10)   EERRRPHKEEEEEAYYPPAPPPYSETDSQASRERRLKKNLALSRESLVV
LSR3.Hs (SEQ ID NO:12)   EERRRPHKEEEEEAYYPPAPPPYSETDSQASRERRLKKNLALSRESLVV
                         *************************************************
```

FIG. 3B

```
                                        FFA
LSR1.Rn (SEQ ID NO:2)   MAPAAGACAGAPDSHPATVVFVCLFLIIFCPDPASAIQVTVSDPYHVVILFQPVTLPCTY
LSR2.Rn (SEQ ID NO:4)   MAPAAGACAGAPDSHPATVVFVCLFLIIFCPDPASAIQVTVSDPYHVVILFQPVTLPCTY
LSR3.Rn (SEQ ID NO:6)   MAPAAGACAGAPDSHPATVVFVCLFLIIFCPDPASAIQVTVSDPYHVVILFQPVTLPCTY
                        ************************************************************

LSR1.Rn (SEQ ID NO:2)   QMSNTLTVPIVIWKYKSFCRDRIADAFSPASVDNQLNAQLAACNPCYNPYVECQDSVRTV
LSR2.Rn (SEQ ID NO:4)   QMSNTLTVPIVIWKYKSFCRDRIADAFSPASVDNQLNAQLAACNPCYNPYVECQDSVRTV
LSR3.Rn (SEQ ID NO:6)   QMSNTLTVPIVIWKYKSFCRDRIADAFSPASVDNQLNAQLAACNPCYNPYVECQDSVRTV
                        ************************************************************

LSR1.Rn (SEQ ID NO:2)   RVVATKQGNAVTLGDYYQGRRITITGNADLTFEQTAWGDSGVYYCSVVSAQDLDGNNEAY
LSR2.Rn (SEQ ID NO:4)   RVVATKQGNAVTLGDYYQGRRITITGNADLTFEQTAWGDSGVYYCSVVSAQDLDGNNEAY
LSR3.Rn (SEQ ID NO:6)   RVVATKQGNAVTLGDYYQGRRITITGNADLTFEQTAWGDSGVYYCSVVSAQDLDGNNEAY
                        ************************************************************

TM
LSR1.Rn (SEQ ID NO:2)   AELIVLGRTSEAPELEPGFRAGPLEDWLFVVVVCLASLLLFLLLGICWCQCCPHTCCCYV
LSR2.Rn (SEQ ID NO:4)   AELIVL--------EL---------DWLFVVVVCLASLLLFLLLGICWCQCCPHTCCCYV
LSR3.Rn (SEQ ID NO:6)   AELIVL--------------------------------------------------
                        ******

LSR1.Rn (SEQ ID NO:2)   RCPCCPDKCCCPEALYAAGKAATSGVPSIYAPSIYTHLSPAKTPPPPPAMIPMGPPYGYP
LSR2.Rn (SEQ ID NO:4)   RCPCCPDKCCCPEALYAAGKAATSGVPSIYAPSIYTHLSPAKTPPPPPAMIPMGPPYGYP
LSR3.Rn (SEQ ID NO:6)   --------------VYAAGKAATSGVPSIYAPSIYTHLSPAKTPPPPPAMIPMGPPYGYP
                                            ****************************************

LSR1.Rn (SEQ ID NO:2)   GDFDRHSSVGGHSSQVPLLRDVDGSVSSEVRSGYRIQANQQDDSMRVLYYMEKELANFDP
LSR2.Rn (SEQ ID NO:4)   GDFDRHSSVGGHSSQVPLLRDVDGSVSSEVRSGYRIQANQQDDSMRVLYYMEKELANFDP
LSR3.Rn (SEQ ID NO:6)   GDFDRHSSVGGHSSQVPLLRDVDGSVSSEVRSGYRIQANQQDDSMRVLYYMEKELANFDP
                        ************************************************************

LSR1.Rn (SEQ ID NO:2)   SRPGPPNGRVERAMSEVTSLHEDDWRSRPSRAPALTPIRDEEWNRHSPQSPRTWEQEPLQ
LSR2.Rn (SEQ ID NO:4)   SRPGPPNGRVERAMSEVTSLHEDDWRSRPSRAPALTPIRDEEWNRHSPQSPRTWEQEPLQ
LSR3.Rn (SEQ ID NO:6)   SRPGPPNGRVERAMSEVTSLHEDDWRSRPSRAPALTPIRDEEWNRHSPQSPRTWEQEPLQ
                        ************************************************************

LSR1.Rn (SEQ ID NO:2)   EQPRGGWGSGRPRARSVDALDDINRPGSTESGRSSPPSSGRRGRAYAPRRSSRDDLYDP
LSR2.Rn (SEQ ID NO:4)   EQPRGGWGSGRPRARSVDALDDINRPGSTESGRSSPPSSGRRGRAYAPRRSSRDDLYDP
LSR3.Rn (SEQ ID NO:6)   EQPRGGWGSGRPRARSVDALDDINRPGSTESGRSSPPSSGRRGRAYAPRRSSRDDLYDP
                        ***********************************************************

LSR1.Rn (SEQ ID NO:2)   DDPRDLPHSRDPHYYDDIRSRDPRADPRSRQRSRDPRDAGFRSRDPQYDGRLLEEALKKK
LSR2.Rn (SEQ ID NO:4)   DDPRDLPHSRDPHYYDDIRSRDPRADPRSRQRSRDPRDAGFRSRDPQYDGRLLEEALKKK
LSR3.Rn (SEQ ID NO:6)   DDPRDLPHSRDPHYYDDIRSRDPRADPRSRQRSRDPRDAGFRSRDPQYDGRLLEEALKKK
                        ************************************************************
```

FIG. 4A

```
                                        +-+-
LSR1.Rn (SEQ ID NO:2)    GSGERRRVYREEEEEEGQYPPAPPPYSETDSQASRERRLKKNLALSRESLVV
LSR2.Rn (SEQ ID NO:4)    GSGERRRVYREEEEEEGQYPPAPPPYSETDSQASRERRLKKNLALSRESLVV
LSR3.Rn (SEQ ID NO:6)    GSGERRRVYREEEEEEGQYPPAPPPYSETDSQASRERRLKKNLALSRESLVV
                            ************************************************
```

FIG. 4B

```
                                              FFA
LSR1.Mm (SEQ ID NO:16)  MAPAASACAGAPGSHPATTIFV CLFLIIYCPDRASAIQVT VPDPYHVVILFQPVTLHCTY
LSR2.Mm (SEQ ID NO:17)  MAPAASACAGAPGSHPATTIFV CLFLIIYCPDRASAIQVT VPDPYHVVILFQPVTLHCTY
LSR1.Mm (SEQ ID NO:18)  MAPAASACAGAPGSHPATTIFV CLFLIIYCPDRASAIQVT VPDPYHVVILFQPVTLHCTY
                        ****************************************************

LSR1.Mm (SEQ ID NO:16)  QMSNTLTAPIVIWKYKSFCRDRVADAFSPASVDNQLNAQLAAGNPGVNPYVECQDSVRTV
LSR2.Mm (SEQ ID NO:17)  QMSNTLTAPIVIWKYKSFCRDRVADAFSPASVDNQLNAQLAAGNPGVNPYVECQDSVRTV
LSR3.Mm (SEQ ID NO:18)  QMSNTLTAPIVIWKYKSFCRDRVADAFSPASVDNQLNAQLAAGNPGVNPYVECQDSVRTV
                        ************************************************************

LSR1.Mm (SEQ ID NO:16)  RVVATKQGNAVTLGDYYQGRRITITGNAGLTFEQTAWGDSGVYYCSVVSAQDLDGNNEAY
LSR2.Mm (SEQ ID NO:17)  RVVATKQGNAVTLGDYYQGRRITITGNAGLTFEQTAWGDSGVYYCSVVSAQDLDGNNEAY
LSR2.Mm (SEQ ID NO:18)  RVVATKQGNAVTLGDYYQGRRITITGNAGLTFEQTAWGDSGVYYCSVVSAQDLDGNNEAY
                        ************************************************************

TM
LSR1.Mm (SEQ ID NO:16)  AELIVLGRTSEAPELTPGFRAGPLEDWLFVVVVCLASLLFFLLLGICWCQCCPHTCCCYV
LSR2.Mm (SEQ ID NO:17)  AELIVL-------ELT---------DWLFVVVVCLASLLFFLLLGICWCQCCPHTCCCYV
LSR3.Mm (SEQ ID NO:18)  AELIVL-------ELT---------------------------------------------
                        ******

LSR1.Mm (SEQ ID NO:16)  RCPCCPDKCCCPEALYAAGKAATSGVPSIYAPSIYTHLSPAKTPPPPPAMIPMRPPYGYP
LSR2.Mm (SEQ ID NO:17)  RCPCCPDKCCCPEALYAAGKAATSGVPSIYAPSIYTHLSPAKTPPPPPAMIPMRPPYGYP
LSR3.Mm (SEQ ID NO:18)  ---------------VYAAGKAATSGVPSIYAPSIYTHLSPAKTPPPPPAMIPMRPPYGYP
                                       *********************************************

LSR1.Mm (SEQ ID NO:16)  GDFDRTSSVGGHSSQVPLLREVDGSVSSEVRSGYRIQANQQDDSMRVLYYMEKELANFDP
LSR2.Mm (SEQ ID NO:17)  GDFDRTSSVGGHSSQVPLLREVDGSVSSEVRSGYRIQANQQDDSMRVLYYMEKELANFDP
LSR3.Mm (SEQ ID NO:18)  GDFDRTSSVGGHSSQVPLLREVDGSVSSEVRSGYRIQANQQDDSMRVLYYMEKELANFDP
                        ************************************************************

LSR1.Mm (SEQ ID NO:16)  SRPGPPNGRVERAMSEVTSLHEDDWRSRPSRAPALTPIRDEEWNRHSPRSPRTWEQEPLQ
LSR2.Mm (SEQ ID NO:17)  SRPGPPNGRVERAMSEVTSLHEDDWRSRPSRAPALTPIRDEEWNRHSPRSPRTWEQEPLQ
LSR3.Mm (SEQ ID NO:18)  SRPGPPNGRVERAMSEVTSLHEDDWRSRPSRAPALTPIRDEEWNRHSPRSPRTWEQEPLQ
                        ************************************************************

LSR1.Mm (SEQ ID NO:16)  EQPRGGWGSGRPRARSVDALDDINRPGSTESGRSSPPSSGRRGRAYAPPRGSRDDLYDP
LSR2.Mm (SEQ ID NO:17)  EQPRGGWGSGRPRARSVDALDDINRPGSTESGRSSPPSSGRRGRAYAPPRGSRDDLYDP
LSR3.Mm (SEQ ID NO:18)  EQPRGGWGSGRPRARSVDALDDINRPGSTESGRSSPPSSGRRGRAYAPPRGSRDDLYDP
                        ***********************************************************

LSR1.Mm (SEQ ID NO:16)  DDPRDLPHSRDPHYYDDLRSRDPRADPRSRQRSHDPRDAGFRSRDPQYDGRLLEEALKKK
LSR2.Mm (SEQ ID NO:17)  DDPRDLPHSRDPHYYDDLRSRDPRADPRSRQRSHDPRDAGFRSRDPQYDGRLLEEALKKK
LSR3.Mm (SEQ ID NO:18)  DDPRDLPHSRDPHYYDDLRSRDPRADPRSRQRSHDPRDAGFRSRDPQYDGRLLEEALKKK
                        ************************************************************
```

FIG. 5A

```
                                        +-+-
LSR1.Mm (SEQ ID NO:16)    GAG ERRRVYREEEEEEEE GHYPPAPPPYSETDSQASRERRMKKNLALSRESLVV
LSR2.Mm (SEQ ID NO:17)    GAG ERRRVYREEEEEEEE GHYPPAPPPYSETDSQASRERRMKKNLALSRESLVV
LSR3.Mm (SEQ ID NO:18)    GAG ERRRVYREEEEEEEE GHYPPAPPPYSETDSQASRERRMKKNLALSRESLVV
                              *************************************************
```

FIG. 5B

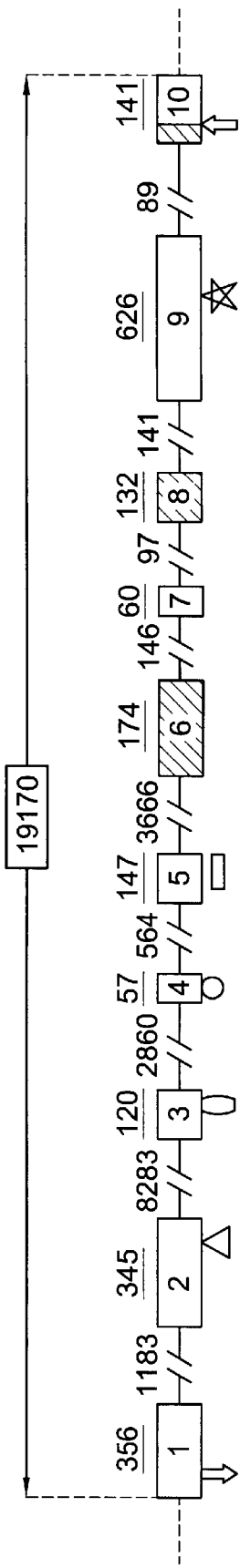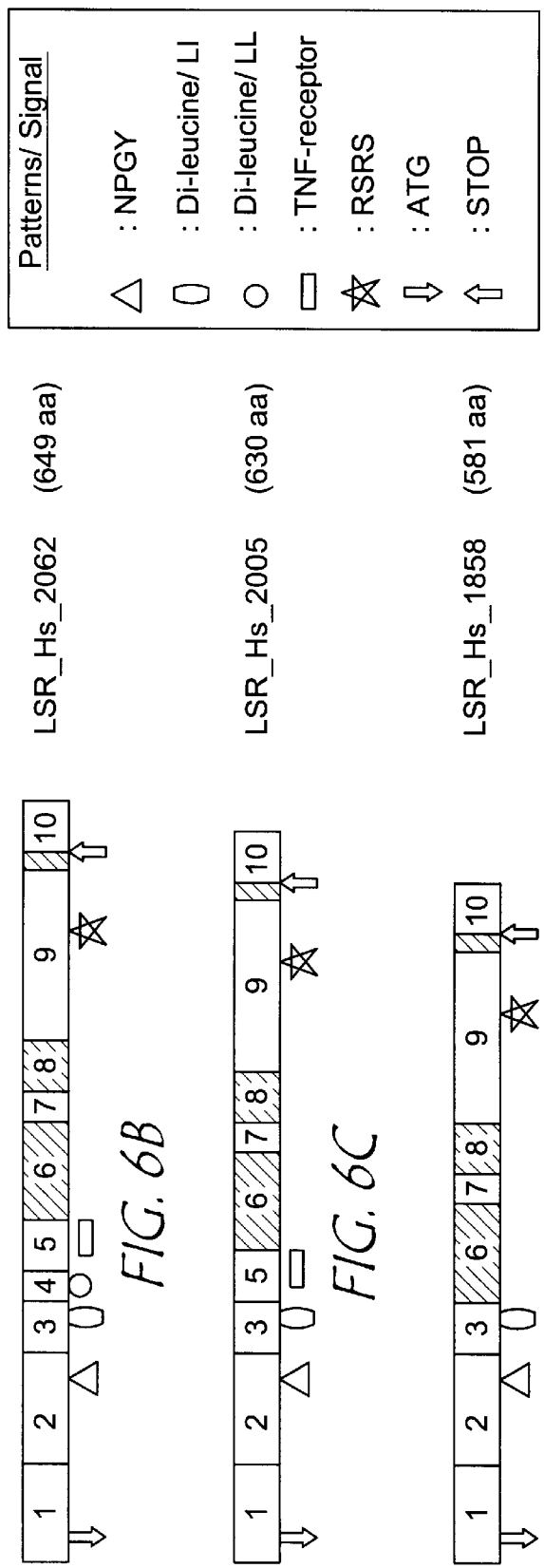
FIG. 6A
FIG. 6B
FIG. 6C
FIG. 6D

```
lsr1.Hs (SEQ ID NO:7)    TGGAGTGTGGCTCGGAGGACCGCGGCGGGTCAAGCACCTTTCTCCCCCATATCTGAAAGC
lsr1.Rn (SEQ ID NO:1)    --------------------ACCGCTCACCAGGTCAGTTGTCCCCGGAAAGCCGAAGGC
lsr1.Mm (SEQ ID NO:13)   ------------------------------------------------------------ lsr1.Hs (SEQ ID NO:7)    ATGCCCTTTGTCCACGTCGTTTACGCTCATTAAAACT--TCCAGAATGCAACAGGACGGA
lsr1.Rn (SEQ ID NO:1)    ATGAGCTTCGCCCAAGTTCTTTTTATGGGTTAGAACTCCTCCAGAGCGGGGGAAAAAGGA
lsr1.Mm (SEQ ID NO:13)   ------------------------------------------------------------ lsr1.Hs (SEQ ID NO:7)    CTTGGAGTAGGGACAAGGAACGGAAGTGGGAAGGGGAGGAGCGTGCACCCCTCCTGGCCT
lsr1.Rn (SEQ ID NO:1)    CTTGGAATAGGGGC------------------GGGACGGAGCACGCACCCTTCTCCGCCT
lsr1.Mm (SEQ ID NO:13)   ------------------------------------------------------------ lsr1.Hs (SEQ ID NO:7)    TGGTGCGCGCCGCGCCCCCTA------AGGTACTTTGGAAGGGACGCGCGGGC-CAGACG
lsr1.Rn (SEQ ID NO:1)    TGGTTCTCGCCGCGCCCCCTACTCTCGGGATACTTGGGAGGGGACGCGCGGGCACCGTCG
lsr1.Mm (SEQ ID NO:13)   ---------------------------------------------------GCACCGTCG
                                                                            ** * * ** lsr1.Hs (SEQ ID NO:7)    CGCCCAGACGGCCGCGATGGCGCTGTTGGCCGGCGGGCTCTCCAGAGGGCTGGGCTCCCA
lsr1.Rn (SEQ ID NO:1)    CTGCTAGACGGCCGCGATGGCGCCGGCGGCCGGCGCGTGTGCTGGGGCGCCTGACTCCCA
lsr1.Mm (SEQ ID NO:13)   CTGCTAGACGGCCGCGATGGCGCCGGCGGCCAGCGCGTGTGCTGGGGCGCCTGGCTCCCA
                          *  * ****************** *  **** *    *   *  *  ** * ****** lsr1.Hs (SEQ ID NO:7)    CCCGGCCGCCGCAGGCCGGGACGCGGTCGTCTTCGTGTGGCTTCTGCTTAGCACCTGGTG
lsr1.Rn (SEQ ID NO:1)    CCCAGCTACCGTGG---------------TCTTCGTGTGTCTCTTTCTCATCATTTTCTG
lsr1.Mm (SEQ ID NO:13)   CCCGGCCACCACGA---------------TCTTCGTGTGTCTTTTTCTCATCATTTACTG
                         *                      ******     *  *  * ** lsr1.Hs (SEQ ID NO:7)    CACAGCTCCTGCCAGGGCCATCCAGGTGACCGTGTCCAACCCCTACCACGTGGTGATCCT
lsr1.Rn (SEQ ID NO:1)    CCCAGACCCTGCCAGTGCCATCCAGGTGACTGTGTCTGACCCCTACCACGTAGTGATCCT
lsr1.Mm (SEQ ID NO:13)   CCCAGACCGTGCCAGTGCCATCCAGGTGACCGTGCCTGACCCCTACCACGTAGTGATCCT
                          * ***  * **** ********** *    ********** ***** lsr1.Hs (SEQ ID NO:7)    CTTCCAGCCTGTGACCCTGCCCTGTACCTACCAGATGACCTCGACCCCCACGCAACCCAT
lsr1.Rn (SEQ ID NO:1)    GTTCCAGCCAGTGACCCTGCCCTGCACCTATCAGATGAGCAACACTCTCACAGTCCCCAT
lsr1.Mm (SEQ ID NO:13)   GTTCCAGCCAGTGACACTACACTGCACCTACCAGATGAGCAATACCCTCACAGCCCCTAT
                          ****** ***  *   * * * **** *  **  * *** * lsr1.Hs (SEQ ID NO:7)    CGTCATCTGGAAGTACAAGTCTTTCTGCCGGGACCGCATCGCCGATGCCTTCTCCCCGGC
lsr1.Rn (SEQ ID NO:1)    CGTGATCTGGAAGTACAAGTCATTCTGCCGGGACCGTATTGCCGATGCCTTCTCTCCTGC
lsr1.Mm (SEQ ID NO:13)   CGTGATCTGGAAGTATAAGTCGTTCTGTCGGGACCGTGTTGCCGACGCCTTCTCCCCTGC
                         *** *********** ***** ***** ********  * ***** ********* ** **
```

FIG. 7A

```
lsrl.Hs  (SEQ ID NO:7)    CAGCGTCGACAACCAGCTCAATGCCCAGCTGGCAGCCGGGAACCCAGGCTACAACCCCTA
lsrl.Rn  (SEQ ID NO:1)    CAGTGTGGACAACCAGCTAAATGCCCAGTTGGCAGCTGGCAACCCCGGCTACAACCCCTA
lsrl.Mm  (SEQ ID NO:13)   CAGCGTGGACAACCAGCTCAACGCCCAGCTGGCGGCTGGCAACCCCGGCTACAACCCCTA
                          *  **********  ****    * *********** lsrl.Hs  (SEQ ID NO:7)    CGTTGAGTGCCAGGACAGCGTGCGCACCGTCAGGGTCGTGGCCACCAAGCAGGGCAACGC
lsrl.Rn  (SEQ ID NO:1)    TGTGGAGTGCCAGGACAGTGTACGCACTGTCAGGGTGGTGGCCACCAAACAGGGCAATGC
lsrl.Mm  (SEQ ID NO:13)   TGTGGAGTGCCAGGACAGCGTACGCACTGTCAGGGTGGTGGCCACCAAACAGGGCAATGC
                           **********  *** **** ******** *** lsrl.Hs  (SEQ ID NO:7)    TGTGACCCTGGGAGATTACTACCAGGGCCGGAGGATTACCATCACCGGAAATGCTGACCT
lsrl.Rn  (SEQ ID NO:1)    GGTGACCCTGGGAGACTACTACCAAGGCAGGAGGATCACCATAACAGGAAATGCTGACCT
lsrl.Mm  (SEQ ID NO:13)   TGTGACCCTGGGAGACTACTACCAGGGCAGGAGAATCACCATCACAGGAAATGCTGGCCT
                          **************** *** * **  ***  ******* lsrl.Hs  (SEQ ID NO:7)    GACCTTTGACCAGACGGCGTGGGGGACAGTGGTGTGTATTACTGCTCCGTGGTCTCAGC
lsrl.Rn  (SEQ ID NO:1)    GACCTTCGAGCAGACAGCCTGGGGAGACAGTGGAGTGTATTACTGCTCTGTGGTCTCGGC
lsrl.Mm  (SEQ ID NO:13)   GACCTTCGAGCAGACGGCCTGGGGAGACAGTGGAGTGTATTACTGCTCCGTGGTCTCAGC
                          ****  ***  *** **** ********** **** lsrl.Hs  (SEQ ID NO:7)    CCAGGACCTCCAGGGGAACAATGAGGCCTACGCAGAGCTCATCGTCCTTGGGAGGACCTC
lsrl.Rn  (SEQ ID NO:1)    CCAAGATCTGGATGGAAACAACGAGGCGTACGCAGAGCTCATCGTCCTTGGCAGGACCTC
lsrl.Mm  (SEQ ID NO:13)   CCAAGATCTGGATGGGAACAACGAGGCGTACGCAGAGCTCATTGTCCTTGGCAGGACCTC
                          *  **  *  * * ********** **** ****** lsrl.Hs  (SEQ ID NO:7)    AGGGGTGGCTGAGCTCTTACCTGGTTTTCAGGCGGGGCCCATAGAAGACTGGCTCTTCGT
lsrl.Rn  (SEQ ID NO:1)    AGAGGCCCCTGAGCTCCTACCTGGTTTTCGGGCGGGGCCCTTGGAAGATTGGCTCTTTGT
lsrl.Mm  (SEQ ID NO:13)   AGAAGCCCCTGAGCTCCTACCTGGTTTTCGGGCGGGGCCCTTGGAAGATTGGCTCTTTGT
                          **  *   ****** ******** *********  * *** ** lsrl.Hs  (SEQ ID NO:7)    GGTTGTGGTATGCCTGGCTGCCTTCCTCATCTTCCTCCTCCTGGGCATCTGCTGGTGCCA
lsrl.Rn  (SEQ ID NO:1)    GGTCGTGGTCTGCCTGGCGAGCCTCCTCCTCTTCCTCCTCCTGGGCATCTGCTGGTGCCA
lsrl.Mm  (SEQ ID NO:13)   GGTCGTGGTCTGCCTGGCAAGCCTCCTCTTCTTCCTCCTCCTGGGCATCTGCTGGTGCCA
                          * * ******   *  *  ** * ***************************** lsrl.Hs  (SEQ ID NO:7)    GTGCTGCCCGCACACTTGCTGCTGCTACGTCAGGTGCCCCTGCTGCCCAGACAAGTGCTG
lsrl.Rn  (SEQ ID NO:1)    GTGCTGTCCTCACACCTGCTGCTGCTATGTCCGATGTCCCTGCTGCCCAGACAAGTGCTG
lsrl.Mm  (SEQ ID NO:13)   GTGCTGTCCCCACACCTGCTGCTGCTATGTCAGATGTCCCTGCTGCCCAGACAAGTGCTG
                          ****  *** ******* * *  * *********************** lsrl.Hs  (SEQ ID NO:7)    CTGCCCCGAGGCCCTGTATGCCGCCGGCAAAGCAGCCACCTCAGGTGTTCCCAGCATTTA
lsrl.Rn  (SEQ ID NO:1)    TTGCCCTGAGGCTCTTTATGCTGCTGGCAAAGCAGCCACCTCAGGTGTCCCGAGCATCTA
lsrl.Mm  (SEQ ID NO:13)   TTGCCCTGAGGCCCTTTATGCTGCTGGCAAAGCAGCCACCTCAGGTGTGCCAAGCATCTA
                          ***** *****  ** ***** ** ********************** ** ****  **
```

FIG. 7B

```
lsrl.Hs (SEQ ID NO:7)    TGCCCCCAGCACCTATGCCCACCTGTCTCCCGCCAAGACCCCACC---CCCACCAGCTAT
lsrl.Rn (SEQ ID NO:1)    TGCCCCCAGCATCTATACCCACCTCTCACCTGCCAAGACCCCACCACCTCCGCCTGCCAT
lsrl.Mm (SEQ ID NO:13)   TGCCCCCAGCATCTATACCCACCTCTCTCCTGCCAAGACTCCGCCACCTCCGCCTGCCAT
                         ********  ***   ***            ** lsrl.Hs (SEQ ID NO:7)    GATTCCCATGGGCCCTGCCTACAACGGGTACCCTGGAGGATACCCTGGAGACGTTGACAG
lsrl.Rn (SEQ ID NO:1)    GATTCCCATGGGCCCTCCCTAT---------------GGGTACCCTGGAGACTTTGACAG
lsrl.Mm (SEQ ID NO:13)   GATTCCCATGCGTCCTCCCTAT---------------GGGTACCCTGGAGACTTTGACAG
                         ********** *  *                  ********** **** lsrl.Hs (SEQ ID NO:7)    GAGTAGCTCAGCTGGTGGCCAAGGCTCCTATGTACCCCTGCTTCGGGACACGGACAGCAG
lsrl.Rn (SEQ ID NO:1)    ACATAGCTCAGTTGGTGGCCACAGCTCCCAAGTACCCCTGCTGCGTGACGTGGATGGCAG
lsrl.Mm (SEQ ID NO:13)   GACCAGCTCAGTTGGTGGCCACAGCTCCCAGGTGCCCCTGCTGCGTGAAGTGGATGGGAG
                          *  **** ****** * ****  *  ****  **   *  * ** lsrl.Hs (SEQ ID NO:7)    TGTGGCCTCTGAAGTCCGCAGTGGCTACAGGATTCAGGCCAGCCAGCAGGACGACTCCAT
lsrl.Rn (SEQ ID NO:1)    TGTATCTTCAGAAGTACGAAGTGGCTACAGGATCCAGGCTAACCAGCAAGATGACTCCAT
lsrl.Mm (SEQ ID NO:13)   CGTATCTTCAGAAGTACGAAGTGGCTACAGGATCCAGGCTAACCAGCAAGATGACTCCAT
                          **  *      ********** **** * ****   ******* lsrl.Hs (SEQ ID NO:7)    GCGGGTCCTGTACTACATGGAGAAGGAGCTGGCCAACTTCGACCCTTCTCGACCTGGCCC
lsrl.Rn (SEQ ID NO:1)    GAGGGTCCTATACTATATGGAGAAAGAGCTAGCCAACTTTGACCCTTCCCGACCTGGCCC
lsrl.Mm (SEQ ID NO:13)   GAGGGTCCTATACTATATGGAGAAGGAGCTAGCCAACTTCGATCCTTCCCGGCCTGGCCC
                         *  **** ** **** * ***   ***  ******** lsrl.Hs (SEQ ID NO:7)    CCCCAGTGGCCGTGTGGAGCGGGCCATGAGTGAAGTCACCTCCCTCCACGAGGACGACTG
lsrl.Rn (SEQ ID NO:1)    TCCCAATGGCAGAGTGGAACGGGCCATGAGTGAAGTAACCTCCCTCCATGAAGATGACTG
lsrl.Mm (SEQ ID NO:13)   TCCCAATGGCCGAGTGGAACGGGCCATGAGTGAAGTAACCTCCCTCCATGAAGATGACTG
                          ** ** * *** ************ *******    *** lsrl.Hs (SEQ ID NO:7)    GCGATCTCGGCCTTCCCGGGGCCCTGCCCTCACCCCGATCCGGGATGAGGAGTGGGGTGG
lsrl.Rn (SEQ ID NO:1)    GCGATCGAGGCCTTCCAGGGCTCCTGCCCTCACCCCCATCAGGGATGAGGAGTGGAATCG
lsrl.Mm (SEQ ID NO:13)   GCGATCTCGGCCTTCCAGGGCTCCTGCCCTCACACCCATCAGGGATGAGGAGTGGAATCG
                         ****  *** *   *********  *  ***********  * lsrl.Hs (SEQ ID NO:7)    CCACTCCCCCGGAGTCCCAGGGGATGGGACCAGGAGCCCGCCAGGGAGCAGGCAGGCGG
lsrl.Rn (SEQ ID NO:1)    CCACTCCCCACAGAGTCCCAGAACATGGGAGCAGGAACCCCTTCAAGAACAACCAAGGGG
lsrl.Mm (SEQ ID NO:13)   CCACTCCCCTCGGAGTCCCAGAACATGGGAGCAGGAACCCCTTCAAGAACAGCCAAGGGG
                         ********* * ********  * **** ** *        ** * ** lsrl.Hs (SEQ ID NO:7)    GGGCTGGCGGGCCAGGCGGCCCCGGGCCCGCTCCGTGGACGCCCTGGACGACCTCACCCC
lsrl.Rn (SEQ ID NO:1)    TGGTTGGGGGTCTGGACGCCCTCGGGCCCGCTCTGTGGATGCTCTAGATGATATCAACCG
lsrl.Mm (SEQ ID NO:13)   TGGTTGGGGGTCTGGGCGGCCTCGGGCCCGCTCTGTGGATGCTCTAGATGACATCAACCG
                         ** *** ** *  *      * ** ****** * ***** ** *** ** ** **   **
```

FIG. 7C

```
lsr1.Hs  (SEQ ID NO:7)    GCCGAGCACCGCCGAGTCAGGGAGCAGGTCTCCCACGAGTAATGGTGGGAGAAGCCGGGC
lsr1.Rn  (SEQ ID NO:1)    GCCTGGCTCCACTGAATCAGGACGGTCTTCTCCCCCAAGTAGTGGACGGAGAGGACGGGC
lsr1.Mm  (SEQ ID NO:13)   GCCTGGCTCCACTGAATCAGGAAGGTCTTCTCCCCCAAGTAGTGGACGGAGAGGGCGGGC
                          *    ***** *      ****** * ** * ***** * ***** lsr1.Hs  (SEQ ID NO:7)    CTACATGCCCCGCGGAGCCGCAGCCGGGACGACCTCTATGACCAAGACGACTCGAGGGA
lsr1.Rn  (SEQ ID NO:1)    CTATGCACCTCCAAGAAGTCGCAGCCGGGATGACCTCTATGACCCGGACGATCCTAGGGA
lsr1.Mm  (SEQ ID NO:13)   CTATGCACCTCCGAGAAGTCGCAGCCGGGATGACCTCTATGACCCCGACGATCCTAGAGA
                          *       **   *  ******** ********** * lsr1.Hs  (SEQ ID NO:7)    CTTCCCACGCTCCCGGGACCCCCACTAC---GACGACTTCAGGTCTCGGGAGCGCCCTCC
lsr1.Rn  (SEQ ID NO:1)    CTTGCCACATTCCCGAGATCCCCACTATTATGACGACATCAGGTCTAGAGA---TCCACG
lsr1.Mm  (SEQ ID NO:13)   CTTGCCACATTCCCGAGATCCCCACTATTATGATGATTTGAGGTCTAGGGA---TCCACG
                          *   *  ******     **  * ****** *         * lsr1.Hs  (SEQ ID NO:7)    TGCCGACCCCAGGTCCCACCACCACCGTACCCGGGACCCTCGGGACAACGGCTCCAGGTC
lsr1.Rn  (SEQ ID NO:1)    TGCTGACCCCAGATCCCGTCAGC---GATCCCGAGATCCTCGGGATGCTGGCTTCAGGTC
lsr1.Mm  (SEQ ID NO:13)   TGCTGACCCCAGATCCCGTCAGC---GATCCCACGATCCTCGGGATGCTGGCTTCAGGTC
                          * ****     *    *  *       ******       **** lsr1.Hs  (SEQ ID NO:7)    CGGGGACCTCCCCTATGATGGGCGGCTACTGGAGGAGGCTGTGAGGAAGAAGGGGTCGGA
lsr1.Rn  (SEQ ID NO:1)    AAGGGACCCTCAGTATGATGGGCGACTATTAGAAGAGGCTTTAAAGAAAAAGGGGTCGGG
lsr1.Mm  (SEQ ID NO:13)   ACGGGACCCTCAGTATGATGGGCGACTCTTAGAAGAGGCTTTAAAGAAAAAGGGGCTGG
                            ******  *  *********    ** * ******  *  *  *** * * lsr1.Hs  (SEQ ID NO:7)    GGAGAGGAGGAGACCCCACAAGGAGGA---------GGAGGAAGAGGCCTACTACCCGCC
lsr1.Rn  (SEQ ID NO:1)    CGAGAGAAGGAGGGTTTACAGGGAGGAAGAAGA---GGAAGAGGAGGGCCAATACCCCCC
lsr1.Mm  (SEQ ID NO:13)   GGAGAGAAGACGCGTTTACAGGGAGGAAGAAGAAGAAGAAGAGGAGGGCCACTATCCCCC
                           ***     *  ****         **** * *     ** lsr1.Hs  (SEQ ID NO:7)    CGCGCCGCCCCGTACTCGGAGACCGACTCGCAGGCGTCCCGAGAGCGCAGGCTCAAGAA
lsr1.Rn  (SEQ ID NO:1)    AGCACCTCCACCTTACTCAGAGACTGACTCGCAGGCCTCACGGGAGAGGAGGCTGAAAAA
lsr1.Mm  (SEQ ID NO:13)   AGCACCTCCGCCTTACTCTGAGACTGACTCGCAGGCCTCGAGGGAGCGGAGGATGAAAAA
                               *** *  ******    *  * lsr1.Hs  (SEQ ID NO:7)    GAACTTGGCCCTGAGTCGGGAAAGTTTAGTCGTCTGATCTGACGTT -------------
lsr1.Rn  (SEQ ID NO:1)    GAATTTGGCCCTGAGTCGGGAAAGTTTAGTCGTCTGATCC-ACGTTTGT-ATGTAGCTT
lsr1.Mm  (SEQ ID NO:13)   GAATTTGGCCCTGAGTCGGGAAAGTTTAGTCGTCTGATCCCACGTTTTGTTATGTAGCTT
                          * *********************************** *** lsr1.Hs  (SEQ ID NO:7)    ------------------------------------------------------------
lsr1.Rn  (SEQ ID NO:1)    TTGTACTTTTTTTTTAATTGGAATCAATATTGATGAAACTTCAAGCCTAATAAAATGTCT
lsr1.Mm  (SEQ ID NO:13)   TTATACTTTTTAATTGGAATATTGATGA--AACTCTTCACCAAGCCTAATAAAA-----
```

FIG. 7D

```
lsr1.Hs (SEQ ID NO:7)     ----------------
lsr1.Rn (SEQ ID NO:1)     AATCACAAAAAAAAAAA
lsr1.Mm (SEQ ID NO:13)    ----------------
```

FIG. 7E

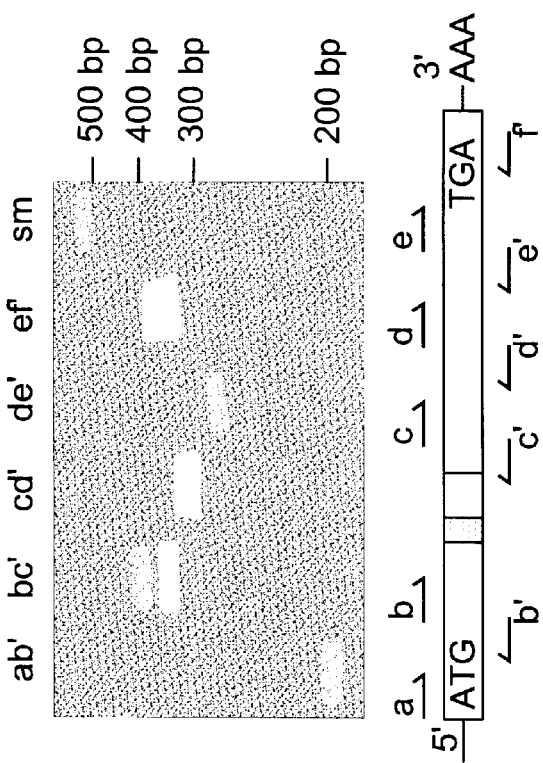
FIG. 11C
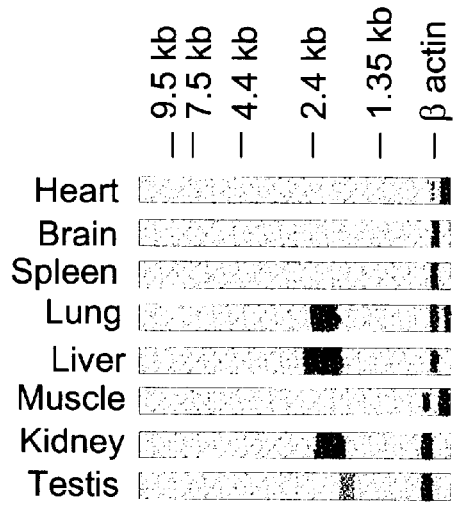
FIG. 11B
FIG. 11A

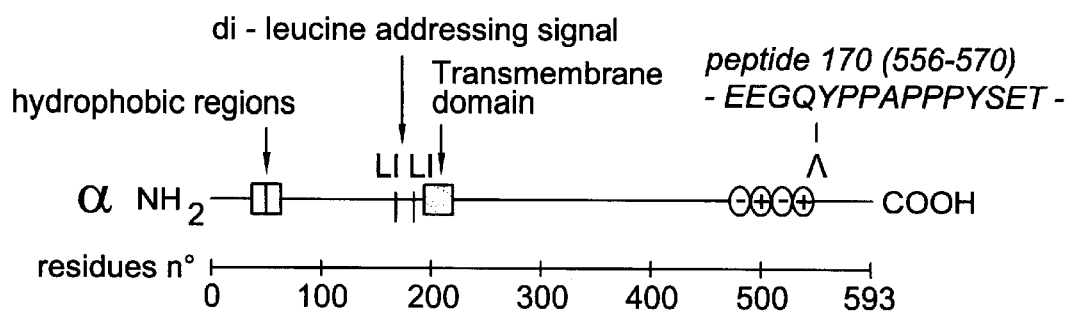
FIG. 14A  Peptide 170
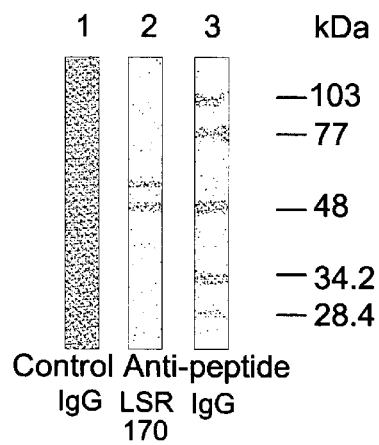
FIG. 14B  Western
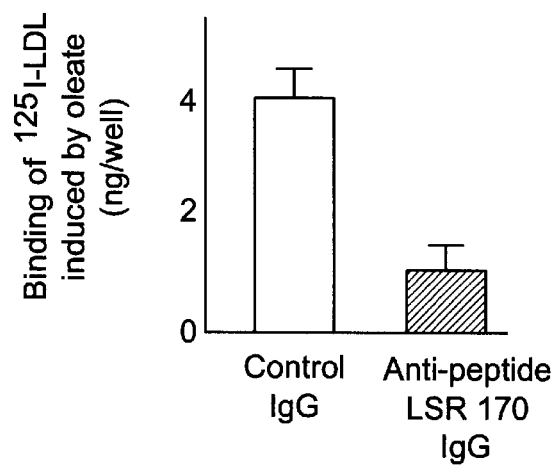
FIG. 14C  Immunionhibition

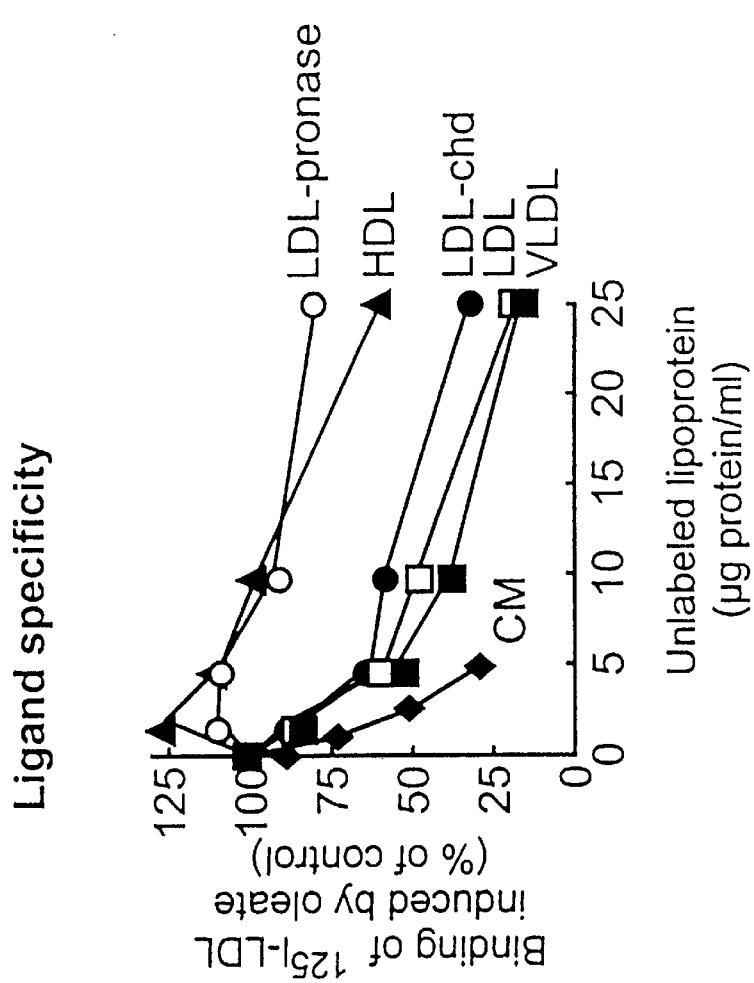
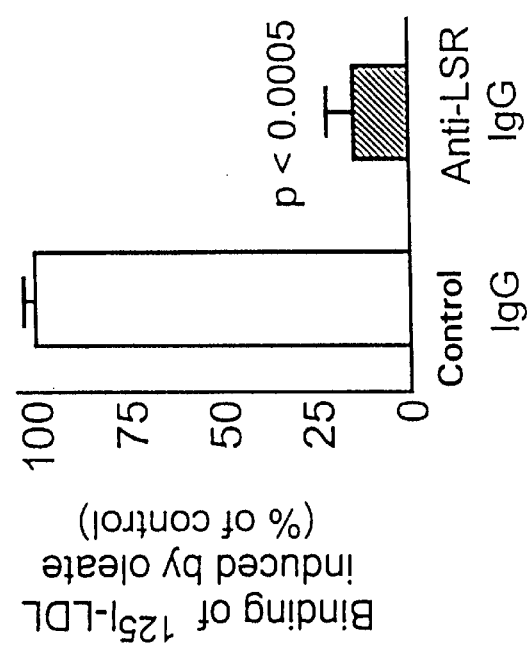
FIG. 17B
FIG. 17A

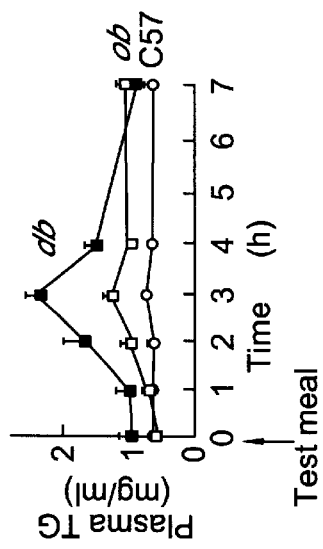
FIG. 28A Weight
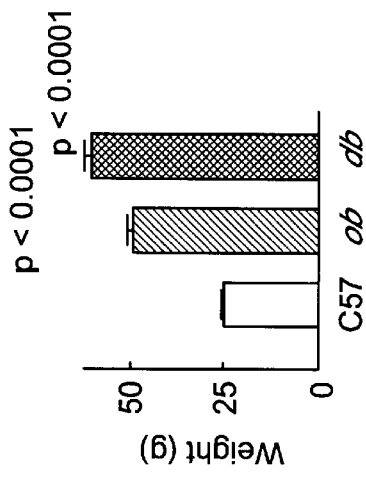
FIG. 28C LSR activity
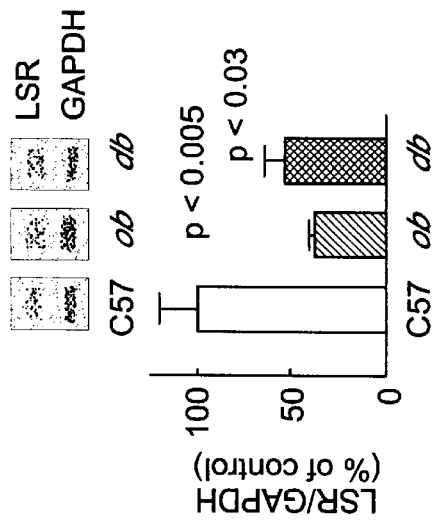
FIG. 28B Postprandial lipemic response
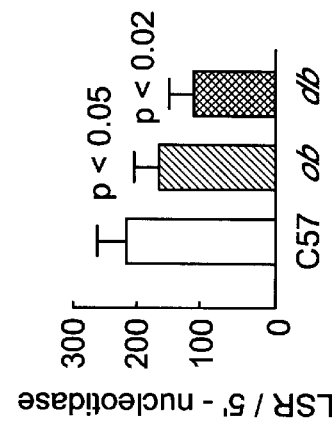
FIG. 28D Northern blot

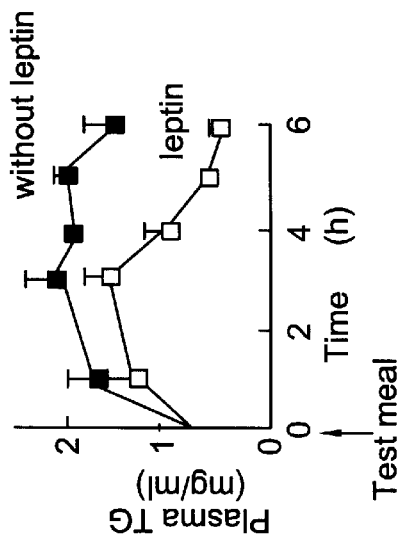
FIG. 29B Postrandial lipemic response
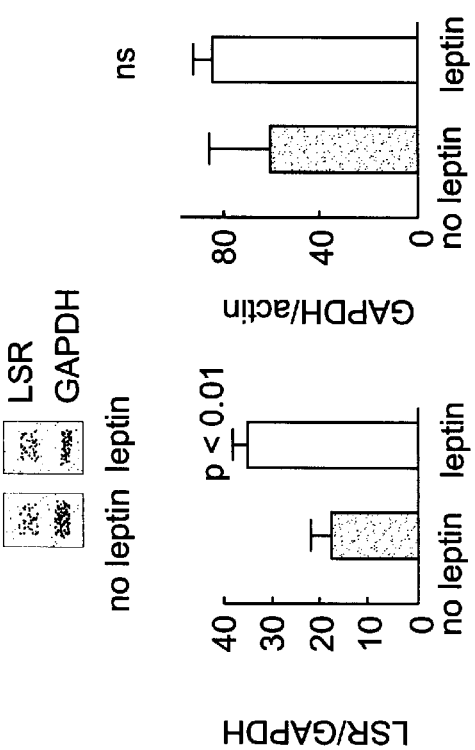
FIG. 29D Northern blot
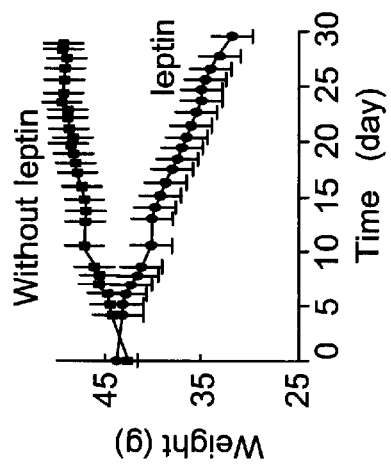
FIG. 29A Weight
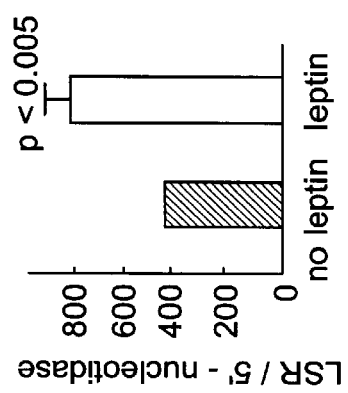
FIG. 29C LSR activity

LSR RECEPTOR, ACTIVITY, CLONING, AND USES FOR DIAGNOSING, PREVENTING AND/OR TREATING OBESITY AND RELATED RISKS OR COMPLICATIONS

INTRODUCTION

The present invention relates to a new complex receptor polypeptide LSR (Lipolysis Stimulated Receptor), characterized by its functional activities, the cloning of the cDNAs complementary to the messenger RNAs encoding each of the subunits of the multimeric complex, vectors and transformed cells, methods of diagnosis and of selection of compounds which can be used as medicament for the prevention and/or treatment of pathologies and/or of pathogeneses such as obesity and anorexia, hyperlipidemias, atherosclerosis, diabetes, hypertension, and more generally the various pathologies associated with abnormalities in the metabolism of cytokines.

Obesity is a public health problem which is both serious and widespread: in industrialized countries, a third of the population has an excess weight of at least 20% relative to the ideal weight. The phenomenon continues to worsen, in regions of the globe whose economies are being modernized, such as the Pacific islands, and in general. In the United States, the number of obese people has passed from 25% at the end of the 70s to 33% at the beginning of the 90s.

Obesity considerably increases the risk of developing cardiovascular or metabolic diseases. It is estimated that if the entire population had an ideal weight, the risk of coronary insufficiency would decrease by 25% and that of cardiac insufficiency and of cerebral vascular accidents by 35%. Coronary insufficiency, atheromatous disease and cardiac insufficiency are at the forefront of the cardiovascular complications induced by obesity. For an excess weight greater than 30%, the incidence of coronary diseases is doubled in subjects under 50 years. Studies carried out for other diseases are equally eloquent. For an excess weight of 20%, the risk of high blood pressure is doubled. For an excess weight of 30%, the risk of developing a non-insulin-dependent diabetes is tripled. That of hyperlipidemias is multiplied by 6.

The list of diseases whose onset is promoted by obesity is long: hyperuricemia (11.4% in obese subjects, against 3.4% in the general population), digestive pathologies, abnormalities in hepatic functions, and even certain cancers.

Whether the physiological changes in obesity are characterized by an increase in the number of adipose cells, or by an increase in the quantity of triglycerides stored in each adipose cell, or by both, this excess weight results mainly from an imbalance between the quantities of calories consumed and those of the calories used by the body. Studies on the causes of this imbalance have been in several directions. Some have focused on studying the mechanism of absorption of foods, and therefore the molecules which control food intake and the feeling of satiety. Other studies have been related to the basal metabolism, that is to say the manner in which the body uses the calories consumed.

The treatments for obesity which have been proposed are of four types. Food restriction is the most frequently used. The obese individuals are advised to change their dietary habits so as to consume fewer calories. This type of treatment is effective in the short-term. However, the recidivation rate is very high. The increase in calorie use through physical exercise is also proposed. This treatment is ineffective when applied alone, but it improves, however, weight loss in subjects on a low-calorie diet. Gastrointestinal surgery, which reduces the absorption of the calories ingested, is effective but has been virtually abandoned because of the side effects which it causes. The medicinal approach uses either the anorexigenic action of molecules involved at the level of the central nervous system, or the effect of molecules which increase energy use by increasing the production of heat. The prototypes of this type of molecule are the thyroid hormones which uncouple oxidative phosphorylations of the mitochondrial respiratory chain. The side effects and the toxicity of this type of treatment make their use dangerous. An approach which aims to reduce the absorption of dietary lipids by sequestering them in the lumen of the digestive tube is also in place. However, it induces physiological imbalances which are difficult to tolerate: deficiency in the absorption of fat-soluble vitamins, flatulence and steatorrhoea. Whatever the envisaged therapeutic approach, the treatments of obesity are all characterized by an extremely high recidivation rate.

The molecular mechanisms responsible for obesity in humans are complex and involve genetic and environmental factors. Because of the low efficiency of the treatments known up until now, it is urgent to define the genetic mechanisms which determine obesity, so as to be able to develop better targeted medicaments.

More than 20 genes have been studied as possible candidates, either because they have been implicated in diseases of which obesity is one of the clinical manifestations, or because they are homologues of genes involved in obesity in animal models. Situated in the 7q31 chromosomal region, the OB gene is one of the most widely studied. Its product, leptin, is involved in the mechanisms of satiety. Leptin is a plasma protein of 16 kDa produced by the adipocytes under the action of various stimuli. Obese mice of the ob/ob type exhibit a deficiency in the leptin gene; this protein is undetectable in the plasma of these animals. The administration of leptin obtained by genetic engineering to ob/ob mice corrects their relative hyperphagia and allows normalization of their weight. This anorexigenic effect of leptin calls into play a receptor of the central nervous system: the ob receptor which belongs to the family of class 1 cytokine receptors. The ob receptor is deficient in obese mice of the db/db strain. The administration of leptin to these mice has no effect on their food intake and does not allow substantial reduction in their weight. The mechanisms by which the ob receptors transmit the signal for satiety are not precisely known. It is possible that neuropeptide Y is involved in this signalling pathway. It is important to specify at this stage that the ob receptors are not the only regulators of appetite. The Melanocortin 4 receptor is also involved since mice made deficient in this receptor are obese (Gura, 1997).

The discovery of leptin and the characterization of the leptin receptor at the level of the central nervous system have opened a new route for the search for medicaments against obesity. This model, however, rapidly proved disappointing. Indeed, with only one exception (Montague et al., 1997), the genes encoding leptin or its ob receptor have proved to be normal in obese human subjects. Furthermore and paradoxically, the plasma concentrations of leptin, the satiety hormone, are abnormally high in most obese human subjects. Most of the therapeutic research efforts in this direction have centred on the characterization of the effect of leptin at the level of the central nervous system.

SUMMARY OF THE INVENTION

The present invention results from a focusing of the research effort on the discovery of the mechanisms of leptin elimination. The most widely accepted working hypothesis is that the plasma levels of leptin are high in obese subjects because this hormone is produced by the adipose tissue and that the fatty mass is increased in obese subjects. The inventors have formulated a different hypothesis and have postulated that the concentrations of leptin are increased in obese individuals because the clearance of this hormone is reduced. This deficiency causes a leptin resistance syndrome and the obese individual develops a suitable response to the high concentrations of leptin. In this perspective, the treatment of obese subjects ought to consist not in an increase in the leptin levels but in a normalization thereof. At this stage, it is essential to recall that the ob type receptors are signalling type receptors. These receptors can bind leptin at the level of the plasma membrane but cannot cause the protein to enter inside the cell for it to be degraded therein. The ob receptors are not endocytosis receptors.

LSR Receptor

The inventors have characterized a receptor, in particular hepatic, called LSR receptor, whose activity is dual. The LSR receptor allows, on the one hand, endocytosis of lipoproteins, when it is activated by the free fatty acids, thus serving as a pathway for the clearance of lipoproteins. This pathway serves mainly, but not exclusively, for the clearance of particles high in triglycerides of intestinal origin (Mann et al., 1995). This activity, expressed most particularly at the hepatic level, is dependent on the presence of free fatty acids which, by binding to the receptor, induce a reversible change in the conformation of this complex and allow it to bind, with a high affinity, various classes of lipoproteins such as those containing apoprotein B or apoprotein E.

On the other hand, under normal conditions, in the absence of free fatty acids, the complex receptor LSR does not bind lipoproteins, but is capable of binding a cytokine, in particular leptin, and then of internalizing it and of degrading it.

The present invention therefore relates to a purified LSR receptor, in particular of hepatic cells, characterized in that it is capable, in the presence of free fatty acids, of binding lipoproteins, and in the absence of free fatty acids, of binding a cytokine, preferably leptin.

According to the invention, this LSR receptor is, in addition, characterized in that the bound lipoproteins or the bound cytokine are incorporated into the cell and then degraded, the bound lipoproteins containing in particular apoprotein B or E.

It should be understood that the invention does not relate to the LSR receptors in a natural form, that is to say that they are not taken in their natural environment but obtained by purification from natural sources, or alternatively obtained by genetic recombination, or alternatively by chemical synthesis and capable, in this case, of containing non-natural amino acids, as will be described below. The production of a recombinant LSR receptor, which may be carried out using one of the nucleotide sequences according to the invention, is particularly advantageous because it makes it possible to obtain an increased level of purity of the receptor.

More particularly, the invention relates to a purified rat LSR receptor, characterized in that it comprises at least one subunit having a molecular weight of about 66 kDa and a subunit having a molecular weight of about 58 kDa.

Preferably, the purified rat LSR receptor of the present invention is characterized in that it contains an α subunit comprising the amino acid sequence of SEQ ID 2 or a sequence homologous thereto, or an α' subunit comprising the amino acid sequence of SEQ ID 4 or a sequence homologous thereto, and one, preferably three, subunits comprising the amino acid sequence of SEQ ID 6 or a sequence homologous thereto.

The invention also relates to a purified mouse LSR receptor, characterized in that it comprises at least one subunit having a molecular weight of about 66 kDa and a subunit having a molecular weight of about 58 kDa.

Preferably, the purified mouse LSR receptor of the present invention is characterized in that it contains an α subunit comprising the amino acid sequence of SEQ ID 16 or a sequence homologous thereto, or an α subunit comprising the amino acid sequence of SEQ ID 17 or a sequence homologous thereto, and one, preferably three, β subunits comprising the amino acid sequence of SEQ ID 18 or a sequence homologous thereto.

The invention also relates to a purified human LSR receptor, characterized in that it comprises at least one subunit having a molecular weight of about 72 kDa and a subunit having a molecular weight of about 64 kDa.

Preferably, the purified human LSR receptor of the present invention is characterized in that it contains an α subunit comprising the amino acid sequence of SEQ ID 8 or a sequence homologous thereto, or an α' subunit comprising the amino acid sequence of SEQ ID 10 or a sequence homologous thereto, and one, preferably three, β subunits comprising the amino acid sequence of SEQ ID 12 or a sequence homologous thereto.

A particularly preferred embodiment of the LSR receptors of the present invention is a recombinant LSR receptor obtained by expressing, in a recombinant host, one or more nucleotide sequences according to the invention. This preferred recombinant receptor consists of an α or α' subunit and one, preferably three, β subunits, in particular an α or α' subunit and three β subunits of a human LSR receptor.

Polypeptide Sequences of LSR

The invention relates to polypeptides, characterized in that they are a constituent of an LSR receptor according to the invention.

It should be understood that the invention does not relate to the polypeptides in a natural form, that is to say that they are not taken in their natural environment. Indeed, the invention relates to the peptides obtained by purification from natural sources, or alternatively obtained by genetic recombination, or alternatively by chemical synthesis, and capable, in this case, of containing non-natural amino acids, as will be described below. The production of a recombinant polypeptide, which may be carried out using one of the nucleotide sequences according to the invention or a fragment of one of these sequences, is particularly advantageous because it makes it possible to obtain an increased level of purity of the desired polypeptide.

The invention therefore relates to a purified, isolated or recombinant polypeptide comprising a sequence of at least 5, preferably at least 10 to 15, consecutive amino acids of an LSR receptor, as well as the homologues, equivalents or variants of the said polypeptide, or one of their fragments. Preferably, the sequence of at least 10 to 15 amino acids of the LSR receptor is a biologically active fragment of an LSR receptor.

More particularly, the invention relates to purified, isolated or recombinant polypeptides comprising a sequence of at least 10 to 15 amino acids of a rat LSR receptor, of a mouse LSR receptor or of a human LSR receptor.

In the present description, the term polypeptide will be used to also designate a protein or a peptide.

Nucleotide Sequences of LSR

The subject of the present invention is also purified nucleic acid sequences, characterized in that they encode an LSR receptor or a polypeptide according to the invention.

The invention relates to a purified nucleic acid, characterized in that it comprises at least 8, preferably at least 10 and more particularly at least 15 consecutive nucleotides of the polynucleotide of a genomic, cDNA or RNA sequence of the LSR receptor, as well as the nucleic acid sequences complementary to this nucleic acid.

More particularly, the invention relates to the purified, isolated or recombinant nucleic acids comprising a sequence of at least 8, preferably at least 10 and more particularly at least 15 consecutive nucleotides of the polynucleotide of a nucleic sequence of a mouse LSR receptor or of a human LSR receptor.

The invention also relates to the variant, mutated, equivalent or homologous nucleic sequences of the nucleic sequences according to the invention, or one of their fragments. It finally relates to the sequences capable of hybridizing specifically with the nucleic sequences according to the invention.

The invention therefore also relates to the nucleic acid sequences contained in the gene encoding the LSR receptor, in particular each of the exons of the said gene or a combination of exons of the said gene, or alternatively a polynucleotide extending over a portion of one or more exons. Preferably, these nucleic acids encode one or more biologically active fragments of the human LSR receptor.

The present invention also relates to the purified nucleic acid sequences encoding one or more elements for regulating the expression of the LSR gene. Also included in the invention are the nucleic acid sequences of the promoter and/or regulator of the gene encoding the receptor according to the invention, or one of their allelic variants, the mutated, equivalent or homologous sequences, or one of their fragments.

The invention also relates to the purified nucleic sequences for hybridization comprising at least 8 nucleotides, characterized in that they can hybridize specifically with a nucleic sequence according to the invention.

Preferably, nucleic acid fragments or oligonucleotides, having as sequences the nucleotide sequences according to the invention can be used as probes or primers.

The invention also comprises methods for screening cDNA and genomic DNA libraries, for the cloning of the isolated cDNAs and/or the genes coding for the receptor according to the invention, and for their promoters and/or regulators, characterized in that they use a nucleic sequence according to the invention.

The nucleic sequences, characterized in that they are capable of being obtained by one of the preceding methods according to the invention or the sequences capable of hybridizing with the said sequences, form part of the invention.

Vectors, Host Cells and Transgenic Animals

The invention also comprises the cloning and/or expression vectors containing a nucleic acid sequence according to the invention.

The vectors according to the invention, characterized in that they comprise elements allowing the expression and/or the secretion of the said sequences in a host cell, also form part of the invention.

The invention comprises, in addition, the host cells, in particular the eukaryotic and prokaryotic cells, transformed with the vectors according to the invention, as well as the mammals, except man, comprising one of the said transformed cells according to the invention.

Among the mammals according to the invention, there will be preferred animals such as mice, rats or rabbits, expressing a polypeptide according to the invention, the phenotype corresponding to the normal or variant LSR receptor, in particular mutated of human origin.

These cells and animals can be used in a method of producing a recombinant polypeptide according to the invention and can also serve as a model for analysis and screening.

The invention also relates to the use of a cell, of a mammal or of a polypeptide according to the invention for studying the expression and the activity of the receptor according to the invention, and the direct or indirect interactions between the said receptor and chemical or biochemical compounds which may be involved in the activity of the said receptor.

The invention also relates to the use of a cell, of a mammal or of a polypeptide according to the invention for screening a chemical or biochemical compound capable of interacting directly or indirectly with the receptor according to the invention, and/or capable of modulating the expression or the activity of the said receptor.

Production of Polypeptides Derived from the LSR Receptor

The invention also relates to the synthesis of synthetic or recombinant polypeptides of the invention, in particular by chemical synthesis or using a nucleic acid sequence according to the invention.

The polypeptides obtained by chemical synthesis and capable of comprising non-natural amino acids corresponding to the said recombinant polypeptides are also included in the invention.

The method of producing a polypeptide of the invention in recombinant form is itself included in the present invention, and is characterized in that the transformed cells are cultured under conditions allowing the expression of a recombinant polypeptide having a polypeptide sequence according to the invention, and in that the said recombinant polypeptide is recovered.

The recombinant polypeptides, characterized in that they are capable of being obtained by the said method of production, also form part of the invention.

Antibodies

The mono- or polyclonal antibodies or fragments thereof, chimeric or immunoconjugated antibodies, characterized in that they are capable of specifically recognizing a polypeptide or a receptor according to the invention, form part of the invention.

There may be noted in particular the advantage of antibodies specifically recognizing certain polypeptides, variants or fragments, which are in particular biologically active, according to the invention.

The invention also relates to methods for the detection and/or purification of a polypeptide according to the invention, characterized in that they use an antibody according to the invention.

The invention comprises, in addition, purified polypeptides, characterized in that they are obtained by a method according to the invention.

Moreover, in addition to their use for the purification of polypeptides, the antibodies of the invention, in particular the monoclonal antibodies, may also be used for the detection of these polypeptides in a biological sample.

More generally, the antibodies of the invention may be advantageously used in any situation where the expression, normal or abnormal, of a polypeptide of the LSR receptor, normal or mutated, needs to be observed.

Detection of Allelic Variability and Diagnosis

Also forming part of the invention are the methods for the determination of an allelic variability, a mutation, a deletion, a loss of heterozygosity or a genetic abnormality, characterized in that they use a nucleic acid sequence or an antibody according to the invention.

These methods relate to, for example, the methods for the diagnosis of the predisposition to obesity, to the associated risks, or to pathologies associated with abnormalities in the metabolism of cytokines, by determining, in a biological sample from the patient, the presence of mutations in at least one of the sequences described above. The nucleic acid sequences analysed may be either the genomic DNA, the cDNA or the mRNA.

Nucleic acids or antibodies based on the present invention can also be used to allow a positive and differential diagnosis in a patient taken in isolation, or a pre-symptomatic diagnosis in an at risk subject, in particular with a familial history.

In addition, the detection of a specific mutation may allow an evolutive diagnosis, in particular as regards the intensity of the pathology or the probable period of its appearance.

Screening of Compounds of Interest

Also included in the invention are the methods for selecting chemical or biochemical compounds capable of interacting, directly or indirectly, with the receptor or the polypeptide or nucleotide sequences according to the invention, and/or allowing the expression or the activity of the LSR receptor to be modulated.

The invention relates in particular to a method for selecting chemical or biochemical compounds capable of interacting with a nucleic acid sequence contained in a gene encoding an LSR receptor, the said method being characterized in that it comprises bringing a host cell expressing an LSR receptor or a fragment of the said receptor into contact with a candidate compound capable of modifying the expression or the regulation of the expression of the said nucleic sequence, and detecting, directly or indirectly, a modification of the expression or of the activity of the LSR receptor.

The invention also relates to a method for selecting chemical or biochemical compounds capable of interacting with the LSR receptor, the said method being characterized in that it comprises bringing an LSR receptor or a fragment of the said receptor, or a host cell expressing an LSR receptor or a fragment of the said receptor, into contact with a candidate compound capable of modifying the LSR activity, and detecting, directly or indirectly, a modification of the activity of the LSR receptor or the formation of a complex between the candidate compound and the said LSR receptor or the said polypeptide.

The invention comprises the compounds capable of interacting directly or indirectly with an LSR receptor as well as the compounds capable of interacting with one or more nucleic sequences of the LSR receptor. It also comprises the chemical or biochemical compounds allowing the expression or the activity of the receptor according to the invention to be modulated. The compounds, characterized in that they were selected by one of the methods according to the present invention, also form part of the invention.

In particular, among these compounds according to the invention, there are preferred the antibodies according to the invention, the polypeptides according to the invention, the nucleic acids, oligonucleotides and vectors according to the invention, or a leptin or one of its derived compounds, preferably one of its protein variants, or leptins which are chemically modified or are obtained by genetic recombination, or the protein gC1qR or one of its analogues, or one of their fragments.

The invention comprises, finally, compounds capable of modulating the expression or the activity of the receptor according to the invention, as medicament for the prevention of pathologies and/or of pathogeneses such as obesity and anorexia, hyperlipidemias, atherosclerosis, diabetes, hypertension, and more generally the various pathologies associated with abnormalities in the metabolism of cytokines.

DETAILED DESCRIPTION

The LSR receptor

The invention relates to a purified LSR receptor (<<Lipolysis Stimulated Receptor>>), preferably hepatic, consisting of at least one α or α' subunit and at least one β subunit. The α subunit has a molecular weight of about 66 kDa in rats and in mice and of about 72 kDa in humans. The α' subunit has a molecular weight of about 64 kDa in rats and in mice and of about 70 kDa in humans. The β subunit has a molecular weight of about 58 kDa in rats and in mice and of about 64 kDa in humans.

The inventors have formulated the hypothesis according to which the most abundant, and probably the most active, form of the LSR receptor is that in which an α or α' subunit and three β subunits exist. It appears, however, possible that the α and α' subunits, on the one hand, and the β subunit, on the other, have distinct biological functions and that these functions can be performed in a cell independently of their assembly in the form of a receptor.

The inventors have also observed that a complex can form between the LSR receptor and the gC1qR receptor having a molecular weight of about 33 kDa, or a homologous protein. It appears that the gC1qR receptor is transiently combined with the LSR receptor and that the presence of a C1q protein or of homologous proteins makes it possible not only to dissociate gC1qR from the LSR receptor but also to activate the LSR receptor, including in the absence of fatty acids.

Activity of the LSR Receptor and Applications

The present invention therefore relates to a receptor, in particular of hepatic cells, characterized in that it is capable, in the presence of free fatty acids, of binding lipoproteins, and in the absence of free fatty acids, of binding a cytokine, preferably the bound leptin, lipoproteins and cytokine being incorporated and then degraded by the cell, it being possible for the said receptor, in addition, to bind the gC1qR protein or one of its analogous proteins.

Clearance of Lipoproteins

The LSR receptor represents the principal pathway for the elimination of lipoproteins of intestinal origin and of particles high in triglycerides, in particular VLDLs and chylomicrons. The LSR receptor can also serve as a pathway for the elimination of LDLs, particles high in cholesterol, which are for the most part removed by the LDL receptor pathway, but of which about 30% are eliminated at the hepatic level by pathways different from the LDL receptor.

The inventors have in fact demonstrated that the LSR receptor is capable of binding lipoproteins, in particular the lipoproteins high in triglycerides, and then of internalizing and degrading them. This lipoprotein clearance activity by the receptor requires the presence of free fatty acids, for example oleate, and is inhibited in the presence of antibodies directed against LSR or against peptides derived from LSR.

Clearance of Cytokines

The inventors have also demonstrated that in the absence of free fatty acids, for example oleate, the LSR receptor is capable of binding cytokines, preferably leptin. The leptin clearance function is, however, only possible if the receptor has not bound fatty acids produced by the hepatic lipase or by the hormone-sensitive lipase of the adipose tissue. Once the cytokines have been bound, the LSR receptor internalizes them and degrades them. This cytokine, preferably leptin, degradation activity is inhibited by antibodies directed against LSR or against peptides derived from LSR.

The inventors have shown that it is the a subunit of the LSR receptor which is most particularly involved in the binding of cytokines, and preferably of leptin.

Furthermore, the inventors have shown, with the aid of mice, that, in vivo, the LSR receptors carry out the hepatic capturing of cytokines, preferably of leptin.

The high levels of leptin in all obese human subjects can be explained by several molecular mechanisms which are capable of reducing the hepatic clearance of leptin, including in particular:

a) alteration of one or more genes for LSR, and/or of their promoters b) facilitation, by post-transcriptional modifications, of the allosteric rearrangement allowing the passage from the cytokine-competent conformation to the lipoprotein receptor conformation;

c) deficiency in the transport of vesicles containing LSR from, or towards, the plasma membrane (this function depends on the integrity of the cytoskeleton)

d) increase in the degradation of LSR;

e) increase in the lipid calorie ration which, by diverting the receptor towards the clearance of lipoproteins, reduces in part its capacity to degrade leptin.

Control of LSR Activity by the Cytokines

Finally, the inventors have demonstrated that cytokines, preferably leptin, modulate the activity of the LSR receptor in the presence of free fatty acids. More particularly, the cytokines increase the lipoprotein clearance activity of the LSR receptor and more precisely, the binding, internalization and degradation of the VLDLs and LDLs. This increase in the LSR activity could be the result of the increase in the apparent number of LSR receptor at the surface of the cells following an increase in protein synthesis and following a mobilization of endocytosis vesicles. In addition, the inventors have shown, with the aid of mice, that, in vivo, cytokines, preferably leptin, are capable of reducing postprandial lipaemic response.

Leptin, and probably other cytokines, are therefore regulators of the activity of LSR. A syndrome of resistance to leptin, or to other cytokines, can lead to a hypertriglyceridemia, which is either permanent or limited to the postprandial phase.

Treatment of Obesity

The role played by LSR in the clearance of leptin makes it possible to formulate a physiopathological model which requires a revision of the strategies used for treating obesity. It is indeed essential to reduce the concentrations of leptin in obese human subjects in order to restore the physiological fluctuations of this hormone.

Accordingly, it is possible to envisage using compounds for the treatment of obesity allowing modulation of the number of LSR receptors, of their recycling rate, or of the change in their conformation, and/or allowing in particular:

1. leptinemia, and therefore the sensations of satiety and of hunger, to be controlled;

2. normal leptin concentrations to be restored and normal regulation of dietary habit by the normal perception of the sensations of hunger and of satiety;

3. triglyceridemia to be controlled;

4. the plasma concentrations of residues of chylomicrons, highly atherogenic particles, to be regulated.

The role played by the LSR receptor in the hepatic clearance of lipoproteins of intestinal region makes it possible to envisage using compounds capable of modulating the expression and/or the activity of LSR in order to modulate the distribution of lipids of dietary origin between the peripheral tissues, in particualr the adipose tissues, and the liver. A treatment of obesity will consist in promoting the hepatic degradation of lipoproteins, and thereby reducing their storage in the adipose tissue, and regulating their plasma concentrations. The latter effect makes it possible to envisage the use of such compounds to reduce the risks associated with obesity, in particular the atherogenic risks.

Treatments of Anorexia and of Cachexia

It is possible to envisage using methods of regulating the activities of LSR to introduce treatments which make it possibile to overcome the vicious circle which characterizes anorexia nervosa. By reducing the number of receptors, it should be possible to promote weight gain in anorexic or undernourished subjects.

Under these conditions, it is advantageous to selectively inhibit the clearance of leptin by using synthetic peptides or pharmacological molecules which either reduce the synthesis of LSR or block its capacity to bind leptin and/or lipoproteins, or alternatively increase the catabolism of the receptor.

Treatment of Abnormalities in the Metabolism of Cytokines

Analysis of the primary structure of the α subunit of LSR, as described below, shows a site homologous to the cytokine binding sites present on their receptors, as well as two routing signals which allow endocytosis and rapid degradation of ligands in the lysozomes. This observation is new in the sense that the cytokine receptors do not allow the internalization and the degradation of ligands. These receptors have been characterized on the basis of their intracellular signalling properties.

Thus, in addition to it having the property of allowing the proteolytic degradation of lipoproteins and of leptin, it is highly probable that the LSR receptor also carries out the degradation of other cytokines. This function can be studied by virtue of the anti-LSR antibodies and of transfected CHO cells expressing the α subunit of LSR as described in Example 4. The involvement of LSR in the clearance of cytokines is essential because these molecules play an important role in the regulation of the metabolism of lipids, of the metabolism of glucose, and in the regulation of food intake and of weight gain.

The molecular mechanisms by which the cytokines modulate the physiological functions involved in obesity and its complications are numerous and complex. It is worth noting, however, the fact that abnormalities in the metabolism of cytokines are associated with hypertriglyceridemia which frequently accompanies viral, bacterial or protozoal infections. Moreover, cytokines, and more particularly Tumor Necrosis Factor (TNF), induce a transient hypertriglyceridemia similar to that observed in certain forms of obesity-related diabetes.

The reduction in the number of LSR receptors expressed in the liver of obese mice could explain a deficiency in the elimination of some cytokines, this deficiency causing metabolic disruptions such as those found in obesity. The use of hepatic cells in culture, and of the various models of obese animals cited below, will make it possible to determine, among all the cytokines and more particularly those which induce weight loss (IL-6, LIF, OSM, CNTF, IL-11, IL-12α, as well as TNFα and TNFβ), those which modulate the expression and/or the activity of LSR. The determination of such cytokines can, for example, be carried out using methods such as those presented in Examples 4 to 6.

Finally, analysis of the primary structure of the α LSR reveals potential phosphorylation sites. This opens the perspective of a regulation of cellular activity by the LSR receptor. A particularly important example would be the involvement of LSR in the regulation of the production of <<Acute Phase Proteins>> under the impetus of various stimuli, including cytokines.

The involvement of LSR in the clearance and the degradation of cytokines may, in addition, not be limited to the liver. Indeed, while it has been demonstrated that the expression of LSR is predominantly hepatic, it is also certain that the expression of this receptor is not limited to this organ. Preliminary Northern-blot analysis on various human tissues has been able to reveal, in addition to the hepatic products, expression products in the kidney and in the testicle. A more thorough analysis will make it possible to show the different tissues expressing LSR in humans. In this perspective, LSR could be involved in the degradation of cytokines not only at the hepatic level, but also at the level of the peripheral tissues. A deficiency in this activity could be involved in the pathogenesis of autoimmune diseases, of multiple sclerosis and of rheumatoid arthritis. Accumulation of cytokines is frequently found in the pathogenesis of these diseases.

Polypeptide Sequences of the LSR Receptor

The invention relates to polypeptides, characterized in that they are a constituent of an LSR receptor according to the invention. The invention relates more particularly to the polypeptides characterized in that they constitute the α, α' or β subunits of the LSR receptor.

The invention relates more particularly to a purified, isolated or recombinant polypeptide comprising a sequence of at least 5, preferably of at least 10 to 15 consecutive amino acids of an LSR receptor, as well as the homologues, equivalents or variants of the said polypeptide, or one of their fragments. Preferably, the sequence of at least 10 to 15 amino acids of the LSR receptor is a biologically active fragment of an LSR receptor.

Preferably, the invention relates to purified, isolated or recombinant polypeptides comprising a sequence of at least 10 to 15 amino acids of a rat LSR receptor, of a mouse LSR receptor or of a human LSR receptor.

In a first preferred embodiment of the invention, the polypeptide is characterized in that it comprises a sequence of at least 10 to 15 consecutive amino acids of a sequence chosen from the group comprising the sequences of SEQ ID 2, SEQ ID 4 and SEQ ID 6, as well as the variants, equivalents or homologues of this polypeptide, or one of their fragments. Preferably, the polypeptide is a homologue or a biologically active fragment of one of the abovementioned sequences.

In a second preferred embodiment of the invention, the polypeptide is characterized in that it comprises a sequence of at least 10 to 15 consecutive amino acids of a sequence chosen from the group comprising the sequences of SEQ ID 16, SEQ ID 17 and SEQ ID 18, as well as the variants, equivalents or homologues of this polypeptide, or one of their fragments. Preferably, the polypeptide is a homologue or a biologically active fragment of one of the abovementioned sequences.

In a third preferred embodiment of the invention, the polypeptide is characterized in that it comprises a sequence of at least 10 to 15 consecutive amino acids of a sequence chosen from the group comprising the sequences of SEQ ID 8, SEQ ID 10 and SEQ ID 12, as well as the variants, equivalents or homologues of this polypeptide, or one of their fragments. Preferably, the polypeptide is a homologue or a biologically active fragment of one of the abovementioned sequences.

Among the preferred polypeptides of the invention, there will be noted particularly the polypeptides having the human sequence SEQ ID 8, SEQ ID 10 or SEQ ID 12, as well as those having the rat sequence SEQ ID 2, SEQ ID 4 or SEQ ID 6, or those having the mouse sequence SEQ ID 16, SEQ ID 17 or SEQ ID 18. The fragments corresponding to the domains represented in FIGS. 1 to 6, whose positions on the sequences corresponding to SEQ ID 2, 8 or 16, are indicated in Tables 1, 3 and 4.

Finally, the invention also relates to the polypeptides of SEQ ID 29 and SEQ ID 30.

The present invention also relates to polypeptides comprising the polypeptides described above, as well as their homologous, equivalent or variant polypeptides, as well as the fragments, preferably biologically active, of the said polypeptides.

Among the polypeptides according to the invention, also preferred are the polypeptides comprising or consisting of an amino acid sequence chosen from the amino acid sequences as described above, characterized in that the said polypeptides are a constituent of the receptor according to the invention.

Analysis of the Polypeptide Sequences of the α, α' and β Subunits of the LSR Receptor The systematic analysis of the products of the 3 rat cDNAs described in the present application is schematically represented in FIG. 1. The α subunit of the rat LSR receptor, a protein encoded by the longer cDNA (LSR-Rn-2097), has the following characteristics.

Potential glycosylation sites are found at positions 12–14 and 577–579. A potential site of attachment of glycosaminoglycans is found at position 14–17.

Several phosphorylation sites are located at the level of the $NH_2$-terminal end (positions 193–196, 597–600, 169–171, 172–174, 401–403, 424–426, 464–466, 467–469, 185–188, 222–225, 436–439, 396–399, 504–507, 530–533, 624–627, 608–615), suggesting that the latter is oriented towards the intracellular region.

Moreover, the protein has, on the $NH_2$-terminal side, a hydrophobic amino acid sequence separated into two parts by 2 amino acids inducing a hairpin structure in which the two arms would consist of hydrophobic amino acids. It is reasonable to assume that this region represents the fatty acid binding site of LSR. The glove-finger structure thus produced can accommodate an aliphatic hydrocarbon chain. The two amino acids are, more precisely in the case of rat LSR, two Prolines situated at positions 31 and 33 of the polypeptide sequence of the α subunit.

Still on the $NH_2$-terminal side is a consensus sequence for binding to clathrin, a protein which lawns the inner surface of the <<coated pits>> (Chen et al., 1990). These specific regions of the plasma membrane allow rapid endocytosis of membrane proteins. Such a consensus sequence is found at the level of the LRP-$α_2$-macroglobulin receptor, of CRAM and of the LDL receptor (Herz et al., 1988; Lee et al., 1990; Goldstein et al., 1995). The consequence of a mutation at this level is a substantial delay in the internalization of the LDLs and induces familial hypercholesterolemia (Davis et al., 1986).

The receptor then possesses a hydrophobic amino acid sequence which constitutes a potential transmembrane domain. The length of this segment allows only one passage across the phospholipid bilayer (Brendel et al., 1992).

Between this clathrin binding signal and the hydrophobic chain corresponding to the single transmembrane segment are 2 motifs LI et LL (Letourneur et al., 1992). These two motifs are found in the following proteins: glut 4 glucose carrier (Verhey et al., 1994); the nonvariant chain and the histocompatibility complex class II (Zhong et al., 1997; Parra-Lopez et al., 1997). These signals control endocytosis and the intracellular addressing of proteins in the peripheral membrane system.

On the C-terminal side, there is then a cysteine-rich region which exhibits homology with the cytokine receptors and more particularly: the TNF 1 and 2 (Tumor Necrosis Factor 1 and 2) receptors; the low-affinity NGF (Nerve Growth factor) receptor; the Shope fibroma virus TNF soluble receptor; CD40, CD27 and CD30, receptors for the cytokines CD40L, CD27L and CD30L; the T cell protein 4-1BB, receptor for the putative cytokine 4-1BBL, the FAS antigen (APO 1), receptor for the FASL protein involved in apoptosis, the T cell OX40 antigen, receptor for the cytokine OX40L, and the vaccinia virus A53 protein (Cytokines and their receptors, 1996; Banner et al., 1993).

In addition to this cysteine-rich segment, there is a region of amino acids which are alternately charged + and − (Brendel et al., 1992). This region provides a potential binding site for the apoprotein ligands Apo B and Apo E.

This region contains, in addition, an RSRS motif found in lamin (Simos et al., 1994) and in SF2' (Krainer et al., 1991).

The LSR α' form encoded by the LSR-Rn-2040 cDNA possesses all the domains described above based on the LSR a sequence encoded by the LSR-Rn-2097 cDNA, with the exception of the LI/LL element, whose Leucine doublet is removed by alternative splicing. Although possessing sequences which are very similar, the subunits a encoded by LSR-Rn-2097 and α' encoded by LSR-Rn-2040 could therefore differ in their recycling rate and their addressing. The β form encoded by LSR-Rn-1893 does not possess a transmembrane domain or a region rich in cysteines and homologous to the cytokine receptors. However, it possesses at the $NH_2$-terminal level the hydrophobic region separated by a repetition of prolines, the region rich in charged amino acids and the RSRS motif. This constituent is probably positioned entirely outside the cell where it is bound via disulphide bridges either to the product of LSR-Rn-2040, or to that of LSR-Rn-2097.

Table 1 below lists the different domains or motifs described above, indicates whether or not they belong to each of the subunits of the LSR receptor, as well as the positions of the start and end of the said domains or motifs, or of regions carrying the said domains or motifs, as indicated in the sequence of SEQ ID 2.

TABLE 1

| Domain or motif | Position on SEQ ID 2 | | Presence on: | | |
|---|---|---|---|---|---|
| | Start | End | α | α' | β |
| Potential fatty acid binding site | 23 | 41 | X | X | X |
| Potential clathrin binding site | 104 | 107 | X | X | X |
| Signal for transport: LI | 183 | 184 | X | X | X |
| LL | 195 | 196 | X | | |
| Transmembrane domain | 204 | 213 | X | X | |
| Potential cytokine receptor site | 214 | 249 | X | X | |
| RSRS motif | 470 | 473 | X | X | X |
| Potential lipoprotein ligand binding site | 544 | 557 | X | X | X |

Comparison of the Polypeptide Sequences of the LSR Receptors in Rats, Mice and Humans The lengths of the polypeptide sequences, as well as the SEQ IDs of their respective sequences in the listing included, of the three types of subunit of the LSR receptors according to the invention, in rats, mice and humans, are indicated in Table 2a below.

TABLE 2a

| Polypeptide | Rat | Mouse | Human |
|---|---|---|---|
| α subunit | 593 aa (SEQ ID 2) | 594 aa (SEQ ID 16) | 649 aa (SEQ ID 8) |
| α' subunit | 574 aa (SEQ ID 4) | 575 aa (SEQ ID 17) | 630 aa (SEQ ID 10) |
| β subunit | 525 aa (SEQ ID 6) | 526 aa (SEQ ID 18) | 581 aa (SEQ ID 12) |

These polypeptide sequences were obtained from each of the three corresponding cDNA sequences, in rats, mice and humans, which will be described in detail later. These polypeptide sequences were obtained from each of the three corresponding cDNA sequences, in rats, mice and humans, which will be described in detail later. The nomenclature used to designate these cDNA sequences, which reflects their length in terms of nucleotides, as well as the SEQ IDs of their respective sequences in the listing included, are presented in Table 2b below.

TABLE 2b

| cDNAc | Rat | Mouse | Human |
|---|---|---|---|
| α subunit | LSR-Rn-2097 (SEQ ID 1) | LSR-Mm-1886 (SEQ ID 13) | LSR-Hs-2062 (SEQ ID 7) |
| α' subunit | LSR-Rn-2040 (SEQ ID 3) | LSR-Mm-1829 (SEQ ID 14) | LSR-Hs-2005 (SEQ ID 9) |
| β subunit | LSR-Rn-1893 (SEQ ID 5) | LSR-Mm-1682 (SEQ ID 15) | LSR-Hs-1858 (SEQ ID 11) |

The protein sequence, corresponding to the a subunit of the LSR receptor, deduced from the LSR-Hs-2062 sequence has a length of 649 amino acids. It is aligned with the protein sequences deduced from LSR-Mm-1886, 594 amino acids long, and from LSR-Rn-2097, 593 amino acids long (FIGS. 2A and 2B). The conservation of the protein sequences is very high (respectively 80.2% and 82.2% identity for 591 and 590 overlapping amino acids). The functional domains identified in the protein sequence of the rat LSR a are found in the human LSR a sequence as well as in that of the murine LSR a (FIGS. 2A and 2B).

The human proteins corresponding to the LSR-Hs-2005 (α') and LSR-Hs-1858 (β) forms have a predicted size of 630 and 581 amino acids respectively. The rat proteins corresponding to the LSR-Rn-2040 (α') and LSR-Rn-1893 (β) forms have a predicted size of 574 and 525 amino acids respectively. The mouse proteins corresponding to the LSR-Mm-1829 (α') and LSR-Mm-1682 (β) forms have a predicted size of 575 and 526 amino acids respectively. The alignment of the three human forms (FIGS. 3A and 3B), of the three forms described in rats (FIGS. 4A and 4B) and of the three forms described in mice (FIGS. 5A and 5B) shows that in the three species, all the protein forms conserve the NPGY signal for binding to clathrin and the RSRS motif. The human (product of LSR-Hs-2062), rat (product of LSR-Rn-2097) and mouse (product of LSR-Mm-1886) long forms (α) exhibit all the functional characteristics of LSR. The three short forms (β) (respective products of LSR-Hs-1817, LSR-Rn-1893 and LSR-Mm-1682) lose the di-leucine domain for lysosomal addressing, the transmembrane domain and the cytokine receptor signature. It is also possible to observe that the three intermediate forms (α') (product of LSR-Hs-2005, of LSR-Rn-2040 and LSR-Mn-1829) lose the di-leucin domain, the transmembrane domain and the domain corresponding to the cytokine receptor signature being conserved (FIGS. 3A, 3B, 4A, 4B, 5A and 5B). FIG. 6 finally represents the proteins derived from the three cDNA forms identified in humans, and the motifs carried by each of them as a result of the splicing from which each is derived.

Table 3 below lists the different domains or motifs described above, as well as the positions of the start and end of the said domains or motifs, or of regions carrying the said domains or motifs, as indicated in the mouse SEQ ID 16 sequence.

TABLE 3

| Domain or motif | Position on SEQ ID 16 | | Presence on: | | |
|---|---|---|---|---|---|
| | Start | End | α | α' | β |
| Potential fatty acid binding site | 23 | 41 | X | X | X |
| Potential clathrin binding site | 104 | 107 | X | X | X |
| Signal for transport: LI | 183 | 184 | X | X | X |
| LL | 195 | 196 | X | | |
| Transmembrane domain | 204 | 213 | X | X | |
| Potential cytokine receptor site | 214 | 249 | X | X | |
| RSRS motif | 470 | 473 | X | X | X |
| Potential lipoprotein ligand binding site | 544 | 558 | X | X | X |

Table 4 below lists the different domains or motifs described above, as well as the positions of the start and end of the said domains or motifs, or of regions carrying the said domains or motifs, as indicated in the human SEQ ID 8 sequence.

TABLE 4

| Domain or motif | Position on SEQ ID 8 | | Presence on: | | |
|---|---|---|---|---|---|
| | Start | End | α | α' | β |
| Potential fatty acid binding site | 76 | 94 | X | X | X |
| Potential clathrin binding site | 157 | 160 | X | X | X |
| Signal for transport: LI | 236 | 237 | X | X | X |
| LL | 248 | 249 | X | | |
| Transmembrane domain | 257 | 266 | X | X | |
| Potential cytokine receptor site | 267 | 302 | X | X | |
| RSRS motif | 527 | 530 | X | X | X |
| Potential lipoprotein ligand binding site | 601 | 613 | X | X | X |

In conclusion, the similarity in the sequence and structure of LSR which is described above makes it possible to extrapolate to humans the observations made in rats and/or mice.

Homologous polypeptide will be understood to mean the polypeptides exhibiting, compared with the natural polypeptide, certain modifications such as in particular a deletion, truncation, extension, chimeric fusion and/or mutation, in particular a point mutation. Among the homologous polypeptides, those in which the amino acid sequence exhibits at least 80%, preferably 90%, homology with the amino acid sequences of the polypeptides according to the invention are preferred.

Equivalent polypeptide will be understood to mean a polypeptide having at least one of the activities of the LSR receptor, in particular the activity of the receptor for lipoproteins or chylomicrons, the activity of the receptor for cytokine, in particular leptin, or the activity of the receptor for the gC1q-R protein or one of its analogous proteins. Equivalent polypeptide will also be understood to mean any polypeptide resulting from the alternative splicing of the genomic nucleic sequence encoding the polypeptides according to the invention.

Variant polypeptide (or protein variant) will be understood to mean all the mutated polypeptides which may exist, in particular in human beings, and which correspond in particular to truncations, deletions and/or additions of amino acid residues, substitutions or mutations, in particular point mutations, as well as the artificial variant polypeptides which will nevertheless be called variant polypeptides. In the present case, the variant polypeptides will be in particular partly associated with the onset and with the development of obesity or anorexia. They may also be associated with the onset and/or development of the risks or complications associated with obesity, in particular at the cardiovascular level, and/or of pathologies associated with abnormalities in the metabolism of cytokines.

Polypeptide fragment is understood to mean a polypeptide or a peptide encoded by a nucleic sequence comprising a minimum of 15 nucleotides or bases, preferably 20 bases or 30 bases. These fragments may comprise in particular a point mutation, compared with the normal polypeptide sequence, or may correspond to specific amino acid sequences of variant polypeptides, artificial or existing in humans, such as those linked to a polymorphism linked in particular to obesity or to the abovementioned pathologies.

Biologically active fragment will be understood to mean in particular a fragment of an amino acid sequence of a polypeptide:

exhibiting at least one of the LSR receptor activities, in particular the lipoprotein receptor activity, or the cytokine, particularly leptin, receptor activity and/or cell signalling activity, and/or capable of being recognized by an antibody specific for the receptor according to the invention, and/or capable of being recognized by a compound capable, for example by neutralizing the binding of a ligand specific for the said receptor, of modulating the activity of the LSR receptor, and/or capable of modulating the addressing and/or cellular location of the LSR receptor, and/or more generally constituting a biologically active domain or motif of the LSR receptor.

Among the preferred biologically active fragments according to the invention, there are in particular:

the fragments comprising a clathrin binding site, the fragments comprising a fatty acid binding site, in particular a fatty acid binding site comprising a hydrophobic amino acid sequence separated into two parts by two contiguous prolines, which induce a hairpin structure whose arms consist of hydrophobic amino acids, the fragments comprising a hydrophobic region constituting a transmembrane domain, the fragments comprising a region capable of controlling endocytosis and intracellular addressing of the proteins in the peripheral membrane system, in particular a fragment comprising a site containing the LI and LL motifs, the fragments comprising a cytokine binding site, in particular a site including a cysteine-rich region, the fragments comprising a region defining a potential binding site for lipoprotein ligands such as ApoB and ApoE, in particular a region comprising a sequence of amino acids alternately charged + and −, and the fragments comprising an RSRS motif.

There are in particular among these fragments polypeptides as defined in Tables 1, 2 and 4, or any fragments of the nucleotides of SEQ ID 2, 8 or 16, comprising the said polypeptides, and any equivalent, homologous or variant fragments.

Other preferred fragments include antigenic peptides such as those having the sequences SEQ ID 29 and 30.

Nucleotide Sequences of the LSR Receptor

The subject of the present invention is isolated nucleic acid sequences, characterized in that they encode an LSR receptor or a polypeptide according to the invention.

More particularly, the invention relates to a purified nucleic acid, characterized in that it comprises at least 8, preferably at least 10 and more particularly at least 15 consecutive nucleotides of the polynucleotide of SEQ ID 19, as well as the nucleic acid sequences complementary to this nucleic acid.

The invention also relates to a purified nucleic acid, characterized in that it comprises at least 8, preferably at least 10 and more particularly at least 15 consecutive nucleotides of the polynucleotide of SEQ ID 41, as well as the nucleic acid sequences complementary to this nucleic acid.

The invention also relates to a purified nucleic acid encoding the human LSR receptor, characterized in that it comprises a nucleotide sequence corresponding to nucleotides 1898 to 21094, particularly to nucleotides 2001 to 20979, more particularly to nucleotides 2145 to 20979 of SEQ ID 19, as well as the nucleic acid sequences complementary to this nucleic acid.

The invention also relates to the nucleic acid sequences contained in the gene encoding the human LSR receptor, in particular each of the exons of the said gene or a combination of exons of the said gene, or alternatively a polynucleotide extending over a portion of one or more exons. Preferably, these nucleic acids encode one or more biologically active fragments of the human LSR receptor.

The invention also relates to a purified nucleic acid, characterized in that it comprises a nucleotide sequence corresponding to nucleotides 1 to 1897 of SEQ ID 19, as well as the nucleic acid sequences complementary to this nucleic acid.

The invention also relates to a purified nucleic acid, characterized in that it comprises a nucleotide sequence corresponding to nucleotides 21095 to 22976 of SEQ ID 19, as well as the nucleic acid sequences complementary to this nucleic acid.

The invention also relates to a purified nucleic acid, characterized in that it comprises a nucleotide sequence chosen from the group comprising the sequences of SEQ ID 7, SEQ ID 9 and SEQ ID 11, as well as the nucleic acid sequences complementary to this nucleic acid.

The invention also relates to a purified nucleic acid, characterized in that it comprises a nucleotide sequence chosen from the group comprising the sequences of SEQ ID 1, SEQ ID 3 and SEQ ID 5, as well as the nucleic acid sequences complementary to this nucleic acid.

The invention also relates to a purified nucleic acid, characterized in that it comprises a nucleotide sequence chosen from the group comprising the sequences of SEQ ID 13, SEQ ID 14 and SEQ ID 15, as well as the nucleic acid sequences complementary to this nucleic acid.

The invention also relates to a purified nucleic acid, characterized in that it comprises a nucleotide sequence corresponding to nucleotides 1898 to 2001 of SEQ ID 19 or preferably to nucleotides 1898 to 2144 of SEQ ID 19, as well as the nucleic acid sequences complementary to this nucleic acid.

The invention also relates to a purified nucleic acid, characterized in that it comprises a nucleotide sequence corresponding to nucleotides 20980 to 21094 of SEQ ID 19, as well as the nucleic acid sequences complementary to this nucleic acid.

Among the nucleic acids according to the invention, the nucleic acids having the nucleotide sequence chosen from the group comprising the sequences of SEQ ID 7, SEQ ID 9 and SEQ ID 11, the sequences of SEQ ID 1, SEQ ID 3 and SEQ ID 5, as well as the sequences of SEQ ID 13, SEQ ID 14 and SEQ ID 15, as well as their complementary sequences, are preferred.

Also forming part of the invention are the variant, mutated, equivalent or homologous sequences of the sequences according to the invention, as well as their fragments and the nucleic sequences capable of hybridizing specifically with the sequences according to the invention.

Human Genomic Sequence

The invention therefore relates to the genomic sequence of the human LSR receptor, preferably the sequence of SEQ ID 19, as well as their complementary sequences or one of their allelic variants, the mutated, equivalent or homologous sequences, or one of their fragments.

The gene for human LSR (SEQ ID 19) comprises 10 exons distributed over 21 094 bp. The size of the exons is respectively: 356, 345, 120, 57, 147, 174, 60, 132, 626 and 141 bp (Table 5).

TABLE 5

| EXON | START | END | 5' SPLIC. | BL 5' | 3' SPLIC. | BL 3' |
|------|-------|-------|-----------|-------|-----------|-------|
| Ex1  | 1898  | 2253  | —         | —     | GTACGG    | +2    |
| Ex2  | 3437  | 3781  | CAG       | +1    | GTATGT    | +1    |
| Ex3  | 12067 | 12186 | CAG       | +2    | GTGAGT    | +1    |
| Ex4  | 15047 | 15103 | CAG       | +2    | GTACGG    | +1    |
| Ex5  | 15668 | 15814 | CAG       | +2    | GTAAGT    | +1    |
| Ex6  | 19481 | 19654 | CAG       | +2    | GTGAGG    | +1    |
| Ex7  | 19801 | 19860 | CAG       | +2    | GTGAGA    | +1    |
| Ex8  | 19958 | 20089 | TAG       | +2    | GTAAGC    | +1    |
| Ex9  | 20231 | 20856 | CAG       | +2    | GTGAGG    | 0     |
| Ex10 | 20946 | 21094 | CAG       | 0     | —         |       |

The EXON column indicates the exons numbered from 1 to 10 in the 5'-3' order of their position on the genomic sequence. The START and END columns indicate respectively the position of the first and of the last nucleotide of the exon considered. The sequences of the splicing site bordering the exon in 5' and 3' are indicated in the 5'SPLIC and 3'SPLIC columns. The BL 5' and BL 3' columns indicate the number of bases in 5' and in 3', respectively, of an exon which will be used in the reading frame of the messenger only after splicing. For example as exon 7 has a free base in 3', this exon can be joined to the 5' end of exon 8 which has 2 free bases in 5'. The combination 1 base+2 bases constitutes the codon which was destroyed by the intron in the genomic sequence. Exon 7 may be joined by its 3' end to any exon having two free bases in 5'; if the new codon created does not correspond to a stop codon, the open reading frame will be conserved.

Exons 1 and 2 as well as 9 and 10 are necessarily co-spliced, thus forming a 5' block corresponding to exons 1 and 2 and a 3' block corresponding to exons 9 and 10. The functional minimal messenger, corresponding to the product of these four exons, could therefore have a size of about 1 331 bp. For the other exons, all the possible combinations make it possible to conserve the open reading frame.

The size of the noncoding exons in 5' could not be determined with precision. Indeed, the rat 5' UTR sequences are too divergent from those of humans to finalize the analysis of these sequences and to identify the real 5' end of the human LSR cDNA. This can be carried out by isolating the 5' end of the human LSR messengers by the 5' end capture methods developed by the inventors (WO 96/34981). The polyadenylation site described below is the only one which is present before the USF2 gene, situated in 3' of the human LSR gene. It is therefore very likely that the untranslated 3' region of this gene is very short (of an estimated size of about 100 bp). All the sizes given in relation to the human LSR cDNA molecules will therefore have to be adjusted according to the size of the untranslated 5' end. The human cDNA sequence obtained taking into account all the exons deduced from the analysis of the genomic sequence have a size of 2 158 bp. This form could correspond to the LSR-Rn-2097 form.

The location of some of the signals for expression of the nucleotide sequence of SEQ ID 19 is presented in Table 6 which follows.

TABLE 6

| Signal            | Start | End   |
|-------------------|-------|-------|
| preferred ATG     | 2145  | 2147  |
| other possible ATG| 2001  | 2003  |
| STOP              | 20977 | 20979 |
| POLY Ad           | 21065 | 21070 |

The characteristic elements of the messenger RNA molecule are described in the Signal column: Initiation of translation (ATG), termination of translation (STOP) and polyadenylation signal (POLY Ad). The Start and End columns indicate the position as nucleotide for the start and end of these signals on the genomic sequence SEQ ID 19. An ATG signal for initiation of translation is preferred to another because it provides an environment which is more suitable for initiation.

The present invention also relates to the purified nucleic acid sequences encoding one or more elements for regulating the expression of the human LSR gene. Also included in the invention are the nucleic acid sequences of the promoter and/or regulator of the gene encoding the receptor according to the invention, or one of their allelic variants, the mutated, equivalent or homologous sequences, or one of their fragments.

The invention relates more particularly to a purified nucleic acid situated in 5' of the coding sequence of the LSR gene. This nucleic acid is characterized in that it comprises a nucleotide sequence corresponding to nucleotides 1 to 1897 of SEQ ID 19, as well as the nucleic acid sequences complementary to this nucleic acid. Shorter fragments of this nucleic acid may also be used as promoters for expression of the LSR gene or of any other sequence encoding a heterologous polypeptide.

The invention also relates to a purified nucleic acid situated in 3' of the transcribed sequence of the LSR gene. This nucleic acid is characterized in that it comprises a nucleotide sequence corresponding to nucleotides 21095 to 22976 of SEQ ID 19, as well as the nucleic acid sequences complementary to this nucleic acid. Shorter fragments of this nucleic acid can also be used as elements regulating the expression of genes.

Finally, the invention also relates to the genomic sequence of the human LSR receptor, preferably the sequence of SEQ ID 41, as well as their complementary sequences, or one or their allelic variants, the mutated, equivalent or homologous sequences, or one of their fragments.

Comparison of the Genomic Organizations in Humans, Rats and Mice

It is advantageous to note that a synteny (conservation of the organization of certain chromosomal regions between species) between the mouse chromosome 7 region where the Lisch7 gene is located, in the immediate vicinity of USF2, and the human chromosome 19 region 19q13, carrying LSR, is well described. The organization of the two Lisch7/LSR and USF2 genes is conserved between species. Likewise, Apo E, which is of a more centromeric location relative to these genes, exists both in mice and in humans. It is remarkable that the LSR lipoprotein receptor and one of their ligands ApoE are located in the same chromosomal region. Indeed, the receptor and the ligand are frequently co-regulated. Such a situation would make it possible to envisage that the phenomena observed in mice are applicable to humans.

Human, Rat and Mouse cDNA Sequences

The invention relates, in addition, to 3 different cDNAs derived from the LSR receptor gene by alternative splicing. These 3 cDNAs have been identified in humans, rats and mice (Table 2b). They encode the three types of LSR receptor subunits, α (long), α' (intermediate) and β (short). The longest cDNA contains the totality of the 10 exons of the gene. The intermediate cDNA does not comprise exon 4. Finally, the shortest cDNA does not contain exons 4 and 5.

The human LSR-Hs-2062 cDNA nucleotide sequence, encoding the a subunit of the LSR receptor, and the rat LSR-Rn-2097 cDNA nucleotide sequence are 78.6% identical over 1 955 bp which overlap. These figures are respectively 78.8% and 1 851 bp when the murine LSR-Mm-1886 sequence (long form) is aligned with the human sequence. This reflects a very high conservation of the nucleic sequences between species. The highest divergence levels are observed in the untranslated 5' end (when the sequence is available), in the first coding exon and in the untranslated 3' end (FIGS. 7A, 7B, 7C, 7D and 7E).

The invention therefore also relates to a purified nucleic acid, characterized in that it is chosen from the group comprising the sequences of SEQ ID 7, SEQ ID 9 and SEQ ID 11, the sequences SEQ ID 1, SEQ ID 3 and SEQ ID 5, and the sequences SEQ ID 13, SEQ ID 14 and SEQ ID 15, as well as the nucleic acid sequences complementary to this nucleic acid, or one of their allelic variants, the mutated, equivalent or homologous sequences, or one of their fragments.

The nucleic acids constituting the coding frames of the abovementioned nucleic acids, between the codons for initiation and for termination of translation, also form part of the invention.

The nucleic acids encoding the polypeptide fragments according to the invention are also part of the invention. It will be particularly noted [lacuna] the nucleic acids encode the fragments described in Tables 1, 3 and 4.

Thus, Table 7 describes the position of such nucleic acid fragments on the human sequence of SEQ ID 7.

TABLE 7

| Domain or motif | Position on the cDNA of SEQ 7 | |
|---|---|---|
| | Start | End |
| Potential fatty acid binding site | 329 | 385 |
| Potential clathrin binding site | 572 | 583 |
| Signal for transport: LI | 809 | 814 |
| LL | 845 | 850 |
| Transmembrane domain | 872 | 901 |
| Potential cytokine receptor site | 902 | 1009 |
| RSRS motif | 1682 | 1693 |
| Potential lipoprotein ligand binding site | 1904 | 1942 |

The invention also relates to a purified nucleic acid corresponding to the sequence of the 5'UTR of the cDNAs encoding the human LSR receptor. This nucleic acid is characterized in that it comprises a nucleotide sequence corresponding to nucleotides 1898 to 2001 of SEQ ID 19 or preferably to nucleotides 1898 to 2144 of SEQ ID 19, as well as the nucleic acid sequences complementary to this nucleic acid. Shorter fragments of this nucleic acid can also be used.

The invention also relates to a purified nucleic acid corresponding to the sequence of the 3'UTR of the cDNAs encoding the LSR receptor. This nucleic acid is characterized in that it comprises a nucleotide sequence corresponding to nucleotides 20980 to 21094 of SEQ ID 19, as well as the nucleic acid sequences complementary to this nucleic acid. Shorter fragments of this nucleic acid can also be used.

The invention also relates to the purified nucleic acids corresponding respectively to the sequences of the 5'UTR or of the 3'UTR of the cDNAs encoding the rat or mouse LSR receptor. Shorter fragments of this nucleic acid can also be used.

The 5'UTR and 3'UTR may contain elements (<<responsive elements>> and <<enhancers>>) which are involved in the regulation of transcription and of translation. These regions have in particular a role in the stability of the mRNAs. Furthermore, the 5'UTR comprises the Shine-Delgarno motif which is essential for the translation of the mRNA.

Nucleic acid, nucleic sequence or nucleic acid sequence are understood to mean an isolated natural, or a synthetic, DNA and/or RNA fragment comprising, or otherwise, non-natural nucleotides, designating a precise succession of nucleotides, modified or otherwise, allowing a fragment, a segment or a region of a nucleic acid to be defined.

Equivalent nucleic sequences are understood to mean nucleic sequences encoding the polypeptides according to the invention taking into account the degeneracy of the genetic code, the complementary DNA sequences and the corresponding RNA sequences, as well as the nucleic sequences encoding the equivalent polypeptides.

Homologous nucleic sequences are understood to mean the nucleic sequences encoding the homologous polypeptides and/or the nucleic sequences exhibiting a level of homology of at least 80%, preferably 90%. According to the invention, the homology is only of the statistical type, which means that the sequences have a minimum of 80%, preferably 90%, of nucleotides in common. They are preferably sequences capable of hybridizing specifically with a sequence of the invention. Preferably, the specific hybridization conditions will be like those found in the examples, or such that they ensure at least 95% homology.

The length of these nucleic sequences for hybridization can vary from 8, 10, 15, 20 or 30 to 200 nucleotides, particularly from 20 to 50 nucleotides, more particularly from 20 to 30 nucleotides.

Allele or allelic variant will be understood to mean the natural mutated sequences corresponding to polymorphisms present in human beings and, in particular, to polymorphisms which can lead to the onset and/or to the development of obesity or of anorexia. These polymorphisms can also lead to the onset and/or to the development of risks or complications associated with obesity, in particular at the cardiovascular level, and/or of pathologies associated with abnormalities in the metabolism of cytokines.

Mutated nucleic sequences are understood to mean the nucleic sequences comprising at least one point mutation compared with the normal sequence.

While the sequences according to the invention are in general normal sequences, they are also mutated sequences since they comprise at least one point mutation and preferably at most 10% of mutations compared with the normal sequence.

Preferably, the present invention relates to mutated nucleic sequences in which the point mutations are not silent, that is to say that they lead to a modification of the amino acid encoded in relation to the normal sequence. Still more preferably, these mutations affect amino acids which structure the LSR complex and/or receptor or the corresponding domains and fragments thereof. These mutations may also affect amino acids carried by the regions corresponding to the receptor sites, for lipoproteins or cytokines, in particular leptin, or to sites for binding of cofactors, in particular or free fatty acids, or alternatively to phosphorylation sites. These mutations may also affect the sequences involved in the transport, addressing and membrane anchorage of LSR.

In general, the present invention relates to the normal LSR polypeptides, the mutated LSR polypeptides as well as fragments thereof and to the corresponding DNA and RNA sequences, the LSR polypeptides designating polypeptides of the receptor according to the invention.

According to the invention, the fragments of nucleic sequences may in particular encode domains of receptors and polypeptides possessing a function or a biological activity as defined above, contain domains or regions situated upstream or downstream of the coding sequence and containing elements for regulating the expression of the LSR gene or alternatively possessing a sequence allowing their use as a probe or as a primer in methods of detection, identification or amplification of nucleic sequences. These fragments preferably have a minimum size of 8, of 10 bases, and fragments of 20 bases, and preferably of 30 bases, will be preferred.

Among the nucleic fragments which may be of interest, in particular for diagnosis, there should be mentioned, for example, the genomic intron sequences of the gene for the LSR complex, such as in particular the joining sequences between the introns and the exons, normal or mutated.

The nucleic acid sequences which can be used as sense or antisense oligonucleotides, characterized in that their sequences are chosen from the sequences according to the invention, also form part of the invention.

Among the nucleic acid fragments of interest, there should thus be mentioned, in particular the antisense oligonucleotides, that is to say whose structure ensures, by hybridization with the target sequence, inhibition of the expression of the corresponding product. There should also be mentioned the sense oligonucleotides which, by interaction with the proteins involved in the regulation of the expression of the corresponding product, will induce either inhibition, or activation of this expression.

The sequences carrying mutations which may be involved in the promoter and/or regulatory sequences of the genes for the LSR complex, which may have effects on the expression of the corresponding proteins, in particular on their level of expression, also form part of the preceding sequences according to the invention.

The nucleic sequences which can be used as primer or probe, characterized in that their nucleic sequence is a sequence of the invention, also form part of the invention.

The present invention relates to all the primers which may be deduced from the nucleotide sequences of the invention and which may make it possible to detect the said nucleotide sequences of the invention, in particular the mutated sequences, using in particular a method of amplification such as the PCR method, or a related method.

The present invention relates to all the probes which may be deduced from the nucleotide sequences of the invention, in particular sequences capable of hybridizing with them, and which may make it possible to detect the said nucleotide sequences of the invention, in particular to discriminate between the normal sequences and the mutated sequences.

The invention also relates to the use of a nucleic acid sequence according to the invention as a probe or a primer for the detection and/or the amplification of a nucleic acid sequence according to the invention.

All the probes and primers according to the invention may be labelled by methods well known to persons skilled in the art, in order to obtain a detectable and/or quantifiable signal.

The present invention also relates to the nucleotide sequences which may comprise non-natural nucleotides, in particular sulphur-containing nucleotides, for example, or nucleotides of α or β structure.

The present invention relates, of course, to both the DNA and RNA sequences, as well as the sequences which hybridize with them, as well as the corresponding double-stranded DNAs.

In the text which follows, the preceding DNA sequences will be called genes for the LSR complex, whether they are normal or pathologic sequences.

It should be understood that the present invention does not relate to the genomic nucleotide sequences in their natural chromosomal environment, that is to say in the natural state. They are sequences which have been isolated, that is to say that they have been collected directly or indirectly, for example by copying (cDNA), their environment having been at least partially modified.

Thus, this may also be both cDNA and genomic DNA, partially modified or carried by sequences which are at least partially different from the sequences carrying them naturally.

These sequences may also be termed non-natural.

The invention also comprises methods for screening cDNA and genomic DNA libraries, for the cloning of the isolated cDNAs, and/or the genes coding for the receptor according to the invention, and for their promoters and/or regulators, characterized in that they use a nucleic sequence according to the invention. Among these methods, there may be mentioned in particular:

the screening of cDNA libraries and the cloning of the isolated cDNAs (Sambrook et al., 1989; Suggs et al., 1981; Woo et al., 1979), with the aid of the nucleic sequences according to the invention, the screening of 5' end tag libraries (WO 96/34981) for nucleic sequences according to the invention, and thus the isolation of tags allowing the cloning of complete cDNAs and the corresponding promoters from genomic DNA libraries, the screening of genomic libraries, for example of BACs, (Chumakov et al., 1992; Chumakov et al., 1995) and, optionally, a genetic analysis by FISH (Cherif et al., 1990) with the aid of sequences according to the invention, allowing isolation and chromosomal location, and then the complete sequencing of the genes encoding the LSR receptor.

Also included in the invention is a sequence, in particular a genomic sequence encoding a receptor or a polypeptide according to the invention, or a nucleic acid sequence of a promoter and/or regulator of a gene encoding a receptor or a polypeptide according to the invention, or one of their allelic variants, a mutated, equivalent or homologous sequence, or one of their fragments, characterized in that it is capable of being obtained by one of the preceding methods according to the invention, or a sequence capable of hybridizing with the said sequences.

Vectors, Host Cells and Transgenic Animals

The invention also comprises the cloning and/or expression vectors containing a nucleic acid sequence according to the invention.

The vectors according to the invention, characterized in that they comprise the elements allowing the expression and/or the secretion of the said sequences in a host cell, also form part of the invention.

The vectors characterized in that they comprise a promoter and/or regulator sequence according to the invention, or a sequence for cellular addressing according to the invention, or one of their fragments, also form part of the invention.

The said vectors will preferably comprise a promoter, signals for initiation and termination of translation, as well as appropriate regions for regulation of transcription. They must be able to be stably maintained in the cell and may optionally possess particular signals specifying the secretion of the translated protein.

These different control signals are chosen according to the cellular host used. To this end, the nucleic acid sequences according to the invention may be inserted into autonomously replicating vectors inside the chosen host, or integrative vectors of the chosen host.

Among the autonomously replicating systems, there will be preferably used according to the host cell, systems of the plasmid or viral type, it being possible for the viral vectors to be in particular adenoviruses (Perricaudet et al., 1992), retroviruses, poxviruses or herpesviruses (Epstein et al., 1992). Persons skilled in the art know the technologies which can be used for each of these systems.

When the integration of the sequence into the chromosomes of the host cell is desired, it will be possible to use, for example, systems of the plasmid or viral type; such viruses will be, for example, retroviruses (Temin, 1986), or AAVs (Carter, 1993).

Such vectors will be prepared according to the methods commonly used by persons skilled in the art, and the clones resulting therefrom may be introduced into an appropriate host by standard methods such as, for example, lipofection, electroporation or heat shock.

The invention comprises, in addition, the host cells, in particular eukaryotic and prokaryotic cells, transformed by the vectors according to the invention, as well as transgenic animals, except humans, comprising one of the said transformed cells according to the invention.

Among the cells which can be used for these purposes, there may of course be mentioned bacterial cells (Olins and Lee, 1993), but also yeast cells (Buckholz, 1993), as well as animal cells, in particular mammalian cell cultures (Edwards and Aruffo, 1993), and in particular Chinese hamster ovary cells (CHO), but also insect cells in which it is possible to use methods using baculoviruses, for example (Luckow, 1993). A preferred cellular host for the expression of the proteins of the invention consists of the CHO cells.

Among the mammals according to the invention, there will be preferred animals such as mice, rats or rabbits, expressing a polypeptide according to the invention, the phenotype corresponding to the normal or variant LSR receptor, in particular mutated of human origin.

Among the animal models more particularly of interest here, there are in particular:
transgenic animals exhibiting a deficiency in one of the components of LSR. They are obtained by homologous recombination on embryonic stem cells, transfer of these stem cells to embryos, selection of the chimeras affected at the level of the reproductive lines, and growth of the said chimeras;
transgenic mice overexpressing one or more of the genes for the LSR complex of murine and/or human origin. The mice are obtained by transfection of multiple copies of the genes for the LSR complex under the control of a strong promoter of an ubiquitous nature, or selective for a type of tissue, preferably the liver;
transgenic animals (preferably mice) made deficient in one or more of the genes for the LSR complex, by inactivation with the aid of the LOXP/CRE recombinase system (Rohlmann et al., 1996) or any other system for inactivating the expression of a gene at a precise age of the animal;
animals (preferably rats, rabbits, mice) overexpressing one or more of the genes for the LSR complex, after viral transcription or gene therapy;
crossings of animals deficient in LSR (in particular mice) with animals deficient in, or overexpressing:
the LDL receptor (Herz et al., 1995; Ishibashi et al., 1993)
hepatic lipase (Homanics et al., 1995; Kobayashi et al., 1996)
apoprotein B (Purcellhuynh et al., 1995; Fan et al., 1995)
apoprotein E (Plump et al., 1992; Zhang et al., 1992; Huang et al., 1996)
apoCIII (Aalto-Setälä et al., 1992; Ito et al., 1990; Maeda et al., 1994).

The production of transgenic animals, and the viral or nonviral transfections will be preferably carried out on the following rat and mouse lines:
Zucker rat (fa/fa) (Iida et al., 1996)
AKR/J mouse (West et al., 1992)
ob/ob mouse (Zhang et al., 1994)
$ob^2j/ob^2j$ mouse (ibid)
tubby mouse (Kleyn et al., 1996; Nobben-Trauth et al., 1996)
fat/fat (Heldin et al., 1995)
agouti mouse (Lu et al., 1994; Manne et al., 1995)
db/db mouse (Chen et al., 1996).

The cells and mammals according to the invention can be used in a method for the production of a polypeptide according to the invention, as described below, and can also serve as a model for analysis and screening.

The transformed cells or mammals as described above can also be used as models so as to study the interactions between the polypeptides of the LSR complex, between these and their partners, chemical or protein compounds, which are involved directly or indirectly in the activities of the receptor for lipoproteins or the receptor for cytokines, and in particular for leptin, and in order to study the different mechanisms and interactions called into play according to the type of activity, or according to whether a normal complex is involved, or a complex in which at least one of the domains is a variant.

In particular, they may be used for the selection of products which interact with the LSR complex, or one of its normal or variant domains, as cofactor or as inhibitor, in particular a competitive inhibitor, or alternatively having an agonist or antagonist activity on the conformational changes in the LSR complex. Preferably, the said transformed cells will be used as a model allowing, in particular, the selection of products which make it possible to combat obesity or the pathologies mentioned above. The said cells may also serve for the detection of the potential risks posed by certain compounds.

Production of Polypeptides Derived From the LSR Receptor

The invention also relates to the synthesis of synthetic or recombinant polypeptides of the invention, in particular by chemical synthesis or by the use of a nucleic acid sequence according to the invention.

The polypeptides according to the present invention can be obtained by chemical synthesis using any of the numerous known peptide syntheses, for example the techniques using solid phases or techniques using partial solid phases, by condensation of fragments or by a conventional synthesis in solution.

When the compounds according to the present invention are synthesized by the solid phase method, the C-terminal amino acid is bound to an inert solid support and comprises groups protecting its amino group at the alpha position (and if necessary, protection on its functional side groups).

At the end of this step, the group protecting the amino-terminal group is removed and the second amino acid, it too comprising the necessary protection, is bound.

The N-terminal protecting groups are removed after each amino acid has been bound; on the other hand, the protection is of course maintained on the side chains. When the polypeptide chain is complete, the peptide is cleaved from its support and the side protecting groups are removed.

The solid phase synthesis technique is well known to a person skilled in the art. See in particular Stewart et al. (1984) and Bodansky (1984).

The polypeptides obtained by chemical synthesis and which may comprise corresponding non-natural amino acids are also included in the invention.

The method for the production of a polypeptide of the invention in recombinant form is itself included in the present invention, and is characterized in that the transformed cells, in particular the cells or mammals of the present invention, are cultured under conditions allowing the expression of a recombinant polypeptide encoded by a nucleic acid sequence according to the invention, and in that the said recombinant polypeptide is recovered.

Also forming part of the invention is a method for the production of a heterologous polypeptide, characterized in that it uses a vector or a host cell containing at least one of the promoter and/or regulatory sequences according to the invention, or at least one of the sequences for cellular addressing according to the invention, or one of their fragments.

The recombinant polypeptides, characterized in that they are capable of being obtained by the said method of production, also form part of the invention.

The recombinant polypeptides obtained as indicated above may be both in glycosylated and nonglycosylated form and may or may not have the natural tertiary structure.

These polypeptides may be produced from the nucleic acid sequences defined above, according to techniques for the production of recombinant polypeptides known to persons skilled in the art. In this case, the nucleic acid sequence used is placed under the control of signals allowing its expression in a cellular host.

An effective system of production of a recombinant polypeptide requires having a vector and a host cell according to the invention.

These cells may be obtained by introducing into the host cells a nucleotide sequence inserted into a vector as defined above, and then culturing the said cells under conditions allowing the replication and/or expression of the transfected nucleotide sequence.

The methods for the purification of a recombinant polypeptide which are used are known to persons skilled in the art. The recombinant polypeptide may be purified from cell lysates and extracts, from the culture medium supernatant, by methods used individually or in combination, such as fractionation, chromatographic methods, immunoaffinity techniques with the aid of specific mono- or polyclonal antibodies, and the like.

A preferred variant consists in producing a recombinant polypeptide fused with a "carrier" protein (chimeric protein). The advantage of this system is that it allows a stabilization and a reduction in proteolysis of the recombinant product, an increase in solubility during in vitro renaturation and/or simplification of the purification when the fusion partner has affinity for a specific ligand.

Antibodies

The mono- or polyclonal antibodies or fragments thereof, chimeric or immuno-conjugated antibodies, characterized in that they are capable of specifically recognizing a polypeptide or receptor according to the invention, also form part of the invention.

Specific polyclonal antibodies may be obtained from a serum of an animal immunized against, for example:
  the LSR receptor purified from membranes of cells carrying the said LSR receptor, by methods well known to persons skilled in the art such as affinity chromatography using, for example, recombinant leptin as specific ligand, or
  a polypeptide according to the invention, in particular produced by genetic recombination or by peptide synthesis, according to the customary procedures, from a nucleic acid sequence according to the invention.

There may be noted in particular the advantage of antibodies specifically recognizing certain polypeptides, variants or fragments, which are in particular biologically active, according to the invention.

The specific monoclonal antibodies may be obtained according to the conventional hybridoma culture method described by Kohler and Milstein, 1975.

The antibodies according to the invention are, for example, chimeric antibodies, humanized antibodies, Fab or F(ab')2 fragments. They may also be in the form of immunoconjugates or of labelled antibodies so as to obtain a detectable and/or quantifiable signal.

The invention also relates to methods for the detection and/or purification of a polypeptide according to the invention, characterized in that they use an antibody according to the invention.

The invention comprises, in addition, purified polypeptides, characterized in that they are obtained by a method according to the invention.

Moreover, in addition to their use for the purification of polypeptides, the antibodies of the invention, in particular the monoclonal antibodies, may also be used for the detection of these polypeptides in a biological sample.

They thus constitute a means for the immunocytochemical or immunohistochemical analysis of the expression of the polypeptide of the LSR receptor on specific tissue sections, for example by immunofluorescence, gold labelling, enzymatic immunoconjugates.

They make it possible in particular to detect abnormal expression of these polypeptides in the biological tissues or samples, which makes them useful for the detection of abnormal expression of the LSR receptor or for monitoring the progress of the method of prevention or treatment.

More generally, the antibodies of the invention may be advantageously used in any situation where the expression of a polypeptide of the LSR receptor, normal or mutated, needs to be observed.

Detection of Allelic Variability and Diagnosis

Also forming part of the invention are the methods for the determination of an allelic variability, a mutation, a deletion, a loss of heterozygosity or a genetic abnormality, characterized in that they use a nucleic acid sequence or an antibody according to the invention.

These methods relate to, for example, the methods for the diagnosis of predisposition to obesity, to the associated risks, or to pathologies associated with abnormalities in the metabolism of cytokines, by determining, in a biological sample from the patient, the presence of mutations in at least one of the sequences described above. The nucleic acid sequences analysed may be either the genomic DNA, the cDNA or the mRNA.

It will also be possible to use nucleic acids or antibodies based on the present invention in order to allow a positive and differential diagnosis in a patient taken in isolation. The nucleic sequences will be preferably used for a pre-symptomatic diagnosis in an at risk subject, in particular with a familial history. It is also possible to envisage an ante-natal diagnosis.

In addition, the detection of a specific mutation may allow an evolutive diagnosis, in particular as regards the intensity of the pathology or the probable period of its appearance.

The methods allowing the detection of a mutation in a gene compared with the natural gene are, of course, highly numerous. They can essentially be divided into two large categories. The first type of method is that in which the presence of a mutation is detected by comparing the mutated sequence with the corresponding nonmutated natural sequence, and the second type is that in which the presence of the mutation is detected indirectly, for example by evidence of the mismatches due to the presence of the mutation.

These methods can use the probes and primers of the present invention which are described. They are generally purified nucleic sequences for hybridization comprising at least 8 nucleotides, characterized in that they can hybridize specifically with a nucleic sequence chosen from the group comprising SEQ ID 1, SEQ ID 3, SEQ ID 5, SEQ ID 7, SEQ ID 9, SEQ ID 11, SEQ ID 13, SEQ ID 14 SEQ ID 15, SEQ ID 19 and SEQ ID 41. Preferably, the specific hybridization conditions are like those defined in the examples, or such that they ensure at least 95% homology. The length of these nucleic sequences for hybridization can vary from 8, 10, 15, 20 or 30 to 200 nucleotides, particularly from 20 to 50 nucleotides, more particularly from 20 to 30 nucleotides.

Among the methods for the determination of an allelic variability, a mutation, a deletion, a loss of heterozygocity or a genetic abnormality, the methods comprising at least one stage for the so-called PCR (polymerase chain reaction) or PCR-like amplification of the target sequence according to the invention likely to exhibit an abnormality with the aid of a pair of primers of nucleotide sequences according to the invention are preferred. The amplified products may be treated with the aid of an appropriate restriction enzyme before carrying out the detection or assay of the targeted product.

PCR-like will be understood to mean all methods using direct or indirect reproductions of nucleic acid sequences, or alternatively in which the labelling systems have been amplified, these techniques are of course known, in general they involve the amplification of DNA by a polymerase; when the original sample is an RNA, it is advisable to carry out a reverse transcription beforehand. There are currently a great number of methods allowing this amplification, for example the so-called NASBA "Nucleic Acid Sequence Based Amplification" (Compton 1991), TAS "Transcription based Amplification System" (Guatelli et al., 1990), LCR "Ligase Chain Reaction" (Landegren et al., 1988), "Endo Run Amplification" (ERA), "Cycling Probe Reaction" (CPR), and SDA "Strand Displacement Amplification" (Walker et al., 1992), methods well known to persons skilled in the art.

The invention comprises, in addition, methods for the diagnosis of pathologies and/or pathogeneses correlated with abnormal expression of a polypeptide and/or a receptor according to the invention, characterized in that an antibody according to the invention is brought into contact with the biological material to be tested, under conditions allowing the possible formation of specific immunological complexes between the said polypeptide and the said antibody, and in that the immunological complexes possibly formed are detected.

Mutations in one or more genes of the LSR complex may be responsible for various modifications of their product(s), which modifications can be used for a diagnostic approach. Indeed, modifications of antigenicity can allow the development of specific antibodies. The discrimination between the various conformations of LSR can be achieved by these methods. All these modifications may be used in a diagnostic approach by virtue of several well-known methods based on the use of mono- or polyclonal antibodies recognizing the normal polypeptide or mutated variants, such as for example using RIA or ELISA.

These diagnostic methods also relate to the methods of diagnosis by imaging in vivo or ex vivo using the monoclonal or polyclonal antibodies according to the invention, particularly those labelled and corresponding to all or part of the mutated polypeptides (imaging with the aid of antibodies coupled to a molecule which is detectable in PET-scan type imaging, for example).

Screening of Compounds of Interest

Also included in the invention are the methods for selecting the chemical or biochemical compound capable of interacting, directly or indirectly, with the receptor according to the invention, and/or allowing the expression or the activity of the said receptor to be modulated, characterized in that they use a receptor, a nucleic acid, a polypeptide, a vector, a cell or a mammal according to the invention.

Screening of Compounds Modifying the Activity of the LSR Receptor

The invention relates to a method for screening compounds modifying the activity of the LSR receptor, consisting in measuring the effect of candidate compounds on various parameters reflecting, directly or indirectly, taken independently or in combination, an LSR receptor activity.

For the screening of compounds capable of modulating the LSR activity for lipoprotein clearance, the preferred principal effect is the effect of the compound on the activity of binding, internalization and degradation of the lipoproteins by the LSR receptor.

This effect can be analysed in the absence or in the presence of free fatty acids, or of any other agent known to induce or to inhibit the activity of LSR on the clearance of lipoproteins, or in the absence or the presence of leptin, or of any other agent capable of inducing or of inhibiting the LSR function of cytokine clearance. It can, in addition, be measured in the absence or in the presence of agents capable of promoting or reducing the lipase activities, either intracellular or extracellular, as well as in the presence or in the absence of alternative known routes of degradation of lipoproteins.

Various indirect parameters can also be measured, including the following the change in weight induced by the administration of the compound the food intake induced by the administration of the compound the postprandial lipemic response induced by the administration of the compound, before, during or after ingestion of a meal, for example high in fat.

The selection of compounds capable of influencing the plasma triglyceride concentrations, and/or the binding, internalization and hepatic degradation of lipoproteins or particles high in triglycerides, will be preferred.

For the screening of compounds capable of modulating the LSR activity of clearance of cytokines, in particular of leptin, the preferred principal effect is the effect of the compound on the activity of binding, internalization and hepatic degradation of cytokines by the LSR receptor, in the absence or in the presence of free fatty acids.

The measurement of the binding, internalization and/or degradation of lipids or of cytokines can be carried out, for example, on hepatocytes or fibroblasts in culture, or on any other cell expressing the LSR receptor at its surface. The cells will be preferably cells expressing a recombinant LSR receptor, more particularly cells expressing a recombinant LSR receptor and whose endogenous LSR receptor would be inactivated or absent. These cells may or may not express the LDL receptor.

The screening of compounds modulating the LSR activity preferably uses cells or model animals according to the invention, in particular mice, rats or humans, more particularly those described above and in the examples which follow.

Screening of Compounds Modifying the Expression of the LSR Receptor

Screening may be used to test compounds capable of modifying the level and/or the specificity of expression of the LSR receptor either by binding competitively to the sites for binding of trariscription factors situated in the LSR-promoter or by binding directly to the transcription factors.

The level of expression of the LSR receptor and its location can be analysed by hybridization in solution with large probes as indicated in Patent PCT WO 97/05277, the teaching of this document being incorporated by reference. Briefly, a cDNA or the genomic DNA for the LSR receptor or alternatively a fragment thereof is inserted at a cloning site situated directly downstream of a bacteriophage (T3, T7 or SP6) RNA polymerase promoter in order to produce an antisense RNA. Preferably, the insert comprises at least 100 consecutive nucleotides of the genomic sequence of the LSR receptor or of one of the cDNAs of the present invention, more particularly one or more of the cDNAs of SEQ ID 9, SEQ ID 11 or SEQ ID 13. The plasmid is linearized and transcribed in the presence of ribonucleotides comprising modified ribonucleotides such as Biotin-UTP and Digoxigenin-UTP. An excess of this labelled RNA is hybridized in solution with the mRNAs isolated from cells or from tissues of interest. The hybridizations are carried out under stringent conditions (40–50° C. for 16 h in a solution containing 80% formamide and 0.4 M NaCl, pH 7–8). The non-hybridized probe is eliminated by digestion with ribonucleases specific for single-stranded RNAs (CL3, T1, PhyM, U2 or A RNases). The presence of modified nucleotides biotin-UTP allows the capture of the hybrids on microtitre plates carrying streptavidine. The presence of the DIG modification allows the detection and quantification of the hybrids by ELISA using anti-DIG antibodies coupled to alkaline phosphatase.

A quantitative analysis of the expression of the gene for the LSR receptor can also be carried out using DNA templates, the term DNA templates designating a one-dimensional, two-dimensional or multi-dimensional arrangement of a plurality of nucleic acids having a sufficient length to allow a specific detection of the expression of mRNAs capable of hybridizing thereto. For example, the DNA templates may contain a plurality of nucleic acids derived from genes for which it is desired to estimate the level of expression. The DNA templates may include the genomic sequences of LSR, that of a cDNA of the present invention, more particularly one or more of the cDNAs of SEQ ID 9, SEQ ID 11 or SEQ ID 13, any sequences complementary thereto or any fragments thereof. Preferably, the fragments comprise at least 15, at least 25, at least 50, at least 100 or at least 500 consecutive nucleotides of the nucleic sequences from which they are derived.

For example, a quantitative analysis of the expression of the LSR receptor can be carried out with a DNA template having the cDNA for the LSR receptor as described in Schena et al. (1995 and 1996). cDNAs for the LSR receptor or fragments thereof are amplified by PCR and bound in the form of a template from a 96-well microplate onto a sylated microscope slide using a very fast automated machine. The DNA template thus produced is incubated in a humid chamber in order to allow its rehydratation. It is then rinsed once in 0.2% SDS for 1 min, twice in water for 1 min and once for 5 min in a sodium borohydride solution. The template is then submerged in water for 2 min at 95° C., transferred into 0.2% SDS for 1 min, rinsed twice with water, dried and stored in the dark at 25° C.

The mRNAs of cells and of tissues are isolated or obtained from a commercial source, for example the company Clontech. The probes are prepared by a reverse transcription cycle. The probes are then hybridized with the DNA template of 1 cm$^2$ under a glass coverslip of 14×14 mm for 6–12 hours at 60° C. The template is washed for 5 min at 25° C. in a washing buffer at low stringency (1×SSC/0.2% SDS) and then for 10 min at room temperature in a highly stringent buffer (0.1×SSC/0.2% SDS). The template is analysed in 0.1×SSC using a laser fluorescence microscope with a set of appropriate filters. Measurements of precise differential expression are obtained by taking the mean of the ratios of two independent hybridizations.

A quantitative analysis of the expression of the LSR receptor can also be carried out with cDNAs for the LSR receptor or fragments thereof on DNA templates according to the description by Pietu et al. (1996). The cDNAs for the LSR receptor or fragments thereof are amplified by PCR and bound to membranes. The mRNAs obtained from different tissues or cells are labelled with radioactive nucleotides. After hybridization and washing under controlled conditions, the hybridized mRNAs are detected with a Phosphor Imager or by autoradiography. The experiments are carried out in duplicate and a quantitative analysis of the differentially expressed mRNAs can be carried out.

Alternatively, the analysis of the expression of the LSR receptor can be made with DNA templates at high density as described by Lockhart et al. (1996) and Sosnowski et al.

(1997). Oligonucleotides of 15 to 50 nucleotides, preferably about 20 nucleotides, extracted from genomic DNA or cDNA sequences for the LSR receptor or of their complementary sequences are synthesized directly on a chip or synthesized and then addressed onto the chip.

LSR cDNA probes labelled with an appropriate compound such as biotin, digoxigenin or a fluorescent molecule are synthesized from a population of mRNA and are fragmented into oligonucleotides of 50 to 100 nucleotides on average. The probes thus obtained are then hybridized to a chip. After washing as described in Lockhart et al (1996) and an application of various electric fields (Sosnowski et al. 1997), the labelled compounds are detected and quantitied. The hybridizations are duplicated. A comparative analysis of the intensity of the signals generated by the probes on the same target oligonucleotide in various cDNA samples indicates a differential expression of the mRNAs for the LSR receptor.

The techniques mentioned above allow the analysis of the levels of expression of the LSR receptor, in the same cell or the same tissue depending on various conditions, for example of induction or of noninduction, but also the analysis of the tissue specificity of this expression, under conditions which can also vary. It will be possible, by virtue of these techniques, to analyse the expression of either of the subunits of the LSR receptor, and more generally of different forms derived from alternative splicing, by adequately defining the probes.

The effect of compounds which are candidates for modulating the level or the specificity of expression, or of splicing of the different forms of the LSR receptor can thus be analysed on a large scale by exposing the cells which are the source of messenger RNA, in particular the model cells according to the invention, whether they express LSR naturally or whether they are recombinant cells, to the said candidate compounds.

Screening of Compounds Interacting With the LSR Receptor

Another aspect of the present invention consists in methods of identifying molecules capable of binding to the LSR receptor. Such molecules can be used to modulate the activity of the LSR receptor. For example, such molecules can be used to stimulate or reduce the degradation of lipoproteins, preferably of lipoproteins high in triglycerides, or of cytokines, preferably of leptin. Such molecules can also be used to inhibit the activation by leptin or the activation by free fatty acids of the LSR activity.

Numerous methods exist for identifying ligands for the LSR receptor. One of these methods is described in U.S. Pat. No. 5,270,170, whose teaching is incorporated by reference. Briefly, a library is constructed which consists of random peptides, comprising a plurality of vectors each encoding a fusion between a peptide which is a candidate for binding to the LSR receptor and a protein binding to DNA such as the Lac repressor encoded by the lad gene. The vectors for the library of random peptides also contain binding sites for the proteins binding to DNA such as the LacO site when the protein is the Lac repressor. The library of random peptides is introduced into a host cell in which the fusion protein is expressed. The host cell is then lysed under conditions allowing the binding of the fusion protein to the sites of the vector.

The vectors which have bound the fusion protein are brought into contact with the immobilized LSR receptor, a subunit of the immobilized LSR receptor or a fragment of the immobilized LSR receptor under conditions allowing the peptides to bind specifically. For example, the LSR receptor, a subunit thereof or a fragment thereof comprising at least 10, at least 20, at least 30, or more than 30 consecutive amino acids can be immobilized by binding to a surface such as a plate or a plastic particle.

The vectors which encode the peptides capable of binding to the LSR receptor are specifically retained at the surface by interactions between the peptide and the LSR receptor, a subunit of the receptor or a fragment thereof.

Alternatively, molecules capable of interacting with the LSR receptor can be identified using a double hybrid system such as the Matchmaker Two Hybrid System 2. According to the instructions of the manual accompanying the Matchmaker Two Hybrid System 2 (Catalogue No. K1604-1, Clontech), whose teaching is incorporated by reference, the nucleic acids encoding the LSR receptor, a subunit thereof or a fragment thereof comprising at least 10, at least 20, at least 30, or more than 30 consecutive amino acids are inserted into an expression vector so that they are in phase with the DNA encoding the DNA binding domain of the transcription activator of yeast GAL4. The nucleic acids of a library encoding proteins or peptides capable of interacting with the LSR receptor are inserted into a second expression vector so that they are in phase with the DNA encoding the activation domain of the GAL4 activator. The yeasts are transformed with the two expression plasmids and they are placed in a medium which makes it possible to select the cells expressing markers contained in each of the vectors as well as those expressing the HIS3 gene whose expression is dependent on GAL4. The transformed cells capable of growing on a histidine-free medium are analysed for expression of LacZ under the dependence of GAL4. The cells which grow in the absence of histidine and express LacZ contain a plasmid which encodes proteins or peptides which interact with the LSR receptor, a subunit thereof or a fragment thereof comprising at least 10, at least 20, at least 30, or more than 30 consecutive amino acids thereof.

To study the interaction of the LSR receptor, a subunit thereof or a fragment thereof comprising at least 10, at least 20, at least 30, or more than 30 consecutive amino acids with small molecules such as those generated by combinatory chemistry, it is possible to use an HPLC-coupled microdialysis as described in Wang et al. (1997), or an affinity capillary electrophoresis as described in Busch et al. (1997), the teaching of these documents being incorporated by reference.

In other methods, the peptides or small molecules capable of interacting with the LSR receptor, a subunit thereof or a fragment thereof comprising at least 10, at least 20, at least 30, or more than 30 consecutive amino acids may be linked to detectable markers such as radioactive, fluorescent or enzymatic markers. These labelled molecules are brought into contact with the immobilized LSR receptor, an immobilized subunit thereof or an immobilized fragment thereof comprising at least 10, at least 20, at least 30, or more than 30 consecutive amino acids under conditions allowing a specific interaction. After elimination of the molecules which are not specifically bound, the bound molecules are detected by appropriate means.

These methods may allow in particular the identification of fatty acids or analogues capable of binding to the fatty acid binding site on the LSR, of lipoproteins or analogues, capable of binding to the lipoprotein binding site on the LSR receptor, of leptin derivatives or analogues capable of binding to the leptin binding site on the LSR, and of derivatives of the gC1qR receptor or analogues capable of binding to the gC1qR binding site on the LSR.

In addition, the peptides or small molecules which bind to LSR, preferably to the binding sites on the LSR receptor for fatty acids, lipoproteins, cytokines, in particular leptin, or gC1qR or one of its analogous proteins, can be identified by competition experiments. In such experiments, the LSR receptor, a subunit thereof or a fragment thereof comprising at least 10, at least 20, at least 30, or more than 30 consecutive amino acids is immobilized on a surface such as a plastic support. Increasing quantities of peptides or of small molecules are brought into contact with the immobilized LSR receptor, an immobilized subunit thereof or an immobilized fragment thereof comprising at least 10, at least 20, at least 30, or more than 30 consecutive amino acids in the presence of a labelled ligand for the receptor, it being possible for this ligand to be, for example, leptin, oleate, the LDLs or gC1qR. The ligand for the LSR receptor may be labelled with a radioactive, fluorescent or enzymatic marker. The capacity of the molecule tested to interact with the LSR receptor, a subunit thereof or a fragment thereof comprising at least 10, at least 20, at least 30, or more than 30 consecutive amino acids is determined by measuring the quantity of labelled ligand bound in the presence of the molecule tested. A decrease in the quantity of bound ligand when the molecule tested is present indicates that the latter is capable of interacting with the LSR receptor, a subunit thereof or a fragment thereof comprising at least 10, at least 20, at least 30, or more than 30 consecutive amino acids.

These methods can in particular allow the identification of fatty acids or analogues capable of binding to the fatty acid binding site on the LSR, of lipoproteins or analogues, capable of binding to the lipoprotein binding site on the LSR receptor, of leptin derivatives or analogues capable of binding to the leptin binding site on the LSR, and of derivatives of the gC1qR receptor or analogues capable of binding to the gC1qR binding site on the LSR. The capacity of such compounds, or of any other candidate compound, to compete with the binding of oleates, lipoproteins, leptin or gC1qR to LSR can be measured in particular.

The BIACORE technology can also be used to carry out the screening of compounds capable of interacting with the LSR receptor. This technology is described in Szabo et al. (1995) and in Edwards and Leartherbarrow (1997), of which the teaching is incorporated by reference, and makes it possible to detect interactions between molecules in real time without the use of labelling. It is based on the phenomenon of SPR (surface plasmon resonance). Briefly, the molecule to be analysed is bound to a surface (typically using a carboxymethyl dextran matrix). A light ray is directed onto the face of the surface which does not contain the sample and is reflected by the said surface. The SPR phenomenon causes a reduction in the intensity of the reflected light with a specific combination of angle and of wavelength. The molecule binding events cause a change in the refractive index at the surface which is detected as a modification of the SPR signal. To carry out a screening of compounds capable of interacting with the LSR receptor, the LSR receptor, a subunit thereof or a fragment thereof comprising at least 10, at least 20, at least 30, or more than 30 consecutive amino acids, is immobilized on a surface. This surface constitutes one face of a cell through which passes the molecule to be tested. The binding of the molecule to the LSR receptor, a subunit thereof or a fragment thereof comprising at least 10, at least 20, at least 30, or more than 30 consecutive amino acids is detected by a change in the SPR signal. The molecules tested may be proteins, peptides, carbohydrates, lipids or small molecules generated, for example, by combinatory chemistry. The candidate proteins can be extracted from any tissue, obtained from any species. The BIACORE technology can also be used by immobilizing eukaryotic or prokaryotic cells or lipid vesicles having an endogenous or recombinant LSR receptor at their surface.

One of the main advantages of this method is that it allows the determination of the association constants between the LSR receptor and the interacting molecules. Thus, it is possible to specifically select the molecules interacting with high or low association constants.

The proteins or other molecules interacting with the LSR receptor, a subunit thereof or a fragment thereof comprising at least 10, at least 20, at least 30, or more than consecutive amino acids can be identified using affinity columns which contain the LSR receptor, a subunit thereof or a fragment thereof comprising at least 10, at least 20, at least 30, or more than 30 consecutive amino acids. The LSR receptor, a subunit thereof or a fragment thereof comprising at least 10, at least 20, at least 30, or more than 30 consecutive amino acids may be attached to the column using conventional techniques including chemical coupling to an appropriate column matrix such as agarose, Affi Gel, or other matrices known to a person skilled in the art. In another aspect of the invention, the affinity column may contain chimeric proteins in which the LSR receptor, a subunit thereof or a fragment thereof comprising at least 10, at least 20, at least 30, or more than 30 consecutive amino acids would be fused, for example, with glutathione S-transferase. The molecules to be tested which are described above are then deposited on the column. The molecules interacting with the LSR receptor, a subunit thereof or a fragment thereof comprising at least 10, at least 20, at least 30, or more than 30 consecutive amino acids are retained by the column and can be isolated by elution. In the case where the molecules tested are proteins, they can then be analysed on a 2-D electrophoresis gel as described in Ramunsen et al. (1997), of which the teaching is incorporated by reference. Alternatively, the proteins or the other molecules retained by the affinity column can be purified by electrophoresis and sequenced. A similar method can be used to isolate antibodies, to screen <<phage display>> products or <<phage display>> derived human antibodies.

Screening of Compounds Interacting with the Promoter and/or Regulatory Sequences of the LSR Receptor The invention also relates to a method of screening compounds interacting with the promoter and/or regulatory sequences of the LSR receptor.

The nucleic acids encoding proteins interacting with the promoter and/or regulatory sequences of the LSR receptor gene, more particularly a nucleotide sequence corresponding to nucleotides 1 to 1897 of SEQ ID 19 or a fragment thereof, can be identified using a single hybrid system such as that described in the manual accompanying the Matchmaker One-Hybrid System from Clontech (Catalogue No. K1603-1), of which the teaching is incorporated by reference. Briefly, the target nucleotide sequence is cloned upstream of a selectable marker gene and integrated into a yeast genome. The yeasts containing the integrated marker gene are transformed by a library containing fusions between cDNAs encoding candidate proteins for binding to the promoter and/or regulatory regions of the gene for the LSR receptor and the yeast transcription factor activating domain such as GAL4. The yeasts are placed in a medium which makes it possible to select the cells expressing the marker gene. The yeasts selected contain a fusion protein capable of binding to the promoter and/or regulatory target region. The cDNAs of the genes encoding the fusion proteins are then sequenced. The corresponding inserts can then be cloned into expression or transcription vectors in vitro. The binding of the polypeptides thus encoded to the promoter target sequences can be confirmed by techniques familiar to persons skilled in the art, including gel retardation or protection to DNAse experiments.

The screening of compounds capable of modifying the expression of the LSR receptor by binding to its regulatory and/or promoter sequences can also be carried out with the aid of <<reporter>> genes. For example, a genomic region situated in 5' of the coding sequence of the LSR receptor, more particularly a nucleotide sequence corresponding to nucleotides 1 to 1897 of SEQ ID 19 or a fragment thereof, can be cloned into a vector such as pSEAP-Basic, pSEAP-Enhancer, pβgal-Basic, pβgal-Enhancer, or pEGFP-1 available from Clontech. Briefly, each of these vectors contains multiple cloning sites situated upstream of a marker gene encoding an easily detectable protein such as alkaline phosphatase, β-galactosidase or GFP (green fluorescent protein). After insertion of the genomic region situated in 5' of the coding sequence of the LSR receptor, more particularly a nucleotide sequence corresponding to nucleotides 1 to 1897 of SEQ ID 19 or a fragment thereof, the level of expression of the marker proteins is measured and compared with a vector containing no insert. The effect of candidate compounds on the expression resulting from the regulatory and/or promoter sequences of LSR can thus be evaluated.

The screening of the compounds capable of binding to the regulatory and/or promoter regions of the gene for the LSR receptor can also be carried out by gel retardation experiments well known to persons skilled in the art and described in Fried and Crothers (1981), Garner and Revzin (1981) and Dent and Latchman (1993), of which the teaching is incorporated by reference. These experiments are based on the principle that a DNA fragment bound to a protein migrates more slowly than the same fragment without protein. Briefly, the target nucleotide sequence is labelled. It is then brought into contact either with a nuclear or total cell extract prepared so as to contain the transcription factors, or with various compounds to be tested. The interaction between the regulatory and/or promoter region of the gene for the LSR receptor and the transcription factor or compound is detected after electrophoresis by retardation of migration.

Compounds

The chemical or biochemical compounds, characterized in that they make it possible to modulate the expression or the activity of the receptor according to the invention, also form part of the invention.

The chemical or biochemical compounds, characterized in that they are capable of interacting, directly or indirectly, with the receptor according to the invention, also form part of the invention.

The chemical or biochemical compounds, characterized in that they are selected by the said methods defined above, also form part of the invention.

In particular, among these compounds according to the invention, a leptin or one of its derived compounds, preferably one of its protein variants, or leptins which are chemically modified or which are obtained by genetic recombination, or one of their fragments, are preferred.

Compounds which make it possible to modulate the expression or the activity of the receptor are understood to mean the compounds which make it possible in particular to reduce, stabilize or increase the number, the recycling rate and/or the change in the conformation of the receptor according to the invention, or to promote or inhibit the overall activity or the activity of one of the domains of the said receptor or alternatively to reestablish normal expression of the said receptor in the case, for example, where a genetic abnormality is observed. These compounds may, for example, interact as ligands specific for the said receptor or for one of its domains as cofactor, or as inhibitor, in particular a competitive inhibitor, or alternatively having an agonist or antagonist activity on the conformational changes in the complex. These compounds may also interact by neutralizing the natural ligands specific for the said receptor and by thereby inhibiting the receptor activity induced by these ligands.

Among these compounds, the compounds which make it possible to modulate the number of polypeptides of the said receptor, its recycling rate and/or the selectivity of their activity, are preferred.

Also preferred are the compounds according to the invention, characterized in that they allow an increase in the total activity or in the expression of the receptor according to the invention, and/or a specific increase in the clearance activity for cytokines, in particular leptin, of the said receptor, and/or a specific increase in the clearance activity for lipoproteins, of the said receptor.

Also preferred are the compounds characterized in that they allow a decrease in the total activity or in the expression of the receptor according to the invention, and/or a specific decrease in the clearance activity for cytokines, in particular leptin, of the said receptor, and/or a specific decrease in the clearance activity for lipoproteins, of the said receptor.

Also preferred are the compounds characterized in that they allow modulation of the elimination of the cytokines, in particular leptin, and/or modulation of the elimination of the lipoproteins, chylomicron residues, and/or triglycerides.

The invention also comprises the compounds according to the invention, characterized in that they allow modulation of the level of cytokines, in particular leptinemia, and/or modulation of the level of lipoproteins, chylomicron residues, and/or triglycerides.

The compounds according to the invention, characterized in that they allow control of the level of cytokines, in particular leptinemia, are more particularly preferred.

Still preferably, the invention comprises the compounds according to the invention, characterized in that they allow control, preferably a decrease, of the level of lipoproteins, a decrease in the plasma concentration of chylomicron residues, and/or a decrease in triglyceridemia.

Among the compounds which are most preferred, there are preferred those characterized in that they are chosen from:
 a. an antibody according to the invention;
 b. a polypeptide according to the invention;
 c. a polypeptide according to the invention, characterized in that it corresponds to a soluble form of the receptor according to the invention;
 d. a vector according to the invention;
 e. a vector according to the invention, characterized in that it has on its outer surface a site for specific recognition of hepatic cells;
 f. a vector according to the invention, characterized in that the product of expression of the nucleic acid inserted by the vector into the target cell is either anchored in or excreted by the said transformed target cell;

g. a sense or antisense oligonucleotide according to the invention;

h. a leptin, or one of its protein variants, or a leptin which is chemically modified or which is modified by genetic recombination, or one of their fragments.

The invention finally relates to the compounds according to the invention as a medicament.

The compounds according to the invention as a medicament for the prevention and/or treatment of pathologies and/or of pathogeneses linked to disorders in dietary habit are preferred in particular.

The compounds according to the invention as a medicament for the prevention and/or treatment of pathologies and/or of pathogeneses linked to disorders in the metabolism of cytokines are also preferred.

Preferably, the invention also relates to the compounds according to the invention as medicament for the prevention or treatment of obesity or anorexia.

The compounds according to the invention as a medicament for the prevention and/or treatment of pathologies and/or of pathogeneses associated with, or induced by obesity, are the preferred compounds.

In particular, there are preferred the compounds according to the invention, as a medicament for the prevention and/or treatment of cardiac insufficiency, of coronary insufficiency, of cerebrovascular accidents, of atheromatous disease, of atherosclerosis, of high blood pressure, of non-insulin-dependent diabetes, of hyperlipidemia and/or of hyperuricemia.

The most preferred are the compounds according to the invention, as a medicament for the prevention and/or treatment of atheromatous disease and/or of atherosclerosis.

Finally, the invention comprises compounds according to the invention for the prevention and/or treatment by gene therapy, of pathologies and/or of pathogeneses linked to disorders in dietary habit, of obesity and/or of pathologies and/or of pathogeneses associated with, or induced by, obesity.

The compounds of the invention as active ingredients of a medicament will be preferably in soluble form, combined with a pharmaceutically acceptable vehicle.

Such compounds which can be used as a medicament offer a new approach for preventing and/or treating pathologies and/or pathogeneses linked to disorders in dietary habit such as obesity or anorexia, and the related risks and/or complications.

Preferably, these compounds will be administered by the systemic route, in particular by the intravenous route, by the intramuscular or intradermal route or by the oral route.

Their modes of administration, optimum dosages and galenic forms can be determined according to the criteria generally taken into account in establishing a treatment suited to a patient, such as for example the age or body weight of the patient, the seriousness of his general condition, the tolerance to treatment and the side effects observed, and the like.

As mentioned above, depending on the cases, it may be advisable to amplify the activity of LSR, by promoting, for example, the expression of its genes or by increasing the activity of their expression products, in pathological cases resulting from the fact that at least one of these genes is not expressed, is insufficiently expressed or is expressed in an abnormal form which does not allow the expression product to carry out its functions, or on the contrary to repress an overexpression or an abnormal expression of these genes. It is therefore advisable in general to compensate for the deficiency or the overexpression of expression products of this gene by a so-called "replacement" therapy allowing the amplification or the reduction in the activities of the LSR complex.

The replacement therapy may be carried out by gene therapy, that is to say by introducing the nucleic acid sequences according to the invention and/or the corresponding genes with the elements which allow their expression in vivo, in the case where one of the genes is insufficiently expressed for example, or alternatively when it is expressed in an abnormal form.

The principles of gene therapy are known. It is possible to use viral vectors according to the invention; it is also possible to envisage nonviral, that is to say synthetic, vectors which mimic viral sequences or alternatively which consist of naked RNA or DNA according to the technique developed in particular by the company VICAL.

In most cases, it is necessary to envisage targeting elements ensuring expression specific for the liver so as to be able to limit the zones of expression of the proteins which remain involved in the clearance of leptin and that of lipoproteins. It is even advantageous, in some cases, to have vectors for transient expression or at least for controlled expression which it will be possible to block when necessary.

Other characteristics and advantages of the invention appear in the remainder of the description with the examples and figures whose legends are represented below.

LEGEND TO THE FIGURES

FIG. 1: Schematic representation of the three forms of the rat LSR protein: LSR 66 ($\alpha$ subunit), LSR 64 ($\alpha'$ subunit), and LSR 58 ($\beta$ subunit).

FIG. 2: Alignment of the protein sequences of the long forms ($\alpha$ subunits) of the human LSR (LSR1.Hs; SEQ ID NO:8), rat LSR (LSR1.Rn; SEQ ID NO:2) and mouse LSR (LSR1.Mm; SEQ ID NO:16). The (*) symbols placed under the alignments indicate the conserved amino acids, the (.) symbols indicate the conservative substitutions of amino acids. Boxed, from the $NH_2$-terminal end to the COOH-terminal end, the potential fatty acid (FFA) binding site boxed, the clathrin binding site [NPGY], the lyosomal addressing consensus: di-leucine LI-X10-LL, the transmembrane TM domain overlined, the motif [RSRS], the potential lipoprotein binding site (+-+-) boxed. Overlined, the signature of the TNF receptor with (arrow); indicated, the amino acids conserved in the signature. The transmembrane domain is situated between the last di-leucine and the TNF signature.

A: Alignment shown from amino acid positions 1 to 539 of SEQ ID NO:8.

B: Alignment shown from amino acid positions 540 to 649 of SEQ ID NO:8.

FIG. 3: Alignment of the protein sequences of the three types of subunits of the human LSR ($\alpha$: LSR1.Hs, SEQ ID NO:8; $\alpha'$: LSR2.Hs, SEQ ID NO:10; $\beta$: LSR3.Hs, SEQ ID NO:12). The meaning of the symbols, of the boxes and of the overlines is the same as that in FIGS. 2A and 2B.

A: Alignment shown from amino acid positions 1 to 540 of SEQ ID NO:8.

B: Alignment shown from amino acid positions 541 to 649 of SEQ ID NO:8.

FIG. 4: Alignment of the protein sequences of the three types of subunits of rat LSR. ($\alpha$: LSR1.Rn, SEQ ID NO:2; $\alpha'$: LSR2.Rn, SEQ ID NO:4; $\beta$: LSR3.Rn, SEQ ID NO:6).

The meaning of the symbols, of the boxes and of the overlines is the same as that in FIGS. 2A and 2B.

A: Alignment shown from amino acid positions 1 to 540 of SEQ ID NO:2.

B: Alignment shown from amino acid positions 541 to 593 of SEQ ID NO:2.

FIG. 5: Alignment of the protein sequences of the three types of subunits of mouse LSR (α: LSR1.Mm, SEQ ID NO: 16; α': LSR2.Mm, SEQ ID NO: 17; β: LSR3.Mm, SEQ ID NO:18). The meaning of the symbols, of the boxes and of the overlines is the same as that in FIGS. 2A and 2B.

A: Alignment shown from amino acid positions 1 to 540 of SEQ ID NO:16.

B: Alignment shown from amino acid positions 541 to 594 of SEQ ID NO:16.

FIG. 6: Schematic representation of the three LSR forms identified in humans, indicating the motifs conserved on each of them.

A: Schematic representation of the genomic organization of the human LSR starting from the first coding exon. The exons are indicated by boxes, the introns by interrupted bars. The size, in nucleotides, of the exons and introns is indicated above them. The elements characterizing the messenger and the encoded protein are presented in this figure. The box on the right gives the meaning of the symbols used.

B: Structure of the LSR-Hs-2062 form of human LSR. This form encodes a protein of 649 amino acids.

C: Structure of the LSR-Hs-2005 form of human LSR. This form encodes a protein of 630 amino acids.

D: Structure of the LSR-Hs-1858 form of human LSR. This form encodes a protein of 581 amino acids.

FIG. 7: Alignment of the nucleotide sequences of the long forms of cDNA (encoding the α subunit) or portions thererof for human LSR (1sr1.HS; nucleotides 1 to 2062 of SEQ ID NO:7), rat LSR (1sr1.Rn; SEQ ID NO:1) and mouse LSR (1sr1.Mm; SEQ ID NO:13). The nucleotides conserved in the three sequences are identified by an * sign placed under the sequences. Dashes are added inside the sequences when the optimum alignment of the sequences cannot be achieved without creating microdeletions.

A: Alignment shown from amino acid positions 1 to 486 of SEQ ID NO:1.

B: Alignment shown from amino acid positions 487 to 1026 of SEQ ID NO:1.

C: Alignment shown from amino acid positions 1027 to 1551 of SEQ ID NO:1.

D: Alignment shown from amino acid positions 1552 to 2080 of SEQ ID NO:1.

E: Alignment shown from amino acid positions 2081 to 2097 of SEQ ID NO:1.

FIG. 8: Identification of the LSR receptor by ligand and Western blotting on solubilized proteins of rat liver membranes (lanes 1, 2 and 4), or on the partially purified protein of 240 kD (lane 3).

Lanes 1, 2 and 3: Ligand blotting. Lane 1: in the absence of oleate and of $^{125}$I-LDL; lane 2: in the presence of oleate and of $^{125}$I-LDL; lane 3: in the presence of oleate and of $^{125}$I-LDL.

Lane 4: Western blotting with anti-LSR antibodies.

FIG. 9: Effect of anti-LSR antibodies on the LSR activity.

A. Binding of $^{125}$I-LDL onto the plasma membranes of rat hepatocytes in the presence of oleate and of increasing concentrations of anti-LSR antibody (■) or of control antibody (□), expressed as % of the total quantity of $^{125}$I-LDL bound in the absence of antibodies.

B. Binding, incorporation and degradation of $^{125}$I-LDL in rat hepatocytes in primary culture in the presence of oleate and of anti-LSR antibody (■) or of control antibody (□), expressed respectively as % of the binding, incorporation and total degradation of $^{125}$I-LDL in the presence of non-specific antibodies.

FIG. 10: Identification of the LSR receptor by immunoprecipitation of $^{35}$S-methionine- and $^{35}$S-cysteine-labelled hepatocyte lysates, in the presence of control antibodies (lane 1), or of anti-LSR antibodies (lanes 2 to 4), after separation by electrophoresis under nonreducing (lanes 2 and 3) or reducing (lanes 1 and 3) conditions.

FIG. 11: Cloning of the cDNA encoding α and β-LSR.

A. Northern-blot analysis showing several sizes of LSR messenger RNA.

B. Multi-tissue Northern-blot analysis of LSR mRNA with a probe specific for LSR and a control probe specific for β-actin.

C. RT-PCR analysis of LSR mRNA using 5 pairs of primers covering the entire sequence and identification of three forms derived from alternative splicing in the amplification fragment obtained by means of the bc' primers. The diagram represents the results of sequence analysis of the three corresponding forms of LSR cDNA: the squared region is absent from the two short forms, the hatched region is absent only from the shortest form.

FIG. 12: Translation in vitro of the two complete cDNAs encoding the longest (66 kDa, lane 2) and the shortest (58 kDa, lane 3) forms of rat LSR, and of a control cDNA, an antisense of the cDNA encoding the longest form of LSR (lane 1).

The products of translation in vitro, labelled with $^{35}$S-methionine, are analysed after electrophoresis under nonreducing conditions.

FIG. 13: Identification of the α- and β-LSR subunits as being responsible for the LSR activity.

A. Diagram showing the location and the sequence of LSR N-terminal peptide used to generate anti-LSR peptide antibodies.

B. Effect of antibodies directed against a synthetic LSR peptide on the LSR activity of rat liver plasma membranes. The LSR activity is measured in the presence of a control antibody (o) or of the anti-LSR peptide antibody (v).

C. Western and Ligand blotting of the α and β subunits of LSR. The Western blotting is carried out using the anti-LSR (lane 1) or anti-LSR peptide (lane 2) antibody. The ligand blotting is carried out in the presence of $^{125}$I-LDL, with (lane 4) or without (lane 3) oleate.

FIG. 14: Identification of the subunits of the LSR receptor and inhibitory effect of antibodies directed against a C-terminal synthetic peptide derived from LSR.

A-Diagram showing the location and the sequence of the synthetic peptide 170.

B-Western blotting of rat hepatocyte lysates using antibodies directed against the synthetic peptide 170 (lane 2), or a control antibody (lane 1); lane 3: molelcular weight markers.

C-Binding of $^{125}$I-LDL by the LSR receptor in the presence of oleate and of control antibodies or antibodies directed against the LSR 170 peptide.

FIG. 15: Effect of a transient transfection of CHO-K1 cells with the plasmids expressing the α and β subunits of the LSR receptor on the binding of LDLs in the presence or in the absence of oleate. Increasing concentration of β plasmid alone (○□); fixed concentration of α plasmid and increasing concentration of β plasmid (●■).

FIG. 16: Effect of a transient transfection of CHO-K1 cells with plasmids expressing the α and β subunits of the LSR receptor on the internalization and degradation of LDLs. Increasing concentration of α plasmid alone (■); fixed concentration of α plasmid and increasing concentration of β plasmid (●). The results are expressed as the difference between the measurements in the presence and in the absence of oleate.

FIG. 17: Characterization of the LSR activity obtained in CHO-K1 cells transiently transfected with the nucleic sequences encoding the α and β subunits of the LSR receptor, compared with the LSR activity obtained in the same cells not transfected (control).

A-Binding of $^{125}$I-LDL in the presence of a control antibody or of an anti-LSR antibody.

B-Binding of $^{125}$I-LDL in the presence of increasing concentrations of unlabelled lipoproteins; rat chylomicrons (♦), human VLDL (■), LDL (□), HDL (♦), LDLs treated with pronase (○), or LDLs modified with cyclohexanedione (LDL-chd, ●).

FIG. 18: Effect of oleate, of RAP-39, of anti-LSR antibodies and of chloroquine on the specific degradation of leptin in primary cultures of rat hepatocytes.

FIG. 19: Western blot analysis with anti-LSR antibodies, of the fraction of rat liver plasma membrane proteins retained on an affinity chromatography column containing leptin.

FIG. 20: Clearance of $^{125}$I-leptin on control (□) ob/ob (■) and db/db (▨) mice in the liver and the kidney. The results are expressed as the difference between the quantities of $^{125}$I-leptin and $^{125}$I-β2-microglobulin found in the liver and in the kidney.

FIG. 21: Apparent number of LSR receptors expressed in the liver of control, ob/ob and db/db mice.

FIG. 22: Effect of anti-LSR antibodies on the proportion between the quantities of $^{125}$I-leptin distributed in the liver and in the kidney.

FIG. 23 Effect of increasing leptin concentrations on the LSR activity of rat hepatocytes in primary cultures. The results represent the differences in activity which are obtained between the cells incubated with and without oleate in the presence either of $^{125}$I-LDL, or of $^{125}$I-VLDL.

FIG. 24: Capacity for inducing, by leptin, the LSR activity of rat hepatocytes in primary culture.

A. Apparent number of receptors expressed at the surface of the hepatocytes in the presence or in the absence of leptin, estimated by the measurement of the quantity of $^{125}$I-LDL bound in the presence of oleate.

B. Effect of cycloheximide, of colchicine and of cytochalasin B on the induction, by leptin, of the LSR activity.

FIG. 25: Effect of leptin on the postprandial lipemic response in control (○), ob/ob (■) and db/db (□) mice, reflected by the variation in the plasma concentration of triglycerides (TG) after ingestion of a high-fat meal, with (B) and without (A) injection of murine recombinant leptin.

FIG. 26: Effect of leptin, in the presence and in the absence of lactoferrin, on the postprandial lipemic response of ob/ob mice, expressed by the measurement of the plasma concentration of triglycerides (TG) after ingestion of a high-fat meal.

FIG. 27: Effect of leptin injection on the apparent number of LSR receptors expressed in the liver of ob/ob and db/db mice.

FIG. 28: Postprandial lipemic response and LSR activity in control (C57BL6), ob/ob and db/db mice.

A-Weight of control, ob/ob and db/db male mice.

B-Postprandial lipemic response in control, ob/ob and db/db mice.

C-Apparent number of LSR receptors estimated by measurement of the binding of LDL and expressed in arbitrary unit by comparison with the 5'-nucleotidase activity, in each plasma membrane preparation.

D-Northern blot on an extract of liver total RNA. GAPDH is used as control.

FIG. 29: Effect of a long-term treatment by leptin on ob/ob mice.

A-Weight change over 30 days

B-Postprandial lipemic response on the 29th day of treatment

C-Apparent number of LSR receptors on day 30, estimated by the measurement of the binding of LDL and expressed in arbitrary unit by comparison with the 5'-nucleotidase activity in each plasma membrane preparation D-Nothern blot analysis of the expression of LSR established on a total extract of liver RNA. GAPDH and actin are used as controls.

FIG. 30: Effect of the oleates on the binding and internalization of the $^{125}$I-LDL in normal human fibroblasts, under normal conditions.

FIG. 31: Effect of increasing concentrations of leptin on the LSR activity of human fibroblasts HF (familial hypercholesterolemia).

FIG. 32: Inhibitory effect of antibodies directed against an NH$_2$-terminal (■) or COOH-terminal (○) peptide of gC1qR, or of control antibodies (□) on the LSR activity of plasma membranes of rat hepatocytes, expressed as a percentage of the quantity of $^{125}$I-LDL bound in the absence of antibodies.

FIG. 33: Effect of increasing concentrations of C1q on the binding, internalization and degradation of $^{125}$I-LDL on rat hepatocytes in primary culture, in the presence (■) or in the absence (□) of oleate.

FIG. 34: Effect of 25 ng/ml of recombinant AdipoQ on the LSR activity in a primary culture of rat hepatocytes.

FIG. 35: Effect of two successive injections of 1 mg of AdipoQ on the postprandial lipemic response in rats after ingestion of a high-fat meal.

FIG. 36: Effect of an intraperitoneal administration of AdipoQ for 3 days on the weight and the concentrations of plasma triglycerides in rats on a normal diet or on a fatty diet.

FIG. 37: Effect of a daily injection of 100 μg of AdipoQ over 5 days, on food intake in ob/ob and db/db obese mice.

EXAMPLES

Experimental Procedures

Materials

Na$^{125}$I is provided by Amersham (Les Ulis, France). Oleic acid, bovine serum albumin (A 2153) (BSA) and Triton X100 are obtained from Sigma (St Quentin Fallavier, France). Human lactoferrin (Serva) and sodium heparin are provided by Biowhittaker (Fontenay sous Bois, France) and Choay laboratories (Gentilly, France) respectively. The enzymatic kits for the determination of triglycerides (TG) are obtained from Boehringer Mannheim (Meylan, France). Suramin sodium is obtained from CBC Chemicals (Woodburg, Conn.). Dulbecco's modified Eagle medium (DMEM), trypsin and foetal calf serum are provided by Life Technologies, Inc. (Eragny, France).

Animals

The mice C57BU6J of the wild type, C57BU6J ob/ob, C57BUKs of the wild type and C57BUKs db/db are obtained from R. Janvier Breeding Center (Le Genest St Isle, France).

Cells

Normal fibroblasts (GM08333) and HF (GM00486A, GM007001B, GM00488C) are provided by the NIGMS human genetic mutant cell repository (Camden, N.J.). The cells were plated on Petri dishes of 36 mm as described above (300,000 normal fibroblasts per well, 150,000 HF fibroblasts per well), and are cultured in a humidified $CO_2$ incubator, in DMEM medium containing 10% (normal fibroblasts) or 20% (HF fibroblasts) foetal calf serum, 2 mM glutamine, 100 U/ml of penicillin and 100 U/ml of streptomycin.

The hepatocytes in primary culture are obtained according to the procedure described above (Mann et al., 1995). The cells are then plated at 900,000 cells per well or $22 \times 10^6$ cells per flask of 165 $cm^2$. The cells are used for the studies after 48 hours in culture.

Preparation and Radiolabelling of the Lipoproteins

The VLDLs (d<1.006 g/ml) and LDLs (1.025<d<1.055 g/ml) are isolated by sequential ultracentrifugation of fresh plasma from volunteers (Bihain and Yen, 1992; Goldstein et al., 1983) and used before 2 weeks. The lipoproteins are radioiodinated (Bilheimer et al., 1972) and used less than one week after the labelling. $^{125}$I-LDL and $^{125}$I-VLDL are filtered (0.22 μm membrane, Gelman) immediately before use.

Preparation and Radiolabelling of Mouse Recombinant Leptin

The leptin cDNA is obtained from the mRNA of adipose tissue of the mouse C57BL6J by PCR. The 5' PCR primer introduces an initiation codon after the signal sequence which is deleted and a sequence encoding a hexahistidine end. The modified sequence encoding murine leptin is cloned into an expression vector pSE280 (Invitrogen, France) and expressed in $E.\ coli$. The sequencing of the plasmid DNA confirms the coding sequence. The bacteria are cultured at 37° C., and the synthesis of the protein is induced by 1 mM isopropyl $-D-thiogalactopyranoside. The bacteria, recovered after gentle centrifugation, are lysed by freeze-thaw and the DNA is digested with a deoxyribonuclease I. The cellular membranes are extracted with the aid of a detergent and the inclusion bodies are separated after centrifugation. After 3 washes in 1% sodium deoxycholate in PBS, the inclusion bodies are solubilized in a 6 M guanidine HCl solution. The renaturation of the recombinant protein is achieved by diluting 1/100 in PBS. The renatured protein is then purified and concentrated on a nickel-based chelate metal affinity chromatography column (Probond, Invitrogen). The elution is carried out with imidazole. The purity of the recombinant leptin is controlled by SDS-PAGE electrophoresis and its activity by the evaluation of satiety in mice C57BL/6J ob/ob after intraperitoneal injection of 25 μg of leptin. The recombinant leptin is then radiolabelled using Iodobeads (Pierce) and according to the method recommended by the manufacturer.

Cloning of the AdipoQ mRNA. Production and Purification of Recombinant AdipoQ Proteins Cloning of the cDNA into an Expression Vector Mouse adipose tissue is obtained from C57BI/6J mice and the mRNA is extracted with the aid of polydTs bound to magnetic beads (Dynabeads, Dynal, France). A cDNA library is constructed from mouse adipose tissue by reverse transcription at 40° C. using a commercial kit (Superscript Life Technologies) using the supplier's instructions. The cDNA specific for AdipoQ is amplified using the following two primers:

5' CTACATGGATCCAGTCATGCCGAAGAT 3' (SEQ ID 37)

5° CGACAACTCGAGTCAGTTGGTATCATGG 3' (SEQ ID 38).

The amplification product is then digested with the restriction enzymes BamHI and XhoI and inserted into an expression vector pTRC HisB (Invitrogen, France) at the corresponding sites. The B version of pTRC allows the expression of heterogeneous sequences downstream of a hexahistidine peptide which carries a recognition site for an enterokinase and an epitope for the anti-Xpress antibody.

Bacterial Transfection and Checking of the Construct

The plasmid thus obtained is transfected into $E.\ coli$ D115 α. Furthermore, the DNA of the plasmid is extracted and the heterologous insert is sequenced.

Cell Culture, Extraction and Purification of the Recombinant Protein

The recombinant bacterial cells are cultured at 37° C. in an LB medium containing antibiotics until the OD at 600 nm reaches 0.2. The production of recombinant protein is then induced by adding 1 mM isopropyl-β-D-thiogalactopyranoside to the culture medium. The bacterial culture is continued for 16 h at 37° C. The cells are recovered by centrifugation. The cells are lysed using lysozyme in a Tris buffer pH 7.4 in the presence of NaCl, PMSF and sodium deoxycholate. The DNA is degraded by sonication. After centrifugation, the recombinant protein is separated from the supernatant using a Probond column (Invitrogen, France). This column contains charged nickel which has affinity for the hexahistidine peptides. The elution is carried out in the presence of imidazole. The protein concentration is estimated by the Lowry method after having dialysed the product of the elution. The purity of the protein obtained is tested by SDS-PAGE electrophoresis, which shows a single band.

Example 1

Identification of the Protein Complex Responsible for the LSR Activity: Partial Purification and Characterization by Means of Polyclonal Antibodies The technique of ligand blotting was used to identify the proteincomplex responsible for the LSR activity. This technique, described in detail by Mann et al., 1995, is detailed below.

Ligand Blotting

The technique consists in isolating, by differential centrifugation (Belcher et al., 1987) rat liver membranes, and in solubilizing the membrane proteins in a solution containing 125 mM octylglucoside, 20 mM Tris and 2 mM EDTA, pH 8. The proteins thus solubilized are separated under nondenaturing conditions on a preparative SDS gel (thickness 5 mm) consisting of a gradient from 4 to 12% polyacrylamide (35–50 mg of protein per gel). For part of the gel, the proteins are then electrotransferred (semi-dry transfer, 21 V, 45 min, Biorad) onto a nitrocellulose membrane. After blocking the free sites of this membrane in a PBS solution containing 3% albumin, the membrane is incubated with 40 µg/ml of $^{125}$I-LDL in the presence (FIG. 8, lane 2) or in the absence (FIG. 8, lane 1) of 0.8 mM oleate. The membrane is then washed five times for 10 minutes in PBS containing 0.5% (v/v) Triton X100, and exposed on a Phosphor Imager screen.

Analysis of the image obtained in the presence (FIG. 8, lane 2) or in the absence (FIG. 8, lane 1) oleate shows the presence of 3 main bands which have bound the LDLs. The apparent MW of the first band is about 240 kDa, that of the second is 1 15 kDa and that of the third is 90 kDa. On the basis of these observations, two hypotheses are formulated: on the one hand, the LSR activity is linked to the presence of several distinct proteins; on the other hand, the same type of image can be explained by a multimeric organization of a protein complex.

In order to check this hypothesis, the inventors undertook the purification of the band having the highest apparent molecular weight (240 kDa). The partial purification of this protein, designated "band A", is carried out by preparative electrophoresis as follows.

Partial Purification of LSR

The technique consists in isolating, by differential centrifugation (Belcher et al., 1987) rat liver membranes, and in solubilizing the membrane proteins in a solution containing 125 mM octylglucoside, 20 mM Tris and 2 mM EDTA, pH 8. The proteins thus solubilized are separated under nondenaturing conditions on a preparative SDS gel (thickness 5 mm) consisting of a gradient from 4 to 12% polyacrylamide (35–50 mg per gel). For part of the gel, the proteins are then electrotransferred (semi-dry transfer, 21 V, 45 min, Biorad) onto a nitrocellulose membrane. After blocking the free sites of this membrane in a PBS solution containing 3% albumin, the membrane is incubated with 40 µg/ml of $^{125}$I-LDL in the presence (FIG. 8, lane 2) or in the absence (FIG. 8, lane 1) of 0.8 mM oleate. The membrane is then washed five times for 10 minutes in PBS containing 0.5% (v/v) Triton X100, and exposed on a Phosphor Imager screen. The proteins of interest are electroeluted (Eletroeluter, Biorad).

The rat liver plasma membrane proteins were prepared and separated on a polyacrylamide gel as above. The precise location of band A was established by ligand blotting carried out after electrotransfer of preprative gel sample removed at various levels.

The gel fragments containing band A are then collected, electroeluted and concentrated (speedvac), and then tested for their capacity to bind the LDLs in the presence of oleate after electrophoresis and transfer onto nitrocellulose membranes (FIG. 8, lane 3; 80 µg of protein/lane).

The proteins thus obtained were also used to produce polyclonal antibodies whose specificity was tested by Western blotting (FIG. 8, lane 4).

Preparation of Polyclonal Antibodies

The LSR proteins used as antigens for the production of anti-LSR antibodies were prepared as indicated above.

The antigen preparation is injected subcutaneously into a rabbit in the presence of complete Freund's adjuvant, followed by a conventional immunization procedure. The titer of the antibody directed against the rat proteins is determined regularly (dot-blot technique). When the latter is judged to be sufficient, the specificity of the antibodies obtained is tested by Western blotting on a preparation of solubilized proteins of rat liver membranes as described above, with anti-rabbit IgG goat antibodies labelled with iodine $I^{125}$ as second antibodies.

The Western blot results after electrophoresis under non-reducing conditions indicate that the antibodies produced from the proteins of band A bind to 3 main protein bands (240 kDa, 115 kDa and 90 kDa) which bind the $^{125}$I-LDL in the presence of oleate (FIG. 8, lane 4). To verify the link between these protein complexes and the LSR activity, the effect of these polyclonal antibodies on the LSR activity was tested.

The methods used are described in detail below (Mann et al., 1995; Troussard et al., 1995). The LSR activity is estimated by measuring the binding of lipoproteins to plasma membranes and by measuring the binding, internalization and degradation of the lipoproteins on primary cultures of rat hepatocytes.

Measurement of the Binding of Lipoproteins on Plasma Membranes

The LSR activity is measured on a preparation of rat liver plasma membranes (Bartles and Hubbard, 1990). These membranes exhibit 10 to 15-fold enrichment with 5-nucleotidase (marker specific for plasma membranes). 100 µg aliquots of proteins are incubated for 30 minutes at 37° C. in the presence or in the absence of 0.8 mM oleate in a final volume of 250 µl supplemented with 100 mM PBS, 2 mM EDTA, 350 mM NaCl, pH 8 (buffer A). The oleate is added in a volume of 5 to 10 µl of isopropanol. The excess and unbound oleate is then removed by 6 washes. The pellets are resuspended in 250 µl of incubation buffer, sonicated for 5 seconds, power 1.90% in the active cycle, and then centrifuged for 15 min at 18,000 rpm. The activated membranes are incubated for 1 hour at 4° C. with various concentrations of antibody and then with 5 µg/ml of $^{125}$I-LDL (1 hour at 4° C.). 25 µl of 2% BSA are added to the incubation mixture. The quantity of $^{125}$I-LDL bound to the membranes is measured by sedimenting the membranes by centrifugation after having deposited 200 µl of the incubation mixture on a layer of 5% (W/V) of BSA in buffer A. The supernatants are removed by aspiration, the tube bottoms are cut off and their radioactivity is counted in a γ counter.

The inhibitory effect of anti-LSR antibodies on the LSR activity, compared to that of any preparation of rabbit immunoglobulins is shown in FIG. 9 A. The inhibition of the LSR activity by the anti-LSR antibodies confirms that the multimeric complex described above is responsible for the activity of the receptor and validates the ligand blotting technique used to identify it. The effect of the anti-band A antibodies was, in addition, tested on the other steps of the activity of the receptor: the internalization and the degradation of lipoproteins by the LSR expressed at the surface of hepatocytes in primary cultures.

Measurement of the Binding, Internalization and Degradation of Lipoproteins by Hepatocytes The LSR activity in the primary cultures of rat hepatocytes is measured by the binding, internalization and degradation of $^{125}$I-LDL and $^{125}$I-VLDL (LDL: low-density lipoprotein; VLDL: very low-density lipoprotein), as described in Bihain and Yen, 1992 and Mann et al., 1995.

To measure the effect of the anti-LSR antibodies on the binding, internalization and degradation of LDLs by LSR, primary cultures of rat hepatocytes (48 h after plating) are incubated in the presence of 20 ng of leptin/well for 30 min at 37° C., followed by the addition of anti-LSR antibodies in the presence or in the absence of oleate. After incubating at room temperature for 30 min, $^{125}$I-LDL (20 µg/ml) is added and then the cells are incubated for 4 h at 37° C. The binding, incorporation and degradation of $^{125}$I-LDL are measured as described in Bihain and Yen, 1992 and Mann, et al., 1995.

The data in FIG. 9B show that the anti-band A antibodies inhibit most of the activity of binding of the LDLs to the LSRs present at the level of the hepatocytes. This inhibition induces a decrease in the same proportions in the internalization and proteolytic degradataion of the lipoproteins.

The anti-band A antibodies are thus characterized as anti-LSR. Their relative specificity was defined by a selective immunoprecipitation method. Extracts of hepatocytes in primary culture are immunoprecipitated by means of the anti-LSR antibodies described above, according to the protocol described below.

Immunoprecipitation of Extracts of Hepatocytes in the Presence of Specific Antibodies Primary cultures of rat hepatocyte (Oukka et al., 1997) are incubated for 60 minutes to 2 hours in the presence of a mixture of $^{35}$S-methionine and $^{35}$S-cysteine (Promix, Amersham). This medium is then removed and the cells are washed and then incubated in PBS containing 1% of Triton X100. This cellular lysate is then incubated in the presence of non-specific antibodies and then of protein A. The equivalent of 40 µg of specific anti-LSR antibodies is then added and the LSR-antibody complexes are precipitated with the aid of a second preparation of protein A. After washing, the complexes are dissociated in the presence of 1% SDS supplemented or otherwise with 5% β-mercaptoethanol, incubated at 100° C. for 5–10 minutes, and separated on a 10% acrylamide gel. The gels are dried and exposed on a Phosphor Imager screen. Each of the lanes contains the equivalent of a 165 cm$^2$ flask, that is to say 22×10$^6$ cells.

Analysis of the immunoprecipitation results indicates that under nonreducing conditions (FIG. 10, lanes 2—without incubation at 100° C.—and 3—with incubation at 100° C.—), the antibodies reveal 3 principal protein bands: 2 of apparent molecular weight 240 kDa and 180 kDa, 1 of apparent molecular weight 68 kDa. The presence of 2 bands of weaker intensity, corresponding to a molecular weight of 115 kDa and 90 kDa, can also be noted. This experimental approach therefore essentially identifies the same protein elements as those identified by the ligand blotting method. It can be observed, moreover, that under reducing conditions (FIG. 10, lanes 1 and 4), the elements of high molecular weight dissociate into 3 elements of apparent molecular weight 68 kDa, 56 kDa and 35 kDa, respectively.

The relative intensity of the 68 kDa and 56 kDa bands is similar whereas that of the 35 kDa band is about ¼ of that of the other two.

Example 2

Cloning of the c-DNA Encoding the α- and β-LSR

The screening of an expression library by means of the anti-LSR antibodies described above was carried out as indicated below.

Screening of an Expression Library

After infection of bacteria with lambda GT11 bacteriophages containing rat liver cDNA (commercially obtained from Clontech Laboratories Inc.) (5' Strech Plus c-DNA Library), the cells are plated on LB MgSO$_4$ medium. After 4 hours of culture at 42° C., a nitrocellulose membrane, previously incubated in a 10 mM IPTG solution, is deposited in the Petri dishes. Four hours later, the first membrane is removed and a second is applied to the Petri dish.

Each membrane is immersed in a Petri dish containing blocking buffer kept stirring for one hour. Next, the antibody is added to a final concentration of 10 µg/ml of blocking buffer (Huynh et al., 1984; Young and Davis, 1983a and 1983b). The membranes are then washed three times for 10 minutes with TNT (10 mM Tris, 150 mM NaCl, 0.05% Tween 20).

The membranes are incubated in the presence of secondary antibodies (alkaline phosphatase-conjugated affinipure F(ab')2 fragment goat anti-rabbit IgG; Immunotech) at a final concentration of 0.08 µg/ml of blocking buffer (TNT+ 5% powdered skimmed milk, Pâturage trademark).

After washing the membranes in TNT, they are incubated in the presence of BCIP (5-bromo-4-chloro-3-indolyl phosphate) and of NBT (nitro blue tetrazolium) until a colour is obtained.

The positive clones are then recovered on the dishes, titrated and subjected to the same immunoscreening procedure so as to confirm that they are true positives (secondary screening). Optionally, a tertiary screening may be carried out. The phage DNA of the selected clones, isolated from a bacterial lysate (Clontech protocol), and digested with the restriction enzyme EcoR1 is inserted at the EcoR1 site of the plasmid pBluescript SK+.

Two clones containing an insert of 1.8 kb were thus obtained, and proved to be of identical sequences. The hybridization of rat liver mRNA (2 µg of polyA+ mRNA ) with a probe corresponding to the BglII-XbaI fragment of this insert revealed two bands of sizes 1.9 kb and 2.1 kb (FIG. 11A) respectively. Northern blot analysis, with a probe corresponding to the XbaI-XbaI fragment of this insert, of the tissue distribution of the corresponding messengers showed that they are preferably expressed in the liver (FIG. 11B). The Nothern blotting was carried out according to the following protocol.

Northern Blotting

The membranes containing the mRNAs of different rat tissues (Clontech) were hybridized with fragments of the cDNA for the LSR gene and of the cDNA for human β-actin (Clontech), labelled with [$^{33}$P]dCTP, in 5×SSPE, 10×Denhardt buffer containing 0.5% SDS, 100 µg/ml of salmon sperm DNA, 50% deionized formamide, at 42° C. for 16 hours. The membranes were then washed in 2×SSC, 0.5% SDS at room temperature and in 1×SSC, 0.1% SDS at 65° C., and then exposed on the Phospor Imager (Molecular Dynamics).

A cDNA corresponding to the 1.9 kb band was reconstructed by 5'RACE PCR from the 1.8 kb fragment and sequenced.

In order to elucidate the presence of multiple bands in Northern blotting, several pairs of primers defining fragments of a rat cDNA sequence were synthesized and used as primers for a PCR amplification (FIG. 11C). The sequences of the oligonucleotides used are listed below:

```
a:  5'-GTTACAGAATTCGCCGCGATGGCGCCGGCG-3'  (SEQ ID 20)
b:  5'-GCCAGGACAGTGTACGCACT-3'            (SEQ ID 21)
c:  5'-ACCTCAGGTGTCCCGAGCAT-3'            (SEQ ID 22)
d:  5'-GAAGATGACTGGCGATCGAG-3'            (SEQ ID 23)
e:  5'-ACCTCTATGACCCGGACGAT-3'            (SEQ ID 24)
b': 5'-CACCACCCTGACAGTGCGTA-3'            (SEQ ID 25)
c': 5'-CTGGGGGCATAGATGCTCGG-3'            (SEQ ID 26)
d': 5'-GCCCTGGAAGGCCTCGATCG-3'            (SEQ ID 27)
e': 5'-CAAGTCCCTAGGATCGTCCG-3'            (SEQ ID 28)
```

Whereas each pair of primers shows a single fragment, the bc' pair makes it possible to amplify three fragments of different sizes. Analysis of the sequences of these fragments makes it possible to reconstitute the sequence of three complete cDNAs for rat LSR, having sizes of 2097 bp (SEQ ID 1), 2040 bp (SEQ ID 3) and 1893 bp (SEQ ID 5) respectively, and all three corresponding to the same precursor messenger by alternative splicing.

These three cDNAs contain an open reading frame starting with an AUG codon at position 219 surrounded by a Kozak consensus sequence (Kozak, 1987 and 1990). The predicted molecular weights of the proteins encoded by these three cDNAs are 66 kDa, 64 kDa and 58 kDa, respectively.

The two cDNAs encoding respectively the longest and the shortest forms of rat LSR were then translated in vitro as indicated below.

Translation in Vitro

The cDNAs are subcloned into the plasmid pcDNA3 transcription and translation in vitro are carried out using the Promega TNT kit. The products of translation, labelled with $^{35}$S-methionine and $^{35}$S-cysteine, are visualized after electrophoresis on a polyacrylamide gradient gel (10%) and exposure on Phospor Imager.

The molecular weights of the products obtained, that is to say 68 kDa and 56 kDa (FIG. 12), corresporid closely to those of the β and β subunits of LSR.

To define if the products of these mRNAs are responsible for the receptor activity, three different experimental approaches were used.

Firstly, two peptides corresponding to residues 169–186 (SAQDLDGNNEAYAELIVLGR: SEQ ID 29) of the LSR produced from the mRNA of size 2097 bp and to residues 556–570 (EEGQYPPAPPPYSET: SEQ ID 30) were synthesized. The sequence of these peptides is common to the three proteins identified above. Antibodies directed against these synthetic peptides were obtained according to the protocols indicated above. FIGS. 13C and 14C show that these anti-LSR peptide antibodies have an inhibitory effect on the binding of the LDLs to the LSRs present on rat plasma membranes, measured according to the protocol described in Example 1.

Secondly, a partial purification of the α and β subunits was obtained by selective solublization with the aid of sarkosyl; a study using Western and ligand blotting showed that the α and β components bind the anti-LSR polyclonal antibodies (FIG. 13B, lane 1), the anti-LSR peptide antibodies (FIG. 13B, lane 2 and FIG. 14B, lane 2), and the LDLs after incubation with oleates (FIG. 13B, lane 4). Ligand blotting was carried out according to the protocol described in Example 1; Western blotting was carried out as indicated below.

Western Blotting

Primary cultures of rat hepatocytes are prepared as indicated in <<Experimental procedures>>. The cells harvested after 48 hours of culture are washed and lysed in PBS containing 1% Triton X100. The lysates are deposited on a 10% SDS-PAGE gel under reducing conditions (2% SDS, 5% β-mercaptoethanol and 20 mM DTT, at 56° C. for 1 h). After transferring onto a nitrocellulose membrane, the Western blotting is carried out with IgG antibodies directed against the LSR receptor.

Thirdly, the labelled proteins LSR 66 and 58 obtained by in vitro translation from the cDNAs LSR-Rn-2097 and LSR-Rn-1893 are used to estimate the effect of oleate on the binding of the LDLs according to the protocol detailed below.

Binding of the LDLs onto the LSR Proteins Expressed in Vitro (<<Flotation>>)

The $^{35}$S-cysteine or $^{35}$S-methionine labelled products of translation in vitro (17 µl) are incubated for 1 hour at 37° C. in the presence of 100 µg/ml of LDL, 1 mM oleate in buffer A, in a final volume of 400 µl. An equal volume of 8% (w/v) BSA is added. The density is adjusted to 1.21 g/ml (assuming an initial density of 1.025 g/ml), with sodium bromide. The samples are then deposited on a sodium bromide solution at 1.063 g/ml, and then centrifuged for 20 hours at 4° C. (Beckman SW41 rotor). A volume of 1 ml is collected at the surface, dialysed against electrophoresis elution buffer, and the radioactivity is counted (Beckman β counter).

Oleate increases the binding of LDL to LSR 56 (respectively LSR 68) by a factor of 2 (5 respectively). It can thus be shown that the α and β subunits of rat LSR, encoded respectively by the cDNAs LSR-Rn-2097 and LSR-Rn-1893 (LSR 56 and LSR 68), preferably bind the LDLs after incubation with oleate.

All these results indicate that the cDNAs LSR-Rn-2097 and LSR-Rn-2040 encode two proteins which are indistinguishable by electrophoresis and whose apparent molecular weight is 68 kDa these proteins correspond to the band comprising the α and α' subunits of LSR, which is identified after immunoprecipitation under reducing conditions. The β subunit of LSR is presumably the product of translation of the cDNA LSR-Rn-1893. The analyses of stoichiometry after immunoprecipitation indicate that the multimeric complex of apparent molecular weight 240 kDa is the result of an assembly of an α subunit with three β subunits. Analysis of the various domains of the proteins corresponding to the α- and β-LCRs is compatible with a lipoprotein receptor function.

Example 3

Analysis of the Activity of a Recombinant LSR Receptor, and its Subunits, in Transfected Cells The inventors also expressed a recombinant LSR receptor in CHO cells according the following protocol.

Transfection With cDNA Sequences Encoding the LSR Receptor

In order to study the activity of each of the recombinant subunits of LSR, as well as the activity of a reconstituted receptor, the inventors used the expression plasmid pcDNA3 (No et al., 1996) to study the expression, in animal cells, of either cDNA encoding the α subunit (α plasmid), or of a cDNA encoding the β subunit (β plasmid), of rat LSR. The LSR cDNAs were subcloned into the plasmid pcDNA3 (Invitrogen) using the EcoRI and/or NotI restriction sites. Once obtained, these constructs are used to transfect CHO (Chinese hamster ovary) animal cells.

After 48 hours of culture, CHO (Chinese hamster ovary) cells (CHO-K1, CCL-61, ATCC, Rockville, Md.) were distributed into 6-well plates (Falcon) at $2.5-2.75 \times 10^5$ cells/well. After 24 h of culture in a Ham F-12 medium containing 10% (v/v) FBS, 2 mM glutamine and 100 units/ml of penicillin and streptomycin, a maximum of 2 μg of plasmid/well were transfected using Superfect (Qiagen) according to the supplier's instructions (10 μl Superfect/well, 2 h at 37° C. in a Ham F-12 medium free of serum). The plates were then washed in PBS in order to remove the transfection reagents and the cells were then cultured in a Ham F-12 medium containing serum. The LSR activity was measured 48 h after transfection according to the protocols detailed in Example 1.

The inventors tested the effect of a co-transfection with the α and β plasmids compared with that of a transfection with the α plasmid alone, or with the β plasmid alone, on the three stages of the activity of the LSR receptor according to the protocols detailed below. FIGS. 15 and 16 show the comparisons between the LSR activities obtained on the recombinant cells expressing the α subunit alone, or the two α and β subunits; similar results are obtained for the β versus α+β comparison, which is compatible with the comparative analysis of the primary sequences of each of the subunits (each of them also carrying the potential binding sites for lipoprotein ligands and fatty acids, such as oleate).

Effect of a Transfection with the LSR (α) Plasmid Alone, or of a Co-transfection with the LSR (α) and LSR (β) Plasmid, on the Binding, Internalization and Degradation of the LDLs The CHO-K1 cells were transiently transfected with increasing concentrations of α plasmid and co-transfected with 0.4 μg of α plasmid and increasing concentrations of β plasmid. After 48 h of culture, the cells were washed once with PBS and incubated for 3 h at 37° C. with 20 μg/ml $^{125}$I-LDL in the presence or in the absence of 1 mM oleate in DMEM containing 0.2% BSA, 5 mM Hepes, and 2 mM CaCl$_2$, pH 7.5. Next, the cells were washed as described above and incubated at 4° C. for 1 h with 10 mM suramin in PBS.

To measure the binding of the LDLs (FIG. 15), the medium was recovered and passed through a γ counter in order to evaluate the quantity of bound $^{121}$I-LDL. The results are the mean values of two measurements. For the measurement of the internalization and the degradation of LDLs (FIG. 16), the quantity of $^{125}$I-LDL internalized and degraded was measured according to the protocols detailed in Example 1.

The co-transfection with α and β plasmids makes it possible to establish three stages of LSR activity (FIGS. 15 and 16).

The inventors also observed that the co-transfection with the α and β plasmids increases the LSR activity compared with a transfection with only an α plasmid. The results suggesting a more efficient activity of the LSR when the ([β]/[α]) ratio between the concentrations of β and α subunits expressed increases, is compatible with the observation that the LSR receptor might consist of the assembly of an α (or α') subunit, and of several, probably three, β subunits.

The results show that only the co-transfection of the β and α subunits allows the overexpression of a completely functional LSR receptor in the sense that it allows the complete proteolytic degradation of the protein.

In order to characterize the lipoprotein degradation activity obtained above in cells transfected with the LSR cDNAs, the inventors finally tested the capacity of anti-LSR antibodies to inhibit the binding of LDLs as measured above, as well as the substrate-specificity thereof.

Characterization of the Lipoprotein Degradation Activity Obtained in Transfected Cells Expressing a Recombinant LSR Receptor The CHO cells were transfected with the α end β plasmids in a concentration ratio of 1 to 3.

FIG. 17A shows that the LDL binding activity obtained in the transfected cells (expressed relative to the same activity observed in nontransfected control cells) is specifically inhibited by the anti-LSR antibodies.

FIG. 17B shows the LDL binding activity obtained in the cells transfected in the presence of various nonlabelled lipoproteins acting as competitive ligands. The results show a ligand specificity similar to that observed for the endogenous LSR activity in rats (Mann et al., 1995): the rat chylomicrons are the preferred substrates for the rat recombinant LSR; then come in particular, in decreasing order of specificity, the VLDLs and then the LDLs.

Example 4

Involvement of LSR in the Clearance of Cytokines

The analysis of the sequence of the α subunit of LSR reveals a cysteine-rich region which corresponds to a Tumor Necrosis Factor type cytokine receptor signature. LSR is, however, distinguishable from the cytokine receptors by the presence of signals allowing rapid endocytosis of the receptor/ligand complex (clathrin motif).

The inventors formulated the hypothesis that this receptor could serve for the removal of cytokines, and in particular of leptin; in order to verify this hypothesis they analysed the degradation of recombinant leptin by hepatocytes in primary culture according to the protocol below.

Degradation of Leptin by Hepatocytes in Primary Culture

Primary cells of rat hepatocytes are incubated for 4 hours at 37° C. with 20 ng/ml of $^{125}$I-leptin in the absence or in the presence of 0.5 mM oleate, 75 μg/ml of RAP, 200 μg/ml of non-specific antibodies or anti-LSR specific antibodies, or 50 μM chloroquinine. The medium is then recovered and the quantity of $^{125}$I-leptin degraded is measured.

As indicated in FIG. 18, the degradation of leptin by hepatocytes in primary culture is inhibited by:
a) polyclonal antibodies directed against LSR. These antibodies also inhibit, in the same proportions, the LSR activity,
b) the 39 kD Receptor Associated Protein (RAP); this protein blocks the LSR activity in vitro and retards the clearance of chylomicrons in vivo (Troussard et al., 1995; Willow et al., 1994)
c) chloroquine; this cellular poison prevents the acidification of the endocytosis vesicles and inhibits the activity of the lysosomal proteases, d) oleate; this free fatty acid induces a change in the conformation of LSR which unmasks the lipoprotein binding site.

This indicates that the FAF (Fatty Acid Free) conformation of LSR is probably the only one which is compatible with the role of binding followed by degradation of leptin. The non-specific immunoglobulins are without effect on the degradation of leptin (FIG. 18).

In order to verify the binding of leptin to LSR, the rat liver plasma membrane proteins were deposited on an affinity chromatography column containing recombinant leptin, according to the protocol detailed below.

Leptin Affinity Chromatography

A Hi-trap column (Pharmacia) is used: 5 mg of leptin are bound onto 1 ml of column according to the methods recommended by the manufacturer. The plasma membrane proteins are solubilized from rat livers as indicated above (Mann et al., 1995), and then dialysed overnight against PBS pH 7.4, 0.1% Tween 20. The column is washed in the same buffer and the protein extract is deposited at a rate of 0.2 ml/minute. The column is washed with 6 ml of the same buffer. It is then eluted with the same buffer supplemented with 100 mM glycine pH 3; 20 fractions of 500 µl are then neutralized with 5 µl of PBS, 0.1% Tween 20, pH 8.50 µl of each fraction are deposited on a nitrocellulose membrane for dot-blot analysis by means of anti-LSR antibodies. The positive fractions (1, 3, 4, 7 and 8) are dialysed against 24 mM ammonium bicarbonate, 0.01% Tween 20, pooled and concentrated in a Speedvac in a final volume of 300 µl. 40 µl of the final product are analysed by Western blotting by means of anti-LSR antibodies.

FIG. 19 shows that the anti-LSR antibodies specifically recognize the α subunit which, after binding to leptin, was released by the glycine buffer.

Experiments of stable transfection of the a subunit will make it possible to measure the affinity of leptin for this new receptor.

All these results suggest that LSR represents one of the pathways for the degradation and elimination of leptin. The in vivo injection of radiolabelled recombinant leptin showed, both in the obese mice and in the control mice, a rapid speed of clearance and a preferential capture of leptin by the liver and the kidney: 50% of the injected dose is found after 10 minutes in these two organs. In order to analyse the mechanisms for the selective capture of leptin, the inventors compared the quantities of leptin and of β2-microglobulin (soluble protein having a molecular weight close to that of leptin, chosen as control) present in the kidney and liver of normal mice and of two obese mouse lines 5 minutes after injection of the same tracer dose of these two radiolabelled proteins.

Measurement of the Clearance of Leptin in Mice

The female control, ob/ob, or db/db mice (6–8 weeks), on an empty stomach, are anaesthetized and receive via the saphenous vein an injection of 80 ng of murine recombinant $^{125}$I-leptin or of $^{125}$I-β$_2$-microglobulin (Sigma, labelled by the Iodobeads method, like leptin). Five minutes later, the animals are infused with a physiological saline solution (15 ml, at 4° C.). The tissues are collected and counted for their radioactivity (Gamma counter). In some cases, an anti-LSR antibody or a control protein are injected 30 minutes after injection of $^{125}$I-leptin. It is important to note that the labelling of leptin with $^{125}$I has no effect on its biological activity.

The results presented in FIG. 20 show that the quantity of leptin selectively captured by the liver is reduced in the obese mice, compared with the control mice; moreover, no difference is observed between the various lines as regards the renal capture of leptin.

The inventors then measured the number of LSR receptors in control, ob/ob and db/db mice according to the following protocol.

Measurement of the Apparent Number of LSR Receptors on Plasma Membranes

The apparent number of LSR receptors on plasma membranes is measured as previously described (Mann et al., 1995) by estimating the quantity of LDL bound to a plasma membrane preparation. The plasma membranes (100 µg) are incubated with 1 mM oleate; they are then washed three times as indicated above, and then incubated for 1 hour at 37° C. with 40 µg/ml of $^{125}$I-LDL. The quantity of $^{125}$I-LDL bound to the plasma membranes is then determined by counting. The mean is established on 3 measurements per animal for 3 different animals in each of the groups.

FIG. 21 shows that the number of LSR receptors in obese animals exhibiting either a deficiency in leptin (ob/ob), or a deficiency in the ob receptor (db/db), is significantly reduced. The reduction in the selective hepatic capture of leptin in obese mice coincides with the reduction, in these animals, of the apparent number of LSR receptors.

The inventors finally tested, according to the protocol presented below, the effect of anti-LSR antibodies on the distribution of leptin between the liver and the kidney, 5 minutes after injection of a tracer dose.

Measurement of the Distribution of Leptin Between the Liver and the Kidney in the Presence of Anti-LSR Antibodies Control mice are anaesthetized and then they are injected intravenously with 1 mg of non-specific IgG antibody or of anti-LSR IgG antibody. After 30 minutes, 80 ng of $^{125}$I-leptin are injected and, after 5 minutes, an infusion of physiological saline solution at 4° C. The tissues are removed immediately and the radioactivity is measured. The results represent the mean and the standard deviation obtained for 3 animals for each of the groups.

As shown in FIG. 22, the hepatic capture of leptin is reduced and the renal capture is increased by the anti-LSR antibodies, compared with the control immunoglobulins.

These results therefore indicate that LSR is responsible for the selective hepatic capture of leptin and that a reduction in the number of receptors is observed in the obese animals. Such a reduction may explain the leptin-resistance syndrome and the increase in the plasma concentration of leptin which is observed in most obese human subjects.

It is also possible that the LSR receptor serves as degradation pathway for other cytokines, in particular those produced by the adipose tissue. The importance of Tumor Necrosis Factor α and Nerve Growth Factor will be noted in particular. These two cytokines exert a significant slimming effect when they are injected into human subjects (Cytokines and their receptors, 1996).

Example 5

Control of the LSR Activity by Cytokines

The α subunit of the LSR receptor binds leptin and possesses potential phosphorylation sites. This makes it a receptor which not only mediates endocytosis, but could also serve in cell signalling.

The inventors therefore tested the hypothesis according to which leptin modulates the activity of LSR, as described below.

Measurement of the LSR Activity of Binding, Internalization and Degradation of Lipoproteins in the Presence of Leptin Rat hepatocytes in primary culture are incubated at 37° C. for 30 min with an increasing concentration of leptin, and then incubated at 37° C. for 4 hours with either 50 µg/ml of $^{125}$I-LDL (specific activity: 209 cpm/ng) or 50 µg/ml of $^{125}$I-VLDL (specific activity: 157 cpm/ng) in the absence or in the presence of 500 µM oleate. The cells are then washed and the quantities of $^{125}$I-lipoproteins bound, incorporated and degraded are measured as described above in Example 1 (Bihain and Yen, 1992). The results shown in FIG. 23 represent the differences obtained between the cells incubated with or without oleate. Each point represents the mean of 3 measurements. The standard deviation for each point is included in the symbol.

The addition of increasing concentrations of leptin to hepatocytes in culture increases the binding, internalization and degradation of VLDLs and LDLs (FIG. 23).

Analysis of the Capacity for Inducing the LSR Activity by Leptin

Measurement, in the Presence of Leptin, of the Apparent Number of LSR Receptors Expressed at the Surface of Rat Hepatocytes in Primary Culture Primary cultures of rat hepatocytes are incubated for 30 min at 37° C. in the presence or in the absence of 20 ng/ml of leptin, for 10 min at 37° C. in the presence of 0.8 mM oleate. The cells are washed with PBS buffer precooled to 4° C., and then incubated for 2 hours at 4° C. in the presence of increasing concentrations of $^{125}$I-LDL. The cells are then washed, lysed and the quantity of bound $^{125}$I-LDL is measured.

Comparative Effects of Leptin in the Presence of Cycloheximide, Colchicine and Cytochalasin B The initial conditions are identical to those described above after incubation with leptin, the cells are incubated for 30 min at 37° C. with 5 µM cycloheximide, 5 µM colchicine or 2.5 µM cytochalasin B. The cells are then incubated for 10 min at 37° C. in the presence of 0.8 mM oleate. The cells are then washed with PBS buffer precooled to 4° C., and then incubated for 2 hours at 4° C. in the presence of 50 µg/ml of $^{125}$I-LDL. 2 measurements are carried out, and the mean results are presented.

It is thus shown that the increase in the LSR activity by leptin is obtained through an increase in the apparent number of receptors expressed at the surface of the hepatocytes (FIG. 24A). This increase results, on the one hand, from an increase in protein synthesis (it is partially inhibited by cycloheximide, an inhibitor of protein synthesis). It involves, on the other hand, the mobilization of the endocytosis vesicles by the microtubule system (it is indeed inhibited by cytochalasin B which blocks microtubular transport) (FIG. 24B).

In order to check the in vivo effect of leptin on the LSR activity, the inventors. characterized the postprandial triglyceridemic response of control, ob/ob and db/db mice after a force-fed test meal according to the following protocols.

Measurement of the Postprandial Lipemic Response in Mice

Control, ob/ob and db/db mice, starved since the day before, are force-fed with a meal which is very high in fat [60% fat (37% saturated, 27% monounsaturated and 36% polyunsaturated fatty acids), 20% protein and 20% carbohydrate] providing 56 kcal of energy/kg of the weight of the animal. Immediately after the meal (time=0 hour), the mice are injected intravenously with 200 µl of physiological saline solution. At various times, 20 µl of blood are collected via the caudal vein in tubes containing 90 µg of disodium EDTA, and after separating the plasma by centrifugation, the plasma concentration of triglyceridemia is determined with the aid of an enzymatic assay kit. Each point on the curves presented corresponds to the mean with standard deviation obtained for 3 measurements per animal and for 3 different animals.

Measurement of the Effect of Leptin on the Postprandial Lipemic Response in Mice The procedure is the same as above, except that immediately after the meal (time=0 hour), the mice are injected intravenously with either 200 µl of physiological saline solution, or 200 µl of the same solution containing 50 µg of murine recombinant leptin.

Measurement of the Postprandial Lipemic Response in Mice in the Presence of Lactoferrin and/or Leptin ob/ob mice, starved since the day before, are force-fed with a meal identical to that described above. Immediately after the meal (time=0 hour), the mice are injected intravenously with 200 µl of saline solution containing either no supplement, or 0.5 µg of leptin, or 2.5 mg of lactoferrin or alternatively a mixture of 0.5 µg of leptin and 2.5 mg of lactoferrin. Blood is collected between 2 and 3 hours after the meal and the plasma concentration of triglycerides (TG) is measured. The values obtained represent the mean with standard deviation obtained for 4 measurements per animal and for 2 different animals [p<0.02 (ob/ob compared with ob/ob+leptin), p<0.01 (ob/ob compared with ob/ob+lactoferrin), NS (ob/ob+lactoferrin compared with ob/ob+leptin +lactoferrin)].

In agreement with the reduction in the number of LSR receptors observed in the obese mice, an amplification of the postprandial lipemic response also exists in the untreated obese mice. The administration of leptin by the intravenous route, at the same time as the test meal, makes it possible to reduce the postprandial lipemic response in the two obese mouse lines and in the control mice (FIG. 25).

This reduction in the lipemic response induced by leptin is suppressed by the administration of lactoferrin (FIG. 26), which blocks the activity of LSR (Yen et al., 1994; Mann et al., 1995). This strongly suggests that the reduction in the lipemic response is explained by an increase in the LSR activity.

Finally, also in vivo, the administration of leptin induces an increase in the apparent number of LSR receptors expressed at the level of the surface of the hepatocytes. This increase is significant both in the ob/ob mice and in the db/db mice (FIG. 27).

Leptin and probably other cytokines are therefore regulators of the activity of LSR. A syndrome of resistance to leptin or to other cytokines can lead to hypertriglyceridemia, which is either permanent or limited to the postprandial phase.

Example 6

Effect of Leptin on the Expression of LSR; Therapeutic Effects

To reinforce correlation between the administration of leptin, the reduction in the postprandial lipemic response, and an enhanced expression or activity of the LSR receptor, and to better evaluate the possible therapeutic implications of the induction of the activity of hepatic clearance of lipoproteins by leptin, the inventors supplemented the preceding analysis with monitoring of the weight variation, of the LSR activity and of the expression of LSR mRNA, in control or obese animals treated with leptin or otherwise.

Postprandial Lipemic Response and LSR Activity in Control and Obese Mice

Control male mice (C57BL6) (n=8) and obese male mice (ob/ob, n=8—animals deficient in the leptin gene—and db/db, n=8—animals deficient in the gene for the leptin receptor—) (aged 17 weeks old) were weighed in order to quantitatively establish the differences in weight between lines (FIG. 28A). The postprandial lipemic responses of the animals of each line were measured in the absence of treatment with leptin as described above. The apparent number of LSR receptors expressed at the surface of the hepatic cells was measured on 4 animals of each line, as described above, and expressed in comparison with the 5'-nucleotidase activity (enzyme selectively measured at the level of the plasma membranes Sigma kit). Finally, Northern blotting made it possible to estimate the level of expression of the LSR receptor in three animals of each line, according to the protocol described above.

The higher postprandial lipemic response in the obese animals (FIG. 28B) is in agreement with the smaller apparent number of hepatic LSR receptors in these same animals (FIG. 28C). Furthermore, the Northern blotting results (FIG. 28D) indicate that this reduction in the apparent number of LSR receptors in the obese animals is accompanied by a reduction in the level of expression of the said receptor in the same animals. The inventors have shown that indeed, a reduction in the number of mRNA encoding the LSR receptor is observed in the obese mice ob/ob and db/db.

The inventors also studied the effect of a long-term treatment of a treatment with leptin on ob/ob mice (FIG. 29).

Effect of a Long-term Treatment with Leptin on ob/ob Mice

The ob/ob obese mice received a daily injection of either leptin, or of an equivalent volume of sterile PBS, for 30 days. The injected doses are 50 µg/animal from day 0 to day 4, 100 µg/animal from day 5 to day 17, and 150 µg/animal from day 18 to day 30. Several parameters indicated below are measured:

- the weight (FIG. 29A): the change in weight is measured for 6 animals, over the duration of the treatment;
- the postprandial lipemic response (FIG. 29B): it is measured according to the protocol detailed in Example 5 on three animals in each group, on day 29;
- the apparent number of LSR receptors (FIG. 29C): it is measured according to the protocol detailed in Example 4 on three animals in each group, on day 30;
- the quantity of LSR mRNA (FIG. 23D): it is estimated by Northern blotting as indicated in the protocol of Example 2.

The inventors thus observed a very significant loss of weight in the ob/ob obese mice treated over 30 days with leptin. Furthermore, the treatment with leptin causes a clear reduction in the postprandial lipemic response. This reduction in the postprandial lipemic response is correlated with an increase in the apparent number of LSR receptors at the surface of the cells and with an increase in the quantity of mRNA encoding the subunits of the LSR receptor.

These results establish in vivo that LSR represents the limiting step in the elimination of dietary lipids. Furthermore, the treatment of this obesity inducing a weight loss causes an increase in the activity of hepatic degradation of dietary lipids, and a reduction in the postprandial lipemic response.

Example 7

Characterization of the Human LSR Receptor

Northern-blot Analysis

Nucleic probes for rat LSR were used to carry out Northern-blot analyses with a membrane (Human Multiple Tissue Northern Blot, Clontech #7760-1) comprising human heart, brain, placenta, lung, liver, skeletal muscle, kidney and pancreas poly A RNAs. A band of about 2 kbp is detected in the liver and in the kidney. Approximate quantification of the hybridization results indicate that LSR is expressed in the liver at least 5 times more than in the kidney.

Cloning of the cDNA; Study of the Splicing Zone

Reverse transcription-PCR experiments on the mRNA made it possible to determine with greater precision the size of exon 1 on the 5' side and splicing sites between exons 1 and 2. However, it is not certain that this end constitutes the start of this exon. In addition, a second initiation site exists in exon 1 which is more downstream from the first and which exhibits a greater probability than the latter. The splicing between exons 1 and 2 was different between the human RNA and the rat RNA.

The amplification was carried out with several pairs of primers:

| | | | |
|---|---|---|---|
| a: | 5'-ATGCAACAGGACGGACTTGGA-3' | (SEQ ID 31) | exon 1 |
| b: | 5'-TCAGACGACTAAACTTTCCCGACTCAGG-3' | (SEQ ID 32) | exon 10 |
| c: | 5'-CTACAACCCCTACGTTGAGT-3' | (SEQ ID 33) | exon 2 |
| d: | 5'-TCGTGACCTGACCTTTGACCAGAC-3' | (SEQ ID 34) | exon 3 |
| e: | 5'-CCTGAGCTACTCCTGTCAACGTCT-3' | (SEQ ID 35) | exon 6 |
| f: | 5'-AGGCCGAGATCGCCAGTCGT-3' | (SEQ ID 36) | exon 9 |

The amplification carried out with the ab pair of primers led to two products 1.8 kb and 2 kb in size after separation on an electrophoresis gel. Given that the sizes of these two products can be explained by an alternative splicing similar to that described in rats, the other amplification primers were drawn. These primers made it possible to identify the three forms of cDNA resulting from the alternative splicing of the RNA.

The first cDNA which contains the totality of the ten exons is called LSR-Hs-2062 and corresponds to SEQ ID 7. It corresponds to the rat cDNA LSR-Rn-2097. The second cDNA contains exons 1, 2, 3, 5, 6, 7, 8, 9 and 10, and is called LSR-Hs-2005. It corresponds to SEQ ID 9. This cDNA corresponds to the rat cDNA LSR-Rn-2040. Finally, the cDNA containing exons 1, 2, 3, 6, 7, 8, 9 and 10 is called LSR-Hs-1858 and its sequence is listed in SEQ ID 11. It corresponds to the rat cDNA LSR-Rn-1893.

It should be noted that it was possible to demonstrate a slippage of the splicing site at the boundary of exon 8. This slippage, of the triplet TAG at position 19953–19955 of SEQ ID 19 to the contiguous triplet AAG at position 19956–19958 of SEQ ID 19, results in the loss of the Glu residue at position 386 of the cDNA of SEQ ID 8.

The sequences of the proteins encoded by the cDNA LSR-Hs-2062, LSR-Hs-2005 and LSR-Hs-1858 correspond respectively to SEQ ID 8, 10 and 12. The biological protein sequences can start at the first ATG codon observed in the reading frame (position 35 of the protein sequence). However, the preferred codon for initiation of translation is more downstream at position 83 of the protein sequence. Furthermore, it is quite possible that this initiation codon is more upstream in the 5' region of exon 1 not yet determined or in a possible exon preceding the latter.

Finally, FIGS. 3A and 3B represents a schematic representation of the various protein forms identified in humans, indicating the conserved motifs.

This analysis makes it possible to conclude that three α, α' and β subunits of LSR, which are equivalent to the LSR 66, LSR 64 and LSR 58 forms in rats, exists in humans.

Identification and Isolation of the Genomic Sequence for Human LSR

Screening of public data banks of nucleic sequences (Genebank, version: 101) both with the sequence of mouse lisch7 (Accession No.: U49507) and with that of rat LSR_2097 isolated by the inventors made it possible to isolate two human genomic DNA sequences. They are cosmids whose accession numbers are AC002128 and AD000684, of respective sizes 45,328 bp and 41,936 bp. These two cosmids partially overlap. The 3' end of the cosmid AC002128 overlaps, over 12838 bp, the 5' end of the cosmid AD000684. On the common portion of 12,838 bp, the sequences are 100% identical, apart from two deletions at positions 822 and 3170 of the cosmid AD000684. The human LSR gene is distributed over the two cosmids. To facilitate the study of this region, a complete genomic sequence was reconstituted: the 45,328 bp of the cosmid AC002128 were added to the sequence of the cosmid AD000684 between the 12,839 base and the 41,936 base. The combination constitutes a sequence of 74,426 bp. A genomic sequence covering the LSR gene, was extracted (SEQ ID 19).

The putative exons of the LSR gene were determined after alignment of the sequence described above with the sequences of the RNAs for mouse Lisch7 and rat LSR. The validity of the splicing sites on either side of the putative exons was verified.

Moreover, a human genomic library consisting of BACs was screened by the methods described in Chumakov et al., 1995 the clones thus isolated were contiged, subcloned and then sequenced in order to obtain the human genomic sequence encoding LSR (SEQ ID 41).

The two sequences thus obtained (SEQ ID 19 and 41) carry minor differences which are mentioned in the accompanying listings.

Example 8

LSR Activity in Humans

Primary cultures of human fibroblasts, isolated from subjects having a deletion affecting the promoter and the first exon of the LDL receptor gene, were obtained.

The incubation of these cells in the presence and in the absence of oleate shows that the latter induces LDL binding, internalization and degradation activity which follows a saturation kinetics (Bihain and Yen, 1992). The affinity of this receptor, induced by oleate, is maximum for the particles high in triglycerides (VLDL and chylomicrons) as well as for triolein and phosphatidylcholine supplemented with recombinant apoprotein E. The affinity of the LDLs for the receptor is lower than that of the VLDLs and the chylomicrons but, however, higher than those of triolein and phosphatidylcholine particles not containing ApoE, or than those of VLDLs isolated from a subject with type III hyperlipidemia and the ApoE $E_{2/2}$ phenotype (Yen et al., 1994).

It was also possible to measure the LSR activity in fibroblasts of normal human subjects (FIG. 30), according to the protocol below.

Measurement of the Binding, Internalization and Degradation of LDLs by Fibroblasts The fibroblasts are cultured beforehand for one week as described above, except that the medium contains 20% foetal bovine serum (Goldstein et al., 1983). Next, they are incubated with increasing concentrations of $^{125}$I-LDL in the absence or in the presence of 1 mM oleate. The cells are then washed, lysed and counted for their radioactivity.

Example 9

Effect of Leptin on the LSR Activity in Humans

The LSR activity of human fibroblasts HF (familial hypercholesterolemia) is also increased after incubation with leptin (FIG. 31), suggesting that as in rats, LSR participates, in humans, in the clearance of cytokines, and its activity is modulated by the latter. The corresponding measurements were carried out as indicated below.

Effect of Leptin on the LSR Activity on Human Fibroblasts

The fibroblasts HF are incubated for 30 minutes at 37° C. with increasing concentrations of leptin, and then for 2 hours at 37° C. with 50 μg/ml of $^{125}$I-LDL, in the presence of 500 μM oleate. The binding, internalization and degradation of the LDLs are measured as indicated in Example 1.

Example 10

Cloning of the cDNA for Mouse LSR; Analysis of the Products of Alternative Splicing The cloning of the cDNA for mouse LSR was carried out using a mouse liver mRNA library. The cloning method used is the same as that for the cDNA for human LSR. The mRNAs were purified and a reverse transcription PCR amplification was carried out with the specific DNA primers. The amplification fragment was cloned to a TA cloning vector (Introgene).

A study of the products of alternative splicing with primers situated in exon 2 and in exon 9 was also carried out in a manner similar to that carried out for the human LSR.

Three products of alternative splicing were observed: LSR-Mm-1886, LSR-Mm-1829 and LSR-Mm-1682. LSR-Mm-1886 contains all the exons from 1 to 10. LSR-Mm-1829 and LSR-Mm-1682 lack exon 4 and exons 4 and 5, respectively. These three biological forms of cDNA indeed correspond to what was observed in humans and rats. The nucleotide sequences of the cDNAs LSR-Mm-1886, LSR-Mm-1829 and LSR-Mm-1682 are illustrated in SEQ ID 13, 14 and 15, respectively. The protein sequences encoded by the cDNAs LSR-Mm-1886, LSR-Mm-1829 and LSR-Mm-1682 are illustrated in SEQ ID 16, 17 and 18.

Example 11

Identification of the γ Subunit of LSR

The α and β subunits of LSR were identified as indicated above. Analysis of the products of translation of the RNAs encoding these two subunits does not allow the presence of a third subunit of molecular weight≈35 kDa to be explained. This subunit is detected only after reduction of the LSR complex (FIG. 10, lane 4).

We purified and obtained the $NH_2$-terminal sequence of this γ subunit.

The purification was carried out by immunoaffinity chromatography according to the following procedure.

Purification of the γ Subunit of LSR

Anti-LSR antibodies (band A) are coupled to a resin [2.5 mg of IgG per 3.5 ml of affi-gel Hz immunoaffinity kit resin (Biorad 153-6060)] which is then incubated with proteins solubilized from total membranes of rat liver (20 mM Tris buffer, 2 mM EDTA, 0.125 M octyl glucoside (5×CMC), 1% inhibitor cocktail, pH=7.4: 160 mg of membrane proteins give 41.3 mg of solubilized proteins (SP) in a volume of 17 ml.

The incubation is carried out for 12 hours: 17 ml filled to 50 ml with 20 mM Tris buffer, 2 mM EDTA, pH 7.4 and the 3.5 ml of resin, with rotary shaking, at room temperature. The resin is washed with 40 ml of 20 mM Tris buffer, 2 mM EDTA, pH 7.4 and then eluted with 20 mM Tris buffer, 2 mM EDTA, 200 mM glycine, pH 2.5 in 30 fractions of 500 μl. The pH of each fraction is neutralized with 100 μl per tube of 1 M Tris buffer, 2 mM EDTA, pH 9. 50 μl of each fraction are deposited on a nitrocellulose membrane for dot-blot analysis: incubation with anti-LSR antibody, and then with a second antibody coupled to alkaline phosphatase.

The positive fractions from 7 to 28 are pooled in pairs and concentrated 2.5-fold in a Speedvac. Western blotting is carried out on the pooled, concentrated and separated fractions on a 10% PAGE-SDS gel. Bands are observed in fractions 7 to 14 (the fractions are pooled).

The two pools are dialysed against 24 mM ammonium bicarbonate and then freeze-dried in a Speedvac. The powder is taken up in 80 μl of 20 mM Tris buffer, 2 mM EDTA, 2% SDS, 3% urea, pH 7.4 and reduced in the presence of 5% β-mercaptoethanol for 30 minutes at 100° C.

After migration and wet transfer in 50 mM Tris, 50 mM borate on a sequencing membrane (PVDF) at 30 mA, the membrane is stained with amido black.

A band with an apparent MW of about 35 kDa was thus identified and sent for sequencing according to the Edman method.

The sequence obtained is LHTGDKAFVEFLTDEIKEE. This sequence corresponds identically to that of a protein of molecular weight 33 kDa identified above as a protein of the cellular surface which binds the globular heads of C1q (gC1q-R) (Ghebrehiwet et al., 1994). A more recent observation indicates that this potential receptor for C1q is also located in the vesicles situated under the cellular surface (van den Berg et al., 1997). This protein also corresponds to a protein previously identified as p34, and which combines with a lamin receptor. This receptor possesses a long $NH_2$-terminal segment oriented inwards in the cell nucleus as well as 8 transmembrane domains. This receptor binds to lamin in a manner which depends on the degree of phosphorylation. Finally, gC1q-R combines with "splicing factor 2" (Honore et al., 1993). The lamin receptor and "splicing factor 2" have in common the characteristic of containing a repeated sequence of serine and arginine (RSRS) situated at the level of the $NH_2$-terminal segment in the case of the lamin receptor and at the level of the carboxy-terminal segment in the case of SF2.

It is remarkable to observe that both α-LSR and β-LSR exhibit repeated segments high in serine and arginine (FIG. 1). Our hypothesis is that the γ-LSR protein represents a molecular chaperone which combines with the α and β subunits of LSR via their RSRS domain.

In order to verify this hypothesis, we obtained polyclonal antibodies directed against two synthetic peptides whose sequence was situated at the carboxy- or $NH_2$-terminal end of the gC1q-R protein:

—$NH_2$-terminal peptide of gC1q-R: LRCVPRVLGSS-VAGY* (amino acids 5 to 19 of gC1q-R) (SEQ ID 39)

—COOH-terminal peptide of gC1q-R: C*YITFLEDLKSFVKSQ (amino acids 268 to 282 of gC1q-R) (SEQ ID 40).

*amino acids differing from the protein sequence, so as to optimize the antigenicity of the peptides.

FIG. 32 shows these antibodies specifically inhibit the activity of LSR. The antibody directed against the COOH-terminal end appears to be the most effective. These results indicate that gC1q-R, or one of its structurally similar homologues, represents a molecular chaperone noncovalently combined with the LSR multimeric complex.

Example 12

Regulation of the LSR Activity by C1q and its Homologues

It has been shown that gC1q-R could bind the globular head of complement factor 1. We sought to use this property of C1q to displace gC1q-R combined with LSR, and we measured the effect of increasing doses of C1q on the binding, internalization and degradation of the LDLs by hepatocytes in primary culture. FIG. 33 shows an increase in the capture and degradation of LDLs induced by human C1q, even in the absence of oleate.

A less substantial, but nevertheless significant, increase is also observed in the presence of oleate. However, under these conditions, the maximum effect is obtained for lower concentrations of C1q.

It therefore appears that gC1q-R exerts on LSR an inhibitory effect which is comparable to that induced by the 39 kD RAP for LRP, the LDL receptor and LSR (Troussard et al., 1995). The displacement of the chaperone gC1q-R using its capacity to bind to complement C1q makes it possible to lift the inhibitory effect. Analysis of the gC1q-R sequence shows that it may be a typical membrane receptor. Indeed, the protein possesses no hydrophobic sequence capable of crossing the phospholipid bilayer.

The effect of complement C1q on the activity of LSR opens major perspectives in the context of the genetics of obesity. It is possible, indeed, that mutations affecting either the gene for C1q, that for gC1q-R, or alternatively that for their analogues such as for example AdipoQ, cerebellin, collagen alpha 1–10, SPA and SPD (pulmonary surfactant proteins), mannan-binding protein, and the scavenger receptor or its homologue LRP (Hu et al., 1996; Drickamer et al., 1986; Krieger and Herz, 1994; Elomaa et al., 1995) modulate the activity of LSR, both as regards clearance of lipoproteins and as regards that of leptin.

Several proteins can interact with gC1q-R because they exhibit homologies with complement C1q. In particular, two proteins isolated in mice, AdipoQ (Hu et al., 1996) and acrp30 (Scherer et al., 1995), and a human protein APM1 (Maeda et al., 1996) exhibit marked homologies. These three proteins, like the components of complement C1q (C1q A, B, C), are secreted proteins; they have an $NH_2$-terminal end which resembles collagen (repetition of Gly-X-Y motifs) and a COOH-terminal end corresponding to the globular domain of complement C1q. These three proteins are preferably expressed in the adipose tissue. There are only 3 amino acids differing between AdipoQ and acrp30. APM1, a protein whose messenger has been characterized as being highly expressed in adipocytes, exhibits 79.7% nucleic acid identity and 80.6% amino acid identity with AdipoQ. APM1 is therefore certainly the human homologue of AdipoQ.

Example 13

Screening of Compounds Modifying the Activity of the LSR Receptor

As described above, the inventors formulated the hypothesis that the LSR <<γ band>>, a protein which is highly homologous to gC1qR, might interact with the LSR receptor like a molecular chaperone and might thus form an <<LSR complex>>, comprising the α or α' and β subunits of the LSR receptor and a gC1qR type molecule. gC1qR has been previously identified as a cell surface protein which binds the globular heads of the complement factor C1q. In addition to C1q, several proteins exhibiting homologies with the C1q proteins, in particular AdipoQ and acrp30 in mice and APM1 in humans, are capable of interacting with the protein homologous to gC1qR in the LSR complex and of modifying the LSR activity.

Screening Parameters

The screening of a compound such as C1q or AdipoQ was carried out through the measurement of various parameters of which the most important is the measurement of the effect of the compound on the activity of the LSR receptor. The various parameters are the following:

change in weight food intake postprandial lipemic response binding, internalization and/or degradation of lipoproteins such as the LDLs.

Change in Weight

Osmotic pumps were surgically inserted into the abdominal cavities of 12 Sprague-Drawley [sic] male rats of 400–450 g. The osmotic pumps contained either 2 ml of PBS (phosphate buffered saline), pH 7.4 (control 6 rats), or 2 ml of recombinant AdipoQ protein (5 mg/ml PBS, 6 rats). These pumps were designed to deliver 10 μl/h (50 μg AdipoQ/h). The animals are weighed and individually housed in metabolic cages. 3 animals in each group are subjected ad libitum either to a normal diet or to a fatty diet (day 0). The fatty diet consists of a normal diet supplemented with 2% (w/w) cholesterol, 10% (w/w) saturated fatty acid in the form of vegetaline, [lacuna] % (w/w) sunflower oil and 15% (w/w) sucrose. On day 3, the animals are weighed and blood samples are obtained from the caudal vein. The quantity of plasma triglycerides was measured using an enzymatic kit.

Food Intake

Recombinant AdipoQ protein (100 μg) or PBS alone were injected daily for 5 days through the caudal vein of ob/ob or db/db mice kept in a metabolic cage. The mice are weighed each day and the quantity of food consumed was also measured. The results correspond to a mean food intake and a standard deviation for 4 mice in each group.

Postprandial Lipemic Response

Male Sprague-Drawley [sic] rats (400–450 g), starved since the day before, were force-fed with a meal which was very high in fat (t=0) (60% fatty acid of which 37% saturated, 27% monounsaturated and 36% polyunsaturated, 20% protein and 20% carbohydrate, the total providing 56 kcal/kg of body weight) and received immediately afterwards an intravenous injection (femoral vein) of either 300 μl of PBS alone or of the same volume containing 1 mg of mouse recombinant AdipoQ protein. Blood samples were collected at various times (0, 2, 4 and 6 h). The quantity of plasma triglycerides was measured using an enzymatic kit. The results are presented as mean values and standard deviations on 3 animals.

LSR Activity or Binding, Internalization and Degradation of Lipoproteins

Primary cultures of rat hepatocytes were prepared and distributed into 6-well plates (9000,000 cells/well). After 48 h, the cells were washed once with PBS (2 ml/well) and incubated for 30 min at 37° C. with 20 ng/ml of recombinant murine leptin. The cells were then incubated for 4 h at 37° C. with increasing concentrations of recombinant murine AdipoQ proteins and 20 μg/ml $^{125}$I-LDL in the presence or in the absence of 0.5 mM oleate. The binding, internalization and degradation of lipoproteins were measured as indicated in Example 1.

C1q

The compound C1q was tested for its capacity to modulate the activity of the LSR receptor (binding, internalization and degradation of lipoproteins). FIG. 33 shows that the compound C1q exhibits the property of increasing the activity in the presence and in the absence of oleate. Thus, it was possible for this compound C1q to be selected as modulator of the LSR activity through the test of activity described above.

AdipoQ

The compound AdipoQ was tested according to the four parameters presented above.

Figure 1:
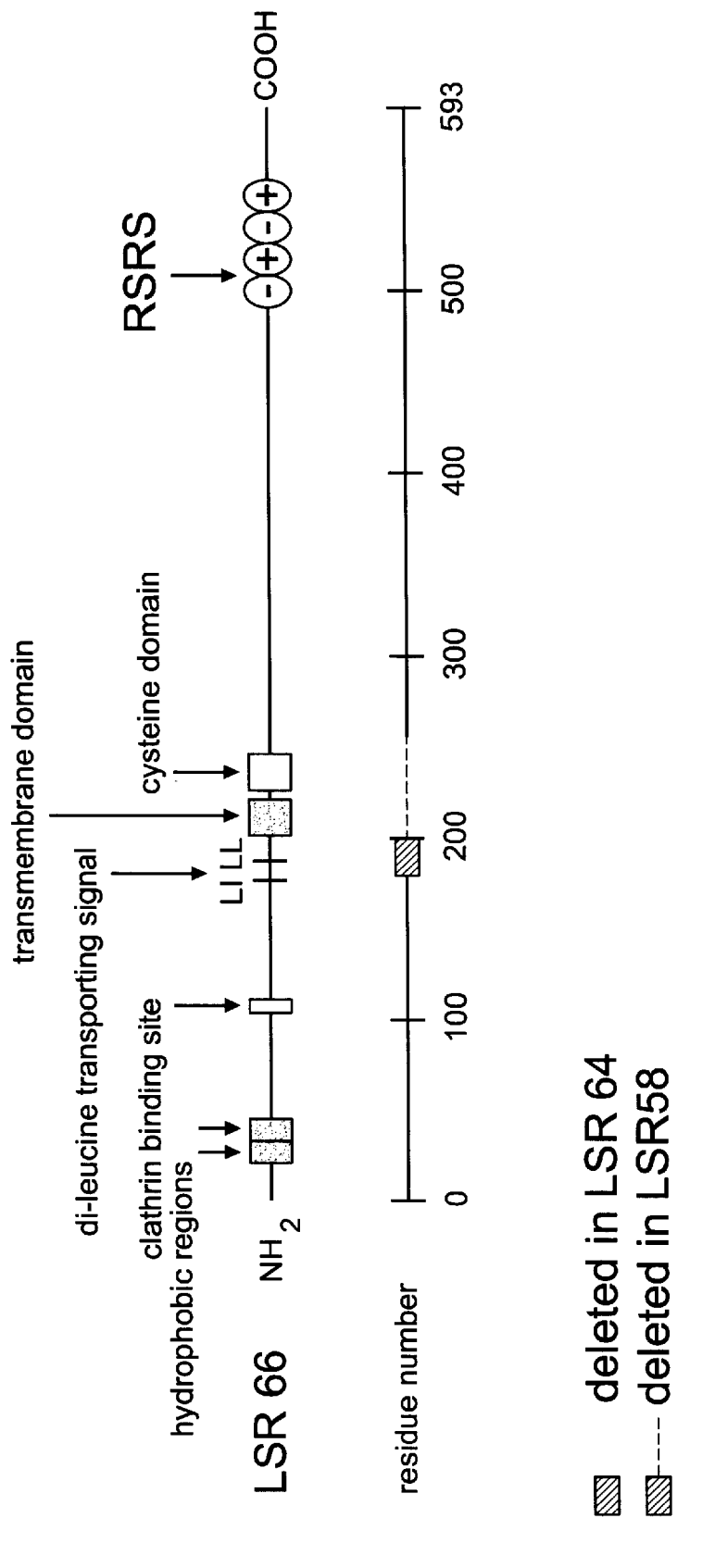
Figure 8:
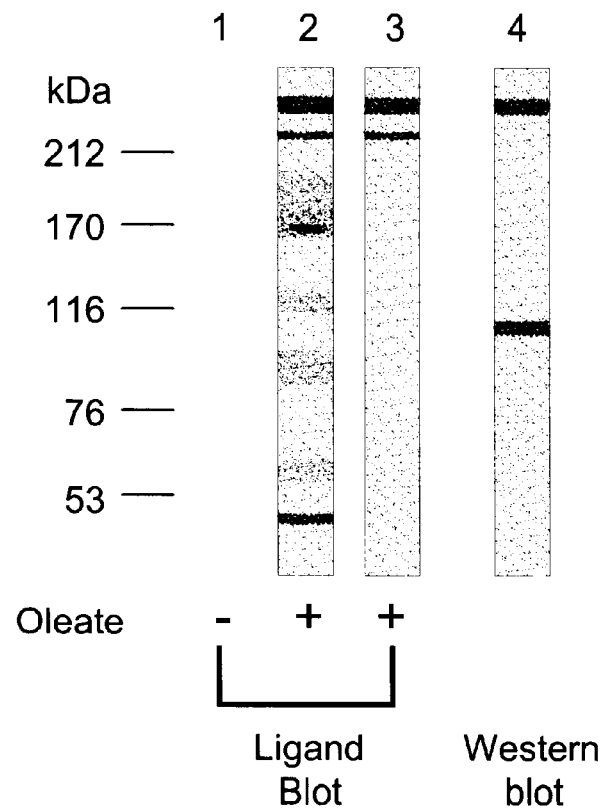
Figures 9A, 9B:
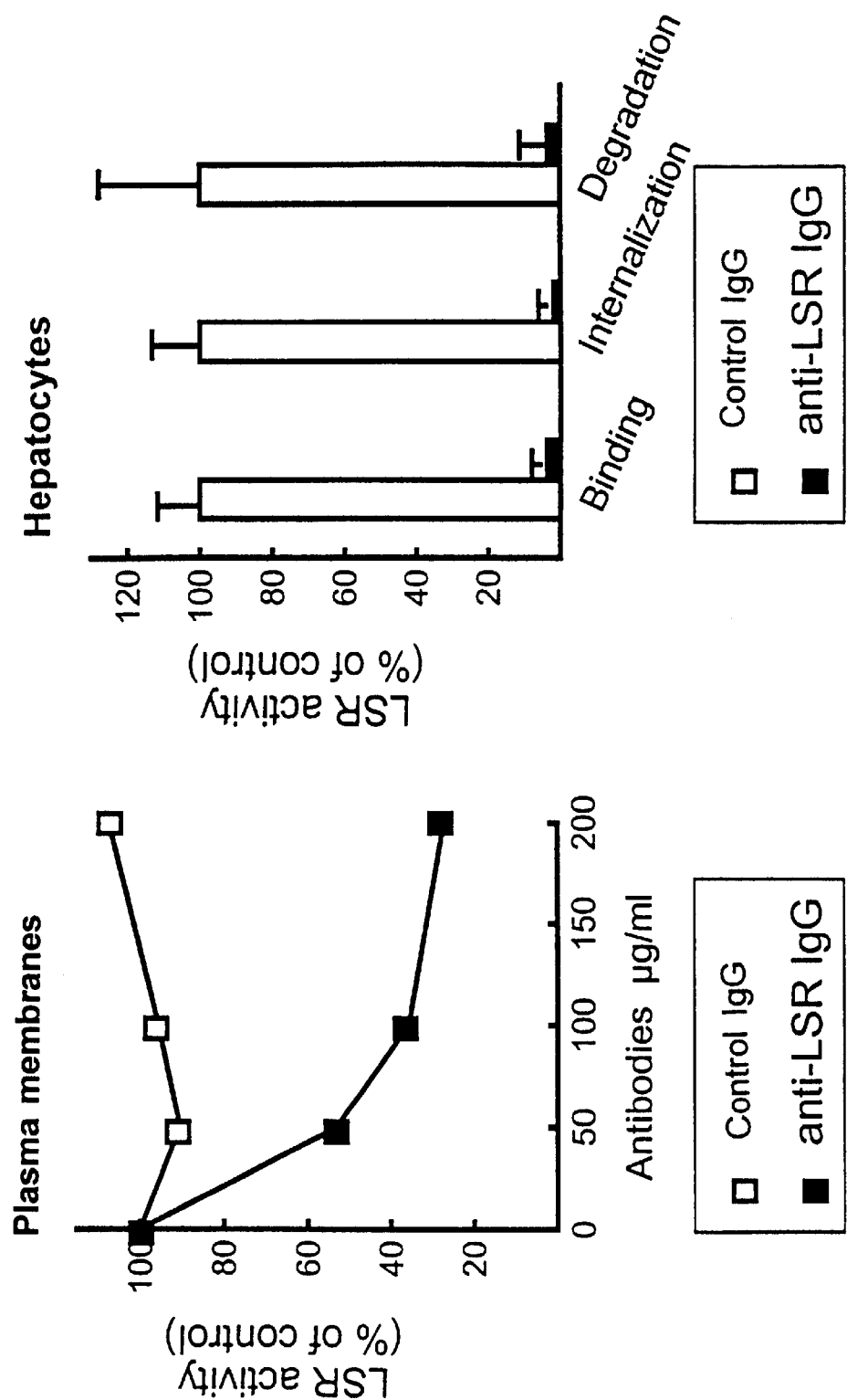
Figure 10:
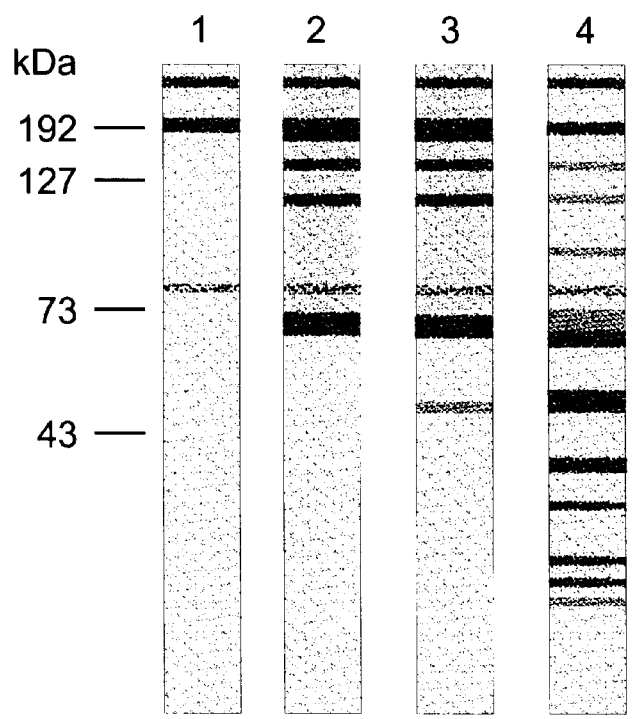
Figure 12:
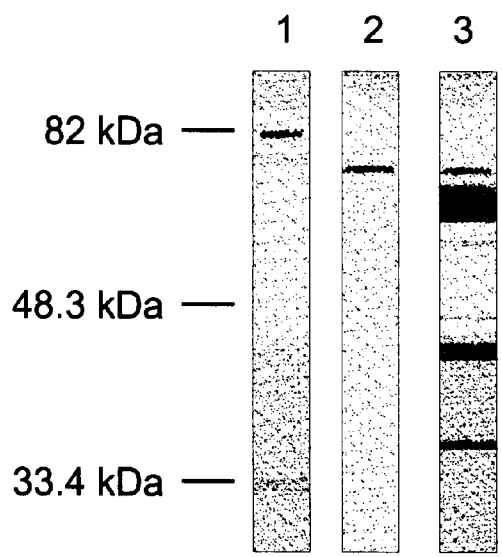
Figure 13A:
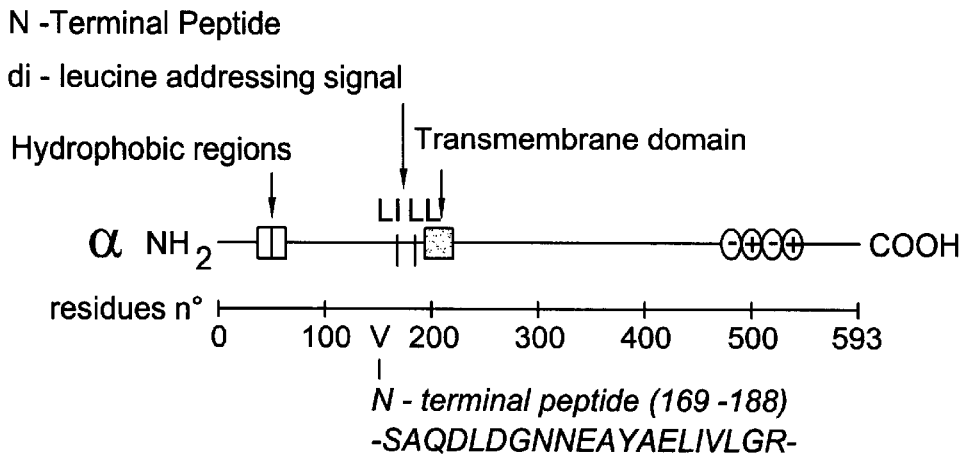
Figure 13B:
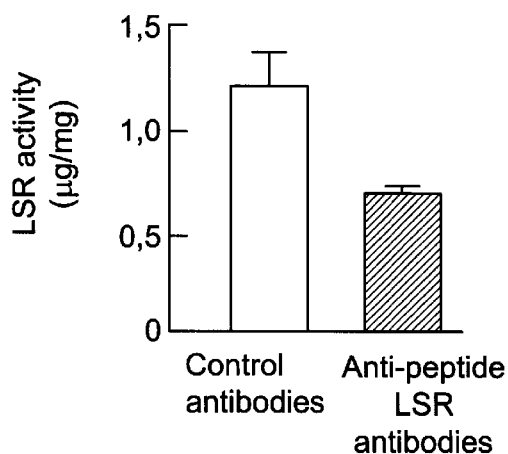
Figure 13C:
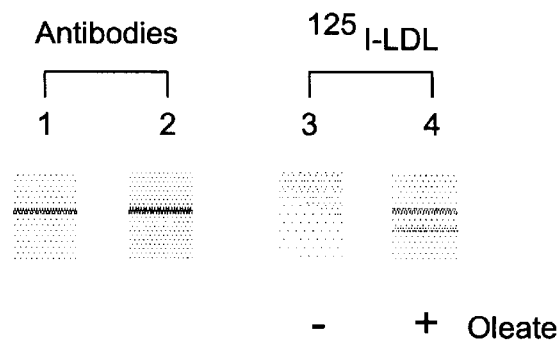
Figure 15:
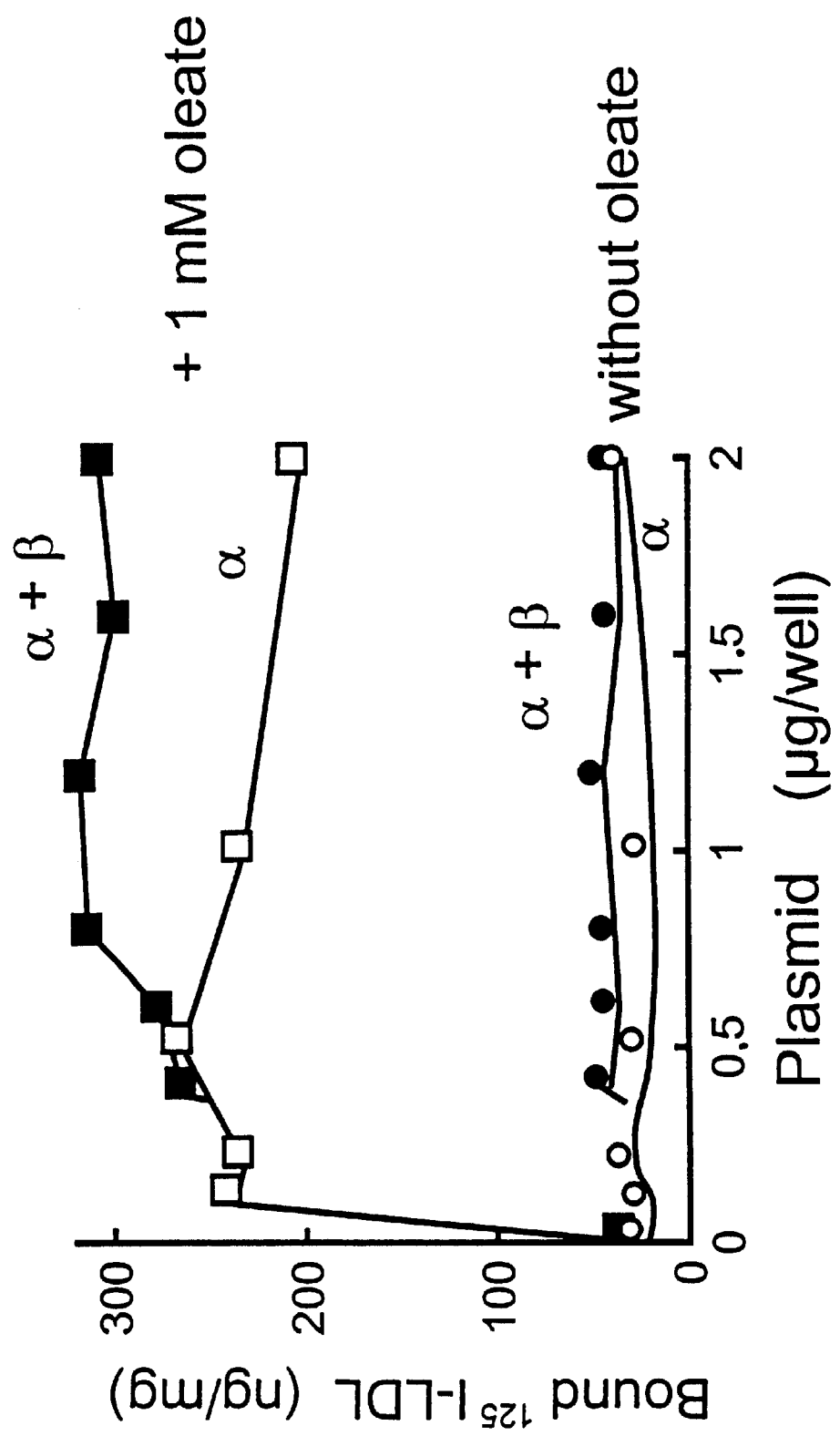
Figures 16A, 16B:
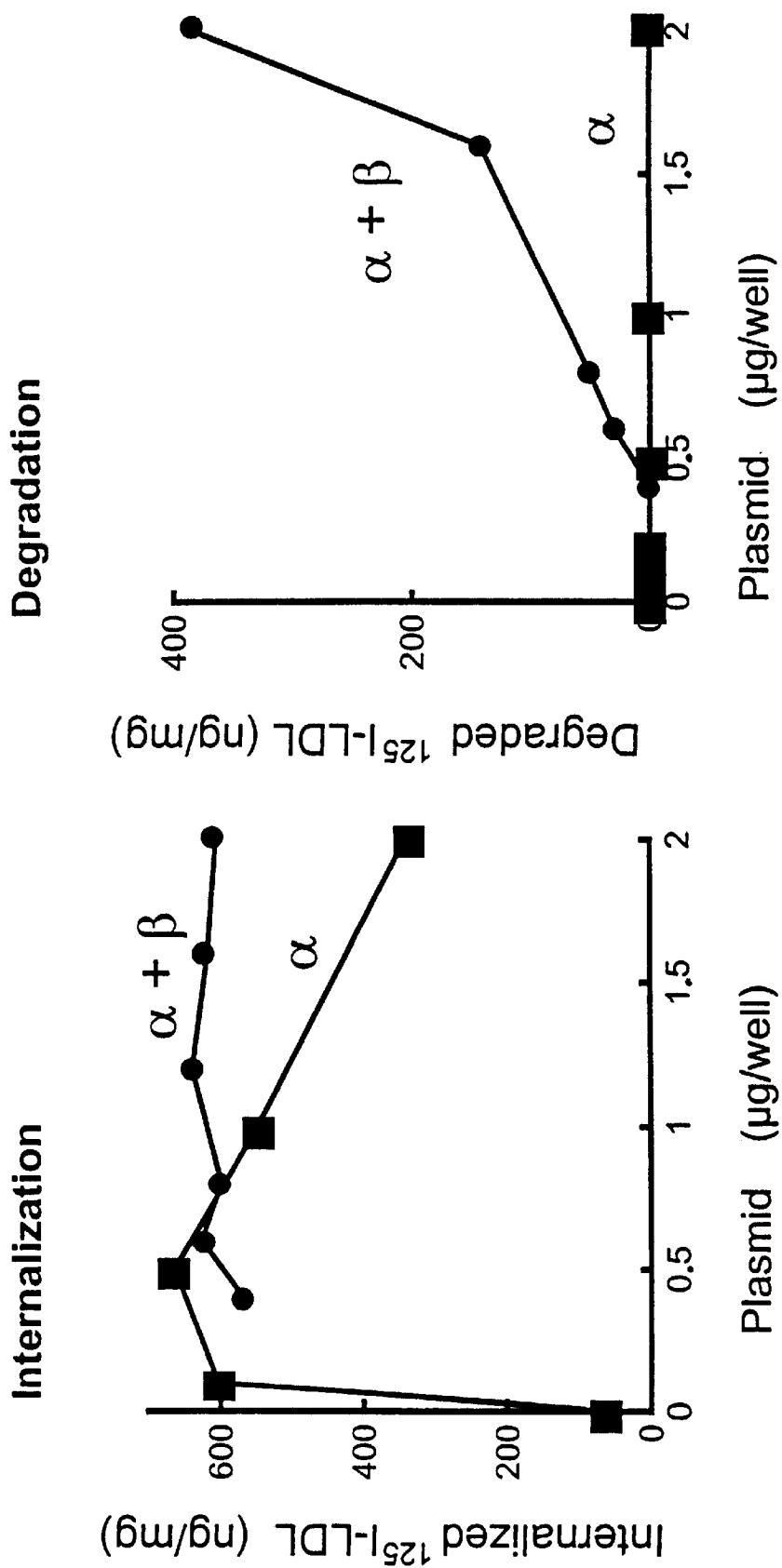
Figure 18:
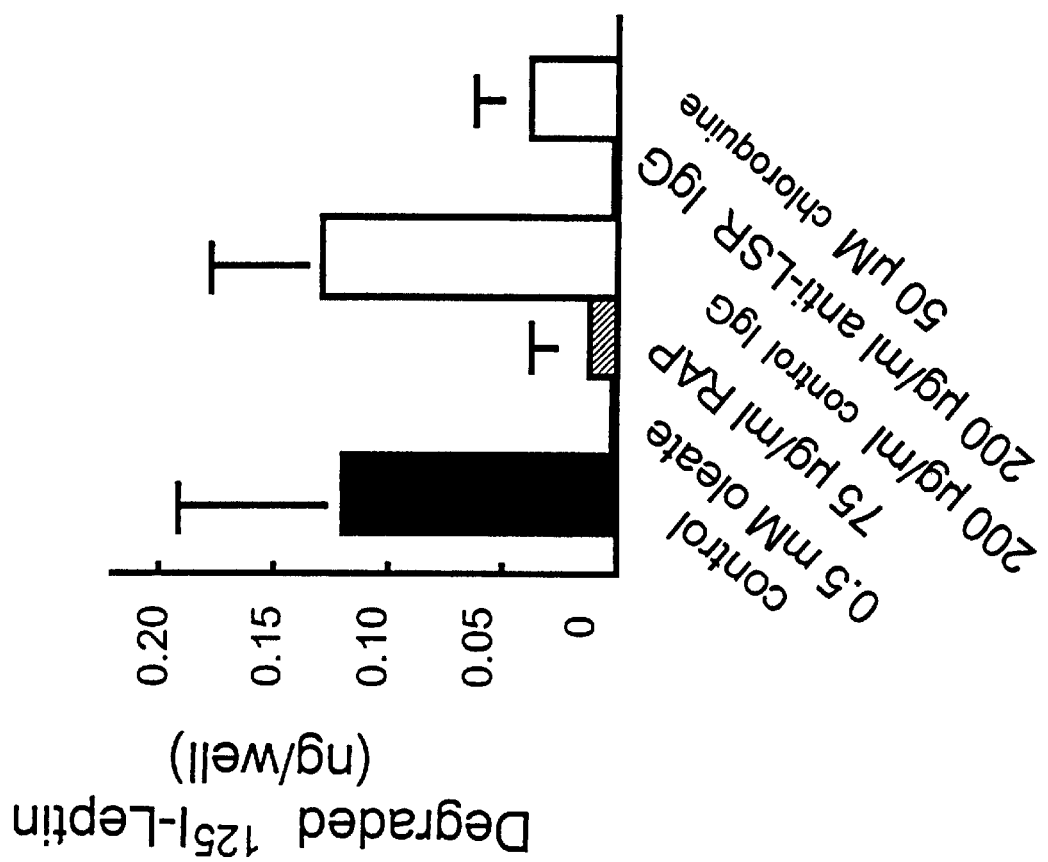
Figure 19:
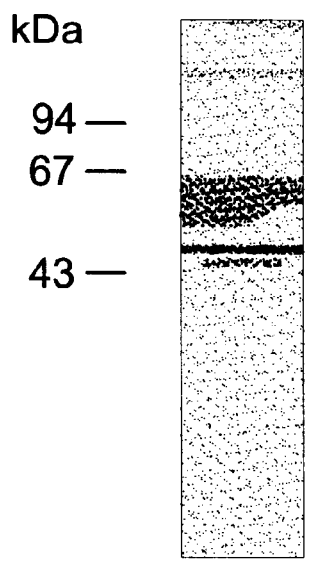
Figure 20:
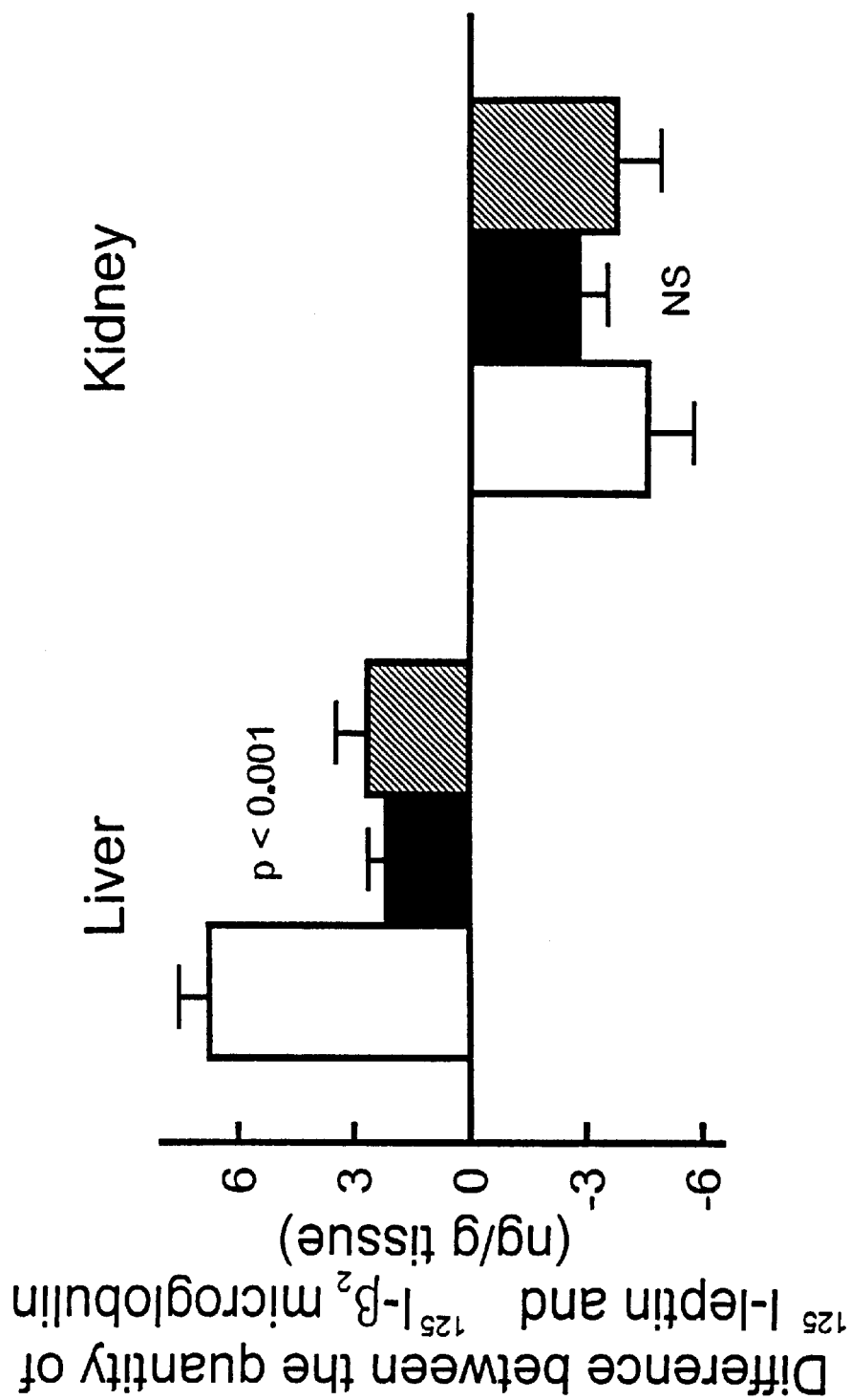
Figure 21:
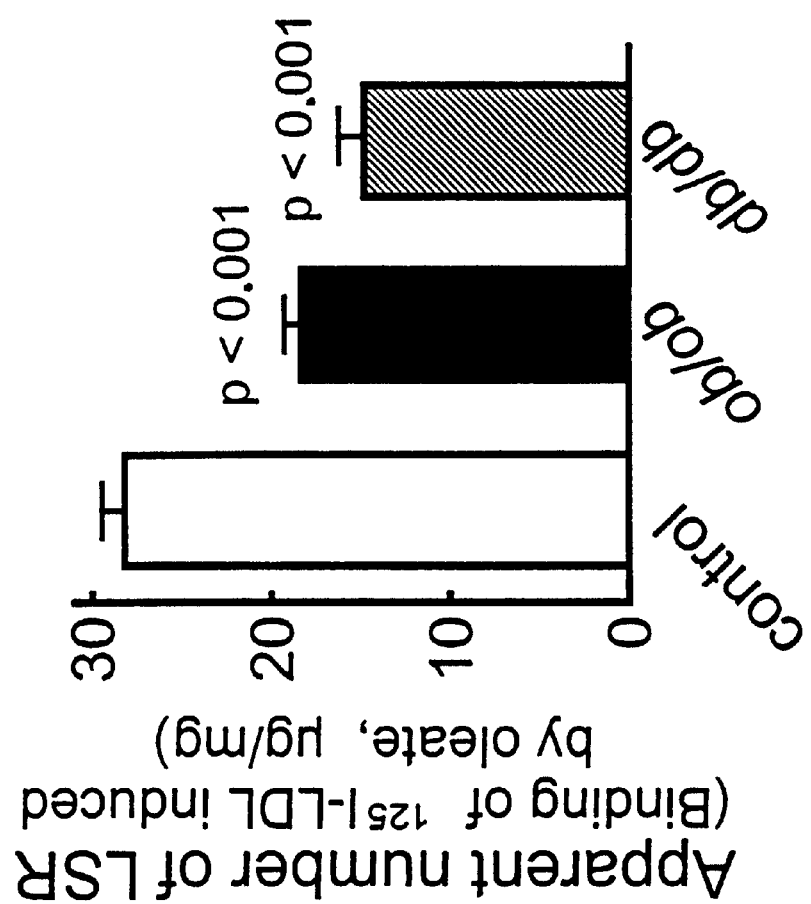
Figure 22:
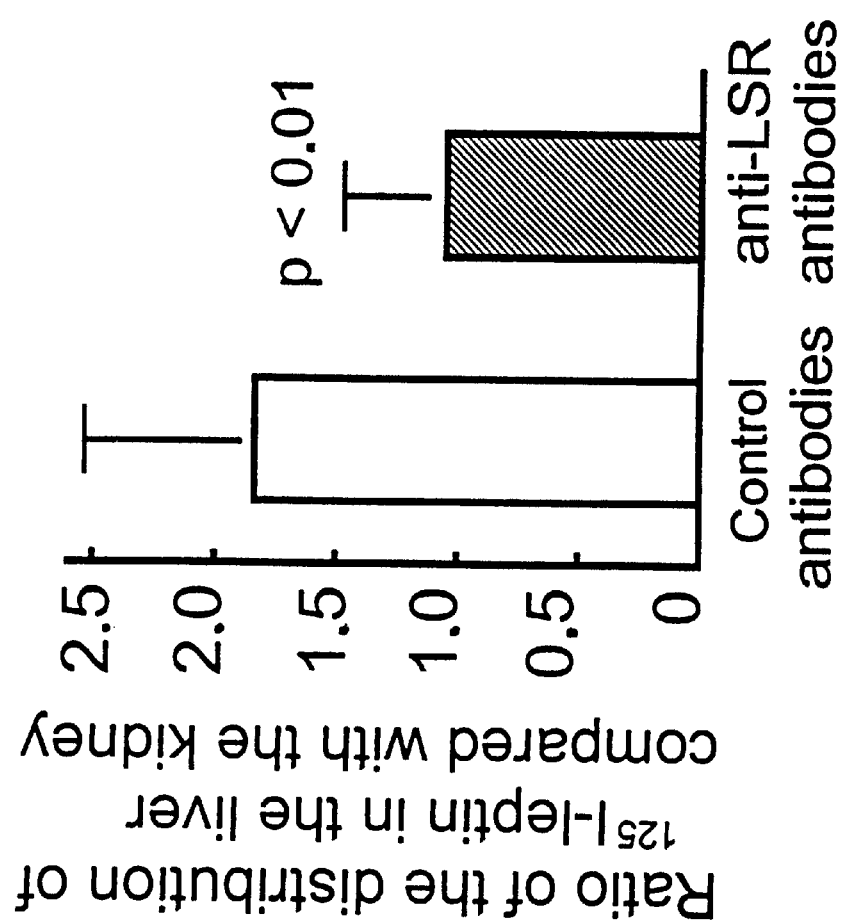
Figure 23:
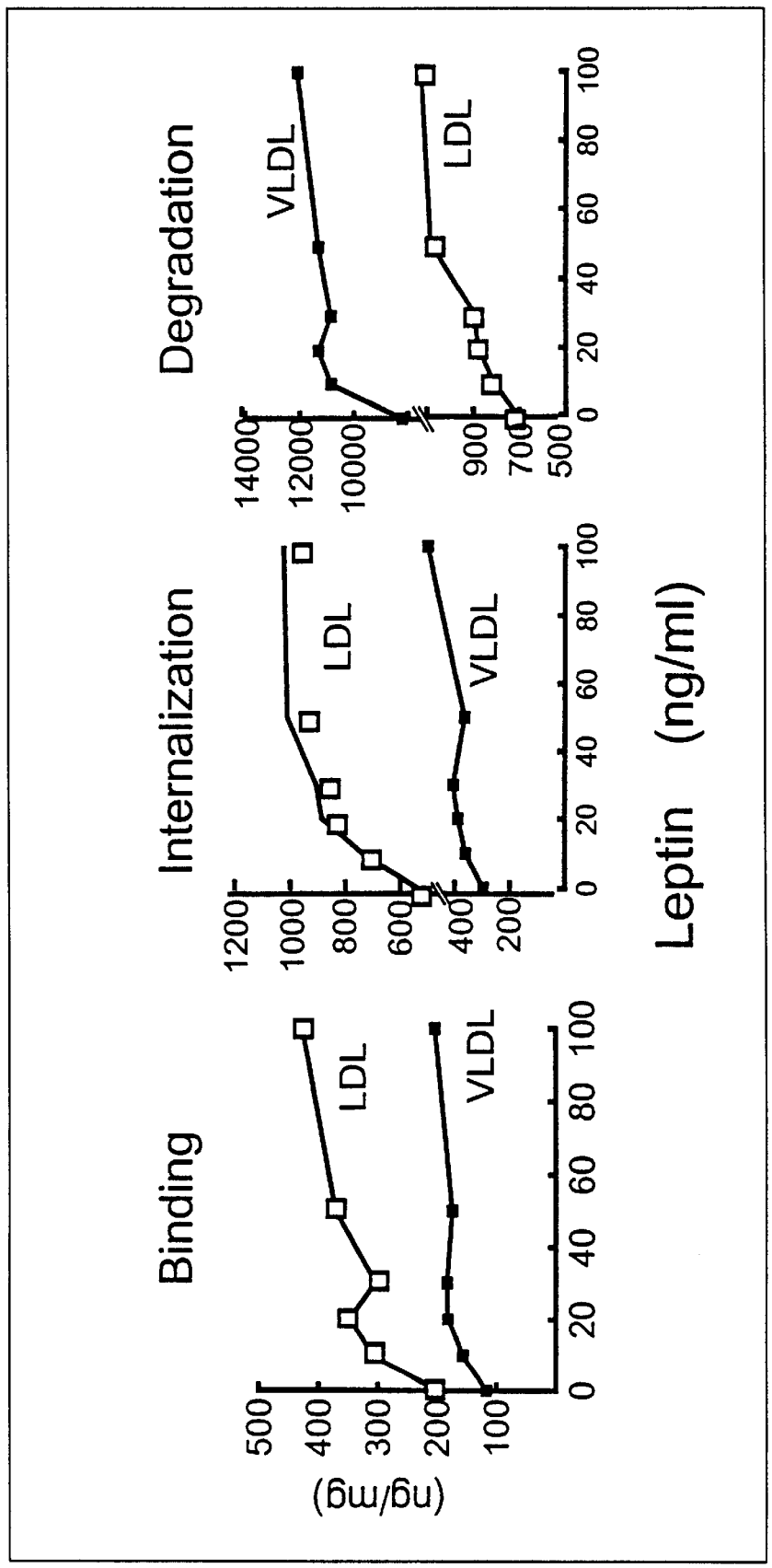
Figure 24B:
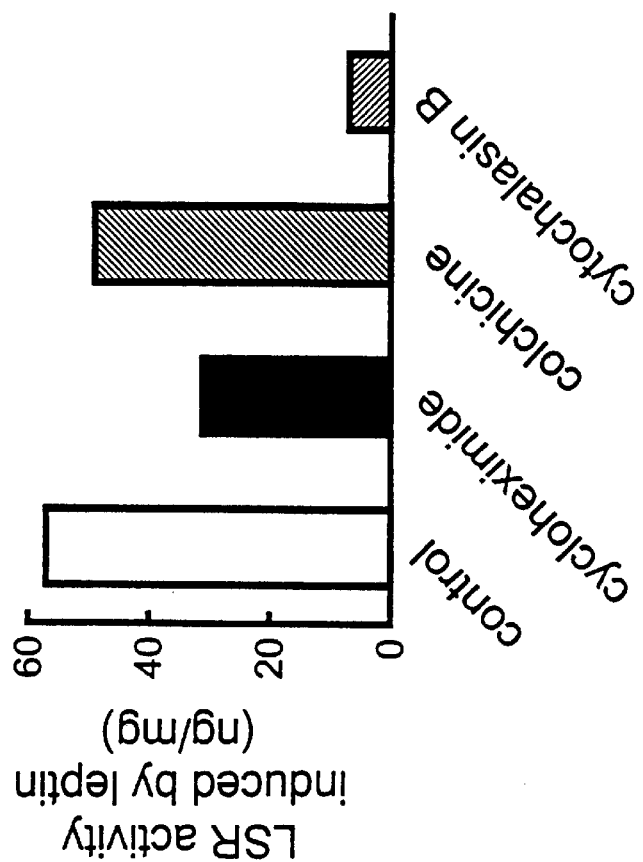
Figure 24A:
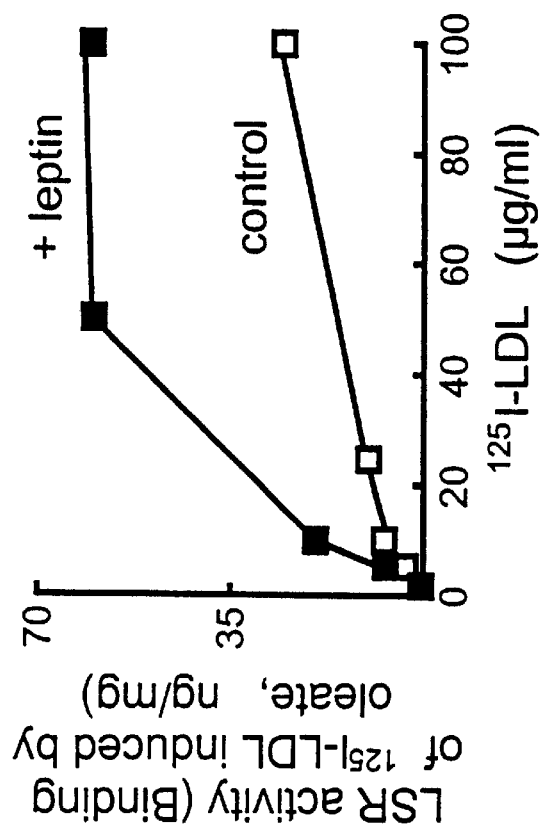
Figures 25A, 25B:
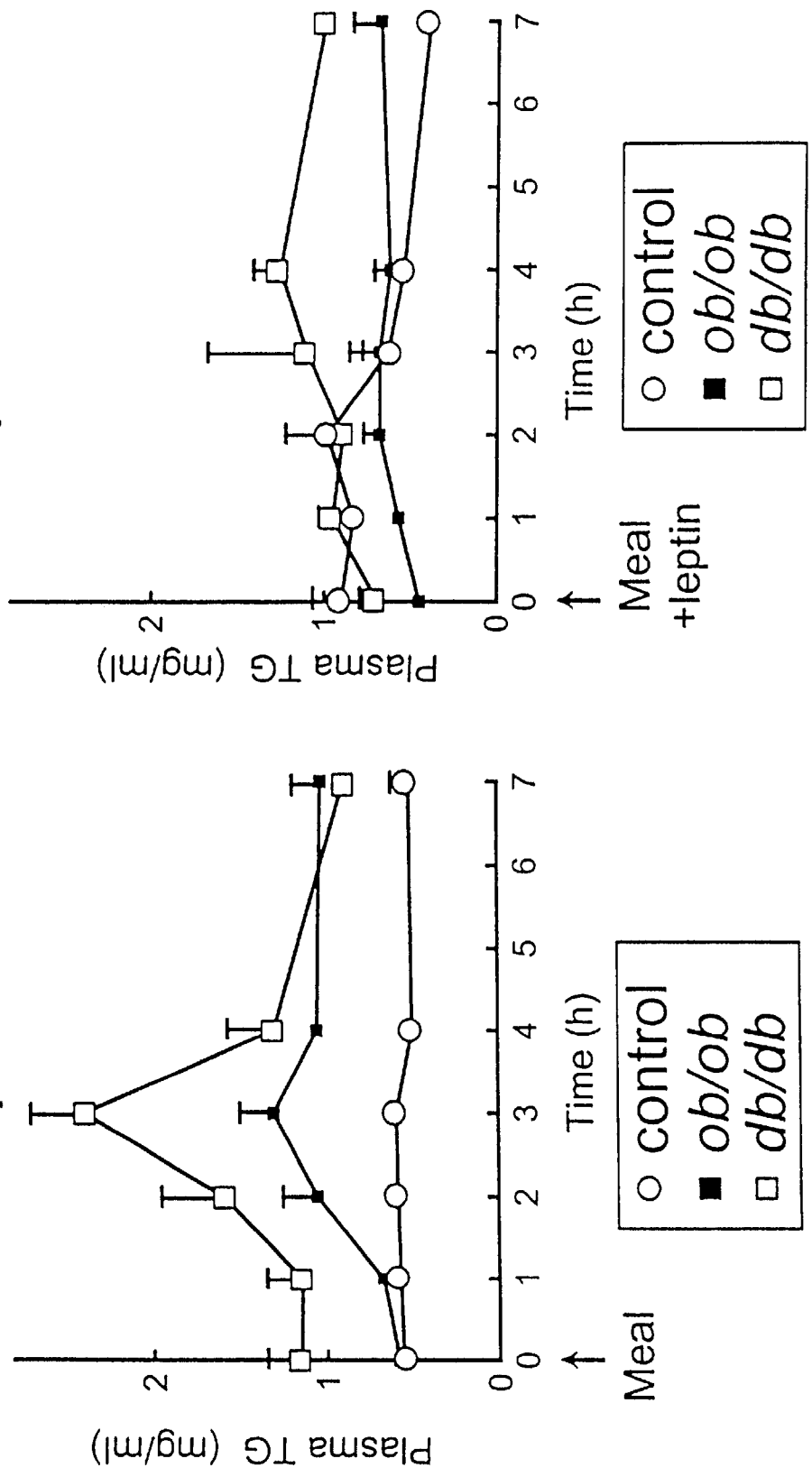
Figure 26:
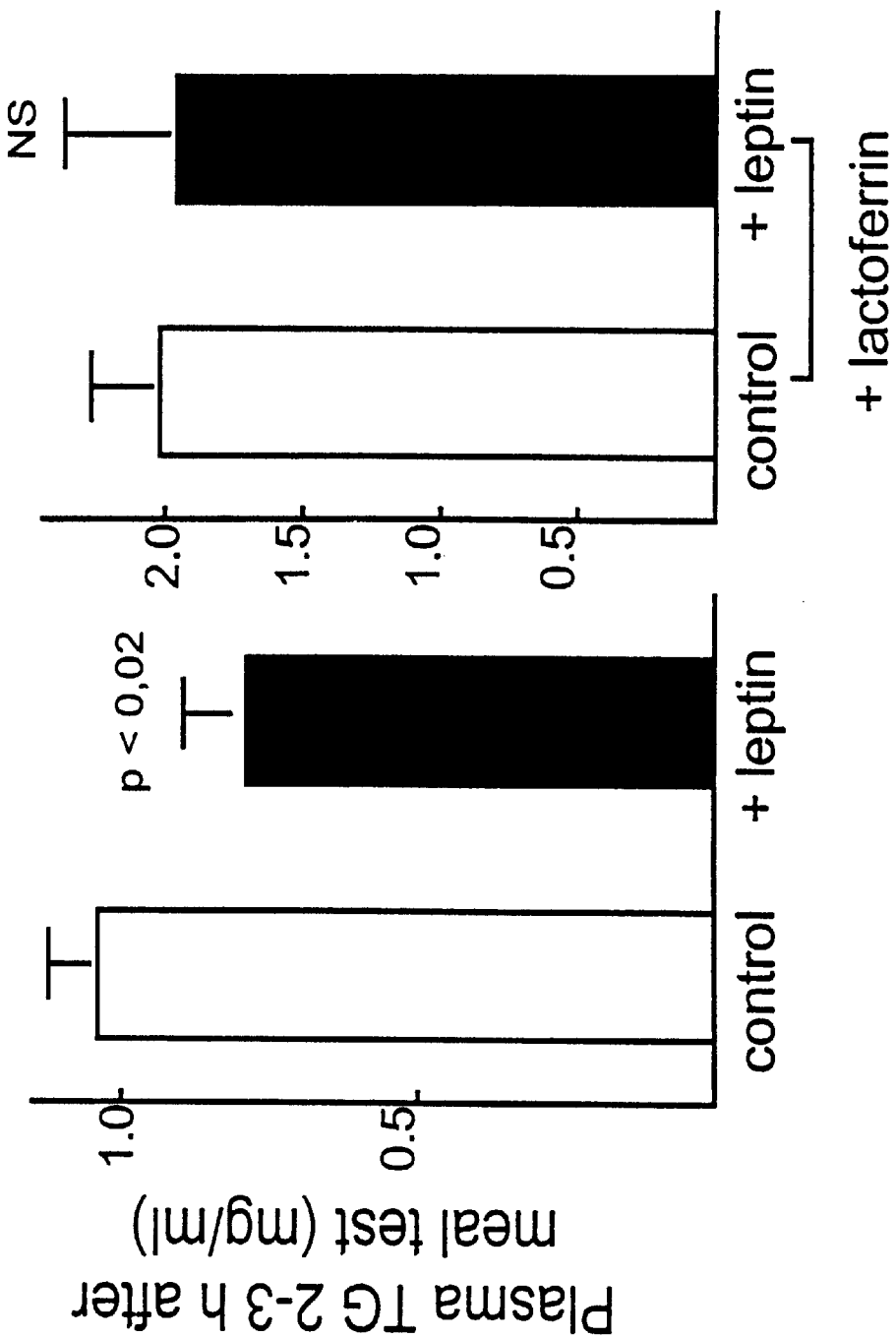
Figure 27:
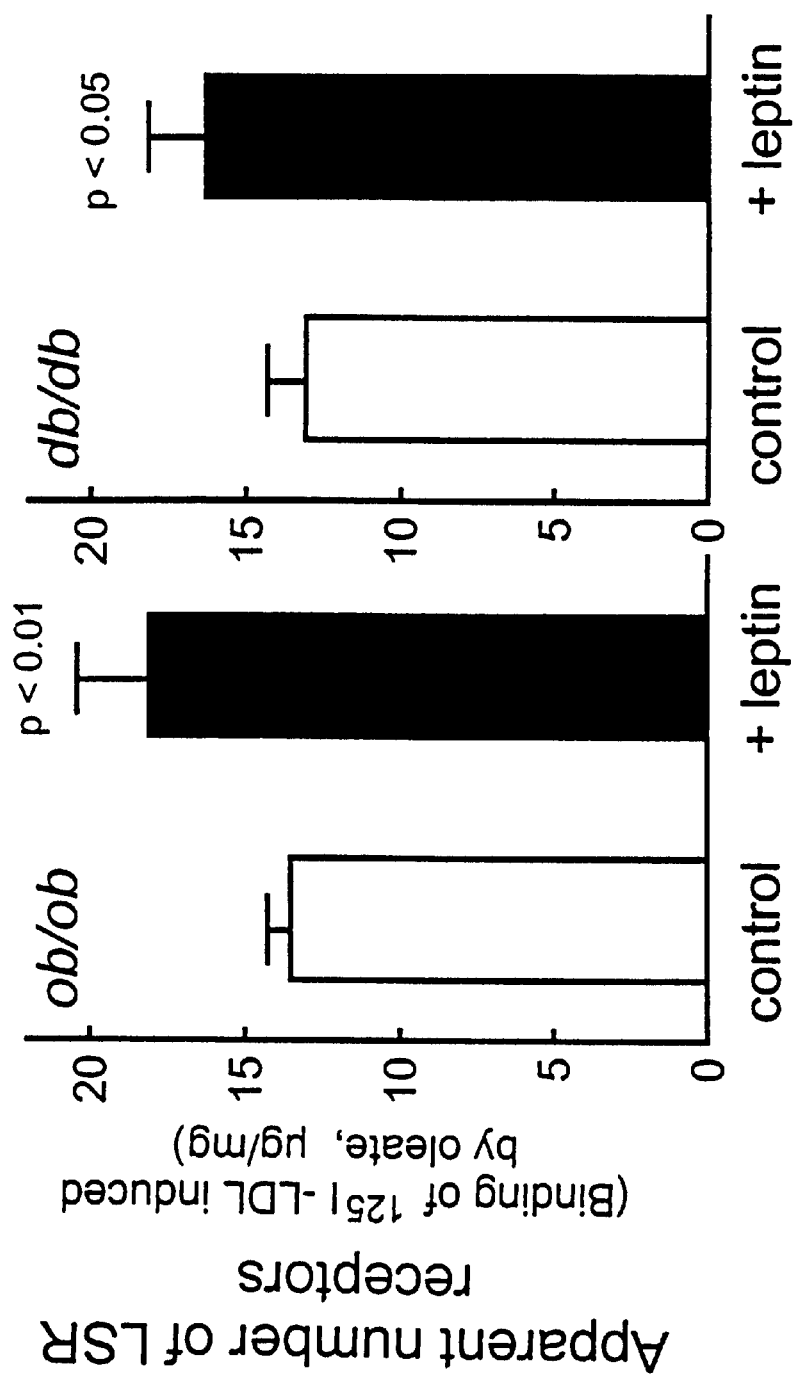
Figure 30:
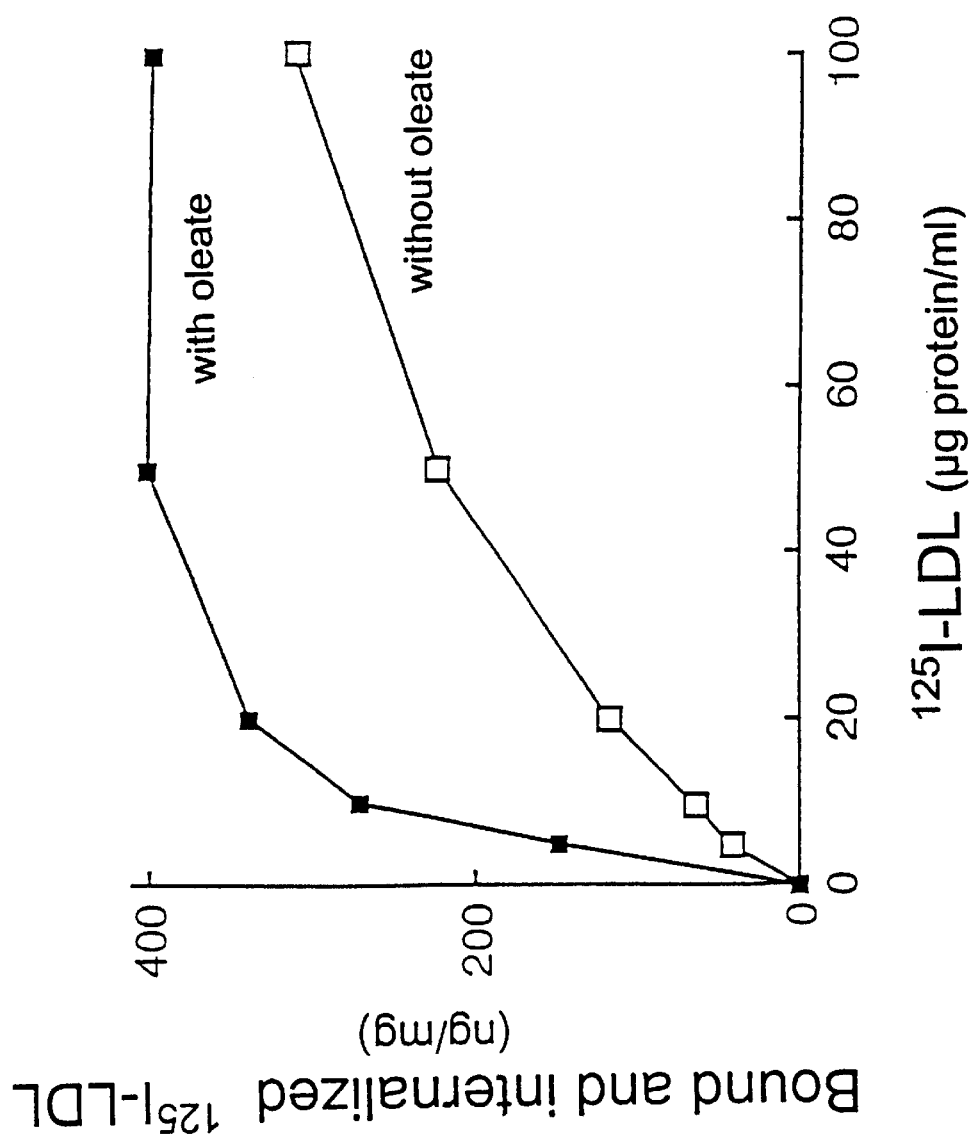
Figure 31:
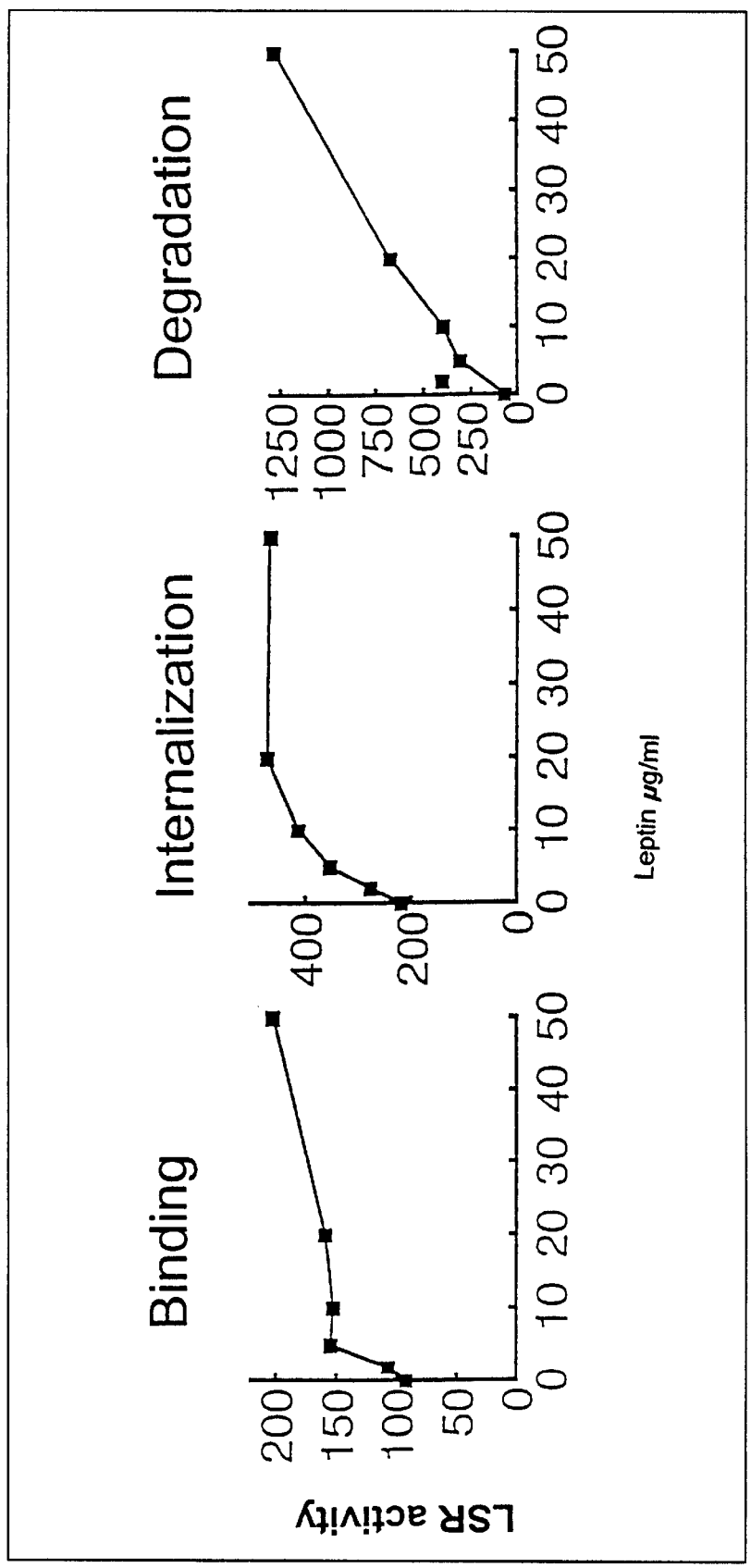
Figure 32:
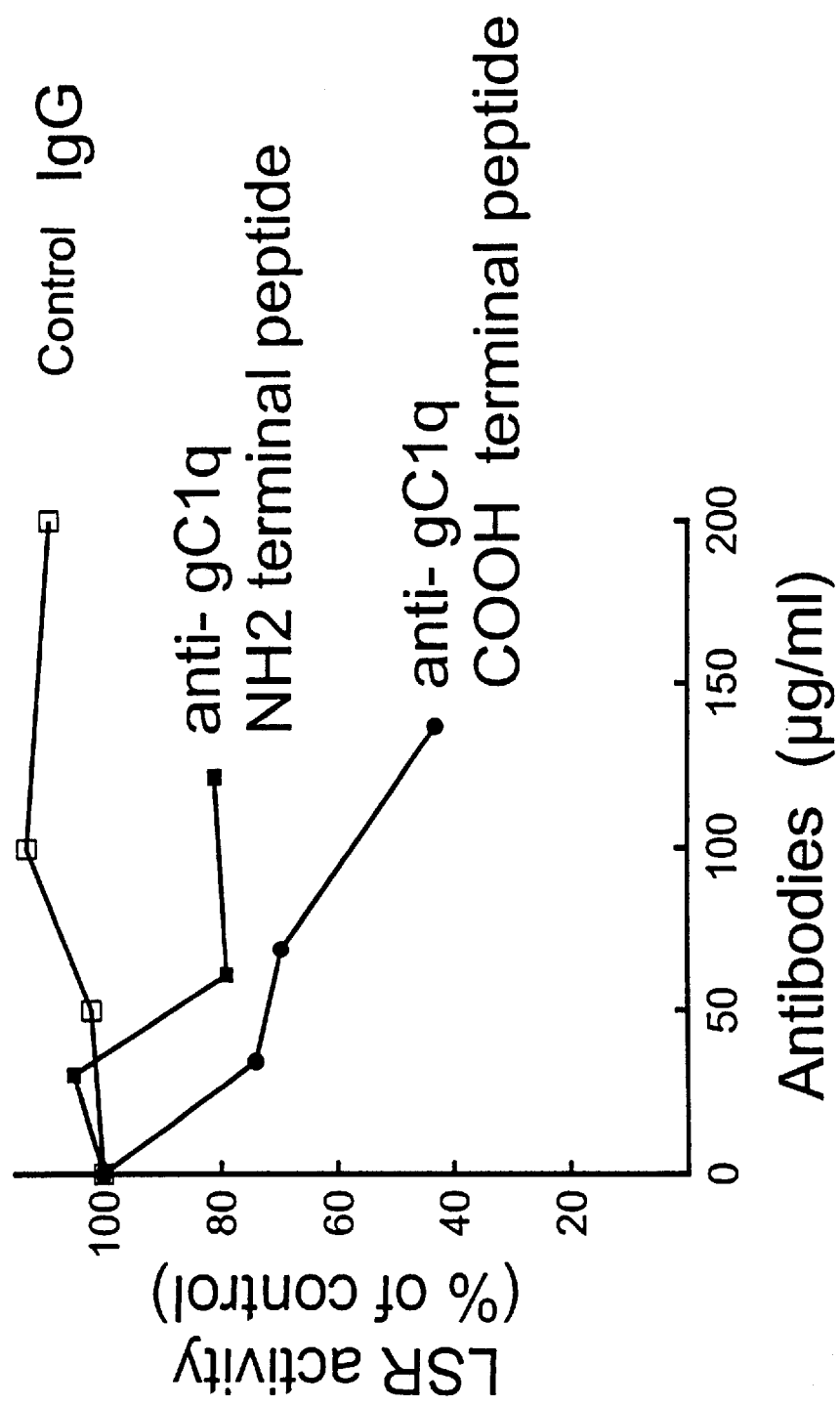
Figure 33:
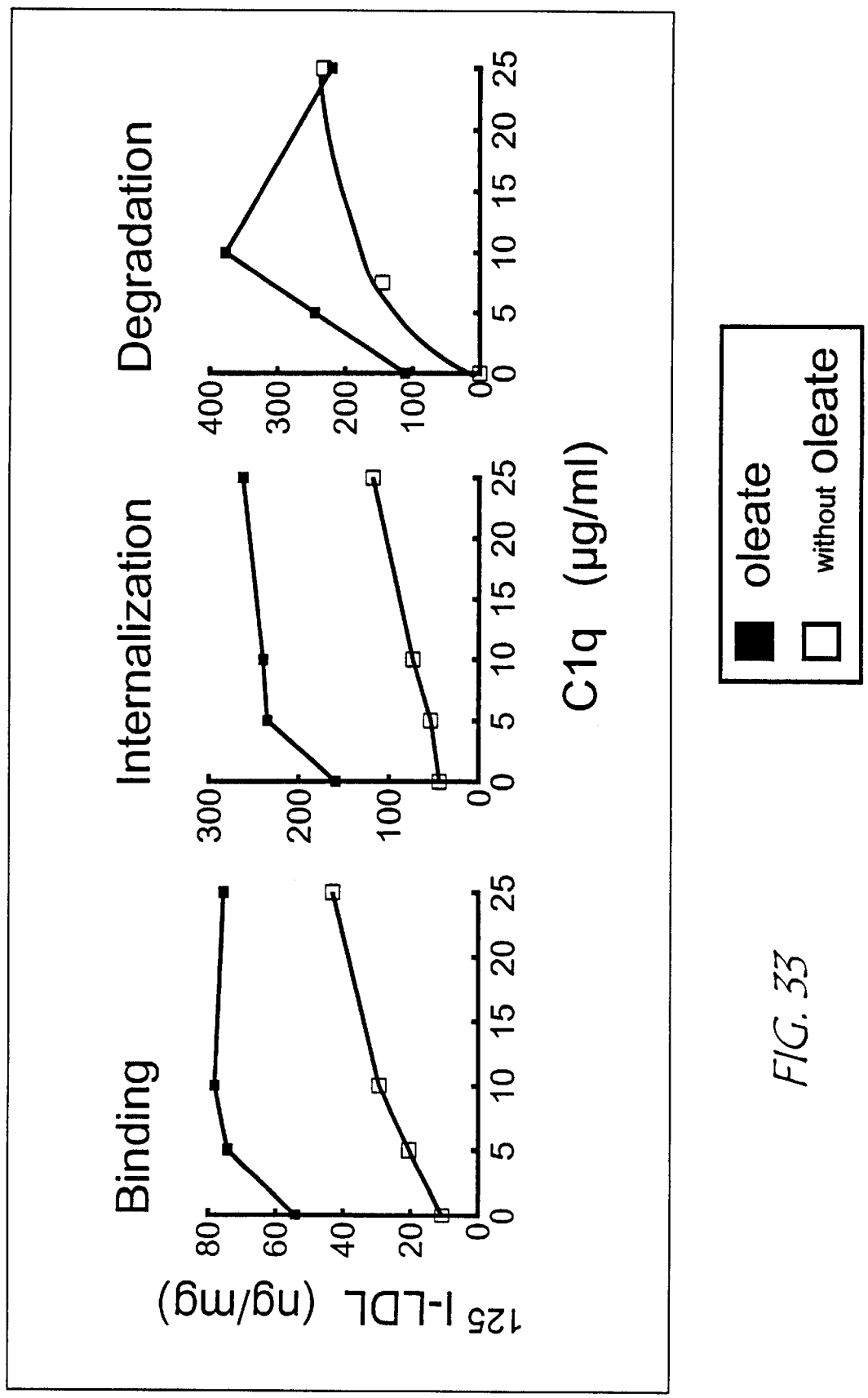
Figure 34:
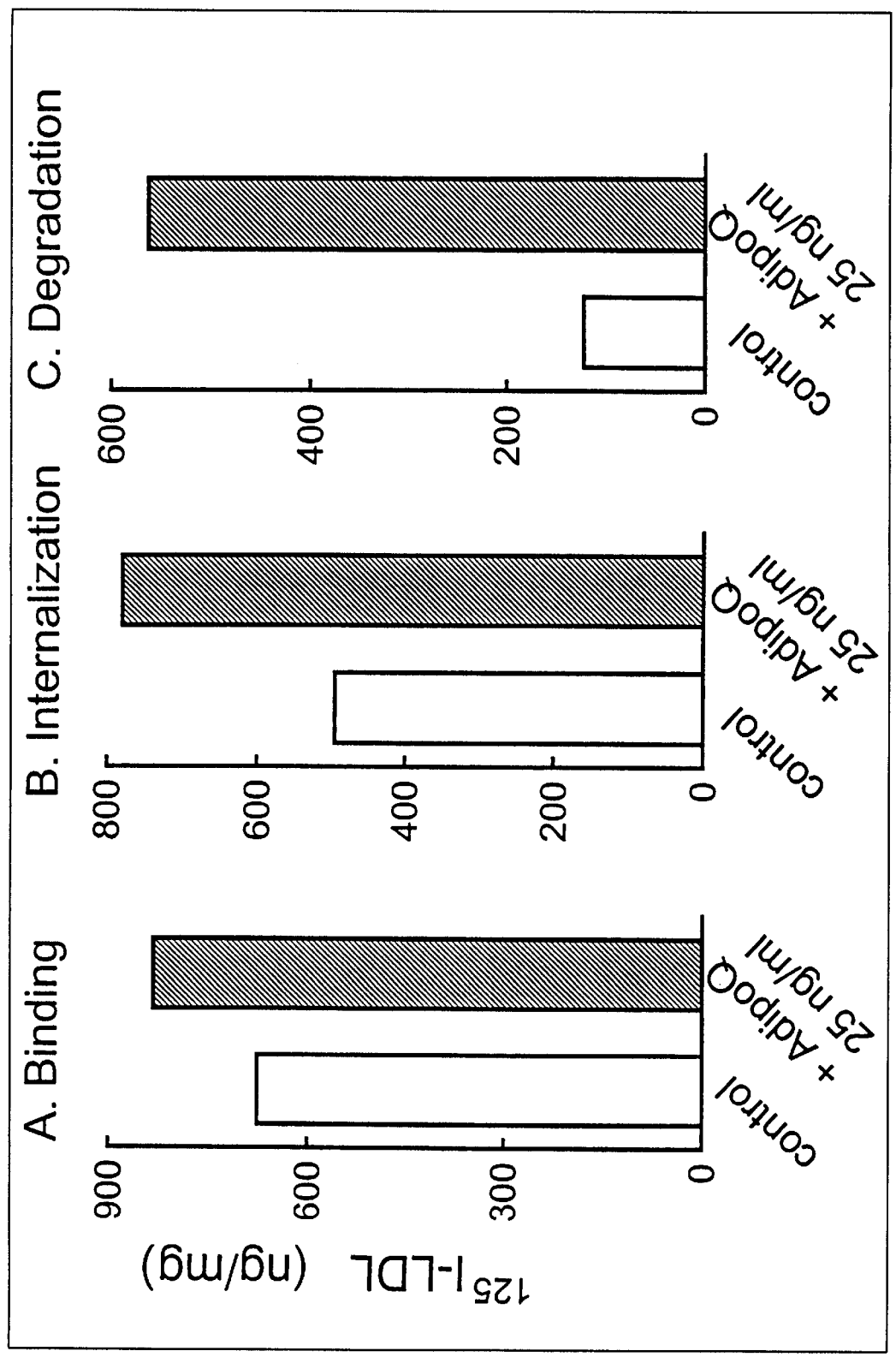
FIG. 34 shows that the compound AdipoQ modulates the LSR activity in the presence of oleate. Indeed, at the concentration of 25 ng/ml, it increases the LSR activity.
Figure 35:
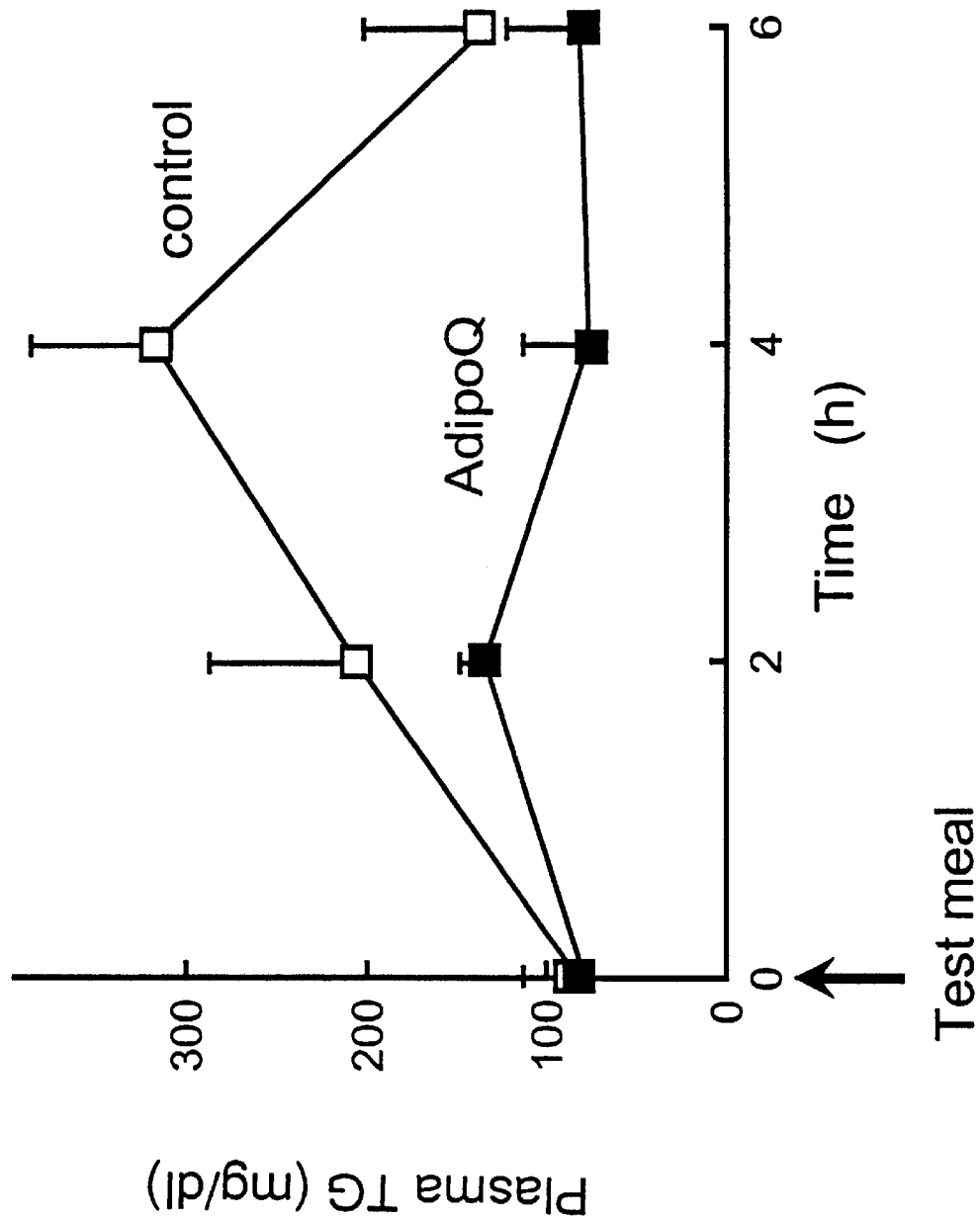
FIG. 35 shows that the administration of AdipoQ makes it possible to massively reduce the postprandial lipemic response.
Figure 36:
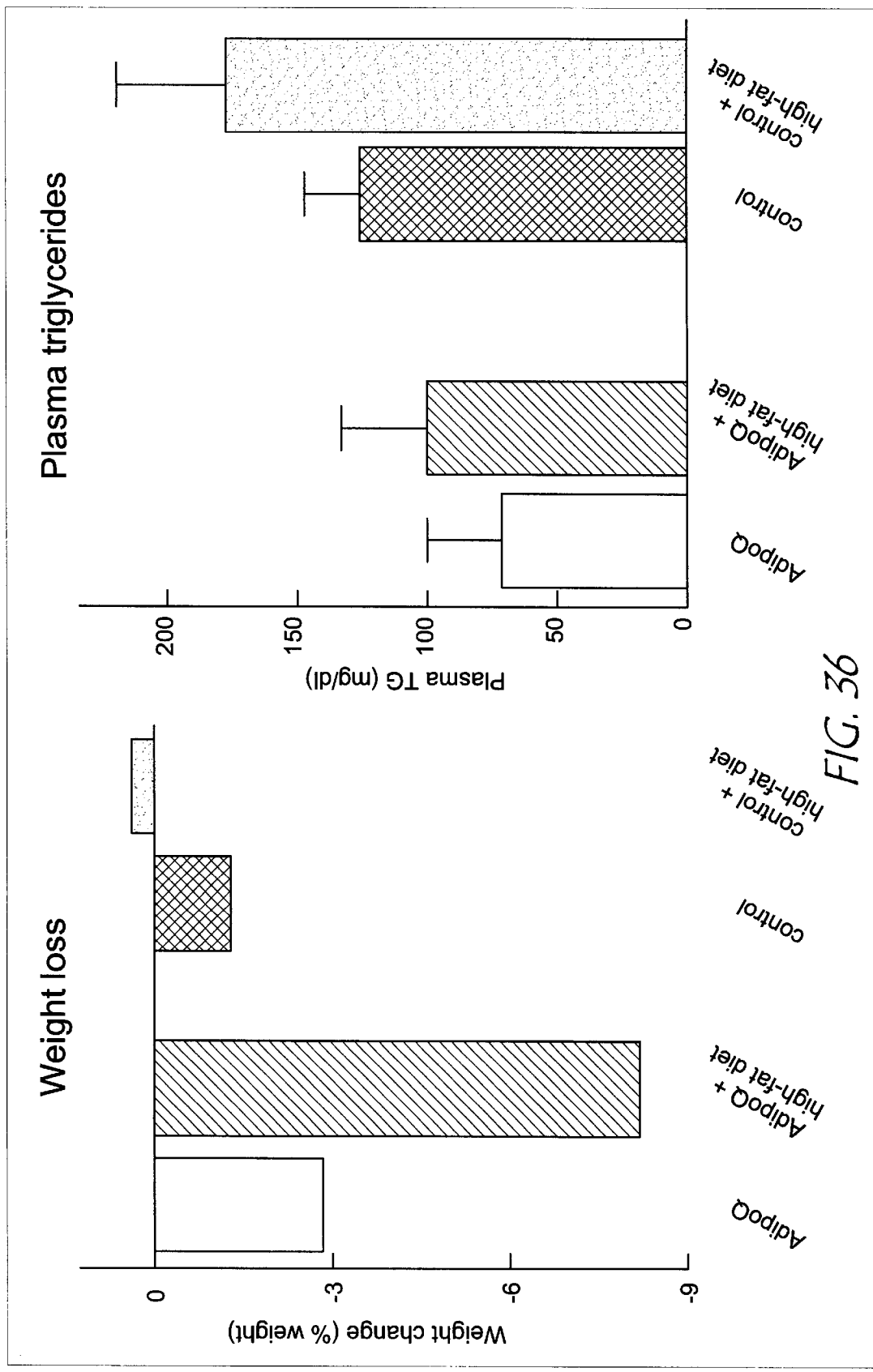
FIG. 36 shows that a 3-day ip infusion treatment with AdipoQ causes a loss in weight which is much greater when the rat is subjected to a fatty diet. Furthermore, the inventors observed that the level of plasma triglycerides is reduced in the animals treated with AdipoQ.
Figure 37:
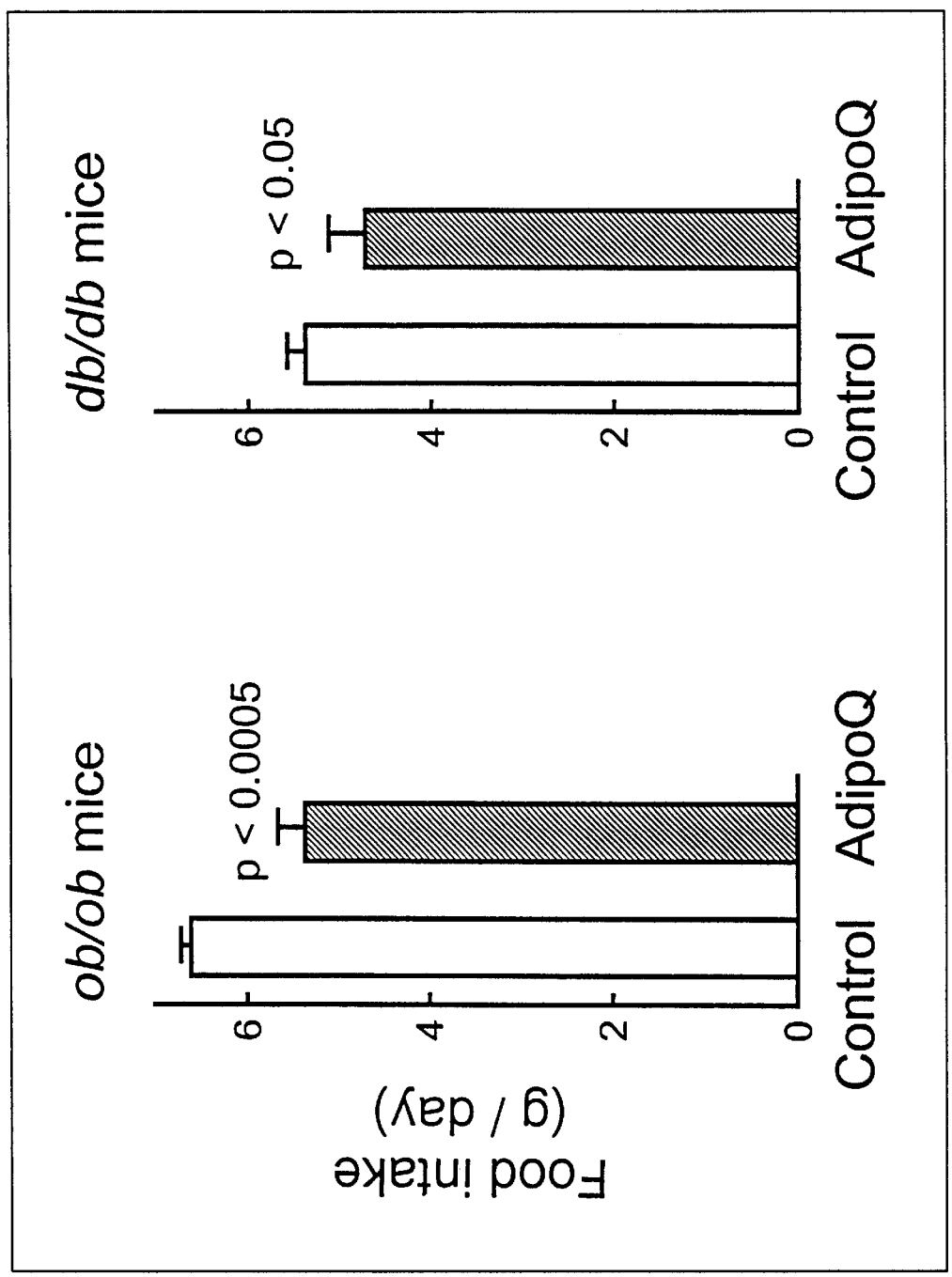
FIG. 37 shows that an injection of AdipoQ reduces the food intake in obese animals.

The increase in the LSR activity induced by 25 ng/ml of AdipoQ can explain the reduction in the postprandial lipemic response and the weight loss.

Thus, the AdipoQ protein is a very valuable compound which could be used in particular in the treatment of obesity. The selection of this protein as a candidate molecule in the treatment of obesity validates the parameters for screening a compound of interest modulating the LSR activity, the most important parameter consisting in measuring the LSR activity.

REFERENCES

Aalto-Setälä, K., Fisher, E. A., Chen, X., Chajek-shaul, T., Hayek, T., Zechner, R., Walsh, A., Ramakrishnan, R., Ginsberg, H. N., and Breslow, J. L. *J. Clin. Invest.* 90: 1889–1900, 1992.

Banner, D. W., D'Arcy, A., Janes, W., Gentz, R., Schoenfeld, H.-J., Broger, C., Loetscher, H., and Lesslauer, W. *Cell* 73: 431–445, 1993.

Bartles, J. R., and Hubbard, A. L. *Methods Enzymol.* 191: 825–841, 1990.

Belcher, J. D., Hamilton, R. L., Brady, S. E., Hornick, C. A., Jaeckle, S., Schneider, W. J., and Havel, R. J. *Proc. Natl. Acad. Sci.* 84: 6785–6789, 1987.

Bihain, B. E., and Yen, F. T. *Biochemistry* 31: 4628–4636, 1992.

Bilheimer, D. W., Eisenberg, S., and Levy, R. I. *Biochim. Biophys. Acta* 260: 212–221, 1972.

Bodansky M., Principles of peptide synthesis, (1984).

Brendel, V., Bucher, P., Nourbakhsh, I., Blaisdell, B. E., and Karlin, S. *Proc. Natl. Acad. Sci. USA* 89: 2002–2006, 1992.

Buckholz, R. G. *Curr. Op. Biotechnology* 4: 538–542, 1993.

Busch et al. *J. Chromatogr.* 777 311–328 (1997)

Carter, B. J. *Curr. Op. Biotechnology* 3: 533–539, 1993.

Chen, W.-J., Goldstein, J.-L., and Brown, M. S. *J. Biol. Chem.* 263: 3116–3123, 1990.

Chen, H., Charlat, O., Targlia, L. A., et al. *Cell* 84: 491495, 1996.

Cherif D., Julier, C., Delattre, O., Derré, J., Lathrop, G. M., and Berger, R. *Proc. Natl. Acad. Sci. USA*. 87: 6639–6643, 1990.

Chumakov, I., Rigault, P., Guillou, S., Ougen, P., Billault, A., Guasconi, G., Gervy, P., Le Gall, I., Soularue, P., Grinas, P., et al. *Nature* 359: 380–386, 1992.

Chumakov, I. M., Rigault, P., Le Gall, I., et al. *Nature* 377: 175–183, 1995.

Compton, J. *Nature* 350: 91–92, 1991.

Cytokines and Their Receptors (Nicola, N. A., ed.). Oxford University Press, Oxford. 1996.

Davis, C. G., Lehrman, M. A., Russell, D. W., Anderson, R. G. W., Brown, M. S., and Goldstein, J. L. *Cell* 45: 15–24, 1986.

Edwards, C. P., and Aruffo, A. *Curr. Op. Biotechnology* 4: 558–563, 1993.

Elomaa, O., Kangas, M., Sahlberg, C., Tuukkanen, J., Sormunen, R., Liakka, A., Thesleff, I., Kraal, G., and Tryggvason, K. *Cell* 80 (4): 603–609, 1995.

Epstein, A. *Médecine/Sciences* 8: 902–911, 1992.

Fan, J. L., Mccormick, S. P. A., Krauss, R. M., Taylor, S., Quan, R., Taylor, J. M., and Young, S. G. *Arterioscler. Thromb. Vasc. Biol* 15: 1889–1899, 1995.

Goldstein, J. L., Basu, S. K., and Brown, M. S. *Methods Enzymol.* 98: 241–260, 1983.

Goldstein, J. L., Hobbs, H. H., Brown, M. S. Familial Hypercholesterolemia In The Metabolic and Molecular Bases of Inherited Disease, Volume II, 7th Edition (Scriver, C. R., Beaudet, A. L., Sly, W. S., Valle, D., ed). Mc Graw-Hill, New-York. pp.1981–2030, 1995.

Guatelli J. C. et al. *Proc. Natl. Acad. Sci. USA* 87: 1874–1878, 1990.

Gura T. *Science* 275: 751–753, 1997.

Heldin, C. H. *Cell* 80: 213–223, 1995.

Herz, J., Hamann, U., Rogne, S., Myklebost, O., Gausepohl, H., and Stanley, K. K. *EMBO J.* 7: 41194127, 1988.

Herz, J., Qiu, S.-Q., Oesterle, A., DeSilva, H. V., Shafi, S., and Havel, R. J. *Proc. Natl. Acad. Sci. USA* 92: 46114615, 1995.

Homanics, G. E., de Silva, H. V., Osada, J., Zhang, S. H., Wong, H., Borensztajn, J., and Maeda, N. *J. Biol. Chem.* 270: 2974–2980, 1995.

Honoré, B., Madsen, P., Rasmussen, H. H., Vandekerckhove, J., Celis, J.E., and Leffers, H. *Gene* 134: 283–287, 1993.

Huang, Y. D., Schwendner, S. W., Rall, S. C., and Mahley, R. W. *J. Biol Chem.* 271: 29146–29151, 1995.

Huynh, T. U., Young R. A. and Davis R. W. DNA cloning techniques: A practical approach, ed Glover D. (IRL Press, Oxford), 1984.

Iida, M., Murakami, T., Ishida, K., Mizuno, A., Kuwajima, M., and Shima, K. *Biochem. Biophys. Res. Commun.* 224: 597–604, 1996.

Ishibashi, S., Brown, M. S., Goldstein, J. L., Gerard, R. D., Hammer, R. E., and Herz, J. *J. Clin. Invest.* 92: 883–893, 1993.

Ito, Y., Azrolan, N., O'Connell, A., Walsh, A., and Breslow, J. L. *Science* 249: 790–793, 1990.

Kleyn, P. W., Fan, W., Kovats, S. G., et al. *Cell* 85: 281–290, 1996.

Kobayashi, J., Applebaum-Bowden, D., Dugi, K. A., Brown, D. R., Kashyap, V. S., Parrott, C., Duarte, C., Maeda, N., and Santamarina-Fojo, S. *J. Biol. Chem.* 271: 26296–26301, 1996.

Köhler et Milstein. *Nature* 256, 495497, 1975.

Kosak M. *Nucleic Acids Res.* 15: 8125–8148, 1987.

Kosak M. *Proc. Natl. Acad. Sci USA* 87: 8301–8305, 1990.

Krainer, A. R., Mayeda, A., Kozak, D., and Binns, G. *Cell* 66: 383–394, 1991.

Krieger, M., and Herz, J. *Ann. Rev. Biochem.* 63: 601–637, 1994.

Landegren U., Kaiser R., Sanders J. & Hood L. *Science* 241: 1077–1080, 1988.

Lee, M. G-S., Bihain, B. E., Russell, D. G., Deckelbaum, R. J., and Van Der Ploeg, L. H. T. *Molec. Cell. Biol.* 10: 4506–4517, 1990.

Letourneur, F., and Klausner, R. D. *Cell* 69: 1143–1157, 1992.

Lockhart et al. *Nature Biotechnology* 14: 1675–1680, 1996

Lu, D., Willard, D., Patel, I. R., et al. *Nature* 371: 799–802, 1994.

Luckow, V. A. *Curr. Op. Biotechnology* 4: 564–572, 1993.

Maeda, N., Li, H., Lee, D., Oliver, P., Quarfordt, S. H., and Osada, J. *J. Biol. Chem.* 269: 23610–23616, 1994.

Mann, C. J., Khallou, J., Chevreuil, O., Troussard, A. A., Guermani, L. M., Launay, K., Delplanque, B., Yen, F. T., and Bihain, B. E. *Biochemistry* 34: 10421–10431, 1995.

Manne, J., Argeson, A. C., Siracusa, L. D. *Proc. Natl. Acad. Sci. USA* 92: 4721–4724, 1995.

Montague, C. T., Farooqi, I. S., Whitehead, J. P., Soos, M. A., Rau, H., Wareham, N. J., Sewter, C. P., Digby, J. E., Mohammed, S. N., Hurst, J. A., Cheetham, C. H., Earley, A. R., Barnett, A. H., Prins, J. B., and O'Rahilly, S. O. *Nature* 387: 903–908, 1997.

No D., Yao T. P. and Evans R. M. *Proc. Natl. Acad. Sci. USA*, 93: 3346–3351, 1996.

Nobben-Trauth, K., Naggert, J. K., North, M. A., and Nishina, P. M. *Nature* 380: 534–538, 1996.

Olins, P. O., and Lee, S. C. *Curr. Op. Biotechnology* 4: 520–525, 1993.

Oukka, M., André, P., Turmel, P., Besnard, N., Angevin, V., Karlsson, L., Trans, P L., Charron, D., Bihain, B., Kosmatopoulos, K., Lotteau, V. *Eur. J. Immunol.* 27: 855–859, 1997.

Parra-Lopez, C. A., Lindner, R., Vidavsky, I., Gross, M., and Unanue, E. R. *J. Immunol.* 158: 2670–2679,1997.

Perricaudet, M., Stratford-Perricaudet, L. and Briand, P. *La Recherche* 23: 471–473, 1992.

Pietu et al. *Genome Research* 6:492–503, 1996

Plump, A. S., Smith, J. D., Hayek, T., Aalto-Setälä, K., Walsh, A., Verstuyft, J. G., Rubin, E. M., and Breslow, J. L. *Cell* 71: 343–353, 1992.

Purcellhuynh, D. A., Farese, R. V., Johnson, D. F., Flynn, L. M., Pierotti, V., Newland, D. L., Linton, M. F., Sanan, D. A., and Young, S. G. *J. Clin. Invest.* 95: 2246–2257, 1995.

Rohlmann, A., Gotthardt, M., Willnow, T. E., Hammer, R. E., and Herz, J. *Nature Biotech.* 14: 1562–1565, 1996.

Sambrook, J., Fritsch, E. F., and Maniatis, T. Molecular cloning: a laboratory manual. Sec. Ed. Cold Spring Harbor Lab., Cold Spring Harbor, N.Y.

Schena et al. *Science* 270:467–470, 1995

Simos, G., Georgatos, S. D. *FEBS Letters* 346: 225–228, 1994.

Sosnowski R G, et al., *Proc Natl Acad Sci U S A* 1997;94:1119–1123

Stewart J. M. et Yound J. D., solid phase peptides synthesis, Pierce Chem. Company, Rockford, 111, 2$^{nd}$ edit., (1984).

Suggs S. V., Wallace R. B., Hirose T., Kawashima E. H. and Itakura K. *PNAS* 78: 6613–6617, 1981.

Szabo A. et al. *Curr Opin Struct Biol* 5, 699–705 (1995)

Temin, H. M. Retrovirus vectors for gene transfer. In Kucherlapati R., ed. Gene Transfer, New York, Plenum Press, 149–187, 1986.

Troussard, A. A., Khallou, J., Mann, C. J., André, P., Strickland, D. K., Bihain, B. E., and Yen, F. T. *J. Biol. Chem.* 270: 17068–17071, 1995.

Verhey, K. J., and Birnbaum, M. J. *J. Biol. Chem.* 269: 2353–2356, 1994.

Walker G. T., Fraiser M. S., Schram J. L., Little M. C., Nadeau J. G., & Malinowski D. P. *Nucleic Acids Res.* 20: 1691–1696, 1992.

Wang et al. *Chromatographia*, 44 205–208 (1997)

West, D. B., Boozer, C. N., Moody, D. L., and Atkinson, R. L. *Am. J. Physiol.* 262: R1025–R1032, 1992.

Willow, T. E., Sheng, Z., Ishibashi, S., Herz, J. *Science*, 264: 1471–1474, 1994.

Woo S. L. C. *Methods Enzymol.* 68: 389, 1979.

Yen, F. T., Mann, C. J., Guermani, L. M., Hannouche, N. F., Hubert, N., Hornick, C. A., Bordeau, V., Agnani, G., and Bihain, B. E. *Biochemistry* 33: 1172–1180, 1994.

Young R. A. and Davis R. W. *PNAS* 80: 1194–1198, 1983a.

Young R. A. and Davis R. W. *Science* 222: 778–782, 1983b.

Zhang, S. H., Reddick, R. L., Piedrahit, J. A., and Maeda, N. *Science* 258: 468471, 1992.

Zhang, Y., Proenca, R., Maffei, M., Barone, M., Leopold, L., Friedman, J. M. *Nature*, 372: 4425–4432, 1994.

Zhong, G., Romagnoli, P., and Germain, R. N. *J. Exp. Med.* 185: 429438, 1997.

---

What is claimed is:

1. A purified or recombinant Lipolysis Stimulated Receptor, wherein said receptor comprises a polypeptide comprising the amino acid sequence of SEQ ID NO:12.

2. The Lipolysis Stimulated Receptor of claim 1, wherein said polypeptide consists of ammino acid sequence of SEQ ID NO:12.

3. A recombinant cell expressing the recombinant Lipolysis Stimulated Receptor of claim 1.

4. A method for selecting a compound useful for enhancing lipoprotein uptake in cells comprising the steps:
   a) contacting the recombinant cell of claim 3 with a candidate compound in the presence of a lipoprotein; and
   b) determining whether the amount of internalized lipoprotein is greater in the presence of said compound has in the absence of said compound, wherein a determination that said amount of internalized lipoprotein is greater in the presence of said compound indicates that said compound is useful for enhancing lipoprotein uptake in cells.

5. The method of claim 4, wherein said candidate compound is a small molecule.

6. A purified or recombinant Lipolysis Stimulated Receptor, wherein said receptor comprises a biologically active polypeptide comprising an amino acid sequence selected from the group consisting of:
   a) an amino acid sequence spanning amino acids 76 to 545 of SEQ ID NO:12;
   b) an amino acid sequence spanning amino acids 76 to 160 of SEQ ID NO:12;
   c) an amino acid sequence spanning amino acids 76 to 237 of SEQ ID NO:12;
   d) an amino acid sequence spanning amino acids 157 to 462 of SEQ ID NO:12;
   e) an amino acid sequence spanning amino acids 236 to 462 of SEQ ID NO:12; and
   f) an amino acid sequence spanning amino acids 236 to 545 of SEQ ID NO:12.

7. The Lipolysis Stimulated Receptor of claim 6, wherein said biologically active polypeptide comprises an amino acid sequence spanning amino acids 76 to 545 of SEQ ID NO:12.

8. The Lipolysis Stimulated Receptor of claim 6, wherein said biologically active polypeptide comprises an amino acid sequence spanning amino acids 76 to 160 of SEQ ID NO:12.

9. The Lipolysis Stimulated Receptor of claim 6, wherein said biologically active polypeptide comprises an amino acid sequence spanning amino acids 76 to 237 of SEQ ID NO:12.

10. The Lipolysis Stimulated Receptor of claim 6, wherein said biologically active polypeptide comprises an amino acid sequence spanning amino acids 157 to 462 of SEQ ID NO:12.

11. The Lipolysis Stimulated Receptor of claim 6, wherein said biologically active polypeptide comprises an amino acid sequence spanning amino acids 236 to 462 of SEQ ID NO:12.

12. The Lipolysis Stimulated Receptor of claim 6, wherein said biologically active polypeptide comprises an amino acid sequence spanning amino acids 236 to 545 of SEQ ID NO:12.

13. A recombinant cell expressing the recombinant Lipolysis Stimulated Receptor of claim 6.

14. A method for selecting a compound useful for enhancing lipoprotein uptake in cells comprising the steps:
   a) contacting the recombinant cell of claim 13 with a candidate compound in the presence of a lipoprotein; and
   b) determining whether the amount of internalized lipoprotein is greater in the presence of said compound than in the absence of said compound, wherein a determination that said amount of internalized lipoprotein is greater in the presence of said compound indicates that said compound is useful for enhancing lipoprotein uptake in cells.

15. The method of claim 14, wherein said candidate compound is a small molecule.

16. A recombinant polypeptide comprising the amino acid sequence of SEQ ID NO:12.

17. The polypeptide of claim 16, wherein said polypeptide consists of SEQ ID NO:12.

18. A recombinant cell expressing the recombinant polypeptide of claim 16.

19. A method for selecting a compound useful for enhancing lipoprotein uptake in cells, comprising the steps of:
   a) contacting the recombinant cell of claim 18 with a candidate compound in the presence of a lipoprotein; and
   b) determining whether the amount of internalized lipoprotein is greater in the presence of said compound than in the absence of said compound wherein a determination that said amount of internalized lipoprotein is greater in the presence of said compound.

20. The method of claim 19, wherein said candidate compound is a small molecule.

21. The polypeptide of claim 16, wherein said polypeptide combines with one or more heterologous polypeptides to form an LSR receptor complex, and wherein said complex comprises an α subunit or an α' subunit, and at least one β subunit.

22. The polypeptide of claim 21, wherein said complex comprises three β subunits.

23. The polypeptide of claim 21, wherein said polypeptide is from a human, and wherein said polypeptide has a molecular weight of 64 kD.

24. The polypeptide of claim 21, wherein said polypeptide is expressed in hepatic cells.

25. The polypeptide of claim 21, wherein said complex has a biological activity selected from the group consisting of lipoprotein binding, lipoprotein internalization, and lipoprotein degradation.

26. The polypeptide of claim 21, wherein said complex has a biological activity that is selected from the group consisting of leptin binding, leptin internalization, and leptin degradation.

27. A composition comprising the polypeptide of claim 16.

28. The composition of claim 27, further comprising a physiologically acceptable carrier.

29. A method of making the polypeptide of claim 16 comprising the steps of:
   a) obtaining a cell capable of expressing said polypeptide;
   b) growing said cells under conditions suitable to produce said polypeptide; and
   c) isolating said polypeptide produced by said cell.

30. The method of claim 29, wherein said cell is prokaryotic.

31. The method of claim 29, wherein said cell is eukaryotic.

32. The method of claim 29, wherein said cell is recombinant for polynucleotide encoding said polypeptide.

33. The method of claim 29, further comprising purifying said polypeptide produced by said cell.

34. An isolated or recombinant biologically active polypeptide comprising an amino acid sequence selected from the group consisting of:

a) an amino acid sequence spanning amino acids 76 to 545 of SEQ ID NO:12;

b) an amino acid sequence spanning amino acids 76 to 160 of SEQ ID NO:12;

c) an amino acid sequence spanning amino acids 76 to 237 of SEQ ID NO:12;

d) an amino acid sequence spanning amino acids 157 to 462 of SEQ ID NO:12;

e) an amino acid sequence spanning amino acids 236 to 462 of SEQ ID NO:12; and f) an amino acid sequence spanning amino acids 236 to 545 of SEQ ID NO:12.

35. The isolated or recombinant biologically active polypeptide of claim 34, wherein said biologically active polypeptide comprises an amino acid sequence spanning amino acids 76 to 545 of SEQ ID NO:12.

36. The isolated or recombinant biologically active polypeptide of claim 34, wherein said biologically active polypeptide comprises an amino acid sequence spanning amino acids 76 to 160 of SEQ ID NO:12.

37. The isolated or recombinant biologically active polypeptide of claim 34, wherein said biologically active polypeptide comprises an amino acid sequence spanning amino acids 76 to 237 of SEQ ID NO:12.

38. The isolated or recombinant biologically active polypeptide of claim 34, wherein said biologically active polypeptide comprises an amino acid sequence spanning amino acids 157 to 462 of SEQ ID NO:12.

39. The isolated or recombinant biologically active polypeptide of claim 34, wherein said biologically active polypeptide comprises an amino acid sequence spanning amino acids 236 to 462 of SEQ ID NO:12.

40. The isolated or recombinant biologically active polypeptide of claim 34, wherein said biologically active polypeptide comprises an amino acid sequence spanning amino acids 236 to 545 of SEQ ID NO:12.

41. A recombinant cell expressing the recombinant polypeptide of claim 34.

42. A method for selecting a compound useful for enhancing lipoprotein uptake in cells, comprising the steps of:

a) contacting the recombinant cell of claim 41 with a candidate compound in the presence of a lipoprotein; and b) determining whether the amount of internalized lipoprotein is greater in the presence of said compound than in the absence of said compound wherein a determination that said amount of internalized lipoprotein is greater in the presence of said compound.

43. The method of claim 42, wherein said candidate compound is a small molecule.

44. The polypeptide of claim 34, wherein said polypeptide combines with one or more heterologous polypeptides to form an LSR receptor complex, and wherein said complex comprises an $\alpha$ subunit or an $\alpha'$ subunit, and at least one $\beta$ subunit.

45. The polypeptide of claim 44, wherein said complex comprises three $\beta$ subunits.

46. The polypeptide of claim 44, wherein said polypeptide is from a human, and wherein said polypeptide has a molecular weight of 64 kD.

47. The polypeptide of claim 44, wherein said polypeptide is expressed in hepatic cells.

48. The polypeptide of claim 44, wherein said complex has a biological activity selected from the group consisting of lipoprotein binding, lipoprotein internalization, and lipoprotein degradation.

49. The polypeptide of claim 44, wherein said complex has a biological activity that is selected from the group consisting of leptin binding, leptin internalization, and leptin degradation.

50. The polypeptide of claim 34, wherein said polypeptide is recombinant.

51. A composition comprising the polypeptide of claim 34.

52. The composition of claim 51, further comprising a physiologically acceptable carrier.

53. A method of making the polypeptide of claim 34 comprising the steps of:

a) obtaining a cell capable of expressing said polypeptide;

b) growing said cells under conditions suitable to produce said polypeptide; and c) isolating said polypeptide produced by said cell.

54. The method of claim 53, wherein said cell is prokaryotic.

55. The method of claim 53, wherein said cell is eukaryotic.

56. The method of claim 53, wherein said cell is recombinant for polynucleotide encoding said polypeptide.

57. The method of claim 53, further comprising purifying said polypeptide produced by said cell.

\* \* \* \* \*

UNITED STATES PATENT AND TRADEMARK OFFICE
CERTIFICATE OF CORRECTION

PATENT NO.    : 6,635,431 B1
DATED         : October 21, 2003
INVENTOR(S)   : Bernard Bihain, Lydie Bougueleret and Frances Yen-Potin It is certified that error appears in the above-identified patent and that said Letters Patent is hereby corrected as shown below:

Column 4,
Line 2, "three, subunits" should read -- three, β subunits --.
Line 12, "an α subunit" should read -- an α' subunit --.

Column 9,
Line 26, "the a subunit" should read -- the α subunit --.

Column 13,
Line 57, "a sequence" should read -- α sequence --.
Line 60, "subunit a encoded" should read -- subunits α encoded --.

Column 15,
Line 1, "the a subunit" should read -- the α subunit --.
Line 9, "rat LSR a are" should read -- rat LSR α are --.
Line 10, "human LSR a sequence" should read -- human LSR α sequence --.
Lines 10 and 11, "murine LSR a" should read -- murine LSR α --.

Column 21,
Line 12, "the a subunit" should read -- the α subunit --.

Column 33,
Line 57, "the lad gene" should read -- the lacI gene --.

Column 36,
Line 15, "more than consecutive" should read -- more than 30 consecutive --.

Column 41,
Line 36, "LSR (1srl.Hs;" should read -- LSR (1sr1.HS; --.
Line 37, "LSR (1srl .Rn;" should read -- LSR (1sr1 .Rn; --.
Line 38, "(1srl.Mm;" should read -- (1sr1.Mm; --.

Column 43,
Line 2, "concentration of β" should read -- concentration of α --.

Column 45,
Lines 7-8, "The mice C57BU6J of the wild type, C57BU6J ob/ob, C57BUKs of the wild type and C57BUKs" should read -- The mice C57BL/6J of the wild type, C57BL/6J ob/ob, C57BL/Ks of the wild type and C57BL/Ks --.

UNITED STATES PATENT AND TRADEMARK OFFICE
CERTIFICATE OF CORRECTION

PATENT NO. : 6,635,431 B1
DATED : October 21, 2003
INVENTOR(S) : Bernard Bihain, Lydie Bougueleret and Frances Yen-Potin It is certified that error appears in the above-identified patent and that said Letters Patent is hereby corrected as shown below:

<u>Column 46,</u>
Line 7, "5°" should read -- 5' --.

<u>Column 51,</u>
Line 44, "corresporid" should read -- correspond --.
Line 45, "β and β subunits" should read -- α and β subunits --.

<u>Column 52,</u>
Line 45, "68 kDa these" should read -- 68 kDa; these --.

<u>Column 53,</u>
Line 52, "$^{121}$I-LDL" should read -- $^{125}$I-LDL --.

<u>Column 55,</u>
Line 25, "pH 8.50 $\mu$l" should read -- pH 8. 50 $\mu$l --.
Line 37, "the a subunit" should read -- the α subunit --.

<u>Column 57,</u>
Line 39, "Coichicine" should read -- Colchicine --.
Line 41, "above after incubation" should read -- above; after incubation --.

<u>Column 59,</u>
Line 23, "membranes Sigma kit)." should read -- membranes; Sigma kit). --.

<u>Column 61,</u>
Line 51, "1995 the clones" should read -- 1995; the clones --.

<u>Column 63,</u>
Line 11, "this y subunit' should read -- this γ subunit --.

<u>Column 67,</u>
Line 32, "491495" should read -- 491-495 --.

<u>Column 68,</u>
Line 4, "41194127" should read -- 4119-4127 --.
Line 7, "46114615" should read -- 4611-4615 --.
Line 16, "1995" should read -- 1996 --.
Line 36, "495497" should read -- 495-497 --.

UNITED STATES PATENT AND TRADEMARK OFFICE
CERTIFICATE OF CORRECTION

PATENT NO. : 6,635,431 B1
DATED : October 21, 2003
INVENTOR(S) : Bernard Bihain, Lydie Bougueleret and Frances Yen-Potin It is certified that error appears in the above-identified patent and that said Letters Patent is hereby corrected as shown below:

Column 70,
Line 34, "486471" should read -- 468-471 --.
Line 38, "429438" should read -- 429-438 --.

Column 183,
Line 6, "consists of ammino" should read -- consists of the amino --.
Line 16, "said compound has" should read -- said compound than --.

Signed and Sealed this

Ninth Day of March, 2004

JON W. DUDAS
*Acting Director of the United States Patent and Trademark Office*

SEQUENCE LISTING

<160> NUMBER OF SEQ ID NOS: 41

<210> SEQ ID NO 1
<211> LENGTH: 2097
<212> TYPE: DNA
<213> ORGANISM: Rattus norvegicus

<400> SEQUENCE: 1

```
accgctcacc aggtcagttg tccccggaaa gccgaaggca tgagcttcgc ccaagttctt      60 tttatggggtt agaactcctc cagagcgggg gaaaaaggac ttggaatagg ggcgggacgg    120
agcacgcacc cttctccgcc ttggttctcg ccgcgccccc tactctcggg atacttggga    180
ggggacgcgc gggcaccgtc gctgctagac ggccgcg atg gcg ccg gcg gcc ggc     235
                                         Met Ala Pro Ala Ala Gly
                                           1               5 gcg tgt gct ggg gcg cct gac tcc cac cca gct acc gtg gtc ttc gtg      283
Ala Cys Ala Gly Ala Pro Asp Ser His Pro Ala Thr Val Val Phe Val
         10                  15                  20 tgt ctc ttt ctc atc att ttc tgc cca gac cct gcc agt gcc atc cag      331
Cys Leu Phe Leu Ile Ile Phe Cys Pro Asp Pro Ala Ser Ala Ile Gln
     25                  30                  35 gtg act gtg tct gac ccc tac cac gta gtg atc ctg ttc cag cca gtg      379
```

-continued

```
Val Thr Val Ser Asp Pro Tyr His Val Val Ile Leu Phe Gln Pro Val
            40                  45                  50 acc ctg ccc tgc acc tat cag atg agc aac act ctc aca gtc ccc atc        427
Thr Leu Pro Cys Thr Tyr Gln Met Ser Asn Thr Leu Thr Val Pro Ile
 55                  60                  65                  70 gtg atc tgg aag tac aag tca ttc tgc cgg gac cgt att gcc gat gcc        475
Val Ile Trp Lys Tyr Lys Ser Phe Cys Arg Asp Arg Ile Ala Asp Ala
                 75                  80                  85 ttc tct cct gcc agt gtg gac aac cag cta aat gcc cag ttg gca gct        523
Phe Ser Pro Ala Ser Val Asp Asn Gln Leu Asn Ala Gln Leu Ala Ala
                     90                  95                 100 ggc aac ccc ggc tac aac ccc tat gtg gag tgc cag gac agt gta cgc        571
Gly Asn Pro Gly Tyr Asn Pro Tyr Val Glu Cys Gln Asp Ser Val Arg
                    105                 110                 115 act gtc agg gtg gtg gcc acc aaa cag ggc aat gcg gtg acc ctg gga        619
Thr Val Arg Val Val Ala Thr Lys Gln Gly Asn Ala Val Thr Leu Gly
            120                 125                 130 gac tac tac caa ggc agg agg atc acc ata aca gga aat gct gac ctg        667
Asp Tyr Tyr Gln Gly Arg Arg Ile Thr Ile Thr Gly Asn Ala Asp Leu
135                 140                 145                 150 acc ttc gag cag aca gcc tgg gga gac agt gga gtg tat tac tgc tct        715
Thr Phe Glu Gln Thr Ala Trp Gly Asp Ser Gly Val Tyr Tyr Cys Ser
                    155                 160                 165 gtg gtc tcg gcc caa gat ctg gat gga aac aac gag gcg tac gca gag        763
Val Val Ser Ala Gln Asp Leu Asp Gly Asn Asn Glu Ala Tyr Ala Glu
                170                 175                 180 ctc atc gtc ctt ggc agg acc tca gag gcc cct gag ctc cta cct ggt        811
Leu Ile Val Leu Gly Arg Thr Ser Glu Ala Pro Glu Leu Leu Pro Gly
            185                 190                 195 ttt cgg gcg ggg ccc ttg gaa gat tgg ctc ttt gtg gtc gtg gtc tgc        859
Phe Arg Ala Gly Pro Leu Glu Asp Trp Leu Phe Val Val Val Val Cys
200                 205                 210 ctg gcg agc ctc ctc ctc ttc ctc ctc ctg ggc atc tgc tgg tgc cag        907
Leu Ala Ser Leu Leu Leu Phe Leu Leu Leu Gly Ile Cys Trp Cys Gln
215                 220                 225                 230 tgc tgt cct cac acc tgc tgc tgt tat gtc cga tgt ccc tgc tgc cca        955
Cys Cys Pro His Thr Cys Cys Cys Tyr Val Arg Cys Pro Cys Cys Pro
                    235                 240                 245 gac aag tgc tgt tgc cct gag gct ctt tat gct gct ggc aaa gca gcc       1003
Asp Lys Cys Cys Cys Pro Glu Ala Leu Tyr Ala Ala Gly Lys Ala Ala
                250                 255                 260 acc tca ggt gtc ccg agc atc tat gcc ccc agc atc tat acc cac ctc       1051
Thr Ser Gly Val Pro Ser Ile Tyr Ala Pro Ser Ile Tyr Thr His Leu
            265                 270                 275 tca cct gcc aag acc cca cca cct ccg cct gcc atg att ccc atg ggc       1099
Ser Pro Ala Lys Thr Pro Pro Pro Pro Ala Met Ile Pro Met Gly
280                 285                 290 cct ccc tat ggg tac cct gga gac ttt gac aga cat agc tca gtt ggt       1147
Pro Pro Tyr Gly Tyr Pro Gly Asp Phe Asp Arg His Ser Ser Val Gly
295                 300                 305                 310 ggc cac agc tcc caa gta ccc ctg ctg cgt gac gtg gat ggc agt gta       1195
Gly His Ser Ser Gln Val Pro Leu Leu Arg Asp Val Asp Gly Ser Val
                    315                 320                 325 tct tca gaa gta cga agt ggc tac agg atc cag gct aac cag caa gat       1243
Ser Ser Glu Val Arg Ser Gly Tyr Arg Ile Gln Ala Asn Gln Gln Asp
                330                 335                 340 gac tcc atg agg gtc cta tac tat atg gag aaa gag cta gcc aac ttt       1291
Asp Ser Met Arg Val Leu Tyr Tyr Met Glu Lys Glu Leu Ala Asn Phe
            345                 350                 355
```

```
gac cct tcc cga cct ggc cct ccc aat ggc aga gtg gaa cgg gcc atg    1339
Asp Pro Ser Arg Pro Gly Pro Pro Asn Gly Arg Val Glu Arg Ala Met
    360                 365                 370 agt gaa gta acc tcc ctc cat gaa gat gac tgg cga tcg agg cct tcc    1387
Ser Glu Val Thr Ser Leu His Glu Asp Asp Trp Arg Ser Arg Pro Ser
375                 380                 385                 390 agg gct cct gcc ctc acc ccc atc agg gat gag gag tgg aat cgc cac    1435
Arg Ala Pro Ala Leu Thr Pro Ile Arg Asp Glu Glu Trp Asn Arg His
                395                 400                 405 tcc cca cag agt ccc aga aca tgg gag cag gaa ccc ctt caa gaa caa    1483
Ser Pro Gln Ser Pro Arg Thr Trp Glu Gln Glu Pro Leu Gln Glu Gln
            410                 415                 420 cca agg ggt ggt tgg ggg tct gga cgc cct cgg gcc cgc tct gtg gat    1531
Pro Arg Gly Gly Trp Gly Ser Gly Arg Pro Arg Ala Arg Ser Val Asp
        425                 430                 435 gct cta gat gat atc aac cgg cct ggc tcc act gaa tca gga cgg tct    1579
Ala Leu Asp Asp Ile Asn Arg Pro Gly Ser Thr Glu Ser Gly Arg Ser
    440                 445                 450 tct ccc cca agt agt gga cgg aga gga cgg gcc tat gca cct cca aga    1627
Ser Pro Pro Ser Ser Gly Arg Arg Gly Arg Ala Tyr Ala Pro Pro Arg
455                 460                 465                 470 agt cgc agc cgg gat gac ctc tat gac ccg gac gat cct agg gac ttg    1675
Ser Arg Ser Arg Asp Asp Leu Tyr Asp Pro Asp Asp Pro Arg Asp Leu
                475                 480                 485 cca cat tcc cga gat ccc cac tat tat gac gac atc agg tct aga gat    1723
Pro His Ser Arg Asp Pro His Tyr Tyr Asp Asp Ile Arg Ser Arg Asp
            490                 495                 500 cca cgt gct gac ccc aga tcc cgt cag cga tcc cga gat cct cgg gat    1771
Pro Arg Ala Asp Pro Arg Ser Arg Gln Arg Ser Arg Asp Pro Arg Asp
        505                 510                 515 gct ggc ttc agg tca agg gac cct cag tat gat ggg cga cta tta gaa    1819
Ala Gly Phe Arg Ser Arg Asp Pro Gln Tyr Asp Gly Arg Leu Leu Glu
    520                 525                 530 gag gct tta aag aaa aag ggg tcg ggc gag aga agg agg gtt tac agg    1867
Glu Ala Leu Lys Lys Lys Gly Ser Gly Glu Arg Arg Arg Val Tyr Arg
535                 540                 545                 550 gag gaa gaa gag gaa gag gag ggc caa tac ccc cca gca cct cca cct    1915
Glu Glu Glu Glu Glu Glu Glu Gly Gln Tyr Pro Pro Ala Pro Pro Pro
                555                 560                 565 tac tca gag act gac tcg cag gcc tca cgg gag agg agg ctg aaa aag    1963
Tyr Ser Glu Thr Asp Ser Gln Ala Ser Arg Glu Arg Arg Leu Lys Lys
            570                 575                 580 aat ttg gcc ctg agt cgg gaa agt tta gtc gtc tga tccacgtttt         2009
Asn Leu Ala Leu Ser Arg Glu Ser Leu Val Val *
        585                 590 gtatgtagct tttgtacttt tttttaatt ggaatcaata ttgatgaaac ttcaagccta   2069
ataaaatgtc taatcacaaa aaaaaaaa                                    2097

<210> SEQ ID NO 2
<211> LENGTH: 593
<212> TYPE: PRT
<213> ORGANISM: Rattus norvegicus

<400> SEQUENCE: 2

Met Ala Pro Ala Ala Gly Ala Cys Ala Gly Ala Pro Asp Ser His Pro
1               5                   10                  15

Ala Thr Val Val Phe Val Cys Leu Phe Leu Ile Ile Phe Cys Pro Asp
            20                  25                  30

Pro Ala Ser Ala Ile Gln Val Thr Val Ser Asp Pro Tyr His Val Val
```

-continued

```
                35                  40                  45
Ile Leu Phe Gln Pro Val Thr Leu Pro Cys Thr Tyr Gln Met Ser Asn
 50                  55                  60
Thr Leu Thr Val Pro Ile Val Ile Trp Lys Tyr Lys Ser Phe Cys Arg
 65                  70                  75                  80
Asp Arg Ile Ala Asp Ala Phe Ser Pro Ala Ser Val Asp Asn Gln Leu
                 85                  90                  95
Asn Ala Gln Leu Ala Ala Gly Asn Pro Gly Tyr Asn Pro Tyr Val Glu
                100                 105                 110
Cys Gln Asp Ser Val Arg Thr Val Arg Val Ala Thr Lys Gln Gly
                115                 120                 125
Asn Ala Val Thr Leu Gly Asp Tyr Tyr Gln Gly Arg Arg Ile Thr Ile
130                 135                 140
Thr Gly Asn Ala Asp Leu Thr Phe Glu Gln Thr Ala Trp Gly Asp Ser
145                 150                 155                 160
Gly Val Tyr Tyr Cys Ser Val Val Ser Ala Gln Asp Leu Asp Gly Asn
                165                 170                 175
Asn Glu Ala Tyr Ala Glu Leu Ile Val Leu Gly Arg Thr Ser Glu Ala
                180                 185                 190
Pro Glu Leu Leu Pro Gly Phe Arg Ala Gly Pro Leu Glu Asp Trp Leu
                195                 200                 205
Phe Val Val Val Cys Leu Ala Ser Leu Leu Phe Leu Leu Leu
                210                 215                 220
Gly Ile Cys Trp Cys Gln Cys Cys Pro His Thr Cys Cys Cys Tyr Val
225                 230                 235                 240
Arg Cys Pro Cys Cys Pro Asp Lys Cys Cys Cys Pro Glu Ala Leu Tyr
                245                 250                 255
Ala Ala Gly Lys Ala Ala Thr Ser Gly Val Pro Ser Ile Tyr Ala Pro
                260                 265                 270
Ser Ile Tyr Thr His Leu Ser Pro Ala Lys Thr Pro Pro Pro Pro
                275                 280                 285
Ala Met Ile Pro Met Gly Pro Tyr Gly Tyr Pro Gly Asp Phe Asp
                290                 295                 300
Arg His Ser Ser Val Gly Gly His Ser Ser Gln Val Pro Leu Leu Arg
305                 310                 315                 320
Asp Val Asp Gly Ser Val Ser Ser Glu Val Arg Ser Gly Tyr Arg Ile
                325                 330                 335
Gln Ala Asn Gln Gln Asp Asp Ser Met Arg Val Leu Tyr Tyr Met Glu
                340                 345                 350
Lys Glu Leu Ala Asn Phe Asp Pro Ser Arg Pro Gly Pro Pro Asn Gly
                355                 360                 365
Arg Val Glu Arg Ala Met Ser Glu Val Thr Ser Leu His Glu Asp Asp
370                 375                 380
Trp Arg Ser Arg Pro Ser Arg Ala Pro Ala Leu Thr Pro Ile Arg Asp
385                 390                 395                 400
Glu Glu Trp Asn Arg His Ser Pro Gln Ser Pro Arg Thr Trp Glu Gln
                405                 410                 415
Glu Pro Leu Gln Glu Gln Pro Arg Gly Gly Trp Gly Ser Gly Arg Pro
                420                 425                 430
Arg Ala Arg Ser Val Asp Ala Leu Asp Asp Ile Asn Arg Pro Gly Ser
                435                 440                 445
Thr Glu Ser Gly Arg Ser Ser Pro Pro Ser Ser Gly Arg Arg Gly Arg
450                 455                 460
```

```
Ala Tyr Ala Pro Pro Arg Ser Arg Ser Arg Asp Asp Leu Tyr Asp Pro
465                 470                 475                 480

Asp Asp Pro Arg Asp Leu Pro His Ser Arg Asp Pro His Tyr Tyr Asp
                485                 490                 495

Asp Ile Arg Ser Arg Asp Pro Arg Ala Asp Pro Arg Ser Arg Gln Arg
            500                 505                 510

Ser Arg Asp Pro Arg Asp Ala Gly Phe Arg Ser Arg Asp Pro Gln Tyr
        515                 520                 525

Asp Gly Arg Leu Leu Glu Glu Ala Leu Lys Lys Lys Gly Ser Gly Glu
    530                 535                 540

Arg Arg Arg Val Tyr Arg Glu Glu Glu Glu Glu Glu Glu Gly Gln Tyr
545                 550                 555                 560

Pro Pro Ala Pro Pro Pro Tyr Ser Glu Thr Asp Ser Gln Ala Ser Arg
                565                 570                 575

Glu Arg Arg Leu Lys Lys Asn Leu Ala Leu Ser Arg Glu Ser Leu Val
            580                 585                 590

Val

<210> SEQ ID NO 3
<211> LENGTH: 2040
<212> TYPE: DNA
<213> ORGANISM: Rattus norvegicus

<400> SEQUENCE: 3
accgctcacc aggtcagttg tccccggaaa gccgaaggca tgagcttcgc ccaagttctt      60
tttatgggtt agaactcctc cagagcgggg gaaaaaggac ttggaatagg ggcgggacgg     120
agcacgcacc cttctccgcc ttggttctcg ccgcgccccc tactctcggg atacttggga    180
ggggacgcgc gggcaccgtc gctgctagac ggccgcg atg gcg ccg gcg gcc ggc     235
                                         Met Ala Pro Ala Ala Gly
                                           1               5 gcg tgt gct ggg gcg cct gac tcc cac cca gct acc gtg gtc ttc gtg     283
Ala Cys Ala Gly Ala Pro Asp Ser His Pro Ala Thr Val Val Phe Val
         10                  15                  20 tgt ctc ttt ctc atc att ttc tgc cca gac cct gcc agt gcc atc cag     331
Cys Leu Phe Leu Ile Ile Phe Cys Pro Asp Pro Ala Ser Ala Ile Gln
     25                  30                  35 gtg act gtg tct gac ccc tac cac gta gtg atc ctg ttc cag cca gtg     379
Val Thr Val Ser Asp Pro Tyr His Val Val Ile Leu Phe Gln Pro Val
 40                  45                  50 acc ctg ccc tgc acc tat cag atg agc aac act ctc aca gtc ccc atc     427
Thr Leu Pro Cys Thr Tyr Gln Met Ser Asn Thr Leu Thr Val Pro Ile
55                  60                  65                  70 gtg atc tgg aag tac aag tca ttc tgc cgg gac cgt att gcc gat gcc     475
Val Ile Trp Lys Tyr Lys Ser Phe Cys Arg Asp Arg Ile Ala Asp Ala
                 75                  80                  85 ttc tct cct gcc agt gtg gac aac cag cta aat gcc cag ttg gca gct     523
Phe Ser Pro Ala Ser Val Asp Asn Gln Leu Asn Ala Gln Leu Ala Ala
             90                  95                 100 ggc aac ccc ggc tac aac ccc tat gtg gag tgc cag gac agt gta cgc     571
Gly Asn Pro Gly Tyr Asn Pro Tyr Val Glu Cys Gln Asp Ser Val Arg
         105                 110                 115 act gtc agg gtg gtg gcc acc aaa cag ggc aat gcg gtg acc ctg gga     619
Thr Val Arg Val Val Ala Thr Lys Gln Gly Asn Ala Val Thr Leu Gly
     120                 125                 130 gac tac tac caa ggc agg agg atc acc ata aca gga aat gct gac ctg     667
Asp Tyr Tyr Gln Gly Arg Arg Ile Thr Ile Thr Gly Asn Ala Asp Leu
```

-continued

```
           135                 140                 145                 150
acc ttc gag cag aca gcc tgg gga gac agt gga gtg tat tac tgc tct      715
Thr Phe Glu Gln Thr Ala Trp Gly Asp Ser Gly Val Tyr Tyr Cys Ser
                    155                 160                 165 gtg gtc tcg gcc caa gat ctg gat gga aac aac gag gcg tac gca gag      763
Val Val Ser Ala Gln Asp Leu Asp Gly Asn Asn Glu Ala Tyr Ala Glu
            170                 175                 180 ctc atc gtc ctt gat tgg ctc ttt gtg gtc gtg tgc ctg gcg agc          811
Leu Ile Val Leu Asp Trp Leu Phe Val Val Val Cys Leu Ala Ser
        185                 190                 195 ctc ctc ctc ttc ctc ctg ggc atc tgc tgg tgc cag tgc tgt cct          859
Leu Leu Leu Phe Leu Leu Gly Ile Cys Trp Cys Gln Cys Cys Pro
    200                 205                 210 cac acc tgc tgc tgc tat gtc cga tgt ccc tgc tgc cca gac aag tgc      907
His Thr Cys Cys Cys Tyr Val Arg Cys Pro Cys Cys Pro Asp Lys Cys
215                 220                 225                 230 tgt tgc cct gag gct ctt tat gct gct ggc aaa gca gcc acc tca ggt      955
Cys Cys Pro Glu Ala Leu Tyr Ala Ala Gly Lys Ala Ala Thr Ser Gly
                235                 240                 245 gtc ccg agc atc tat gcc ccc agc atc tat acc cac ctc tca cct gcc     1003
Val Pro Ser Ile Tyr Ala Pro Ser Ile Tyr Thr His Leu Ser Pro Ala
            250                 255                 260 aag acc cca cca cct ccg cct gcc atg att ccc atg ggc cct ccc tat     1051
Lys Thr Pro Pro Pro Pro Pro Ala Met Ile Pro Met Gly Pro Pro Tyr
        265                 270                 275 ggg tac cct gga gac ttt gac aga cat agc tca gtt ggt ggc cac agc     1099
Gly Tyr Pro Gly Asp Phe Asp Arg His Ser Ser Val Gly Gly His Ser
    280                 285                 290 tcc caa gta ccc ctg ctg cgt gac gtg gat ggc agt gta tct tca gaa     1147
Ser Gln Val Pro Leu Leu Arg Asp Val Asp Gly Ser Val Ser Ser Glu
295                 300                 305                 310 gta cga agt ggc tac agg atc cag gct aac cag caa gat gac tcc atg     1195
Val Arg Ser Gly Tyr Arg Ile Gln Ala Asn Gln Gln Asp Asp Ser Met
                315                 320                 325 agg gtc cta tac tat atg gag aaa gag cta gcc aac ttt gac cct tcc     1243
Arg Val Leu Tyr Tyr Met Glu Lys Glu Leu Ala Asn Phe Asp Pro Ser
            330                 335                 340 cga cct ggc cct ccc aat ggc aga gtg gaa cgg gcc atg agt gaa gta     1291
Arg Pro Gly Pro Pro Asn Gly Arg Val Glu Arg Ala Met Ser Glu Val
        345                 350                 355 acc tcc ctc cat gaa gat gac tgg cga tcg agg cct tcc agg gct cct     1339
Thr Ser Leu His Glu Asp Asp Trp Arg Ser Arg Pro Ser Arg Ala Pro
    360                 365                 370 gcc ctc acc ccc atc agg gat gag gag tgg aat cgc cac tcc cca cag     1387
Ala Leu Thr Pro Ile Arg Asp Glu Glu Trp Asn Arg His Ser Pro Gln
375                 380                 385                 390 agt ccc aga aca tgg gag cag gaa ccc ctt caa gaa caa cca agg ggt     1435
Ser Pro Arg Thr Trp Glu Gln Glu Pro Leu Gln Glu Gln Pro Arg Gly
                395                 400                 405 ggt tgg ggg tct gga cgc cct cgg gcc cgc tct gtg gat gct cta gat     1483
Gly Trp Gly Ser Gly Arg Pro Arg Ala Arg Ser Val Asp Ala Leu Asp
            410                 415                 420 gat atc aac cgg cct ggc tcc act gaa tca gga cgg tct tct ccc cca     1531
Asp Ile Asn Arg Pro Gly Ser Thr Glu Ser Gly Arg Ser Ser Pro Pro
        425                 430                 435 agt agt gga cgg aga gga cgg gcc tat gca cct cca aga agt cgc agc     1579
Ser Ser Gly Arg Arg Gly Arg Ala Tyr Ala Pro Pro Arg Ser Arg Ser
    440                 445                 450 cgg gat gac ctc tat gac ccg gac gat cct agg gac ttg cca cat tcc     1627
```

```
                                                                              Arg Asp Asp Leu Tyr Asp Pro Asp Asp Pro Arg Asp Leu Pro His Ser
                                                                              455             460             465             470 cga gat ccc cac tat tat gac gac atc agg tct aga gat cca cgt gct              1675
Arg Asp Pro His Tyr Tyr Asp Asp Ile Arg Ser Arg Asp Pro Arg Ala
            475                 480                 485 gac ccc aga tcc cgt cag cga tcc cga gat cct cgg gat gct ggc ttc              1723
Asp Pro Arg Ser Arg Gln Arg Ser Arg Asp Pro Arg Asp Ala Gly Phe
        490                 495                 500 agg tca agg gac cct cag tat gat ggg cga cta tta gaa gag gct tta              1771
Arg Ser Arg Asp Pro Gln Tyr Asp Gly Arg Leu Leu Glu Glu Ala Leu
            505                 510                 515 aag aaa aag ggg tcg ggc gag aga agg agg gtt tac agg gag gaa gaa              1819
Lys Lys Lys Gly Ser Gly Glu Arg Arg Arg Val Tyr Arg Glu Glu Glu
        520                 525                 530 gag gaa gag gag ggc caa tac ccc cca gca cct cca cct tac tca gag              1867
Glu Glu Glu Glu Gly Gln Tyr Pro Pro Ala Pro Pro Pro Tyr Ser Glu
535                 540                 545                 550 act gac tcg cag gcc tca cgg gag agg agg ctg aaa aag aat ttg gcc              1915
Thr Asp Ser Gln Ala Ser Arg Glu Arg Arg Leu Lys Lys Asn Leu Ala
                555                 560                 565 ctg agt cgg gaa agt tta gtc gtc tga tccacgtttt gtatgtagct                    1962
Leu Ser Arg Glu Ser Leu Val Val  *
            570 tttgtacttt tttttttaatt ggaatcaata ttgatgaaac ttcaagccta ataaaatgtc           2022 taatcacaaa aaaaaaaa                                                          2040

<210> SEQ ID NO 4
<211> LENGTH: 574
<212> TYPE: PRT
<213> ORGANISM: Rattus norvegicus

<400> SEQUENCE: 4

Met Ala Pro Ala Ala Gly Ala Cys Ala Gly Ala Pro Asp Ser His Pro
1               5                   10                  15

Ala Thr Val Val Phe Val Cys Leu Phe Leu Ile Ile Phe Cys Pro Asp
            20                  25                  30

Pro Ala Ser Ala Ile Gln Val Thr Val Ser Asp Pro Tyr His Val Val
        35                  40                  45

Ile Leu Phe Gln Pro Val Thr Leu Pro Cys Thr Tyr Gln Met Ser Asn
    50                  55                  60

Thr Leu Thr Val Pro Ile Val Ile Trp Lys Tyr Lys Ser Phe Cys Arg
65                  70                  75                  80

Asp Arg Ile Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Ala Thr Lys Gln Gly
        115                 120                 125

Asn Ala Val Thr Leu Gly Asp Tyr Tyr Gln Gly Arg Arg Ile Thr Ile
    130                 135                 140

Thr Gly Asn Ala Asp Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Asp Trp Leu Phe Val Val
            180                 185                 190
```

-continued

Val Val Cys Leu Ala Ser Leu Leu Phe Leu Leu Gly Ile Cys
            195                 200                 205

Trp Cys Gln Cys Cys Pro His Thr Cys Cys Tyr Val Arg Cys Pro
    210                 215                 220

Cys Cys Pro Asp Lys Cys Cys Pro Glu Ala Leu Tyr Ala Ala Gly
225                 230                 235                 240

Lys Ala Ala Thr Ser Gly Val Pro Ser Ile Tyr Ala Pro Ser Ile Tyr
                245                 250                 255

Thr His Leu Ser Pro Ala Lys Thr Pro Pro Pro Ala Met Ile
                260                 265                 270

Pro Met Gly Pro Pro Tyr Gly Tyr Pro Gly Asp Phe Asp Arg His Ser
            275                 280                 285

Ser Val Gly Gly His Ser Ser Gln Val Pro Leu Leu Arg Asp Val Asp
    290                 295                 300

Gly Ser Val Ser Ser Glu Val Arg Ser Gly Tyr Arg Ile Gln Ala Asn
305                 310                 315                 320

Gln Gln Asp Asp Ser Met Arg Val Leu Tyr Tyr Met Glu Lys Glu Leu
                325                 330                 335

Ala Asn Phe Asp Pro Ser Arg Pro Gly Pro Pro Asn Gly Arg Val Glu
                340                 345                 350

Arg Ala Met Ser Glu Val Thr Ser Leu His Glu Asp Asp Trp Arg Ser
            355                 360                 365

Arg Pro Ser Arg Ala Pro Ala Leu Thr Pro Ile Arg Asp Glu Glu Trp
    370                 375                 380

Asn Arg His Ser Pro Gln Ser Pro Arg Thr Trp Glu Gln Glu Pro Leu
385                 390                 395                 400

Gln Glu Gln Pro Arg Gly Gly Trp Gly Ser Gly Arg Pro Arg Ala Arg
                405                 410                 415

Ser Val Asp Ala Leu Asp Asp Ile Asn Arg Pro Gly Ser Thr Glu Ser
                420                 425                 430

Gly Arg Ser Ser Pro Ser Ser Gly Arg Arg Gly Arg Ala Tyr Ala
            435                 440                 445

Pro Pro Arg Ser Arg Ser Arg Asp Asp Leu Tyr Asp Pro Asp Asp Pro
    450                 455                 460

Arg Asp Leu Pro His Ser Arg Asp Pro His Tyr Tyr Asp Asp Ile Arg
465                 470                 475                 480

Ser Arg Asp Pro Arg Ala Asp Pro Arg Ser Arg Gln Arg Ser Arg Asp
                485                 490                 495

Pro Arg Asp Ala Gly Phe Arg Ser Arg Asp Pro Gln Tyr Asp Gly Arg
            500                 505                 510

Leu Leu Glu Glu Ala Leu Lys Lys Gly Ser Gly Glu Arg Arg Arg
    515                 520                 525

Val Tyr Arg Glu Glu Glu Glu Glu Gly Gln Tyr Pro Pro Ala
    530                 535                 540

Pro Pro Pro Tyr Ser Glu Thr Asp Ser Gln Ala Ser Arg Glu Arg Arg
545                 550                 555                 560

Leu Lys Lys Asn Leu Ala Leu Ser Arg Glu Ser Leu Val Val
                565                 570

<210> SEQ ID NO 5
<211> LENGTH: 1893
<212> TYPE: DNA
<213> ORGANISM: Rattus norvegicus

<400> SEQUENCE: 5

-continued

```
accgctcacc aggtcagttg tccccggaaa gccgaaggca tgagcttcgc ccaagttctt      60
tttatgggtt agaactcctc cagagcgggg gaaaaaggac ttggaatagg ggcgggacgg     120
agcacgcacc cttctccgcc ttggttctcg ccgcgccccc tactctcggg atacttggga    180
ggggacgcgc gggcaccgtc gctgctagac ggccgcg atg gcg ccg gcg gcc ggc     235
                                          Met Ala Pro Ala Ala Gly
                                            1               5 gcg tgt gct ggg gcg cct gac tcc cac cca gct acc gtg gtc ttc gtg      283
Ala Cys Ala Gly Ala Pro Asp Ser His Pro Ala Thr Val Val Phe Val
         10                  15                  20 tgt ctc ttt ctc atc att ttc tgc cca gac cct gcc agt gcc atc cag      331
Cys Leu Phe Leu Ile Ile Phe Cys Pro Asp Pro Ala Ser Ala Ile Gln
     25                  30                  35 gtg act gtg tct gac ccc tac cac gta gtg atc ctg ttc cag cca gtg      379
Val Thr Val Ser Asp Pro Tyr His Val Val Ile Leu Phe Gln Pro Val
 40                  45                  50 acc ctg ccc tgc acc tat cag atg agc aac act ctc aca gtc ccc atc      427
Thr Leu Pro Cys Thr Tyr Gln Met Ser Asn Thr Leu Thr Val Pro Ile
55                  60                  65                  70 gtg atc tgg aag tac aag tca ttc tgc cgg gac cgt att gcc gat gcc      475
Val Ile Trp Lys Tyr Lys Ser Phe Cys Arg Asp Arg Ile Ala Asp Ala
                 75                  80                  85 ttc tct cct gcc agt gtg gac aac cag cta aat gcc cag ttg gca gct      523
Phe Ser Pro Ala Ser Val Asp Asn Gln Leu Asn Ala Gln Leu Ala Ala
         90                  95                 100 ggc aac ccc ggc tac aac ccc tat gtg gag tgc cag gac agt gta cgc      571
Gly Asn Pro Gly Tyr Asn Pro Tyr Val Glu Cys Gln Asp Ser Val Arg
     105                 110                 115 act gtc agg gtg gtg gcc acc aaa cag ggc aat gcg gtg acc ctg gga      619
Thr Val Arg Val Val Ala Thr Lys Gln Gly Asn Ala Val Thr Leu Gly
 120                 125                 130 gac tac tac caa ggc agg agg atc acc ata aca gga aat gct gac ctg      667
Asp Tyr Tyr Gln Gly Arg Arg Ile Thr Ile Thr Gly Asn Ala Asp Leu
135                 140                 145                 150 acc ttc gag cag aca gcc tgg gga gac agt gga gtg tat tac tgc tct      715
Thr Phe Glu Gln Thr Ala Trp Gly Asp Ser Gly Val Tyr Tyr Cys Ser
                 155                 160                 165 gtg gtc tcg gcc caa gat ctg gat gga aac aac gag gcg tac gca gag      763
Val Val Ser Ala Gln Asp Leu Asp Gly Asn Asn Glu Ala Tyr Ala Glu
         170                 175                 180 ctc atc gtc ctt gtt tat gct gct ggc aaa gca gcc acc tca ggt gtc      811
Leu Ile Val Leu Val Tyr Ala Ala Gly Lys Ala Ala Thr Ser Gly Val
     185                 190                 195 ccg agc atc tat gcc ccc agc atc tat acc cac ctc tca cct gcc aag      859
Pro Ser Ile Tyr Ala Pro Ser Ile Tyr Thr His Leu Ser Pro Ala Lys
 200                 205                 210 acc cca cca cct ccg cct gcc atg att ccc atg ggc cct ccc tat ggg      907
Thr Pro Pro Pro Pro Ala Met Ile Pro Met Gly Pro Pro Tyr Gly
215                 220                 225                 230 tac cct gga gac ttt gac aga cat agc tca gtt ggt ggc cac agc tcc      955
Tyr Pro Gly Asp Phe Asp Arg His Ser Ser Val Gly Gly His Ser Ser
                 235                 240                 245 caa gta ccc ctg ctg cgt gac gtg gat ggc agt gta tct tca gaa gta     1003
Gln Val Pro Leu Leu Arg Asp Val Asp Gly Ser Val Ser Ser Glu Val
         250                 255                 260 cga agt ggc tac agg atc cag gct aac cag caa gat gac tcc atg agg     1051
Arg Ser Gly Tyr Arg Ile Gln Ala Asn Gln Gln Asp Asp Ser Met Arg
     265                 270                 275
```

```
gtc cta tac tat atg gag aaa gag cta gcc aac ttt gac cct tcc cga    1099
Val Leu Tyr Tyr Met Glu Lys Glu Leu Ala Asn Phe Asp Pro Ser Arg
    280                 285                 290 cct ggc cct ccc aat ggc aga gtg gaa cgg gcc atg agt gaa gta acc    1147
Pro Gly Pro Pro Asn Gly Arg Val Glu Arg Ala Met Ser Glu Val Thr
295                 300                 305                 310 tcc ctc cat gaa gat gac tgg cga tcg agg cct tcc agg gct cct gcc    1195
Ser Leu His Glu Asp Asp Trp Arg Ser Arg Pro Ser Arg Ala Pro Ala
                315                 320                 325 ctc acc ccc atc agg gat gag gag tgg aat cgc cac tcc cca cag agt    1243
Leu Thr Pro Ile Arg Asp Glu Glu Trp Asn Arg His Ser Pro Gln Ser
            330                 335                 340 ccc aga aca tgg gag cag gaa ccc ctt caa gaa caa cca agg ggt ggt    1291
Pro Arg Thr Trp Glu Gln Glu Pro Leu Gln Glu Gln Pro Arg Gly Gly
        345                 350                 355 tgg ggg tct gga cgc cct cgg gcc cgc tct gtg gat gct cta gat gat    1339
Trp Gly Ser Gly Arg Pro Arg Ala Arg Ser Val Asp Ala Leu Asp Asp
    360                 365                 370 atc aac cgg cct ggc tcc act gaa tca gga cgg tct tct ccc cca agt    1387
Ile Asn Arg Pro Gly Ser Thr Glu Ser Gly Arg Ser Ser Pro Pro Ser
375                 380                 385                 390 agt gga cgg aga gga cgg gcc tat gca cct cca aga agt cgc agc cgg    1435
Ser Gly Arg Arg Gly Arg Ala Tyr Ala Pro Pro Arg Ser Arg Ser Arg
                395                 400                 405 gat gac ctc tat gac ccg gac gat cct agg gac ttg cca cat tcc cga    1483
Asp Asp Leu Tyr Asp Pro Asp Asp Pro Arg Asp Leu Pro His Ser Arg
            410                 415                 420 gat ccc cac tat tat gac gac atc agg tct aga gat cca cgt gct gac    1531
Asp Pro His Tyr Tyr Asp Asp Ile Arg Ser Arg Asp Pro Arg Ala Asp
        425                 430                 435 ccc aga tcc cgt cag cga tcc cga gat cct cgg gat gct ggc ttc agg    1579
Pro Arg Ser Arg Gln Arg Ser Arg Asp Pro Arg Asp Ala Gly Phe Arg
    440                 445                 450 tca agg gac cct cag tat gat ggg cga cta tta gaa gag gct tta aag    1627
Ser Arg Asp Pro Gln Tyr Asp Gly Arg Leu Leu Glu Glu Ala Leu Lys
455                 460                 465                 470 aaa aag ggg tcg ggc gag aga agg agg gtt tac agg gag gaa gaa gag    1675
Lys Lys Gly Ser Gly Glu Arg Arg Arg Val Tyr Arg Glu Glu Glu Glu
                475                 480                 485 gaa gag gag ggc caa tac ccc cca gca cct cca cct tac tca gag act    1723
Glu Glu Glu Gly Gln Tyr Pro Pro Ala Pro Pro Pro Tyr Ser Glu Thr
            490                 495                 500 gac tcg cag gcc tca cgg gag agg agg ctg aaa aag aat ttg gcc ctg    1771
Asp Ser Gln Ala Ser Arg Glu Arg Arg Leu Lys Lys Asn Leu Ala Leu
        505                 510                 515 agt cgg gaa agt tta gtc gtc tga tccacgtttt gtatgtagct tttgtacttt   1825
Ser Arg Glu Ser Leu Val Val *
    520                 525 tttttttaatt ggaatcaata ttgatgaaac ttcaagccta ataaaatgtc taatcacaaa  1885
aaaaaaaa                                                            1893

<210> SEQ ID NO 6
<211> LENGTH: 525
<212> TYPE: PRT
<213> ORGANISM: Rattus norvegicus

<400> SEQUENCE: 6

Met Ala Pro Ala Ala Gly Ala Cys Ala Gly Ala Pro Asp Ser His Pro
1               5                   10                  15
```

-continued

```
Ala Thr Val Val Phe Val Cys Leu Phe Leu Ile Ile Phe Cys Pro Asp
             20                  25                  30

Pro Ala Ser Ala Ile Gln Val Thr Val Ser Asp Pro Tyr His Val Val
             35                  40                  45

Ile Leu Phe Gln Pro Val Thr Leu Pro Cys Thr Tyr Gln Met Ser Asn
 50                  55                  60

Thr Leu Thr Val Pro Ile Val Ile Trp Lys Tyr Lys Ser Phe Cys Arg
 65                  70                  75                  80

Asp Arg Ile Ala Asp Ala Phe Ser Pro Ala Ser Val Asp Asn Gln Leu
                 85                  90                  95

Asn Ala Gln Leu Ala Ala Gly Asn Pro Gly Tyr Asn Pro Tyr Val Glu
             100                 105                 110

Cys Gln Asp Ser Val Arg Thr Val Arg Val Val Ala Thr Lys Gln Gly
             115                 120                 125

Asn Ala Val Thr Leu Gly Asp Tyr Tyr Gln Gly Arg Arg Ile Thr Ile
130                 135                 140

Thr Gly Asn Ala Asp Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                 165                 170                 175

Asn Glu Ala Tyr Ala Glu Leu Ile Val Leu Val Tyr Ala Ala Gly Lys
             180                 185                 190

Ala Ala Thr Ser Gly Val Pro Ser Ile Tyr Ala Pro Ser Ile Tyr Thr
             195                 200                 205

His Leu Ser Pro Ala Lys Thr Pro Pro Pro Pro Ala Met Ile Pro
             210                 215                 220

Met Gly Pro Pro Tyr Gly Tyr Pro Gly Asp Phe Asp Arg His Ser Ser
225                 230                 235                 240

Val Gly Gly His Ser Ser Gln Val Pro Leu Leu Arg Asp Val Asp Gly
                 245                 250                 255

Ser Val Ser Ser Glu Val Arg Ser Gly Tyr Arg Ile Gln Ala Asn Gln
             260                 265                 270

Gln Asp Asp Ser Met Arg Val Leu Tyr Tyr Met Glu Lys Glu Leu Ala
             275                 280                 285

Asn Phe Asp Pro Ser Arg Pro Gly Pro Pro Asn Gly Arg Val Glu Arg
             290                 295                 300

Ala Met Ser Glu Val Thr Ser Leu His Glu Asp Asp Trp Arg Ser Arg
305                 310                 315                 320

Pro Ser Arg Ala Pro Ala Leu Thr Pro Ile Arg Asp Glu Glu Trp Asn
                 325                 330                 335

Arg His Ser Pro Gln Ser Pro Arg Thr Trp Glu Gln Glu Pro Leu Gln
             340                 345                 350

Glu Gln Pro Arg Gly Gly Trp Gly Ser Gly Arg Pro Arg Ala Arg Ser
             355                 360                 365

Val Asp Ala Leu Asp Asp Ile Asn Arg Pro Gly Ser Thr Glu Ser Gly
370                 375                 380

Arg Ser Ser Pro Pro Ser Ser Gly Arg Arg Gly Arg Ala Tyr Ala Pro
385                 390                 395                 400

Pro Arg Ser Arg Ser Arg Asp Asp Leu Tyr Asp Pro Asp Asp Pro Arg
                 405                 410                 415

Asp Leu Pro His Ser Arg Asp His Tyr Tyr Asp Asp Ile Arg Ser
             420                 425                 430

Arg Asp Pro Arg Ala Asp Pro Arg Ser Arg Gln Arg Ser Arg Asp Pro
```

```
                435                 440                 445
Arg Asp Ala Gly Phe Arg Ser Arg Asp Pro Gln Tyr Asp Gly Arg Leu
            450                 455                 460

Leu Glu Glu Ala Leu Lys Lys Lys Gly Ser Gly Glu Arg Arg Val
465                 470                 475                 480

Tyr Arg Glu Glu Glu Glu Glu Gly Gln Tyr Pro Pro Ala Pro
                485                 490                 495

Pro Pro Tyr Ser Glu Thr Asp Ser Gln Ala Ser Arg Glu Arg Leu
            500                 505                 510

Lys Lys Asn Leu Ala Leu Ser Arg Glu Ser Leu Val Val
            515                 520                 525

<210> SEQ ID NO 7
<211> LENGTH: 2158
<212> TYPE: DNA
<213> ORGANISM: Homo sapiens
<220> FEATURE:
<221> NAME/KEY: Misc_Feature
<222> LOCATION: 1259..1261
<223> OTHER INFORMATION: Potential splicing site AAG
<221> NAME/KEY: Misc_Feature
<222> LOCATION: 1657
<223> OTHER INFORMATION: Potential insertion of a AGG

<400> SEQUENCE: 7
tggagtgtgg ctcggaggac cgcggcgggt caagcacctt tctcccccat atctgaaagc      60 atgcccttg tccacgtcgt ttacgctcat taaaacttcc aga atg caa cag gac       115
                                             Met Gln Gln Asp
                                              1 gga ctt gga gta ggg aca agg aac gga agt ggg aag ggg agg agc gtg     163
Gly Leu Gly Val Gly Thr Arg Asn Gly Ser Gly Lys Gly Arg Ser Val
 5                  10                  15                  20 cac ccc tcc tgg cct tgg tgc gcg ccg cgc cct cta agg tac ttt gga     211
His Pro Ser Trp Pro Trp Cys Ala Pro Arg Pro Leu Arg Tyr Phe Gly
                25                  30                  35 agg gac gcg cgg gcc aga cgc gcc cag acg gcc gcg atg gcg ctg ttg     259
Arg Asp Ala Arg Ala Arg Arg Ala Gln Thr Ala Ala Met Ala Leu Leu
            40                  45                  50 gcc ggc ggg ctc tcc aga ggg ctg ggc tcc cac ccg gcc gcc gca ggc     307
Ala Gly Gly Leu Ser Arg Gly Leu Gly Ser His Pro Ala Ala Ala Gly
        55                  60                  65 cgg gac gcg gtc gtc ttc gtg tgg ctt ctg ctt agc acc tgg tgc aca     355
Arg Asp Ala Val Val Phe Val Trp Leu Leu Leu Ser Thr Trp Cys Thr
    70                  75                  80 gct cct gcc agg gcc atc cag gtg acc gtg tcc aac ccc tac cac gtg     403
Ala Pro Ala Arg Ala Ile Gln Val Thr Val Ser Asn Pro Tyr His Val
85                  90                  95                 100 gtg atc ctc ttc cag cct gtg acc ctg ccc tgt acc tac cag atg acc     451
Val Ile Leu Phe Gln Pro Val Thr Leu Pro Cys Thr Tyr Gln Met Thr
                105                 110                 115 tcg acc ccc acg caa ccc atc gtc atc tgg aag tac aag tct ttc tgc     499
Ser Thr Pro Thr Gln Pro Ile Val Ile Trp Lys Tyr Lys Ser Phe Cys
            120                 125                 130 cgg gac cgc atc gcc gat gcc ttc tcc ccg gcc agc gtc gac aac cag     547
Arg Asp Arg Ile Ala Asp Ala Phe Ser Pro Ala Ser Val Asp Asn Gln
        135                 140                 145 ctc aat gcc cag ctg gca gcc ggg aac cca ggc tac aac ccc tac gtt     595
Leu Asn Ala Gln Leu Ala Ala Gly Asn Pro Gly Tyr Asn Pro Tyr Val
    150                 155                 160 gag tgc cag gac agc gtg cgc acc gtc agg gtc gtg gcc acc aag cag     643
```

-continued

```
Glu Cys Gln Asp Ser Val Arg Thr Val Arg Val Val Ala Thr Lys Gln
165                 170                 175                 180 ggc aac gct gtg acc ctg gga gat tac tac cag ggc cgg agg att acc        691
Gly Asn Ala Val Thr Leu Gly Asp Tyr Tyr Gln Gly Arg Arg Ile Thr
                185                 190                 195 atc acc gga aat gct gac ctg acc ttt gac cag acg gcg tgg ggg gac        739
Ile Thr Gly Asn Ala Asp Leu Thr Phe Asp Gln Thr Ala Trp Gly Asp
            200                 205                 210 agt ggt gtg tat tac tgc tcc gtg gtc tca gcc cag gac ctc cag ggg        787
Ser Gly Val Tyr Tyr Cys Ser Val Val Ser Ala Gln Asp Leu Gln Gly
        215                 220                 225 aac aat gag gcc tac gca gag ctc atc gtc ctt ggg agg acc tca ggg        835
Asn Asn Glu Ala Tyr Ala Glu Leu Ile Val Leu Gly Arg Thr Ser Gly
    230                 235                 240 gtg gct gag ctc tta cct ggt ttt cag gcg ggg ccc ata gaa gac tgg        883
Val Ala Glu Leu Leu Pro Gly Phe Gln Ala Gly Pro Ile Glu Asp Trp
245                 250                 255                 260 ctc ttc gtg gtt gtg gta tgc ctg gct gcc ttc ctc atc ttc ctc ctc        931
Leu Phe Val Val Val Cys Leu Ala Ala Phe Leu Ile Phe Leu Leu
                265                 270                 275 ctg ggc atc tgc tgg tgc cag tgc tgc ccg cac act tgc tgc tgc tac        979
Leu Gly Ile Cys Trp Cys Gln Cys Cys Pro His Thr Cys Cys Cys Tyr
            280                 285                 290 gtc agg tgc ccc tgc tgc cca gac aag tgc tgc tgc ccc gag gcc ctg       1027
Val Arg Cys Pro Cys Cys Pro Asp Lys Cys Cys Cys Pro Glu Ala Leu
        295                 300                 305 tat gcc gcc ggc aaa gca gcc acc tca ggt gtt ccc agc att tat gcc       1075
Tyr Ala Ala Gly Lys Ala Ala Thr Ser Gly Val Pro Ser Ile Tyr Ala
310                 315                 320 ccc agc acc tat gcc cac ctg tct ccc gcc aag acc cca ccc cca cca       1123
Pro Ser Thr Tyr Ala His Leu Ser Pro Ala Lys Thr Pro Pro Pro Pro
325                 330                 335                 340 gct atg att ccc atg ggc cct gcc tac aac ggg tac cct gga gga tac       1171
Ala Met Ile Pro Met Gly Pro Ala Tyr Asn Gly Tyr Pro Gly Gly Tyr
                345                 350                 355 cct gga gac gtt gac agg agt agc tca gct ggt ggc caa ggc tcc tat       1219
Pro Gly Asp Val Asp Arg Ser Ser Ser Ala Gly Gly Gln Gly Ser Tyr
            360                 365                 370 gta ccc ctg ctt cgg gac acg gac agc agt gtg gcc tct gaa gtc cgc       1267
Val Pro Leu Leu Arg Asp Thr Asp Ser Ser Val Ala Ser Glu Val Arg
        375                 380                 385 agt ggc tac agg att cag gcc agc cag cag gac gac tcc atg cgg gtc       1315
Ser Gly Tyr Arg Ile Gln Ala Ser Gln Gln Asp Asp Ser Met Arg Val
390                 395                 400 ctg tac tac atg gag aag gag ctg gcc aac ttc gac cct tct cga cct       1363
Leu Tyr Tyr Met Glu Lys Glu Leu Ala Asn Phe Asp Pro Ser Arg Pro
405                 410                 415                 420 ggc ccc ccc agt ggc cgt gtg gag cgg gcc atg agt gaa gtc acc tcc       1411
Gly Pro Pro Ser Gly Arg Val Glu Arg Ala Met Ser Glu Val Thr Ser
                425                 430                 435 ctc cac gag gac gac tgg cga tct cgg cct tcc cgg ggc cct gcc ctc       1459
Leu His Glu Asp Asp Trp Arg Ser Arg Pro Ser Arg Gly Pro Ala Leu
            440                 445                 450 acc ccg atc cgg gat gag gag tgg ggt ggc cac tcc ccc cgg agt ccc       1507
Thr Pro Ile Arg Asp Glu Glu Trp Gly Gly His Ser Pro Arg Ser Pro
        455                 460                 465 agg gga tgg gac cag gag ccc gcc agg gag cag gca ggc ggg ggc tgg       1555
Arg Gly Trp Asp Gln Glu Pro Ala Arg Glu Gln Ala Gly Gly Gly Trp
470                 475                 480
```

```
cgg gcc agg cgg ccc cgg gcc cgc tcc gtg gac gcc ctg gac gac ctc     1603
Arg Ala Arg Arg Pro Arg Ala Arg Ser Val Asp Ala Leu Asp Asp Leu
485                 490                 495                 500 acc ccg ccg agc acc gcc gag tca ggg agc agg tct ccc acg agt aat     1651
Thr Pro Pro Ser Thr Ala Glu Ser Gly Ser Arg Ser Pro Thr Ser Asn
            505                 510                 515 ggt ggg aga agc cgg gcc tac atg ccc ccg cgg agc cgc agc cgg gac     1699
Gly Gly Arg Ser Arg Ala Tyr Met Pro Pro Arg Ser Arg Ser Arg Asp
        520                 525                 530 gac ctc tat gac caa gac gac tcg agg gac ttc cca cgc tcc cgg gac     1747
Asp Leu Tyr Asp Gln Asp Asp Ser Arg Asp Phe Pro Arg Ser Arg Asp
    535                 540                 545 ccc cac tac gac gac ttc agg tct cgg gag cgc cct cct gcc gac ccc     1795
Pro His Tyr Asp Asp Phe Arg Ser Arg Glu Arg Pro Pro Ala Asp Pro
550                 555                 560 agg tcc cac cac cac cgt acc cgg gac cct cgg gac aac ggc tcc agg     1843
Arg Ser His His His Arg Thr Arg Asp Pro Arg Asp Asn Gly Ser Arg
565                 570                 575                 580 tcc ggg gac ctc ccc tat gat ggg cgg cta ctg gag gag gct gtg agg     1891
Ser Gly Asp Leu Pro Tyr Asp Gly Arg Leu Leu Glu Glu Ala Val Arg
            585                 590                 595 aag aag ggg tcg gag gag agg agg aga ccc cac aag gag gag gag gaa     1939
Lys Lys Gly Ser Glu Glu Arg Arg Arg Pro His Lys Glu Glu Glu Glu
        600                 605                 610 gag gcc tac tac ccg ccc gcg ccg ccc ccg tac tcg gag acc gac tcg     1987
Glu Ala Tyr Tyr Pro Pro Ala Pro Pro Pro Tyr Ser Glu Thr Asp Ser
    615                 620                 625 cag gcg tcc cga gag cgc agg ctc aag aag aac ttg gcc ctg agt cgg     2035
Gln Ala Ser Arg Glu Arg Arg Leu Lys Lys Asn Leu Ala Leu Ser Arg
630                 635                 640 gaa agt tta gtc gtc tga tctgacgttt tctacgtagc ttttgtattt            2083
Glu Ser Leu Val Val  *
645 tttttttaa tttgaaggaa cactgatgaa gccctgccat acccctcccg agtctaataa    2143
aacgtataat cacaa                                                    2158

<210> SEQ ID NO 8
<211> LENGTH: 649
<212> TYPE: PRT
<213> ORGANISM: Homo sapiens
<220> FEATURE:
<221> NAME/KEY: Misc_Feature
<222> LOCATION: 386
<223> OTHER INFORMATION: Potential deletion of a Glu
<221> NAME/KEY: Misc_Feature
<222> LOCATION: 518
<223> OTHER INFORMATION: Potential insertion of a Arg

<400> SEQUENCE: 8

Met Gln Gln Asp Gly Leu Gly Val Gly Thr Arg Asn Gly Ser Gly Lys
1               5                   10                  15

Gly Arg Ser Val His Pro Ser Trp Pro Trp Cys Ala Pro Arg Pro Leu
            20                  25                  30

Arg Tyr Phe Gly Arg Asp Ala Arg Ala Arg Ala Gln Thr Ala Ala
        35                  40                  45

Met Ala Leu Leu Ala Gly Gly Leu Ser Arg Gly Leu Gly Ser His Pro
    50                  55                  60

Ala Ala Gly Arg Asp Ala Val Val Phe Val Trp Leu Leu Leu Ser
65                  70                  75                  80

Thr Trp Cys Thr Ala Pro Ala Arg Ala Ile Gln Val Thr Val Ser Asn
```

-continued

```
              85                  90                  95
Pro Tyr His Val Ile Leu Phe Gln Pro Val Thr Leu Pro Cys Thr
            100                 105                 110

Tyr Gln Met Thr Ser Thr Pro Thr Gln Pro Ile Val Ile Trp Lys Tyr
            115                 120                 125

Lys Ser Phe Cys Arg Asp Arg Ile Ala Asp Ala Phe Ser Pro Ala Ser
            130                 135                 140

Val Asp Asn Gln Leu Asn Ala Gln Leu Ala Ala Gly Asn Pro Gly Tyr
145                 150                 155                 160

Asn Pro Tyr Val Glu Cys Gln Asp Ser Val Arg Thr Val Arg Val Val
                165                 170                 175

Ala Thr Lys Gln Gly Asn Ala Val Thr Leu Gly Asp Tyr Tyr Gln Gly
            180                 185                 190

Arg Arg Ile Thr Ile Thr Gly Asn Ala Asp Leu Thr Phe Asp Gln Thr
            195                 200                 205

Ala Trp Gly Asp Ser Gly Val Tyr Tyr Cys Ser Val Val Ser Ala Gln
            210                 215                 220

Asp Leu Gln Gly Asn Asn Glu Ala Tyr Ala Glu Leu Ile Val Leu Gly
225                 230                 235                 240

Arg Thr Ser Gly Val Ala Glu Leu Leu Pro Gly Phe Gln Ala Gly Pro
                245                 250                 255

Ile Glu Asp Trp Leu Phe Val Val Val Cys Leu Ala Ala Phe Leu
            260                 265                 270

Ile Phe Leu Leu Leu Gly Ile Cys Trp Cys Gln Cys Cys Pro His Thr
            275                 280                 285

Cys Cys Cys Tyr Val Arg Cys Pro Cys Cys Pro Asp Lys Cys Cys Cys
            290                 295                 300

Pro Glu Ala Leu Tyr Ala Ala Gly Lys Ala Ala Thr Ser Gly Val Pro
305                 310                 315                 320

Ser Ile Tyr Ala Pro Ser Thr Tyr Ala His Leu Ser Pro Ala Lys Thr
                325                 330                 335

Pro Pro Pro Pro Ala Met Ile Pro Met Gly Pro Ala Tyr Asn Gly Tyr
            340                 345                 350

Pro Gly Gly Tyr Pro Gly Asp Val Asp Arg Ser Ser Ala Gly Gly
            355                 360                 365

Gln Gly Ser Tyr Val Pro Leu Leu Arg Asp Thr Asp Ser Ser Val Ala
370                 375                 380

Ser Glu Val Arg Ser Gly Tyr Arg Ile Gln Ala Ser Gln Gln Asp Asp
385                 390                 395                 400

Ser Met Arg Val Leu Tyr Tyr Met Glu Lys Glu Leu Ala Asn Phe Asp
                405                 410                 415

Pro Ser Arg Pro Gly Pro Pro Ser Gly Arg Val Glu Arg Ala Met Ser
            420                 425                 430

Glu Val Thr Ser Leu His Glu Asp Asp Trp Arg Ser Arg Pro Ser Arg
            435                 440                 445

Gly Pro Ala Leu Thr Pro Ile Arg Asp Glu Glu Trp Gly Gly His Ser
            450                 455                 460

Pro Arg Ser Pro Arg Gly Trp Asp Gln Glu Pro Ala Arg Glu Gln Ala
465                 470                 475                 480

Gly Gly Gly Trp Arg Ala Arg Arg Pro Arg Ala Arg Ser Val Asp Ala
                485                 490                 495

Leu Asp Asp Leu Thr Pro Pro Ser Thr Ala Glu Ser Gly Ser Arg Ser
            500                 505                 510
```

```
Pro Thr Ser Asn Gly Gly Arg Ser Arg Ala Tyr Met Pro Pro Arg Ser
        515                 520                 525
Arg Ser Arg Asp Asp Leu Tyr Asp Gln Asp Asp Ser Arg Asp Phe Pro
    530                 535                 540
Arg Ser Arg Asp Pro His Tyr Asp Asp Phe Arg Ser Arg Glu Arg Pro
545                 550                 555                 560
Pro Ala Asp Pro Arg Ser His His Arg Thr Arg Asp Pro Arg Asp
                565                 570                 575
Asn Gly Ser Arg Ser Gly Asp Leu Pro Tyr Asp Gly Arg Leu Leu Glu
            580                 585                 590
Glu Ala Val Arg Lys Lys Gly Ser Glu Glu Arg Arg Pro His Lys
        595                 600                 605
Glu Glu Glu Glu Ala Tyr Tyr Pro Pro Ala Pro Pro Tyr Ser
    610                 615                 620
Glu Thr Asp Ser Gln Ala Ser Arg Glu Arg Leu Lys Lys Asn Leu
625                 630                 635                 640
Ala Leu Ser Arg Glu Ser Leu Val Val
                645

<210> SEQ ID NO 9
<211> LENGTH: 2101
<212> TYPE: DNA
<213> ORGANISM: Homo sapiens

<400> SEQUENCE: 9
tggagtgtgg ctcggaggac cgcggcgggt caagcaccett tctcccccat atctgaaagc      60 atgcccttttg tccacgtcgt ttacgctcat taaaacttcc aga atg caa cag gac      115
                                              Met Gln Gln Asp
                                               1 gga ctt gga gta ggg aca agg aac gga agt ggg aag ggg agg agc gtg      163
Gly Leu Gly Val Gly Thr Arg Asn Gly Ser Gly Lys Gly Arg Ser Val
5                   10                  15                  20 cac ccc tcc tgg cct tgg tgc gcg ccg cgc ccc cta agg tac ttt gga      211
His Pro Ser Trp Pro Trp Cys Ala Pro Arg Pro Leu Arg Tyr Phe Gly
                25                  30                  35 agg gac gcg cgg gcc aga cgc gcc cag acg gcc gcg atg gcg ctg ttg      259
Arg Asp Ala Arg Ala Arg Arg Ala Gln Thr Ala Ala Met Ala Leu Leu
            40                  45                  50 gcc ggc ggg ctc tcc aga ggg ctg ggc tcc cac ccg gcc gcc gca ggc      307
Ala Gly Gly Leu Ser Arg Gly Leu Gly Ser His Pro Ala Ala Ala Gly
        55                  60                  65 cgg gac gcg gtc gtc ttc gtg tgg ctt ctg ctt agc acc tgg tgc aca      355
Arg Asp Ala Val Val Phe Val Trp Leu Leu Leu Ser Thr Trp Cys Thr
    70                  75                  80 gct cct gcc agg gcc atc cag gtg acc gtg tcc aac ccc tac cac gtg      403
Ala Pro Ala Arg Ala Ile Gln Val Thr Val Ser Asn Pro Tyr His Val
85                  90                  95                  100 gtg atc ctc ttc cag cct gtg acc ctg ccc tgt acc tac cag atg acc      451
Val Ile Leu Phe Gln Pro Val Thr Leu Pro Cys Thr Tyr Gln Met Thr
                105                 110                 115 tcg acc ccc acg caa ccc atc gtc atc tgg aag tac aag tct ttc tgc      499
Ser Thr Pro Thr Gln Pro Ile Val Ile Trp Lys Tyr Lys Ser Phe Cys
            120                 125                 130 cgg gac cgc atc gcc gat gcc ttc tcc ccg gcc agc gtc gac aac cag      547
Arg Asp Arg Ile Ala Asp Ala Phe Ser Pro Ala Ser Val Asp Asn Gln
        135                 140                 145 ctc aat gcc cag ctg gca gcc ggg aac cca ggc tac aac ccc tac gtt      595
```

-continued

```
Leu Asn Ala Gln Leu Ala Ala Gly Asn Pro Gly Tyr Asn Pro Tyr Val
    150                 155                 160 gag tgc cag gac agc gtg cgc acc gtc agg gtc gtg gcc acc aag cag        643
Glu Cys Gln Asp Ser Val Arg Thr Val Arg Val Val Ala Thr Lys Gln
165                 170                 175                 180 ggc aac gct gtg acc ctg gga gat tac tac cag ggc cgg agg att acc        691
Gly Asn Ala Val Thr Leu Gly Asp Tyr Tyr Gln Gly Arg Arg Ile Thr
                185                 190                 195 atc acc gga aat gct gac ctg acc ttt gac cag acg gcg tgg ggg gac        739
Ile Thr Gly Asn Ala Asp Leu Thr Phe Asp Gln Thr Ala Trp Gly Asp
            200                 205                 210 agt ggt gtg tat tac tgc tcc gtg gtc tca gcc cag gac ctc cag ggg        787
Ser Gly Val Tyr Tyr Cys Ser Val Val Ser Ala Gln Asp Leu Gln Gly
        215                 220                 225 aac aat gag gcc tac gca gag ctc atc gtc ctt gac tgg ctc ttc gtg        835
Asn Asn Glu Ala Tyr Ala Glu Leu Ile Val Leu Asp Trp Leu Phe Val
    230                 235                 240 gtt gtg gta tgc ctg gct gcc ttc ctc atc ttc ctc ctg ggc atc            883
Val Val Val Cys Leu Ala Ala Phe Leu Ile Phe Leu Leu Leu Gly Ile
245                 250                 255                 260 tgc tgg tgc cag tgc tgc ccg cac act tgc tgc tgc tac gtc agg tgc        931
Cys Trp Cys Gln Cys Cys Pro His Thr Cys Cys Cys Tyr Val Arg Cys
                265                 270                 275 ccc tgc tgc cca gac aag tgc tgc tgc ccc gag gcc ctg tat gcc gcc        979
Pro Cys Cys Pro Asp Lys Cys Cys Cys Pro Glu Ala Leu Tyr Ala Ala
            280                 285                 290 ggc aaa gca gcc acc tca ggt gtt ccc agc att tat gcc ccc agc acc       1027
Gly Lys Ala Ala Thr Ser Gly Val Pro Ser Ile Tyr Ala Pro Ser Thr
        295                 300                 305 tat gcc cac ctg tct ccc gcc aag acc cca ccc cca gct atg att           1075
Tyr Ala His Leu Ser Pro Ala Lys Thr Pro Pro Pro Ala Met Ile
    310                 315                 320 ccc atg ggc cct gcc tac aac ggg tac cct gga gga tac cct gga gac       1123
Pro Met Gly Pro Ala Tyr Asn Gly Tyr Pro Gly Gly Tyr Pro Gly Asp
325                 330                 335                 340 gtt gac agg agt agc tca gct ggt ggc caa ggc tcc tat gta ccc ctg       1171
Val Asp Arg Ser Ser Ser Ala Gly Gly Gln Gly Ser Tyr Val Pro Leu
                345                 350                 355 ctt cgg gac acg gac agc agt gtg gcc tct gaa gtc cgc agt ggc tac       1219
Leu Arg Asp Thr Asp Ser Ser Val Ala Ser Glu Val Arg Ser Gly Tyr
            360                 365                 370 agg att cag gca agc cag cag gac gac tcc atg cgg gtc ctg tac tac       1267
Arg Ile Gln Ala Ser Gln Gln Asp Asp Ser Met Arg Val Leu Tyr Tyr
        375                 380                 385 atg gag aag gag ctg gcc aac ttc gac cct tct cga cct ggc ccc ccc       1315
Met Glu Lys Glu Leu Ala Asn Phe Asp Pro Ser Arg Pro Gly Pro Pro
    390                 395                 400 agt ggc cgt gtg gag cgg gcc atg agt gaa gtc acc tcc ctc cac gag       1363
Ser Gly Arg Val Glu Arg Ala Met Ser Glu Val Thr Ser Leu His Glu
405                 410                 415                 420 gac gac tgg cga tct cgg cct tcc cgg ggc cct gcc ctc acc ccg atc       1411
Asp Asp Trp Arg Ser Arg Pro Ser Arg Gly Pro Ala Leu Thr Pro Ile
                425                 430                 435 cgg gat gag gag tgg ggt ggc cac tcc ccc cgg agt ccc agg gga tgg       1459
Arg Asp Glu Glu Trp Gly Gly His Ser Pro Arg Ser Pro Arg Gly Trp
            440                 445                 450 gac cag gag ccc gcc agg gag cag gca ggc ggg ggc tgg cgg gcc agg       1507
Asp Gln Glu Pro Ala Arg Glu Gln Ala Gly Gly Gly Trp Arg Ala Arg
        455                 460                 465
```

-continued

| | | | | | | | | | | | | | | | |
|---|---|---|---|---|---|---|---|---|---|---|---|---|---|---|---|
| cgg | ccc | cgg | gcc | cgc | tcc | gtg | gac | gcc | ctg | gac | gac | ctc | acc | ccg | ccg | 1555
| Arg | Pro | Arg | Ala | Arg | Ser | Val | Asp | Ala | Leu | Asp | Asp | Leu | Thr | Pro | Pro |
| | 470 | | | | 475 | | | | 480 | | | | | | | agc acc gcc gag tca ggg agc agg tct ccc acg agt aat ggt ggg aga 1603
Ser Thr Ala Glu Ser Gly Ser Arg Ser Pro Thr Ser Asn Gly Gly Arg
485            490                495                500 agc cgg gcc tac atg ccc ccg cgg agc cgc agc cgg gac gac ctc tat 1651
Ser Arg Ala Tyr Met Pro Pro Arg Ser Arg Ser Arg Asp Asp Leu Tyr
            505                510                515 gac caa gac gac tcg agg gac ttc cca cgc tcc cgg gac ccc cac tac 1699
Asp Gln Asp Asp Ser Arg Asp Phe Pro Arg Ser Arg Asp Pro His Tyr
        520                525                530 gac gac ttc agg tct cgg gag cgc cct cct gcc gac ccc agg tcc cac 1747
Asp Asp Phe Arg Ser Arg Glu Arg Pro Pro Ala Asp Pro Arg Ser His
            535                540                545 cac cac cgt acc cgg gac cct cgg gac aac ggc tcc agg tcc ggg gac 1795
His His Arg Thr Arg Asp Pro Arg Asp Asn Gly Ser Arg Ser Gly Asp
        550                555                560 ctc ccc tat gat ggg cgg cta ctg gag gag gct gtg agg aag aag ggg 1843
Leu Pro Tyr Asp Gly Arg Leu Leu Glu Glu Ala Val Arg Lys Lys Gly
565            570                575                580 tcg gag gag agg agg aga ccc cac aag gag gag gag gaa gag gcc tac 1891
Ser Glu Glu Arg Arg Arg Pro His Lys Glu Glu Glu Glu Glu Ala Tyr
            585                590                595 tac ccg ccc gcg ccg ccc ccg tac tcg gag acc gac tcg cag gcg tcc 1939
Tyr Pro Pro Ala Pro Pro Pro Tyr Ser Glu Thr Asp Ser Gln Ala Ser
            600                605                610 cga gag cgc agg ctc aag aag aac ttg gcc ctg agt cgg gaa agt tta 1987
Arg Glu Arg Arg Leu Lys Lys Asn Leu Ala Leu Ser Arg Glu Ser Leu
            615                620                625 gtc gtc tga tctgacgttt tctacgtagc ttttgtattt ttttttttaa 2036
Val Val *
    630 tttgaaggaa cactgatgaa gccctgccat accccctcccg agtctaataa aacgtataat 2096 cacaa 2101

<210> SEQ ID NO 10
<211> LENGTH: 630
<212> TYPE: PRT
<213> ORGANISM: Homo sapiens

<400> SEQUENCE: 10

Met Gln Gln Asp Gly Leu Gly Val Gly Thr Arg Asn Gly Ser Gly Lys
1               5                   10                  15

Gly Arg Ser Val His Pro Ser Trp Pro Trp Cys Ala Pro Arg Pro Leu
            20                  25                  30

Arg Tyr Phe Gly Arg Asp Ala Arg Ala Arg Ala Gln Thr Ala Ala
            35                  40                  45

Met Ala Leu Leu Ala Gly Gly Leu Ser Arg Gly Leu Gly Ser His Pro
    50                  55                  60

Ala Ala Gly Arg Asp Ala Val Val Phe Val Trp Leu Leu Leu Ser
65                  70                  75                  80

Thr Trp Cys Thr Ala Pro Ala Arg Ala Ile Gln Val Thr Val Ser Asn
                85                  90                  95

Pro Tyr His Val Val Ile Leu Phe Gln Pro Val Thr Leu Pro Cys Thr
            100                 105                 110

Tyr Gln Met Thr Ser Thr Pro Thr Gln Pro Ile Val Ile Trp Lys Tyr
        115                 120                 125

```
Lys Ser Phe Cys Arg Asp Arg Ile Ala Asp Ala Phe Ser Pro Ala Ser
    130                 135                 140
Val Asp Asn Gln Leu Asn Ala Gln Leu Ala Ala Gly Asn Pro Gly Tyr
145                 150                 155                 160
Asn Pro Tyr Val Glu Cys Gln Asp Ser Val Arg Thr Val Arg Val Val
                165                 170                 175
Ala Thr Lys Gln Gly Asn Ala Val Thr Leu Gly Asp Tyr Tyr Gln Gly
            180                 185                 190
Arg Arg Ile Thr Ile Thr Gly Asn Ala Asp Leu Thr Phe Asp Gln Thr
        195                 200                 205
Ala Trp Gly Asp Ser Gly Val Tyr Tyr Cys Ser Val Val Ser Ala Gln
    210                 215                 220
Asp Leu Gln Gly Asn Asn Glu Ala Tyr Ala Glu Leu Ile Val Leu Asp
225                 230                 235                 240
Trp Leu Phe Val Val Val Cys Leu Ala Ala Phe Leu Ile Phe Leu
                245                 250                 255
Leu Leu Gly Ile Cys Trp Cys Gln Cys Cys Pro His Thr Cys Cys Cys
            260                 265                 270
Tyr Val Arg Cys Pro Cys Cys Pro Asp Lys Cys Cys Cys Pro Glu Ala
        275                 280                 285
Leu Tyr Ala Ala Gly Lys Ala Thr Ser Gly Val Pro Ser Ile Tyr
    290                 295                 300
Ala Pro Ser Thr Tyr Ala His Leu Ser Pro Ala Lys Thr Pro Pro Pro
305                 310                 315                 320
Pro Ala Met Ile Pro Met Gly Pro Ala Tyr Asn Gly Tyr Pro Gly Gly
                325                 330                 335
Tyr Pro Gly Asp Val Asp Arg Ser Ser Ser Ala Gly Gly Gln Gly Ser
            340                 345                 350
Tyr Val Pro Leu Leu Arg Asp Thr Asp Ser Ser Val Ala Ser Glu Val
        355                 360                 365
Arg Ser Gly Tyr Arg Ile Gln Ala Ser Gln Gln Asp Asp Ser Met Arg
    370                 375                 380
Val Leu Tyr Tyr Met Glu Lys Glu Leu Ala Asn Phe Asp Pro Ser Arg
385                 390                 395                 400
Pro Gly Pro Pro Ser Gly Arg Val Glu Arg Ala Met Ser Glu Val Thr
                405                 410                 415
Ser Leu His Glu Asp Asp Trp Arg Ser Arg Pro Ser Arg Gly Pro Ala
            420                 425                 430
Leu Thr Pro Ile Arg Asp Glu Glu Trp Gly Gly His Ser Pro Arg Ser
        435                 440                 445
Pro Arg Gly Trp Asp Gln Glu Pro Ala Arg Glu Gln Ala Gly Gly Gly
    450                 455                 460
Trp Arg Ala Arg Arg Pro Arg Ala Arg Ser Val Asp Ala Leu Asp Asp
465                 470                 475                 480
Leu Thr Pro Pro Ser Thr Ala Glu Ser Gly Ser Arg Ser Pro Thr Ser
                485                 490                 495
Asn Gly Gly Arg Ser Arg Ala Tyr Met Pro Pro Arg Ser Arg Ser Arg
            500                 505                 510
Asp Asp Leu Tyr Asp Gln Asp Asp Ser Arg Asp Phe Pro Arg Ser Arg
        515                 520                 525
Asp Pro His Tyr Asp Asp Phe Arg Ser Arg Glu Arg Pro Pro Ala Asp
    530                 535                 540
```

```
Pro Arg Ser His His Arg Thr Arg Asp Pro Arg Asp Asn Gly Ser
545                 550                 555                 560

Arg Ser Gly Asp Leu Pro Tyr Asp Gly Arg Leu Leu Glu Glu Ala Val
            565                 570                 575

Arg Lys Lys Gly Ser Glu Glu Arg Arg Pro His Lys Glu Glu Glu
            580                 585                 590

Glu Glu Ala Tyr Tyr Pro Pro Ala Pro Pro Tyr Ser Glu Thr Asp
            595                 600                 605

Ser Gln Ala Ser Arg Glu Arg Arg Leu Lys Lys Asn Leu Ala Leu Ser
        610                 615                 620

Arg Glu Ser Leu Val Val
625                 630

<210> SEQ ID NO 11
<211> LENGTH: 1954
<212> TYPE: DNA
<213> ORGANISM: Homo sapiens

<400> SEQUENCE: 11
tggagtgtgg ctcggaggac cgcggcgggt caagcacctt tctcccccat atctgaaagc      60 atgcccttg tccacgtcgt ttacgctcat taaaacttcc aga atg caa cag gac       115
                                            Met Gln Gln Asp
                                              1 gga ctt gga gta ggg aca agg aac gga agt ggg aag ggg agg agc gtg       163
Gly Leu Gly Val Gly Thr Arg Asn Gly Ser Gly Lys Gly Arg Ser Val
  5                  10                  15                  20 cac ccc tcc tgg cct tgg tgc gcg ccg cgc cca cta agg tac ttt gga       211
His Pro Ser Trp Pro Trp Cys Ala Pro Arg Pro Leu Arg Tyr Phe Gly
             25                  30                  35 agg gac gcg cgg gcc aga cgc gcc cag acg gcc gcg atg gcg ctg ttg       259
Arg Asp Ala Arg Ala Arg Ala Gln Thr Ala Ala Met Ala Leu Leu
         40                  45                  50 gcc ggc ggg ctc tcc aga ggg ctg ggc tcc cac ccg gcc gcc gca ggc       307
Ala Gly Gly Leu Ser Arg Gly Leu Gly Ser His Pro Ala Ala Ala Gly
         55                  60                  65 cgg gac gcg gtc gtc ttc gtg tgg ctt ctg ctt agc acc tgg tgc aca       355
Arg Asp Ala Val Val Phe Val Trp Leu Leu Leu Ser Thr Trp Cys Thr
 70                  75                  80 gct cct gcc agg gcc atc cag gtg acc gtg tcc aac ccc tac cac gtg       403
Ala Pro Ala Arg Ala Ile Gln Val Thr Val Ser Asn Pro Tyr His Val
 85                  90                  95                 100 gtg atc ctc ttc cag cct gtg acc ctg ccc tgt acc tac cag atg acc       451
Val Ile Leu Phe Gln Pro Val Thr Leu Pro Cys Thr Tyr Gln Met Thr
                 105                 110                 115 tcg acc ccc acg caa ccc atc gtc atc tgg aag tac aag tct ttc tgc       499
Ser Thr Pro Thr Gln Pro Ile Val Ile Trp Lys Tyr Lys Ser Phe Cys
             120                 125                 130 cgg gac cgc atc gcc gat gcc ttc tcc ccg gcc agc gtc gac aac cag       547
Arg Asp Arg Ile Ala Asp Ala Phe Ser Pro Ala Ser Val Asp Asn Gln
         135                 140                 145 ctc aat gcc cag ctg gca gcc ggg aac cca ggc tac aac ccc tac gtt       595
Leu Asn Ala Gln Leu Ala Ala Gly Asn Pro Gly Tyr Asn Pro Tyr Val
     150                 155                 160 gag tgc cag gac agc gtg cgc acc gtc agg gtc gtg gcc acc aag cag       643
Glu Cys Gln Asp Ser Val Arg Thr Val Arg Val Val Ala Thr Lys Gln
165                 170                 175                 180 ggc aac gct gtg acc ctg gga gat tac tac cag ggc cgg agg att acc       691
Gly Asn Ala Val Thr Leu Gly Asp Tyr Tyr Gln Gly Arg Arg Ile Thr
                 185                 190                 195
```

-continued

| | |
|---|---|
| atc acc gga aat gct gac ctg acc ttt gac cag acg gcg tgg ggg gac<br>Ile Thr Gly Asn Ala Asp Leu Thr Phe Asp Gln Thr Ala Trp Gly Asp<br>200          205          210 | 739 |
| agt ggt gtg tat tac tgc tcc gtg gtc tca gcc cag gac ctc cag ggg<br>Ser Gly Val Tyr Tyr Cys Ser Val Val Ser Ala Gln Asp Leu Gln Gly<br>215          220          225 | 787 |
| aac aat gag gcc tac gca gag ctc atc gtc ctt gtg tat gcc gcc ggc<br>Asn Asn Glu Ala Tyr Ala Glu Leu Ile Val Leu Val Tyr Ala Ala Gly<br>230          235          240 | 835 |
| aaa gca gcc acc tca ggt gtt ccc agc att tat gcc ccc agc acc tat<br>Lys Ala Ala Thr Ser Gly Val Pro Ser Ile Tyr Ala Pro Ser Thr Tyr<br>245          250          255          260 | 883 |
| gcc cac ctg tct ccc gcc aag acc cca ccc cca cca gct atg att ccc<br>Ala His Leu Ser Pro Ala Lys Thr Pro Pro Pro Pro Ala Met Ile Pro<br>265          270          275 | 931 |
| atg ggc cct gcc tac aac ggg tac cct gga gga tac cct gga gac gtt<br>Met Gly Pro Ala Tyr Asn Gly Tyr Pro Gly Gly Tyr Pro Gly Asp Val<br>280          285          290 | 979 |
| gac agg agt agc tca gct ggt ggc caa ggc tcc tat gta ccc ctg ctt<br>Asp Arg Ser Ser Ser Ala Gly Gly Gln Gly Ser Tyr Val Pro Leu Leu<br>295          300          305 | 1027 |
| cgg gac acg gac agc agt gtg gcc tct gaa gtc cgc agt ggc tac agg<br>Arg Asp Thr Asp Ser Ser Val Ala Ser Glu Val Arg Ser Gly Tyr Arg<br>310          315          320 | 1075 |
| att cag gcc agc cag cag gac gac tcc atg cgg gtc ctg tac tac atg<br>Ile Gln Ala Ser Gln Gln Asp Asp Ser Met Arg Val Leu Tyr Tyr Met<br>325          330          335          340 | 1123 |
| gag aag gag ctg gcc aac ttc gac cct tct cga cct ggc ccc ccc agt<br>Glu Lys Glu Leu Ala Asn Phe Asp Pro Ser Arg Pro Gly Pro Pro Ser<br>345          350          355 | 1171 |
| ggc cgt gtg gag cgg gcc atg agt gaa gtc acc tcc ctc cac gag gac<br>Gly Arg Val Glu Arg Ala Met Ser Glu Val Thr Ser Leu His Glu Asp<br>360          365          370 | 1219 |
| gac tgg cga tct cgg cct tcc cgg ggc cct gcc ctc acc ccg atc cgg<br>Asp Trp Arg Ser Arg Pro Ser Arg Gly Pro Ala Leu Thr Pro Ile Arg<br>375          380          385 | 1267 |
| gat gag gag tgg ggt ggc cac tcc ccc cgg agt ccc agg gga tgg gac<br>Asp Glu Glu Trp Gly Gly His Ser Pro Arg Ser Pro Arg Gly Trp Asp<br>390          395          400 | 1315 |
| cag gag ccc gcc agg gag cag gca ggg ggc tgg cgg gcc agg cgg<br>Gln Glu Pro Ala Arg Glu Gln Ala Gly Gly Trp Arg Ala Arg Arg<br>405          410          415          420 | 1363 |
| ccc cgg gcc cgc tcc gtg gac gcc ctg gac gac ctc acc ccg ccg agc<br>Pro Arg Ala Arg Ser Val Asp Ala Leu Asp Asp Leu Thr Pro Pro Ser<br>425          430          435 | 1411 |
| acc gcc gag tca ggg agc agg tct ccc acg agt aat ggt ggg aga agc<br>Thr Ala Glu Ser Gly Ser Arg Ser Pro Thr Ser Asn Gly Gly Arg Ser<br>440          445          450 | 1459 |
| cgg gcc tac atg ccc ccg cgg agc cgc agc cgg gac gac ctc tat gac<br>Arg Ala Tyr Met Pro Pro Arg Ser Arg Ser Arg Asp Asp Leu Tyr Asp<br>455          460          465 | 1507 |
| caa gac gac tcg agg gac ttc cca cgc tcc cgg gac ccc cac tac gac<br>Gln Asp Asp Ser Arg Asp Phe Pro Arg Ser Arg Asp Pro His Tyr Asp<br>470          475          480 | 1555 |
| gac ttc agg tct cgg gag cgc cct cct gcc gac ccc agg tcc cac cac<br>Asp Phe Arg Ser Arg Glu Arg Pro Pro Ala Asp Pro Arg Ser His His<br>485          490          495          500 | 1603 |
| cac cgt acc cgg gac cct cgg gac aac ggc tcc agg tcc ggg gac ctc<br>His Arg Thr Arg Asp Pro Arg Asp Asn Gly Ser Arg Ser Gly Asp Leu | 1651 |

```
                        505                 510                 515
ccc tat gat ggg cgg cta ctg gag gag gct gtg agg aag aag ggg tcg      1699
Pro Tyr Asp Gly Arg Leu Leu Glu Glu Ala Val Arg Lys Lys Gly Ser
            520                 525                 530 gag gag agg agg aga ccc cac aag gag gag gaa gag gcc tac tac          1747
Glu Glu Arg Arg Arg Pro His Lys Glu Glu Glu Glu Ala Tyr Tyr
        535                 540                 545 ccg ccc gcg ccg ccc ccg tac tcg gag acc gac tcg cag gcg tcc cga      1795
Pro Pro Ala Pro Pro Pro Tyr Ser Glu Thr Asp Ser Gln Ala Ser Arg
    550                 555                 560 gag cgc agg ctc aag aag aac ttg gcc ctg agt cgg gaa agt tta gtc      1843
Glu Arg Arg Leu Lys Lys Asn Leu Ala Leu Ser Arg Glu Ser Leu Val
565                 570                 575                 580 gtc tga tctgacgttt tctacgtagc ttttgtattt ttttttttaa tttgaaggaa       1899
Val * cactgatgaa gccctgccat accccctcccg agtctaataa aacgtataat cacaa        1954
```

<210> SEQ ID NO 12
<211> LENGTH: 581
<212> TYPE: PRT
<213> ORGANISM: Homo sapiens

<400> SEQUENCE: 12

```
Met Gln Gln Asp Gly Leu Gly Val Gly Thr Arg Asn Gly Ser Gly Lys
1               5                   10                  15

Gly Arg Ser Val His Pro Ser Trp Pro Trp Cys Ala Pro Arg Pro Leu
            20                  25                  30

Arg Tyr Phe Gly Arg Asp Ala Arg Ala Arg Ala Gln Thr Ala Ala
        35                  40                  45

Met Ala Leu Leu Ala Gly Gly Leu Ser Arg Gly Leu Gly Ser His Pro
    50                  55                  60

Ala Ala Ala Gly Arg Asp Ala Val Val Phe Val Trp Leu Leu Leu Ser
65                  70                  75                  80

Thr Trp Cys Thr Ala Pro Ala Arg Ala Ile Gln Val Thr Val Ser Asn
                85                  90                  95

Pro Tyr His Val Val Ile Leu Phe Gln Pro Val Thr Leu Pro Cys Thr
            100                 105                 110

Tyr Gln Met Thr Ser Thr Pro Thr Gln Pro Ile Val Ile Trp Lys Tyr
        115                 120                 125

Lys Ser Phe Cys Arg Asp Arg Ile Ala Asp Ala Phe Ser Pro Ala Ser
    130                 135                 140

Val Asp Asn Gln Leu Asn Ala Gln Leu Ala Ala Gly Asn Pro Gly Tyr
145                 150                 155                 160

Asn Pro Tyr Val Glu Cys Gln Asp Ser Val Arg Thr Val Arg Val Val
                165                 170                 175

Ala Thr Lys Gln Gly Asn Ala Val Thr Leu Gly Asp Tyr Tyr Gln Gly
            180                 185                 190

Arg Arg Ile Thr Ile Thr Gly Asn Ala Asp Leu Thr Phe Asp Gln Thr
        195                 200                 205

Ala Trp Gly Asp Ser Gly Val Tyr Tyr Cys Ser Val Val Ser Ala Gln
    210                 215                 220

Asp Leu Gln Gly Asn Asn Glu Ala Tyr Ala Glu Leu Ile Val Leu Val
225                 230                 235                 240

Tyr Ala Ala Gly Lys Ala Ala Thr Ser Gly Val Pro Ser Ile Tyr Ala
                245                 250                 255
```

```
Pro Ser Thr Tyr Ala His Leu Ser Pro Ala Lys Thr Pro Pro Pro
            260                 265                 270

Ala Met Ile Pro Met Gly Pro Ala Tyr Asn Gly Tyr Pro Gly Gly Tyr
            275                 280                 285

Pro Gly Asp Val Asp Arg Ser Ser Ala Gly Gly Gln Gly Ser Tyr
            290                 295                 300

Val Pro Leu Leu Arg Asp Thr Asp Ser Val Ala Ser Glu Val Arg
305                 310                 315                 320

Ser Gly Tyr Arg Ile Gln Ala Ser Gln Gln Asp Asp Ser Met Arg Val
                325                 330                 335

Leu Tyr Tyr Met Glu Lys Glu Leu Ala Asn Phe Asp Pro Ser Arg Pro
                340                 345                 350

Gly Pro Pro Ser Gly Arg Val Glu Arg Ala Met Ser Glu Val Thr Ser
                355                 360                 365

Leu His Glu Asp Asp Trp Arg Ser Arg Pro Ser Arg Gly Pro Ala Leu
                370                 375                 380

Thr Pro Ile Arg Asp Glu Glu Trp Gly His Ser Pro Arg Ser Pro
385                 390                 395                 400

Arg Gly Trp Asp Gln Glu Pro Ala Arg Glu Gln Ala Gly Gly Trp
                405                 410                 415

Arg Ala Arg Arg Pro Arg Ala Arg Ser Val Asp Ala Leu Asp Asp Leu
                420                 425                 430

Thr Pro Pro Ser Thr Ala Glu Ser Gly Ser Arg Ser Pro Thr Ser Asn
                435                 440                 445

Gly Gly Arg Ser Arg Ala Tyr Met Pro Pro Arg Ser Arg Ser Arg Asp
                450                 455                 460

Asp Leu Tyr Asp Gln Asp Ser Arg Asp Phe Pro Arg Ser Arg Asp
465                 470                 475                 480

Pro His Tyr Asp Asp Phe Arg Ser Arg Glu Arg Pro Ala Asp Pro
                485                 490                 495

Arg Ser His His His Arg Thr Arg Asp Pro Arg Asp Asn Gly Ser Arg
                500                 505                 510

Ser Gly Asp Leu Pro Tyr Asp Gly Arg Leu Leu Glu Glu Ala Val Arg
                515                 520                 525

Lys Lys Gly Ser Glu Glu Arg Arg Pro His Lys Glu Glu Glu
                530                 535                 540

Glu Ala Tyr Tyr Pro Pro Ala Pro Pro Tyr Ser Glu Thr Asp Ser
545                 550                 555                 560

Gln Ala Ser Arg Glu Arg Arg Leu Lys Lys Asn Leu Ala Leu Ser Arg
                565                 570                 575

Glu Ser Leu Val Val
            580

<210> SEQ ID NO 13
<211> LENGTH: 1886
<212> TYPE: DNA
<213> ORGANISM: Mus musculus

<400> SEQUENCE: 13
gcaccgtcgc tgctagacgg ccgcg atg gcg ccg gcg gcc agc gcg tgt gct      52
                           Met Ala Pro Ala Ala Ser Ala Cys Ala
                             1               5 ggg gcg cct ggc tcc cac ccg gcc acc acg atc ttc gtg tgt ctt ttt     100
Gly Ala Pro Gly Ser His Pro Ala Thr Thr Ile Phe Val Cys Leu Phe
 10                  15                  20                  25
```

-continued

| | | |
|---|---|---|
| ctc atc att tac tgc cca gac cgt gcc agt gcc atc cag gtg acc gtg<br>Leu Ile Ile Tyr Cys Pro Asp Arg Ala Ser Ala Ile Gln Val Thr Val<br>30                35                40 | | 148 |
| cct gac ccc tac cac gta gtg atc ctg ttc cag cca gtg aca cta cac<br>Pro Asp Pro Tyr His Val Val Ile Leu Phe Gln Pro Val Thr Leu His<br>    45                50                55 | | 196 |
| tgc acc tac cag atg agc aat acc ctc aca gcc cct atc gtg atc tgg<br>Cys Thr Tyr Gln Met Ser Asn Thr Leu Thr Ala Pro Ile Val Ile Trp<br>        60                65                70 | | 244 |
| aag tat aag tcg ttc tgt cgg gac cgt gtt gcc gac gcc ttc tcc cct<br>Lys Tyr Lys Ser Phe Cys Arg Asp Arg Val Ala Asp Ala Phe Ser Pro<br>75                80                85 | | 292 |
| gcc agc gtg gac aac cag ctc aac gcc cag ctg gcg gct ggc aac ccc<br>Ala Ser Val Asp Asn Gln Leu Asn Ala Gln Leu Ala Ala Gly Asn Pro<br>90                95                100               105 | | 340 |
| ggc tac aac ccc tat gtg gag tgc cag gac agc gta cgc act gtc agg<br>Gly Tyr Asn Pro Tyr Val Glu Cys Gln Asp Ser Val Arg Thr Val Arg<br>            110               115               120 | | 388 |
| gtg gtg gcc acc aaa cag ggc aat gct gtg acc ctg gga gac tac tac<br>Val Val Ala Thr Lys Gln Gly Asn Ala Val Thr Leu Gly Asp Tyr Tyr<br>        125               130               135 | | 436 |
| cag ggc agg aga atc acc atc aca gga aat gct ggc ctg acc ttc gag<br>Gln Gly Arg Arg Ile Thr Ile Thr Gly Asn Ala Gly Leu Thr Phe Glu<br>140               145               150 | | 484 |
| cag acg gcc tgg gga gac agt gga gtg tat tac tgc tcc gtg gtc tca<br>Gln Thr Ala Trp Gly Asp Ser Gly Val Tyr Tyr Cys Ser Val Val Ser<br>155               160               165 | | 532 |
| gcc caa gat ctg gat ggg aac aac gag gcg tac gca gag ctc att gtc<br>Ala Gln Asp Leu Asp Gly Asn Asn Glu Ala Tyr Ala Glu Leu Ile Val<br>170               175               180               185 | | 580 |
| ctt ggc agg acc tca gaa gcc cct gag ctc cta cct ggt ttt cgg gcg<br>Leu Gly Arg Thr Ser Glu Ala Pro Glu Leu Leu Pro Gly Phe Arg Ala<br>            190               195               200 | | 628 |
| ggg ccc ttg gaa gat tgg ctc ttt gtg gtc gtg gtc tgc ctg gca agc<br>Gly Pro Leu Glu Asp Trp Leu Phe Val Val Val Cys Leu Ala Ser<br>        205               210               215 | | 676 |
| ctc ctc ttc ttc ctc ctc ctg ggc atc tgc tgg tgc cag tgc tgt ccc<br>Leu Leu Phe Phe Leu Leu Leu Gly Ile Cys Trp Cys Gln Cys Cys Pro<br>220               225               230 | | 724 |
| cac acc tgc tgc tgc tat gtc aga tgt ccc tgc tgc cca gac aag tgc<br>His Thr Cys Cys Cys Tyr Val Arg Cys Pro Cys Cys Pro Asp Lys Cys<br>235               240               245 | | 772 |
| tgt tgc cct gag gcc ctt tat gct gct ggc aaa gca gcc acc tca ggt<br>Cys Cys Pro Glu Ala Leu Tyr Ala Ala Gly Lys Ala Ala Thr Ser Gly<br>250               255               260               265 | | 820 |
| gtg cca agc atc tat gcc ccc agc atc tat acc cac ctc tct cct gcc<br>Val Pro Ser Ile Tyr Ala Pro Ser Ile Tyr Thr His Leu Ser Pro Ala<br>            270               275               280 | | 868 |
| aag act ccg cca cct ccg cct gcc atg att ccc atg cgt cct ccc tat<br>Lys Thr Pro Pro Pro Pro Ala Met Ile Pro Met Arg Pro Pro Tyr<br>        285               290               295 | | 916 |
| ggg tac cct gga gac ttt gac agg acc agc tca gtt ggt ggc cac agc<br>Gly Tyr Pro Gly Asp Phe Asp Arg Thr Ser Ser Val Gly Gly His Ser<br>300               305               310 | | 964 |
| tcc cag gtg ccc ctg ctg cgt gaa gtg gat ggg agc gta tct tca gaa<br>Ser Gln Val Pro Leu Leu Arg Glu Val Asp Gly Ser Val Ser Ser Glu<br>315               320               325 | | 1012 |
| gta cga agt ggc tac agg atc cag gct aac cag caa gat gac tcc atg<br>Val Arg Ser Gly Tyr Arg Ile Gln Ala Asn Gln Gln Asp Asp Ser Met<br>330               335               340               345 | | 1060 |

-continued

```
agg gtc cta tac tat atg gag aag gag cta gcc aac ttc gat cct tcc        1108
Arg Val Leu Tyr Tyr Met Glu Lys Glu Leu Ala Asn Phe Asp Pro Ser
            350                 355                 360 cgg cct ggc cct ccc aat ggc cga gtg gaa cgg gcc atg agt gaa gta        1156
Arg Pro Gly Pro Pro Asn Gly Arg Val Glu Arg Ala Met Ser Glu Val
        365                 370                 375 acc tcc ctc cat gaa gat gac tgg cga tct cgg cct tcc agg gct cct        1204
Thr Ser Leu His Glu Asp Asp Trp Arg Ser Arg Pro Ser Arg Ala Pro
            380                 385                 390 gcc ctc aca ccc atc agg gat gag gag tgg aat cgc cac tcc cct cgg        1252
Ala Leu Thr Pro Ile Arg Asp Glu Glu Trp Asn Arg His Ser Pro Arg
        395                 400                 405 agt ccc aga aca tgg gag cag gaa ccc ctt caa gaa cag cca agg ggt        1300
Ser Pro Arg Thr Trp Glu Gln Glu Pro Leu Gln Glu Gln Pro Arg Gly
410                 415                 420                 425 ggt tgg ggg tct ggg cgg cct cgg gcc cgc tct gtg gat gct cta gat        1348
Gly Trp Gly Ser Gly Arg Pro Arg Ala Arg Ser Val Asp Ala Leu Asp
            430                 435                 440 gac atc aac cgg cct ggc tcc act gaa tca gga agg tct tct ccc cca        1396
Asp Ile Asn Arg Pro Gly Ser Thr Glu Ser Gly Arg Ser Ser Pro Pro
        445                 450                 455 agt agt gga cgg aga ggg cgg gcc tat gca cct ccg aga agt cgc agc        1444
Ser Ser Gly Arg Arg Gly Arg Ala Tyr Ala Pro Pro Arg Ser Arg Ser
        460                 465                 470 cgg gat gac ctc tat gac ccc gac gat cct aga gac ttg cca cat tcc        1492
Arg Asp Asp Leu Tyr Asp Pro Asp Asp Pro Arg Asp Leu Pro His Ser
        475                 480                 485 cga gat ccc cac tat tat gat gat ttg agg tct agg gat cca cgt gct        1540
Arg Asp Pro His Tyr Tyr Asp Asp Leu Arg Ser Arg Asp Pro Arg Ala
490                 495                 500                 505 gac ccc aga tcc cgt cag cga tcc cac gat cct cgg gat gct ggc ttc        1588
Asp Pro Arg Ser Arg Gln Arg Ser His Asp Pro Arg Asp Ala Gly Phe
            510                 515                 520 agg tca cgg gac cct cag tat gat ggg cga ctc tta gaa gag gct tta        1636
Arg Ser Arg Asp Pro Gln Tyr Asp Gly Arg Leu Leu Glu Glu Ala Leu
        525                 530                 535 aag aaa aaa ggg gct ggg gag aga aga cgc gtt tac agg gag gaa gaa        1684
Lys Lys Lys Gly Ala Gly Glu Arg Arg Arg Val Tyr Arg Glu Glu Glu
        540                 545                 550 gaa gaa gaa gag gag ggc cac tat ccc cca gca cct ccg cct tac tct        1732
Glu Glu Glu Glu Glu Gly His Tyr Pro Pro Ala Pro Pro Pro Tyr Ser
    555                 560                 565 gag act gac tcg cag gcc tcg agg gag cgg agg atg aaa aag aat ttg        1780
Glu Thr Asp Ser Gln Ala Ser Arg Glu Arg Arg Met Lys Lys Asn Leu
570                 575                 580                 585 gcc ctg agt cgg gaa agt tta gtc gtc tga tcccacgttt tgttatgtag          1830
Ala Leu Ser Arg Glu Ser Leu Val Val *
                590 cttttatact tttttaattg gaatattgat gaaactcttc accaagccta ataaaa         1886

<210> SEQ ID NO 14
<211> LENGTH: 1829
<212> TYPE: DNA
<213> ORGANISM: Mus musculus

<400> SEQUENCE: 14
gcaccgtcgc tgctagacgg ccgcg atg gcg ccg gcg gcc agc gcg tgt gct          52
                            Met Ala Pro Ala Ala Ser Ala Cys Ala
                              1               5
```

-continued

| | | |
|---|---|---|
| ggg gcg cct ggc tcc cac ccg gcc acc acg atc ttc gtg tgt ctt ttt<br>Gly Ala Pro Gly Ser His Pro Ala Thr Thr Ile Phe Val Cys Leu Phe<br>10                    15                          20                      25 | 100 |
| ctc atc att tac tgc cca gac cgt gcc agt gcc atc cag gtg acc gtg<br>Leu Ile Ile Tyr Cys Pro Asp Arg Ala Ser Ala Ile Gln Val Thr Val<br>                  30                          35                        40 | 148 |
| cct gac ccc tac cac gta gtg atc ctg ttc cag cca gtg aca cta cac<br>Pro Asp Pro Tyr His Val Val Ile Leu Phe Gln Pro Val Thr Leu His<br>                  45                          50                        55 | 196 |
| tgc acc tac cag atg agc aat acc ctc aca gcc cct atc gtg atc tgg<br>Cys Thr Tyr Gln Met Ser Asn Thr Leu Thr Ala Pro Ile Val Ile Trp<br>                60                          65                        70 | 244 |
| aag tat aag tcg ttc tgt cgg gac cgt gtt gcc gac gcc ttc tcc cct<br>Lys Tyr Lys Ser Phe Cys Arg Asp Arg Val Ala Asp Ala Phe Ser Pro<br>        75                        80                        85 | 292 |
| gcc agc gtg gac aac cag ctc aac gcc cag ctg gcg gct ggc aac ccc<br>Ala Ser Val Asp Asn Gln Leu Asn Ala Gln Leu Ala Ala Gly Asn Pro<br>90                    95                        100                      105 | 340 |
| ggc tac aac ccc tat gtg gag tgc cag gac agc gta cgc act gtc agg<br>Gly Tyr Asn Pro Tyr Val Glu Cys Gln Asp Ser Val Arg Thr Val Arg<br>                  110                        115                      120 | 388 |
| gtg gtg gcc acc aaa cag ggc aat gct gtg acc ctg gga gac tac tac<br>Val Val Ala Thr Lys Gln Gly Asn Ala Val Thr Leu Gly Asp Tyr Tyr<br>            125                        130                      135 | 436 |
| cag ggc agg aga atc acc atc aca gga aat gct ggc ctg acc ttc gag<br>Gln Gly Arg Arg Ile Thr Ile Thr Gly Asn Ala Gly Leu Thr Phe Glu<br>        140                        145                      150 | 484 |
| cag acg gcc tgg gga gac agt gga gtg tat tac tgc tcc gtg gtc tca<br>Gln Thr Ala Trp Gly Asp Ser Gly Val Tyr Tyr Cys Ser Val Val Ser<br>        155                        160                      165 | 532 |
| gcc caa gat ctg gat ggg aac aac gag gcg tac gca gag ctc att gtc<br>Ala Gln Asp Leu Asp Gly Asn Asn Glu Ala Tyr Ala Glu Leu Ile Val<br>170                    175                        180                      185 | 580 |
| ctt gat tgg ctc ttt gtg gtc gtg gtc tgc ctg gca agc ctc ctc ttc<br>Leu Asp Trp Leu Phe Val Val Val Val Cys Leu Ala Ser Leu Leu Phe<br>                  190                        195                      200 | 628 |
| ttc ctc ctc ctg ggc atc tgc tgg tgc cag tgc tgt ccc cac acc tgc<br>Phe Leu Leu Leu Gly Ile Cys Trp Cys Gln Cys Cys Pro His Thr Cys<br>            205                        210                      215 | 676 |
| tgc tgc tat gtc aga tgt ccc tgc tgc cca gac aag tgc tgt tgc cct<br>Cys Cys Tyr Val Arg Cys Pro Cys Cys Pro Asp Lys Cys Cys Cys Pro<br>        220                        225                      230 | 724 |
| gag gcc ctt tat gct gct ggc aaa gca gcc acc tca ggt gtg cca agc<br>Glu Ala Leu Tyr Ala Ala Gly Lys Ala Ala Thr Ser Gly Val Pro Ser<br>        235                        240                      245 | 772 |
| atc tat gcc ccc agc atc tat acc cac ctc tct cct gcc aag act ccg<br>Ile Tyr Ala Pro Ser Ile Tyr Thr His Leu Ser Pro Ala Lys Thr Pro<br>250                    255                        260                      265 | 820 |
| cca cct ccg cct gcc atg att ccc atg cgt cct ccc tat ggg tac cct<br>Pro Pro Pro Pro Ala Met Ile Pro Met Arg Pro Pro Tyr Gly Tyr Pro<br>                  270                        275                      280 | 868 |
| gga gac ttt gac agg acc agc tca gtt ggt ggc cac agc tcc cag gtg<br>Gly Asp Phe Asp Arg Thr Ser Ser Val Gly Gly His Ser Ser Gln Val<br>                285                        290                      295 | 916 |
| ccc ctg ctg cgt gaa gtg gat ggg agc gta tct tca gaa gta cga agt<br>Pro Leu Leu Arg Glu Val Asp Gly Ser Val Ser Ser Glu Val Arg Ser<br>            300                        305                      310 | 964 |
| ggc tac agg atc cag gct aac cag caa gat gac tcc atg agg gtc cta<br>Gly Tyr Arg Ile Gln Ala Asn Gln Gln Asp Asp Ser Met Arg Val Leu<br>        315                        320                      325 | 1012 |

```
tac tat atg gag aag gag cta gcc aac ttc gat cct tcc cgg cct ggc       1060
Tyr Tyr Met Glu Lys Glu Leu Ala Asn Phe Asp Pro Ser Arg Pro Gly
330             335                 340                 345 cct ccc aat ggc cga gtg gaa cgg gcc atg agt gaa gta acc tcc ctc       1108
Pro Pro Asn Gly Arg Val Glu Arg Ala Met Ser Glu Val Thr Ser Leu
                350                 355                 360 cat gaa gat gac tgg cga tct cgg cct tcc agg gct cct gcc ctc aca       1156
His Glu Asp Asp Trp Arg Ser Arg Pro Ser Arg Ala Pro Ala Leu Thr
            365                 370                 375 ccc atc agg gat gag gag tgg aat cgc cac tcc cct cgg agt ccc aga       1204
Pro Ile Arg Asp Glu Glu Trp Asn Arg His Ser Pro Arg Ser Pro Arg
        380                 385                 390 aca tgg gag cag gaa ccc ctt caa gaa cag cca agg ggt ggt tgg ggg       1252
Thr Trp Glu Gln Glu Pro Leu Gln Glu Gln Pro Arg Gly Gly Trp Gly
    395                 400                 405 tct ggg cgg cct cgg gcc cgc tct gtg gat gct cta gat gac atc aac       1300
Ser Gly Arg Pro Arg Ala Arg Ser Val Asp Ala Leu Asp Asp Ile Asn
410                 415                 420                 425 cgg cct ggc tcc act gaa tca gga agg tct tct ccc cca agt agt gga       1348
Arg Pro Gly Ser Thr Glu Ser Gly Arg Ser Ser Pro Pro Ser Ser Gly
                430                 435                 440 cgg aga ggg cgg gcc tat gca cct ccg aga agt cgc agc cgg gat gac       1396
Arg Arg Gly Arg Ala Tyr Ala Pro Pro Arg Ser Arg Ser Arg Asp Asp
            445                 450                 455 ctc tat gac ccc gac gat cct aga gac ttg cca cat tcc cga gat ccc       1444
Leu Tyr Asp Pro Asp Asp Pro Arg Asp Leu Pro His Ser Arg Asp Pro
        460                 465                 470 cac tat tat gat gat ttg agg tct agg gat cca cgt gct gac ccc aga       1492
His Tyr Tyr Asp Asp Leu Arg Ser Arg Asp Pro Arg Ala Asp Pro Arg
    475                 480                 485 tcc cgt cag cga tcc cac gat cct cgg gat gct ggc ttc agg tca cgg       1540
Ser Arg Gln Arg Ser His Asp Pro Arg Asp Ala Gly Phe Arg Ser Arg
490                 495                 500                 505 gac cct cag tat gat ggg cga ctc tta gaa gag gct tta aag aaa aaa       1588
Asp Pro Gln Tyr Asp Gly Arg Leu Leu Glu Glu Ala Leu Lys Lys Lys
                510                 515                 520 ggg gct ggg gag aga aga cgc gtt tac agg gag gaa gaa gaa gaa gaa       1636
Gly Ala Gly Glu Arg Arg Arg Val Tyr Arg Glu Glu Glu Glu Glu Glu
            525                 530                 535 gag gag ggc cac tat ccc cca gca cct ccg cct tac tct gag act gac       1684
Glu Glu Gly His Tyr Pro Pro Ala Pro Pro Pro Tyr Ser Glu Thr Asp
        540                 545                 550 tcg cag gcc tcg agg gag cgg agg atg aaa aag aat ttg gcc ctg agt       1732
Ser Gln Ala Ser Arg Glu Arg Arg Met Lys Lys Asn Leu Ala Leu Ser
    555                 560                 565 cgg gaa agt tta gtc gtc tga tcccacgttt tgttatgtag cttttatact         1783
Arg Glu Ser Leu Val Val *
570                 575 tttttaattg gaatattgat gaaactcttc accaagccta ataaaa                    1829

<210> SEQ ID NO 15
<211> LENGTH: 1682
<212> TYPE: DNA
<213> ORGANISM: Mus musculus

<400> SEQUENCE: 15
gcaccgtcgc tgctagacgg ccgcg atg gcg ccg gcg gcc agc gcg tgt gct         52
                            Met Ala Pro Ala Ala Ser Ala Cys Ala
                              1               5
```

-continued

| | |
|---|---|
| ggg gcg cct ggc tcc cac ccg gcc acc acg atc ttc gtg tgt ctt ttt<br>Gly Ala Pro Gly Ser His Pro Ala Thr Thr Ile Phe Val Cys Leu Phe<br>10                  15                         20                  25 | 100 |
| ctc atc att tac tgc cca gac cgt gcc agt gcc atc cag gtg acc gtg<br>Leu Ile Ile Tyr Cys Pro Asp Arg Ala Ser Ala Ile Gln Val Thr Val<br>                  30                         35                         40 | 148 |
| cct gac ccc tac cac gta gtg atc ctg ttc cag cca gtg aca cta cac<br>Pro Asp Pro Tyr His Val Val Ile Leu Phe Gln Pro Val Thr Leu His<br>                        45                         50                       55 | 196 |
| tgc acc tac cag atg agc aat acc ctc aca gcc cct atc gtg atc tgg<br>Cys Thr Tyr Gln Met Ser Asn Thr Leu Thr Ala Pro Ile Val Ile Trp<br>                       60                         65                      70 | 244 |
| aag tat aag tcg ttc tgt cgg gac cgt gtt gcc gac gcc ttc tcc cct<br>Lys Tyr Lys Ser Phe Cys Arg Asp Arg Val Ala Asp Ala Phe Ser Pro<br> 75                         80                        85 | 292 |
| gcc agc gtg gac aac cag ctc aac gcc cag ctg gcg gct ggc aac ccc<br>Ala Ser Val Asp Asn Gln Leu Asn Ala Gln Leu Ala Ala Gly Asn Pro<br>90                  95                       100                  105 | 340 |
| ggc tac aac ccc tat gtg gag tgc cag gac agc gta cgc act gtc agg<br>Gly Tyr Asn Pro Tyr Val Glu Cys Gln Asp Ser Val Arg Thr Val Arg<br>                     110                      115                     120 | 388 |
| gtg gtg gcc acc aaa cag ggc aat gct gtg acc ctg gga gac tac tac<br>Val Val Ala Thr Lys Gln Gly Asn Ala Val Thr Leu Gly Asp Tyr Tyr<br>           125                       130                     135 | 436 |
| cag ggc agg aga atc acc atc aca gga aat gct ggc ctg acc ttc gag<br>Gln Gly Arg Arg Ile Thr Ile Thr Gly Asn Ala Gly Leu Thr Phe Glu<br>140                            145                         150 | 484 |
| cag acg gcc tgg gga gac agt gga gtg tat tac tgc tcc gtg gtc tca<br>Gln Thr Ala Trp Gly Asp Ser Gly Val Tyr Tyr Cys Ser Val Val Ser<br>           155                       160                     165 | 532 |
| gcc caa gat ctg gat ggg aac aac gag gcg tac gca gag ctc att gtc<br>Ala Gln Asp Leu Asp Gly Asn Asn Glu Ala Tyr Ala Glu Leu Ile Val<br>170                            175                       180                  185 | 580 |
| ctt gtt tat gct gct ggc aaa gca gcc acc tca ggt gtg cca agc atc<br>Leu Val Tyr Ala Ala Gly Lys Ala Ala Thr Ser Gly Val Pro Ser Ile<br>                     190                      195                     200 | 628 |
| tat gcc ccc agc atc tat acc cac ctc tct cct gcc aag act ccg cca<br>Tyr Ala Pro Ser Ile Tyr Thr His Leu Ser Pro Ala Lys Thr Pro Pro<br>           205                       210                     215 | 676 |
| cct ccg cct gcc atg att ccc atg cgt cct ccc tat ggg tac cct gga<br>Pro Pro Pro Ala Met Ile Pro Met Arg Pro Pro Tyr Gly Tyr Pro Gly<br>220                            225                        230 | 724 |
| gac ttt gac agg acc agc tca gtt ggt ggc cac agc tcc cag gtg ccc<br>Asp Phe Asp Arg Thr Ser Ser Val Gly Gly His Ser Ser Gln Val Pro<br>    235                       240                      245 | 772 |
| ctg ctg cgt gaa gtg gat ggg agc gta tct tca gaa gta cga agt ggc<br>Leu Leu Arg Glu Val Asp Gly Ser Val Ser Ser Glu Val Arg Ser Gly<br>250                            255                      260                  265 | 820 |
| tac agg atc cag gct aac cag caa gat gac tcc atg agg gtc cta tac<br>Tyr Arg Ile Gln Ala Asn Gln Gln Asp Asp Ser Met Arg Val Leu Tyr<br>           270                       275                     280 | 868 |
| tat atg gag aag gag cta gcc aac ttc gat cct tcc cgg cct ggc cct<br>Tyr Met Glu Lys Glu Leu Ala Asn Phe Asp Pro Ser Arg Pro Gly Pro<br>                    285                      290                     295 | 916 |
| ccc aat ggc cga gtg gaa cgg gcc atg agt gaa gta acc tcc ctc cat<br>Pro Asn Gly Arg Val Glu Arg Ala Met Ser Glu Val Thr Ser Leu His<br>300                            305                      310 | 964 |
| gaa gat gac tgg cga tct cgg cct tcc agg gct cct gcc ctc aca ccc<br>Glu Asp Asp Trp Arg Ser Arg Pro Ser Arg Ala Pro Ala Leu Thr Pro<br>      315                     320                      325 | 1012 |

-continued

```
atc agg gat gag gag tgg aat cgc cac tcc cct cgg agt ccc aga aca    1060
Ile Arg Asp Glu Glu Trp Asn Arg His Ser Pro Arg Ser Pro Arg Thr
330                 335                 340                 345 tgg gag cag gaa ccc ctt caa gaa cag cca agg ggt ggt tgg ggg tct    1108
Trp Glu Gln Glu Pro Leu Gln Glu Gln Pro Arg Gly Gly Trp Gly Ser
            350                 355                 360 ggg cgg cct cgg gcc cgc tct gtg gat gct cta gat gac atc aac cgg    1156
Gly Arg Pro Arg Ala Arg Ser Val Asp Ala Leu Asp Asp Ile Asn Arg
        365                 370                 375 cct ggc tcc act gaa tca gga agg tct tct ccc cca agt agt gga cgg    1204
Pro Gly Ser Thr Glu Ser Gly Arg Ser Ser Pro Pro Ser Ser Gly Arg
    380                 385                 390 aga ggg cgg gcc tat gca cct ccg aga agt cgc agc cgg gat gac ctc    1252
Arg Gly Arg Ala Tyr Ala Pro Pro Arg Ser Arg Ser Arg Asp Asp Leu
395                 400                 405 tat gac ccc gac gat cct aga gac ttg cca cat tcc cga gat ccc cac    1300
Tyr Asp Pro Asp Asp Pro Arg Asp Leu Pro His Ser Arg Asp Pro His
410                 415                 420                 425 tat tat gat gat ttg agg tct agg gat cca cgt gct gac ccc aga tcc    1348
Tyr Tyr Asp Asp Leu Arg Ser Arg Asp Pro Arg Ala Asp Pro Arg Ser
            430                 435                 440 cgt cag cga tcc cac gat cct cgg gat gct ggc ttc agg tca cgg gac    1396
Arg Gln Arg Ser His Asp Pro Arg Asp Ala Gly Phe Arg Ser Arg Asp
        445                 450                 455 cct cag tat gat ggg cga ctc tta gaa gag gct tta aag aaa aaa ggg    1444
Pro Gln Tyr Asp Gly Arg Leu Leu Glu Glu Ala Leu Lys Lys Lys Gly
    460                 465                 470 gct ggg gag aga aga cgc gtt tac agg gag gaa gaa gaa gaa gaa gag    1492
Ala Gly Glu Arg Arg Arg Val Tyr Arg Glu Glu Glu Glu Glu Glu Glu
475                 480                 485 gag ggc cac tat ccc cca gca cct ccg cct tac tct gag act gac tcg    1540
Glu Gly His Tyr Pro Pro Ala Pro Pro Pro Tyr Ser Glu Thr Asp Ser
490                 495                 500                 505 cag gcc tcg agg gag cgg agg atg aaa aag aat ttg gcc ctg agt cgg    1588
Gln Ala Ser Arg Glu Arg Arg Met Lys Lys Asn Leu Ala Leu Ser Arg
            510                 515                 520 gaa agt tta gtc gtc tga tcccacgttt tgttatgtag cttttatact           1636
Glu Ser Leu Val Val *
                525 tttttaattg gaatattgat gaaactcttc accaagccta ataaaa                 1682

<210> SEQ ID NO 16
<211> LENGTH: 594
<212> TYPE: PRT
<213> ORGANISM: Mus musculus

<400> SEQUENCE: 16

Met Ala Pro Ala Ala Ser Ala Cys Ala Gly Ala Pro Gly Ser His Pro
1               5                   10                  15

Ala Thr Thr Ile Phe Val Cys Leu Phe Leu Ile Ile Tyr Cys Pro Asp
            20                  25                  30

Arg Ala Ser Ala Ile Gln Val Thr Val Pro Asp Pro Tyr His Val Val
        35                  40                  45

Ile Leu Phe Gln Pro Val Thr Leu His Cys Thr Tyr Gln Met Ser Asn
    50                  55                  60

Thr Leu Thr Ala Pro Ile Val Ile Trp Lys Tyr Lys Ser Phe Cys Arg
65                  70                  75                  80

Asp Arg Val Ala Asp Ala Phe Ser Pro Ala Ser Val Asp Asn Gln Leu
```

-continued

```
                        85                  90                      95
Asn Ala Gln Leu Ala Ala Gly Asn Pro Gly Tyr Asn Pro Tyr Val Glu
                    100             105             110

Cys Gln Asp Ser Val Arg Thr Val Arg Val Ala Thr Lys Gln Gly
            115             120             125

Asn Ala Val Thr Leu Gly Asp Tyr Tyr Gln Gly Arg Arg Ile Thr Ile
        130             135             140

Thr Gly Asn Ala Gly Leu Thr Phe Glu Gln Thr Ala Trp Gly Asp Ser
145             150             155             160

Gly Val Tyr Tyr Cys Ser Val Val Ser Ala Gln Asp Leu Asp Gly Asn
                165             170             175

Asn Glu Ala Tyr Ala Glu Leu Ile Val Leu Gly Arg Thr Ser Glu Ala
            180             185             190

Pro Glu Leu Leu Pro Gly Phe Arg Ala Gly Pro Leu Glu Asp Trp Leu
        195             200             205

Phe Val Val Val Cys Leu Ala Ser Leu Leu Phe Phe Leu Leu Leu
    210             215             220

Gly Ile Cys Trp Cys Gln Cys Cys Pro His Thr Cys Cys Cys Tyr Val
225             230             235             240

Arg Cys Pro Cys Cys Pro Asp Lys Cys Cys Cys Pro Glu Ala Leu Tyr
                245             250             255

Ala Ala Gly Lys Ala Ala Thr Ser Gly Val Pro Ser Ile Tyr Ala Pro
            260             265             270

Ser Ile Tyr Thr His Leu Ser Pro Ala Lys Thr Pro Pro Pro Pro
        275             280             285

Ala Met Ile Pro Met Arg Pro Tyr Gly Tyr Pro Gly Asp Phe Asp
    290             295             300

Arg Thr Ser Ser Val Gly Gly His Ser Ser Gln Val Pro Leu Leu Arg
305             310             315             320

Glu Val Asp Gly Ser Val Ser Ser Glu Val Arg Ser Gly Tyr Arg Ile
                325             330             335

Gln Ala Asn Gln Gln Asp Asp Ser Met Arg Val Leu Tyr Tyr Met Glu
            340             345             350

Lys Glu Leu Ala Asn Phe Asp Pro Ser Arg Pro Gly Pro Pro Asn Gly
        355             360             365

Arg Val Glu Arg Ala Met Ser Glu Val Thr Ser Leu His Glu Asp Asp
370             375             380

Trp Arg Ser Arg Pro Ser Arg Ala Pro Ala Leu Thr Pro Ile Arg Asp
385             390             395             400

Glu Glu Trp Asn Arg His Ser Pro Arg Ser Pro Arg Thr Trp Glu Gln
                405             410             415

Glu Pro Leu Gln Glu Gln Pro Arg Gly Gly Trp Gly Ser Gly Arg Pro
            420             425             430

Arg Ala Arg Ser Val Asp Ala Leu Asp Asp Ile Asn Arg Pro Gly Ser
        435             440             445

Thr Glu Ser Gly Arg Ser Ser Pro Pro Ser Ser Gly Arg Arg Gly Arg
450             455             460

Ala Tyr Ala Pro Pro Arg Ser Arg Ser Arg Asp Asp Leu Tyr Asp Pro
465             470             475             480

Asp Asp Pro Arg Asp Leu Pro His Ser Arg Asp Pro His Tyr Tyr Asp
                485             490             495

Asp Leu Arg Ser Arg Asp Pro Arg Ala Asp Pro Arg Ser Arg Gln Arg
            500             505             510
```

-continued

```
Ser His Asp Pro Arg Asp Ala Gly Phe Arg Ser Arg Asp Pro Gln Tyr
        515                 520                 525

Asp Gly Arg Leu Leu Glu Glu Ala Leu Lys Lys Lys Gly Ala Gly Glu
        530                 535                 540

Arg Arg Arg Val Tyr Arg Glu Glu Glu Glu Glu Glu Glu Glu Gly His
545                 550                 555                 560

Tyr Pro Pro Ala Pro Pro Tyr Ser Glu Thr Asp Ser Gln Ala Ser
                565                 570                 575

Arg Glu Arg Met Lys Lys Asn Leu Ala Leu Ser Arg Glu Ser Leu
                580                 585                 590

Val Val

<210> SEQ ID NO 17
<211> LENGTH: 575
<212> TYPE: PRT
<213> ORGANISM: Mus musculus

<400> SEQUENCE: 17

Met Ala Pro Ala Ala Ser Ala Cys Ala Gly Ala Pro Gly Ser His Pro
1               5                   10                  15

Ala Thr Thr Ile Phe Val Cys Leu Phe Leu Ile Ile Tyr Cys Pro Asp
                20                  25                  30

Arg Ala Ser Ala Ile Gln Val Thr Val Pro Asp Pro Tyr His Val Val
            35                  40                  45

Ile Leu Phe Gln Pro Val Thr Leu His Cys Thr Tyr Gln Met Ser Asn
        50                  55                  60

Thr Leu Thr Ala Pro Ile Val Ile Trp Lys Tyr Lys Ser Phe Cys Arg
65                  70                  75                  80

Asp Arg Val Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Val Ala Thr Lys Gln Gly
        115                 120                 125

Asn Ala Val Thr Leu Gly Asp Tyr Tyr Gln Gly Arg Arg Ile Thr Ile
    130                 135                 140

Thr Gly Asn Ala Gly Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Asp Trp Leu Phe Val Val
            180                 185                 190

Val Val Cys Leu Ala Ser Leu Leu Phe Phe Leu Leu Leu Gly Ile Cys
        195                 200                 205

Trp Cys Gln Cys Cys Pro His Thr Cys Cys Cys Tyr Val Arg Cys Pro
    210                 215                 220

Cys Cys Pro Asp Lys Cys Cys Cys Pro Glu Ala Leu Tyr Ala Ala Gly
225                 230                 235                 240

Lys Ala Ala Thr Ser Gly Val Pro Ser Ile Tyr Ala Pro Ser Ile Tyr
                245                 250                 255

Thr His Leu Ser Pro Ala Lys Thr Pro Pro Pro Pro Ala Met Ile
            260                 265                 270

Pro Met Arg Pro Pro Tyr Gly Tyr Pro Gly Asp Phe Asp Arg Thr Ser
        275                 280                 285
```

-continued

```
Ser Val Gly Gly His Ser Ser Gln Val Pro Leu Leu Arg Glu Val Asp
        290                 295                 300

Gly Ser Val Ser Ser Glu Val Arg Ser Gly Tyr Arg Ile Gln Ala Asn
305                 310                 315                 320

Gln Gln Asp Asp Ser Met Arg Val Leu Tyr Tyr Met Glu Lys Glu Leu
                325                 330                 335

Ala Asn Phe Asp Pro Ser Arg Pro Gly Pro Pro Asn Gly Arg Val Glu
                340                 345                 350

Arg Ala Met Ser Glu Val Thr Ser Leu His Glu Asp Asp Trp Arg Ser
            355                 360                 365

Arg Pro Ser Arg Ala Pro Ala Leu Thr Pro Ile Arg Asp Glu Glu Trp
    370                 375                 380

Asn Arg His Ser Pro Arg Ser Pro Arg Thr Trp Glu Gln Glu Pro Leu
385                 390                 395                 400

Gln Glu Gln Pro Arg Gly Gly Trp Gly Ser Gly Arg Pro Arg Ala Arg
                405                 410                 415

Ser Val Asp Ala Leu Asp Asp Ile Asn Arg Pro Gly Ser Thr Glu Ser
                420                 425                 430

Gly Arg Ser Ser Pro Pro Ser Ser Gly Arg Arg Gly Arg Ala Tyr Ala
            435                 440                 445

Pro Pro Arg Ser Arg Ser Arg Asp Asp Leu Tyr Asp Pro Asp Asp Pro
    450                 455                 460

Arg Asp Leu Pro His Ser Arg Asp Pro His Tyr Tyr Asp Asp Leu Arg
465                 470                 475                 480

Ser Arg Asp Pro Arg Ala Asp Pro Arg Ser Arg Gln Arg Ser His Asp
                485                 490                 495

Pro Arg Asp Ala Gly Phe Arg Ser Arg Asp Pro Gln Tyr Asp Gly Arg
                500                 505                 510

Leu Leu Glu Glu Ala Leu Lys Lys Gly Ala Gly Glu Arg Arg Arg
            515                 520                 525

Val Tyr Arg Glu Glu Glu Glu Glu Glu Gly His Tyr Pro Pro
    530                 535                 540

Ala Pro Pro Pro Tyr Ser Glu Thr Asp Ser Gln Ala Ser Arg Glu Arg
545                 550                 555                 560

Arg Met Lys Lys Asn Leu Ala Leu Ser Arg Glu Ser Leu Val Val
                565                 570                 575

<210> SEQ ID NO 18
<211> LENGTH: 526
<212> TYPE: PRT
<213> ORGANISM: Mus musculus

<400> SEQUENCE: 18

Met Ala Pro Ala Ala Ser Ala Cys Ala Gly Ala Pro Gly Ser His Pro
1               5                   10                  15

Ala Thr Thr Ile Phe Val Cys Leu Phe Leu Ile Ile Tyr Cys Pro Asp
                20                  25                  30

Arg Ala Ser Ala Ile Gln Val Thr Val Pro Asp Pro Tyr His Val Val
            35                  40                  45

Ile Leu Phe Gln Pro Val Thr Leu His Cys Thr Tyr Gln Met Ser Asn
        50                  55                  60

Thr Leu Thr Ala Pro Ile Val Ile Trp Lys Tyr Lys Ser Phe Cys Arg
65                  70                  75                  80

Asp Arg Val Ala Asp Ala Phe Ser Pro Ala Ser Val Asp Asn Gln Leu
```

```
                    85                  90                      95
Asn Ala Gln Leu Ala Ala Gly Asn Pro Gly Tyr Asn Pro Tyr Val Glu
                100                 105                 110

Cys Gln Asp Ser Val Arg Thr Val Arg Val Ala Thr Lys Gln Gly
                115                 120                 125

Asn Ala Val Thr Leu Gly Asp Tyr Tyr Gln Gly Arg Arg Ile Thr Ile
                130                 135                 140

Thr Gly Asn Ala Gly Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Val Tyr Ala Ala Gly Lys
                180                 185                 190

Ala Ala Thr Ser Gly Val Pro Ser Ile Tyr Ala Pro Ser Ile Tyr Thr
                195                 200                 205

His Leu Ser Pro Ala Lys Thr Pro Pro Pro Ala Met Ile Pro
210                 215                 220

Met Arg Pro Pro Tyr Gly Tyr Pro Gly Asp Phe Asp Arg Thr Ser Ser
225                 230                 235                 240

Val Gly Gly His Ser Ser Gln Val Pro Leu Leu Arg Glu Val Asp Gly
                245                 250                 255

Ser Val Ser Ser Glu Val Arg Ser Gly Tyr Arg Ile Gln Ala Asn Gln
                260                 265                 270

Gln Asp Asp Ser Met Arg Val Leu Tyr Tyr Met Glu Lys Glu Leu Ala
                275                 280                 285

Asn Phe Asp Pro Ser Arg Pro Gly Pro Pro Asn Gly Arg Val Glu Arg
                290                 295                 300

Ala Met Ser Glu Val Thr Ser Leu His Glu Asp Asp Trp Arg Ser Arg
305                 310                 315                 320

Pro Ser Arg Ala Pro Ala Leu Thr Pro Ile Arg Asp Glu Glu Trp Asn
                325                 330                 335

Arg His Ser Pro Arg Ser Pro Arg Thr Trp Glu Gln Glu Pro Leu Gln
                340                 345                 350

Glu Gln Pro Arg Gly Gly Trp Gly Ser Gly Arg Pro Arg Ala Arg Ser
                355                 360                 365

Val Asp Ala Leu Asp Asp Ile Asn Arg Pro Gly Ser Thr Glu Ser Gly
370                 375                 380

Arg Ser Ser Pro Pro Ser Ser Gly Arg Arg Gly Arg Ala Tyr Ala Pro
385                 390                 395                 400

Pro Arg Ser Arg Ser Arg Asp Asp Leu Tyr Asp Pro Asp Asp Pro Arg
                405                 410                 415

Asp Leu Pro His Ser Arg Asp Pro His Tyr Tyr Asp Asp Leu Arg Ser
                420                 425                 430

Arg Asp Pro Arg Ala Asp Pro Arg Ser Arg Gln Arg Ser His Asp Pro
                435                 440                 445

Arg Asp Ala Gly Phe Arg Ser Arg Asp Pro Gln Tyr Asp Gly Arg Leu
                450                 455                 460

Leu Glu Glu Ala Leu Lys Lys Lys Gly Ala Gly Glu Arg Arg Arg Val
465                 470                 475                 480

Tyr Arg Glu Glu Glu Glu Glu Glu Gly His Tyr Pro Pro Ala
                485                 490                 495

Pro Pro Pro Tyr Ser Glu Thr Asp Ser Gln Ala Ser Arg Glu Arg Arg
                500                 505                 510
```

```
Met Lys Lys Asn Leu Ala Leu Ser Arg Glu Ser Leu Val Val
        515                 520                 525
```

```
<210> SEQ ID NO 19
<211> LENGTH: 22976
<212> TYPE: DNA
<213> ORGANISM: Homo sapiens
<220> FEATURE:
<221> NAME/KEY: exon
<222> LOCATION: 1898..2253
<221> NAME/KEY: exon
<222> LOCATION: 3437..3781
<221> NAME/KEY: exon
<222> LOCATION: 12065..12184
<221> NAME/KEY: exon
<222> LOCATION: 15045..15101
<221> NAME/KEY: exon
<222> LOCATION: 15666..15812
<221> NAME/KEY: exon
<222> LOCATION: 19479..19652
<221> NAME/KEY: exon
<222> LOCATION: 19799..19858
<221> NAME/KEY: exon
<222> LOCATION: 19956..20087
<221> NAME/KEY: exon
<222> LOCATION: 20229..20854
<221> NAME/KEY: exon
<222> LOCATION: 20944..21094
<221> NAME/KEY: Misc_Feature
<222> LOCATION: 19956..19958
<223> OTHER INFORMATION: Potential variant splicing site AAG

<400> SEQUENCE: 19
aacagtttgg cagttcctca aaaggttaaa aatagaacta ccaagtcacc cagcaattcc      60
attcttaggc atatattcaa aagaaatgaa agcagatatt tgtacaccag tgttcacagc     120
tgcactattt acaatagtca aaggtagaa acaacctagg tccatccaca aatgaatgga     180
taaataaaac gtagcatata catacaatgg tacactagtc cgctgtaaaa agaaattttg     240
atcttactgc atgctacatg gcttcgacat actacaacat ggatggacct tgaaaacatt     300
attctttgtg aaataaacta gacacaggac aaatgttaga cgattccact tatatgaggc     360
acctagaatg ggcaatttgg taagcaaagt agaatagaaa ttactagggg cacaggtagc     420
agggaatggg gagttactgt ttaatggtca cagagtttat gttggggatg atgaaacagt     480
ttcgggata aagagtggtg attggtacac gacattgtga atatacttaa tgccactgaa     540
ttttacactt gaagtggtta aagcgataaa tattatagtt tgcatatttt atcataaaaa     600
tatttttta aacgatgaag ggacgtgaac gggttgaaat tttataaaaa gtggccaggg     660
aaggtgtcac tgcaatggtg tcctacagga ggaggaagat catgtggaca tctgcgggaa     720
gggtgttctg gcagagggag tagcacgggc gatggctctg aggactgtga gaagtatagt     780
tggaaacagc gaggaggcca gggtgtccga agctgagtaa gccagagaga gtgggaggag     840
gtgagataag aggggaagg tcagtttctg ctgagagtga ggaggagcca caggagggct     900
gtgagcaggt ggacgtgatc tggcttgagt tttaacaggg ccagtagaac aaagcacgcc     960
tgggtaccga aaccagccac tggccagttg gcaacctggg ggagtctaac gcgaggaagc    1020
gcccagggtt ccccaggat gcgctttccc tcgccgccac ctggagacag cagagtcacg    1080
cccagcgctg cgcaggctga tcgccgcgcc gcgccccgc cctcggtcgc aggtggctcg    1140
ttccgggaat tcctaagcgg aaaccggtcc caagccccgc gccttcgctc ggccccttta    1200
agagccagaa tttccggagg gctgacccgg gggctaggga tgcccagggg ccgaaccaca    1260
agttgggaac gggtgggga ggtggcgaaa acttccgaag tggaattcca acttttcctg    1320
```

```
gccctgattc cccttgggca tccctgaggg ggcagagctt cccttccggg gactttagag   1380
ggttcctcag gtcatctaac tgggagacac aggaggcccg aagcgccccc cctccacccg   1440
gtccggagga accccagtgg aagtggagaa gtcaggcgcc accaacaagc ctctcccagc   1500
caggactttg cttagactcg ctcctcccgg cagggcgcac ctaggcgggt ccatcgccag   1560
ccggggagag gggtttgggc agggagggaa caggtgcgcg gcgggacccg ccctatctca   1620
acaggtgaat cgctccaagt gggtctcggt tgcatggatc tcggtgcgct tggtttggcc   1680
ggagcagatg ggggccggaa gggacctgtg tccgcaggc gccctcccag cgggccagtc   1740
acttggttcg ggccctgggg gacggagcgc acctgggtca gcccacttcc ggggagggag   1800
gcagaggaac cctcccccgc cgctcacccc taagcccagc cctcggctcc cacccttgtg   1860
tacctgggcc gaaccattca ccggagcgcg cagcgggtgg agtgtggctc ggaggaccgc   1920
ggcgggtcaa gcacctttct cccccatatc tgaaagcatg cccttttgtcc acgtcgttta   1980
cgctcattaa aacttccaga atgcaacagg acggacttgg agtagggaca aggaacggaa   2040
gtgggaaggg gaggagcgtg caccctcct ggccttggtg cgcgccgcgc ccctaaggt   2100
actttggaag ggacgcgcgg gccagacgcg cccagacggc cgcgatggcg ctgttggccg   2160
gcgggctctc cagagggctg ggctccaccc ggccgccgc aggccgggac gcggtcgtct   2220
tcgtgtggct tctgcttagc acctggtgca caggtacggg gcacggggcc tctgacgctg   2280
cggaacgccg gagggaactg tagaggggga tggatggagt tggaggcggc gggaagcggg   2340
aagcggggt ctcagaggct gggaccttcc gatcccctgg gtcttgggcg atctgttgcg   2400
cgcgggagtg agaggaattc cccatttgtg ccggggagcg ctccccgcgc ccttatctgg   2460
aagatagcag gaagtgaaac tccctggacg gtgagacccg gagcggcagg gagaatggaa   2520
ctctttgtgg ggagggagtg gaagaccgcc cgatctctgg gaaaagaaaa gccgggatgg   2580
gacttgggcg caccgggga tttctaagtt ttggagtaac ggggagaggg cacggagggg   2640
ctggatcaga cgcttcctag agggacagag acgaaggaac aatgcctagg cctcgggtgg   2700
gtgtgggact gggactccc catcccccgc accccaccca cctcccgcgg ctccggatt   2760
atacgtgcgt aagagtctgg tgggatggat ttacggactt gaaaccgact tctgctggca   2820
ggctttcacc tggatgggat atttgggtgg tgatgaggtc ttcccgaga cacttttggt   2880
tcagtcattt gaaatgactt tagagtaggg tgaggtggtg ggaggctgat ggagatattg   2940
tgggggcttt agtccctcca tggcaaagca gttcaggcaa acaactccat ggttttccct   3000
ccaaattcaa aaggccccgg gtaacctgga atccttcgta gtcggttttg aagtggggcc   3060
ttgggcgctg ggggcatcaa catggccatc tgggcttgcc tgcccaggcc acacagaggc   3120
cccttgttgt gggtgaatgg caaagggaag aggggactgg tgtggttcag aggccacagg   3180
ctgggaagag ggatggcggg cgagtccaag gaaactggcg gtgtcaccgt gcacctgcca   3240
cttcagcccc acgggtctat aaaatgggca tgattatcgt ggctacctca ctggtcctgg   3300
caattaagga acaatgtgtg ccaggcactc tgtaaaccac atacttgcga gtgtcaagct   3360
ggtgacaggt ggcgttcctg ttgaagcacc tccctgagct cacagcaacc cttgctgtct   3420
ctcctcttgc cctcagctcc tgccagggcc atccaggtga ccgtgtccaa ccctaccac   3480
gtggtgatcc tcttccagcc tgtgaccctg ccctgtacct accagatgac ctcgaccccc   3540
acgcaaccca tcgtcatctg gaagtacaag tcttctgcc gggaccgcat cgccgatgcc   3600
ttctccccgg ccagcgtcga caaccagctc aatgcccagc tggcagccgg gaacccaggc   3660
```

```
tacaacccct acgttgagtg ccaggacagc gtgcgcaccg tcagggtcgt ggccaccaag    3720
cagggcaacg ctgtgaccct gggagattac taccagggcc ggaggattac catcaccgga    3780
agtatgttgg gcagggcagg gggatgaggc tgggcttgcc cgggtggtgg gactggcgtc    3840
cttgtgcggg acctggagtc cccatctgaa agctcttgag tgccagtgtc tgaaaggacc    3900
attgaaggga gcaattcttt ttttttttt ttttgaagat ggagtcttgc tctggactcc    3960
aggctggagt gcagtggtgc gatctcagct cactgcaacc tccacctccc aggttcaagc    4020
aattctcttg cctcagcctc ccgagtagct gggactccag gtgcgtgcca ccacgcccag    4080
ttaatttttg tatttttagt agagatgggg tttcaccatg ttggccaggc tggtctcaaa    4140
ctcctgacct caaatgatct gcccgccttg cctcgcaaa gtgctgagag acaccatacc    4200
cagcctaaag ggagcgattc tattctacta ttcttccttc tgctaatcct tccattcttt    4260
aatttaataa cgaagatttt ttgagtacct gtcatatacc aggtgctgtt ctgggccctg    4320
ggaatacagc tgttaacaaa atcatcaaac cacttccctc gtggagccca cattgcagtg    4380
agagagacaa acacgacaca cactctcaag tccttgaaga taaagaaaac tgggtaacgg    4440
agagaagagg ccagggtttg ttctataatc attaataaca cgagcagtaa gaagtaaaat    4500
ttatctaagt aacaacttat aaagggtcta ctgtgtgcta agctctcatc caggttccca    4560
aggattaact cagaccacac agtaattgaa tagattctat cattgtcatc ttacagaggc    4620
ccagagagag aaagtgactt gcctagtgtc atagctggta acggggctgg gattctaact    4680
cagccacttt gggtctagtg gccaagctcc taatcccttt gcttgcctag ggtggtccgc    4740
agaggactca cagaggagat ggcaggagtg aactgcaggg gcaagagagc ttaatggaga    4800
aagcctgtga catgccagga actgcacaca tattctccca ttgagtcctc tcctctaccc    4860
tcctgacagc tgaggcacag agaggttacc ttgttcaaat gggtgcatag gaagtcaaag    4920
tctggagctg gggtttgaac ccaggcagcc ctgagaacct tgttcttttt ttttgagacg    4980
gagtctcgct ctgtcgccca ggctggagtg cagtggcggg atctcggctc actgcaactc    5040
cgcctcccgg gttcacgcca ttctcctgcc tcagcctccc aagtagctgg gactacaggc    5100
gcccgccact acgcccggct aattttttgt atttttagta gagacggggt ttcaccgttt    5160
tagccgggat ggtctcgatc tcctgacctc gtgatccgcc cgcctcggcc tcccaaagtg    5220
ctgggattac aggcgtgagc caccgcgccc ggccccttgt tcttaactgt aatgctgcct    5280
cctgatagga tgtgcctgtt gggactaagt aaggggcagt cattcattca ttcatttggt    5340
atttatcaag catcgactat gtgtcgttgg tgctggggat agaggtgatt gggatggctg    5400
aagtttctgt cgtcaaggag atgacattct ggtggagtga gactggcagt aaataagcag    5460
ataaagaaag agtatgagaa tttcaaagtc tgggcacggt ggctcacgtc tgtaatctca    5520
gcactttggg aggccaaggt gggtggatca cctgaggtca ggagttccag accagcctgg    5580
ccaacatggt gaaaccccgt ctctactaaa aatacaaaga ttagccaggc atggtggcac    5640
atgcctgtaa tccagctac tcaggaggct gaggcatgag aatcgcttga acccaggagg    5700
cagaggttgc agtgagctga gatcgcacca ctgtactgca gtctgggcga cagagtgaga    5760
ctctgtctca aaaaaaaaa aaaaaaaaa gactccgtca aggtataaga atgtcagaga    5820
gtactaagtg ttgcaaagaa aataacacca ggctgggtgc attggctcat gcctgtaaat    5880
ttcagcactt tgggaggcca aggcaggagg atcacttgag cctaggagtt tgagaccagc    5940
ctggacaaca aaatgagacc ccatgtctac aaaaatttta aaaatttaaa aattagctgg    6000
gcatggtggc atgtgcctgt ggtcccggct gctcaggagg ctgaggtggg aggattgctt    6060
```

-continued

```
gggcttgaga ggtcaaggct tcagtgagtc atgatcgtgc cactgcattc cagcctgggt    6120
gacagagtga gaccctgtct tgaaatgaaa agaaaatagg ctgggcgcag tggctcacac    6180
ctgtaatccc agcactttgg gaggccgagg tgggtggatc acctgaggtc aggagatcga    6240
gaccagcctg gccaacatgg tgaaatccca tctctactaa aaatacaaaa tttagccggg    6300
cgtggtggtg ggcgcctgta atcccagcta ctcgggaggc tgaggcagga gaatcgcttg    6360
aacctgggag gcgaaggttg cggtgcgcca agattgcgcc actgcactct agcctgggaa    6420
acagtgagac tccgtcttaa aaaaaaaga aaaagaaaa tagcactggg tgatgtgcta    6480
catggaatga cttgggctgt gaatatgatt tgaggagggc ctgggcctgg gccttacaga    6540
acctagaagg cagagaggaa ggggaggggc agggtgccag ggatgaaggc tcacgtacct    6600
catgtcttag tgtgtgttca ctgtcttaaa caagaattta agttgggca tggggcagag    6660 cggggaaggg agcatcccct tgcagacccc aagaagccag gaactggagc acattctgct    6720
agaggatcga tgggaagcag ggttccaggg gctgagccta tgtcagtcct gtttcagagg    6780
aggcaccagg cttgcttgcc ctgaatttct gtgggcagct cagccatgag catcctactg    6840
ttattgaggt cacagggctg cttaggcccc ctcctctcta acccagggat tgtgcctgcc    6900
tggaccaggc gtgactgcta agcttctgcc aggacaagcc aaatactgag ggtgcttcct    6960
ctgctggacg caaaagtcca ggatgacccc ccaggctctg tctcggggaa ggggccctgc    7020
atgctccagg ggcctcacag gcctgggtct ttcaaaccac ccccacctgg gcctgtgttt    7080
gatcaaggcc ctgagtgtaa acatccattg tgtgtgtcct ttcaggaaat cccatagcca    7140
taggagcttc ctctgtttca gctttgagga tggggaaaag tggactcccc gtggtgttcc    7200
tagggtcacc cactgtgctg gggtttttct gttgttgttg ttttttttct gttgcccagg    7260
ctggagtgca gtggtgcaat ctcagctcac tgcaacctct gcctcgcaag ttcaagtgat    7320
tctccgcctc agcctcctga gtagctggga ttacaggtgc acaccaccac acctggctaa    7380
tttttgtatc tttttggtag agatgggatt tcgccatgtt ggccaggctg gtctcaaact    7440
cctgacctca ggtgatctgc ctgccttggc ctcccaaagt tctgggatta cagatgtgag    7500
ccaccatgcc cggcctatcc tggtttcaaa agtgaaaata gtcctggata aggtagaagg    7560
ctgtccactc caggcatccc tccggtccgg tggctcattc cctgctttgt ccttccatgc    7620
tttgggtgat ggaccagcac ctggacagga ggccctgttc cacctcctcg ggctccttgg    7680
ggtccaagtg cccccacctc cagctgcact gcagcagaga gcccatggga cctctgaaat    7740
catgaaggtc acctttgcgg tgtataaaga aggaaccaga ggttggagat gtggaggagg    7800
cctggctgct gttcccactg gagacctggc atcttctccc cgacctaaaa caatgaaagc    7860
agtgctcagc ccggatgaga tcacggccag cccaagacca ggaacagggt acgccctgca    7920
ggaagaaggt gtgcccagac cttaggatgg atcaaaagaa gccggaaaac tatattttt    7980 gtgagttttg aaaatgtcag acaggtcaaa caaaacacag tgaggtccag cctcggccta    8040
caagatgcca gatttcaacc cctggcctat atgatctgtt tgcctggca ggcggttcct    8100 gtccacctct tttgtttata gcagggacca gctcttgagc tccagtgttg aagaggcacg    8160
gtcagggtct gatctgaaga cactggtggc tcatgcctgt aatcccagca cttcaggagg    8220
ccgaggcagg aggattgctt gaggacagga gctgggagac cagcctgggc aacacagtga    8280
gacccagaga ctacaaaaaa ataaatttag cggggcatga tggcacaccc tgctactctg    8340
gagatgggaa gattgcttga gcctaggagt tcgaagctgc agtgacccat gatcgcacca    8400
```

-continued

```
ctgcactcca gcctgggcga ccaagctagg ccctctcaaa aaagatacag gtggaaaaat    8460
gatggacgaa gagggcattg tggcaaacct ggggatttag gagaacctag tttggaattc    8520
tatgaggatt caatgaaaga atgtgtgtag aggggcccag cacatagtaa gagctcaata    8580
aacggtgggg gctaggggcg gtggctcatg cctgtaatcc cagcactttg ggaggctgag    8640
gcaggtggat cacttgagcc ctggagttca agatcaacct ggacaacaaa gcaagatccc    8700
atctcaaaat taaaaaacaa caccaacaac aaaaaaacag tggcttagat gcctgatcat    8760
tagggtaagt cgtgtcctca acccctttcac atctgctctg aaggtcacca tatccggaag   8820
ccttccctgg cctccttgtt taaaatggca cagcccccac tccacgcctg gcactctctg    8880
ctgtccctga ttcgttttct ccatacagct tatctttgtc tgatatgtga catagttaac    8940
attttatatt tgtctttctt tcctagttag aatctgaact ctagaagggc aagggcaagg    9000
atttataact caaaggttcc gggcttaggc ctcttttata ttcttgattt tgaggttaat    9060
taagagctca ggcctagcga ggtggctcat gcctggaatc ccagcacttt gggaggccca    9120
ggcgggcaga tcacttgagg tcaggagttc agacctgcc tggccaacac agtgaaaaac     9180
ctgtctctac taaaaataca aaaattagcc agttatgttg gcaggcgcct ataatcccag    9240
ctactcaaga ggctgaggca ggagaatcgc ttgaacccag gaggcagagg ctgcagtgag    9300
ccaagatcgt gccactgcac tccagcctgg gcaacagagc gagactccat ctcaaaaaaa    9360
aaaaaaaaat taagagctca aagagtttgt tttcataggc agcagaatga gaaaagttta    9420
caaaatagtt taaatgacaa taaagtcatt atagattaac ataaataaaa tacctttttat   9480
gaaaaaaata atcattttct gaaatcagac aaaacattgt gaatgagaag gtggcatggt    9540
tttatttttt tgcaagtctc cgaagcctgg ctggatagaa gagcctggct tctcagagct    9600
gcttcagtct gttgtgatat ctattgtatg tcacgtagcc tctggaaaac tccacagtta    9660
gtattgttgg gaaaataact ttgacctcag gatctcctga aaacgtcttg ggaaccccca    9720
gggtctagag gctgcagttt gagaactgtt gctgtggtat cccaggtgtc tcaaatactg    9780
cctagaacat aggtggtact cagtaattat tgttgaagga tgaatgaatg aatgaatgaa    9840
tgaatgaatg aaagaaagaa agaaatgtgt ctttgaatcc agccatgtgc ccagaatgat    9900
gagacagatg acaaaagcta agggacttta gcatgaggag aggggggttcg tttcctttt    9960
tttcttttt ttttgagatg gagtctcact ctactgccca ggctagagtg cagtggtgca   10020
atctcagctc actgcaatct ctgcctcctg agttcaagca attctcctgc ctcagcctcc   10080
agggtagctg ggactacagg tgcgtgccac catgcctagc taatttttta catttttggt   10140
agagatgggg ttttaccatg ttggccgggc tggtctggaa ctcctgacct caagtgatcc   10200
acctgcctca gcctcccaaa gtgttaggat tacaggtgtg agccaccatg tccggccaag   10260
agggtgttca tttctgctcc ttgccaggta ttgtgtcagg cactggggac ccagcagtgg   10320
ctgagacaga cagggctctg cctcacggag cccacatttt caccaggcaa aggatggtcg   10380
gccccctaagc tggagataa gacttcagca gttgggtggg ggagccgtgg gagaagccca   10440
gcccacaggg ggacagtgca aatctagaac caaggcgatg gcagggtgga ggctggcacg   10500
gtagctagag accacgtcgt gccaaggggcc ttggggacca tgggactatg ggaccttagg   10560
gaaggcgtct ggaatgctgt agccagacac tgttgcaagg aggattttc tgtagacatg    10620
aggccttcct tatgaagaaa gcaagggttc tttcattcct gggggtgcca ggtgctgtgg   10680
actgcagcac gcgtggttgc tgccgtcaca gagctgtcat gcaggagggc agcgcgtcct   10740
tgggaaggtg gcaggcaggt caggctagga ggaaagaggc cgggaagctg agggcatttc   10800
```

```
ctgcccgaga tgcccaatgt agcctacttc tgtccccagt ggcttaaggc agagttgcct    10860
ggtaggtgcc ctggtcccac cctggtgaaa ggctgaaggt atttaattag tgcctgagaa    10920
gcagagagga acaggatgt gccaaaacac tttgatggat ggtagagtta acaggctcct     10980
tgcctgcagc tgcttcagac aagagcgtcc ccaagccctg ggcctgacct ggaatgtggg    11040
gatggaaggg gaggggagg aaccaaggca ctgggagggt aagtctctct ctcccacata     11100
gacacaccca ctccttatgg gtgcctgggc atctcctggt acctagaatc tggcctgttt    11160
atctccacac ccatccctgg ggtctacact aggccctgtg ggtggcagtt cacatcaggg    11220
gagttctgac tttggctctg agaggtggtt cagagatggc tgtaagttga aagcacaga    11280 ctgctgggtg tggtggttca cgcctgtaat cccagcactt gggaggctg aggtgggggt    11340 ggatcacctg aggtctggag ttcaaaacca acttggtcaa catggcgaaa ctccatctct    11400
actaaaaatg caaaaattag ccaggtgtgg tggcaggtgc ctataatccc agctacatgg    11460
gaggctgagg caggagaatt gcttgaatct gggaggcgaa gattgtagtg agccgagatt    11520
agttcgcacc attgcatgcc agcctgggca acaagagtga aactccgatt caaacaaaaa    11580
aaaaaaaaag ctgggcatgg tggagtgcct gtagtcctaa ctactcaggt gggaggattg    11640
cttgagtcca ggaggttgaa gttgcagtgg gctataatta ccactgca ctccagccag      11700 ggccacagag tgagaccctg tctctaaaga aagaaaaaa aaacaacct caggctccga      11760 gggcaccatt actgctctat actgaagagc tgtgcagctt ttccagaccc gaaatgtcat    11820
ccacaaaaca gaagtgataa tggtcctgcc tcacagactt cttgcagtag tccaggtgtt    11880
tagaacgggg tgtaaaaggc cgtgtgccct tggtaggaat cttttgcatat gcatttgatc   11940 atctgcagcc tgcccagccc actgcttgcc ccctcctggg tgtgctggga agggtctttt    12000
ggccctccag gggttaggtg ccccagcctc caaggtgccc tcacgccttt tcatcccgac    12060
tcagatgctg acctgaccct tgaccagacg gcgtgggggg acagtggtgt gtattactgc    12120
tccgtggtct cagcccagga cctccagggg aacaatgagg cctacgcaga gctcatcgtc    12180
cttggtgagt gggcctggga agggggaggc atggcccttc cttttgtccg cttctgttct    12240
gtctgccctc ccctgtgtcc gccctctgcc ctccagctta ccctctgggc tctgtcgcct    12300
gctctgctct ccccaggct ctgccagtca cttaggctcc cctgtgccct gcaccccagg    12360
cagggaccac tggcccacag tgcctccaat cacccaagcc aaactaagag aagagtggag    12420
acaattggag actctgcctt ttcaaagtct cattttaaa aaaaatccag acttggggtc     12480
cgggtgcggt agttcatgcc tgtaatccca gcactttggg aggccgaggc gggtggatca    12540
cttgaggcca ggagttcgag actagcctgg ccaacgtggc aaaatcccgt ctctataaaa    12600
aatataaaag ccaggcgtgg tggtgcacat gcctgtaatc ccagttactc agaaggctga    12660
ggcatgagga ttgcttgaac ctgggaggca gaggatgcag taagccaaga tcaagccact    12720
gcactccagc ctgggcgaca gagtgagact ctgtccaaaa aaaaaaaaa tccagacgtg     12780 gtcagagtcc atgggcagtg aatgaggaca gttgatggtg tgcaaaatcg acccacctct    12840
tgctacatcc ccaaggcctc atctcacccg agtccctcgc caaagcacag cggttttgcc    12900
gtgtgccctg ctgggatggc gctgcatggc acacacactg tgtaagtttg agtgcagctg    12960
aaacgaagcc gattccagac acccagggc agggcgggt gtccgtgtgg ctgggaggcc     13020
tccttgtgtt aggggggatgt tgccatcggc caggtgccct gctgtaagcc aacacatgga   13080
gtcttgtatg acatgtgctc tgcatgagtg atgccgctgg gctgtacact gccatcttca    13140
```

```
catgtgtgaa tgagcacgtg actgggggt acttgggctg caagacagag ttcatgtgtg   13200
ggggatggaa cacgtgcacc agtgacccag gaacctctgc ctgttcttcg gtaaaatgca   13260
ccatttgcat cagcagttcc caaaattagt ctccaggtct atttacactc taaaacatta   13320
tcgagggtct ccaagagctt ttgtttgttt ctgtgggttt tatgtctatc tgttgcttaa   13380
catattagga attaaaatgg ggagattttc ctttttttt ttttttttg agatggagtc   13440 tcgttctgtc gcccaggctg gagtgcagtg gctcgatctc ggctcactgc aagcttcacc   13500
tcctgggttc acgccattct cctgcctcag cctcccaggt agctgggact acaggcaccc   13560
gccaccacac ccggctaatt ttttttgtat ttttagtaga gactgggttt caccatgtta   13620
gccaggatgg tctcgatctc ctgacctcgt gatccaccca cctgggcctc ccaaagtgct   13680
gggattacag gcatgagcca ctgcccggcc ttaaaatggg gagattttc aagcccaaga   13740 tacacaagga agactgggca acatggcaag accctgactc tacaaaaaat tttaaaatta   13800
accaggcatg gtggcatgca cctgtgagcc cagcttcttg ggaggctgag gcaggagtat   13860
cgcttgcacc caggaggtca aggctgcagt gagccgtgac tatgctactg cactctagca   13920
tgagtgacag agaccctggc tcaagaaaca caaacacaca cacacacaca cacacgcata   13980
tagtccatta ggcatcaggg cgatgatggc atcagggagc ctgggaaact ctactggaca   14040
ttcatgggag aacaagtgaa aaaggcaaat aacatcttag tgttattcta aaatttcttc   14100
ttttggcctt gtggacagga ccacgctttg agagctgtga ctgacatgcc tctgtcctgt   14160
tgcgagggcc tatagtgcca agtgcatgag ctctggggag ggcttcgtgg gtgcagagct   14220
gggcctgtgg aggcccctca gacacaaaac tggtggggct cagagctcca ggggcactcg   14280
agggaagaca agaaccggct ctgagatgcg tgaatgtgac agtgcatgag tagagatgga   14340
gaccttgtgg gtcccagaac caggactgca tatgactttc atatgtgggt atttttgcct   14400
tcatgggtcc cttcctgttt taaaaaaaat gtgtgattat gttgtcacaa agagtttatt   14460
cctgtatatt gtgttaattt gtgttcagat ttgtaaagta aaattaaacc atttcagcca   14520
ggtgtggtga cacatgcctg tagccctagc tacttacccc agaggctgag gtgggaggat   14580
cgcctgagcc cacgaggttg aagctgcagt gagccatgat cacacccctg cactccagac   14640
tgggcgacag agctgagatc ctatttcgtg gccctaggt ccctgtgcct gctggaacag   14700
gacatcccta tcaccgtggt tggagccctt tggggtgcta agacctatga atgagggaaa   14760 cttaggtgc ccaagctgag gtagagccct cagaaccccc tgggatttgt attggagccc   14820
tcgtggcata acacaggtgg attatgcaat gggagtttct tacctataag cacccacatg   14880
tgggcgggtg gagggtagga gccatgcact agggcttcag cccccagccc cttcccgctt   14940
cagggcacac cttgcacttg gccagcctgg agctgggctt tcgggggtgg cacagcctgg   15000
gctggctctg gccagcataa tctgtttctc ttttgtccct ccaggagga cctcaggggt   15060 ggctgagctc ttacctggtt ttcaggcggg gcccatagaa ggtacggggg gtggatcctg   15120
agttgggctc tcgggagct cccatacatc acctactgct tctgactcta gttagtatcc   15180
ccttccccac taaaccctgc tcactgtgga cccctcacta acctggcctg actgtggctc   15240
tgaggcatct agtggtctgg cgctgggcct aggctaggct gggctgagga gagcctgggg   15300
tgcaggccag ggctctgtga ctggcacctg cggtgctctt gagggtgtgg cgtctgggca   15360
gctggctctc tctttggtct gggggctgca gtctgtctcc ctctgtgcag gctgcctcgt   15420
tttctgcctt gtgttttttg cacctggggg agggccgtaa ctggggaatg gccgggatgg   15480
tagaatgggg agtgtgctgt gcccagcctc tggcacaaaa aatccagcca gggctgcagg   15540
```

```
ttccttggtg agctttgcaa atcgtccccg acctcagtgc tggctccgca ccatgtaccc    15600
ctgctgtgcc gttagccctg ttccctccca ggcctccggg ctcagggcct gttgtctttc    15660
tgcagactgg ctcttcgtgg ttgtggtatg cctggctgcc ttcctcatct tcctcctcct    15720
gggcatctgc tggtccagt gctgcccgca cacttgctgc tgctacgtca ggtgcccctg     15780
ctgcccagac aagtgctgct gccccgaggc ccgtaagtgt cccgctcatg gccaccctgg    15840
tttgggcaac atcctgcatc caagggaagg aggtggccat ccacctgccc ccaggacagt    15900
ggcgttggtc tggagggtgt gaatttagcc agtggggaga agtaggctg aggagggtct     15960 gctgtttaga ttgtcgttta cttcctccaa ctttttagttt attttttattt atgttgttct  16020 tttcttttgt aagtataatc catacacatg gtaaaaatgt ccaacagtac aagatactag    16080
tcacatggaa gtaaagccct ctaaaaaaac caaatcttgg ctaggcgcag tgattacgcc    16140
tgtaatccca gcactttggg aggccaagac gagtggatca cttgaggtca ggagttccag    16200
atcagcctgg ccaacatggt aaaacccagt ctctactaa aatacaaaa attagctggg      16260 catggtggtg atcgcctgta atcccagcta ctcaggagac tgaggcatga gaatcgctta    16320
aacccaagaa gtggaggttg cagtgagctg agatcacgcc actgcactcc agcctgggcg    16380
acagagtgag actctgtctc aaaaaaaaaa gaaaaaaaaa tgttaagtga aaagttaag     16440 aaaccaaaca aggtttacaa cactacatga tttaagcaaa aaaaattttt tttgttttag    16500
agaaagggtc tcattctgtc atccaggcag tgcagtgcga tcatagctct ctgcagcctc    16560
aaactcccgg gttcaagcag tcctcccgcc tcagcctctg gagcagctgg gactgtaggc    16620
acacaccacc atgcccagct aatttttttga ttttgtttt ttgtagagac ggggtctcag   16680
tatgttgccc agcctgatct caaactcctg gcctcaggtg atcctcccaa gtcagcctcc    16740
ccaaagtgct gggattacag gcatgtgcca ccatgctggc caattttttaa aaattttctg  16800 tagagacagg gtcttgctat gttgcccagg ctggtcttga actcttgacc tcaagtgatc    16860
ctgcctcagg ctcccaaagt gatgggatta caggcatgaa ctaccacacc tggccttaaa    16920
cttaagcaaa tttttttttt tttttggaga cagtttcact ctgtcgccca ggctggagta    16980
aagtggcgtg atctctgctc actgcaacct ccgccccccg ggtttaagct attctcctgc    17040
ctcagcctcc cgagtagctg ggatataggc gcctgccacc acgcctgact aatttttgta   17100 ttttttagtag agacgggtt ttgccatgtt ggccaggctg gtctcgaact cctgacctca    17160
ggcagtccgc tcccccgcac ccctaccttg gcctcccaaa gtgttaggac tacaggtgtg    17220
agccaccatg cctggccaaa tttaagcaaa tgtttgaaaa cataccccca caggaatgct    17280
gcacatttta cccagctact atgtctaggg tcgtatctag cacaccagca tggctactgt    17340
ggagagctgg gactggatgt gagatgagag ctaagggga agtaagcaaa ccaagcaggg     17400
gaaggtaaga aagacagaa gacagagaga gagggaccta actctatgag aggagtcaga    17460
catgtgcaat tgaaaaagac ttgctcctgt ctctcttctg tgaatgtttg tgaatatccc    17520
aacgggacac tttcacagag gagctgattg acgtggtcac agccatcagc cttgggacac    17580
cagaccacag tgtgtacact aagtggcact gatggacact tcagcatccc tctagctgct    17640
gtcccgtttc ccctcctcgg ggaccacagc tgttgccagt ccttggtttc cttcaggagg   17700
gtgtctgggt agaccagcct gtgtgcacac agtccaagat acatgaacag tgaagtgcca    17760
ggcaatcctt gcaagcatgg gcaggtggag agctgaggcc tgcttgacac cttcctgctc    17820
agaagcccag tgagcagttt ccctcccctag ggctcagtgt catcccctat aaaatggggc   17880
```

```
ttatggcaga gctcaccaca ctgggtgcat ctggggattt ggcgagctca tgtgcacacc   17940
attgagcatg gggcccaacc tatataaaat attctacgtc tgtcagctgc tgggcactgc   18000
cactatcagc ctcagtagtg actgagggac agggcaccag tcagaccct ggtgcacaca    18060 gagtgacccc agagaagcag ccttccctct ctgagtcctg tttccttctg ttaggtcctg   18120
acttcatggg ttgttgttag cattaaggaa gtcgctggct aattttatag tcattgaagt   18180
cagtggtgtg caacctggtt cctcaaagga tcacttccct gaaaaaattc cactgctccc   18240
tggaggctta tgcaggccat cccatcccct ccctcttgtt gtgttcagct gacagctttt   18300
tgctcagtga gtaagtgtta ggtccatttc acagatgggc tgcaaccaag tttgcagtga   18360
acccactaag accagagcta gggccaggac taaatgctgg tcccaatgcc acattcccct   18420
gtccccacac cacatttcct ccatccggag accctgttac cccaacccag ggccccatta   18480
actccctggc agaggccctg ttacatctgc tgctgccaca gcctccgccc acccttcagg   18540
aggcagcagg tcccactgct gatgataaag ttgcaggctg cctgagctaa tgaagggggct  18600 tcctctaggc tgtgcactta gtcttctgct tccaaaccaa atcagaggtg aggcaccctc   18660
tctgggccca tctctctcct ccattttcct gttggggtcc cagggaggaa gccacttgcc   18720
tagggcccag gaattttgca agcctcttgc cctaggagg aaggaaggga ggaggatctt    18780
accttgaact gtcaagccta gagcctggtg gggcaggcag aaatgggtgc agtccatgag   18840
ttagaaacac tagaggagac actttgctgc ttggccgggg caggcaagtt aattcccgag   18900
gctcctgcca ctgcatctca atctggaagg tgaccaggtg ggcaggaccc acgtctccca   18960
gatgactcat tttttctaga acagggggctt ggctgccaaa gaggatactt gatttcggct  19020
tgtggggaca gtggtggacc cagcatctgg gctttatata aagggcagct ttgttgccct   19080
gtaaacacac agaccatggg tggccacttc ttccagtaag ttagctgggg agttggaagt   19140
ttaggtaaaa ccttttgatt gacaaatgtt ggcgaattac catgctgtta aatgaaacat   19200
tgttctgcca ccctggggct gtgggtgcct gcgtgcaccc tctgaaaaat cacacaggaa   19260
gtggggtggg gtctctgtga agctggtgtc ccccagcctc agggatgctg cagaaatgga   19320
atgaggacca acagggactc agatgtccaa ggaagctcta cagcggagag gacggcttgg   19380
gaaggaggtc caggcccagg tccctccgga acccaatggg tatggggcag cctggctcct   19440
gcctcatccc ccttctcctg ttgattgtgt cctcacagtg tatgccgccg gcaaagcagc   19500
cacctcaggt gttcccagca tttatgcccc cagcacctat gcccacctgt ctcccgccaa   19560
gaccccaccc ccaccagcta tgattcccat gggccctgcc tacaacgggt accctggagg   19620 atacctgga gacgttgaca ggagtagctc aggtgaggcc gggggaagca ggaacagctg    19680
gtgggagtgt gctgggcatc tggacactga ggggcagggg ctggaaggaa gagtgtcttg   19740
ggagccgagg aggggctctg ctcctggtgc gcggccactg acagccactc tcccccagct   19800
ggtggccaag gctcctatgt acccctgctt cgggacacgg acagcagtgt ggcctctggt   19860
gagaatccat cgtcccgaag ttggatgtgc ctgtaaggga gaggggtggg ccaggatcca   19920
tcctcccaaa ccgaccacca cccccctgtc cctagaagtc cgcagtggct acaggattca   19980
ggccagccag caggacgact ccatgcgggt cctgtactac atggagaagg agctggccaa   20040
cttcgaccct tctcgacctg gccccccag tggccgtgtg gagcggggta agcaggagcc    20100
ttggggtctg agggcttttta aggtgggggg gtgaaacatg tctccctgat acctgccgca   20160
gggactcttg gtgcaaaccc tggaccccgg gctcctccag cagtcagtga cacccccctt   20220
ccctgcagcc atgagtgaag tcacctccct ccacgaggac gactggcgat ctcggccttc   20280
```

```
ccggggcccct gccctcaccc cgatccggga tgaggagtgg ggtggccact ccccccggag   20340
tcccagggga tgggaccagg agcccgccag ggagcaggca ggcggggggct ggcgggccag   20400 gcggccccgg gcccgctccg tggacgccct ggacgacctc accccgccga gcaccgccga   20460
gtcagggagc aggtctccca cgagtaatgg tgggagaagc cgggcctaca tgccccgcg    20520 gagccgcagc cgggacgacc tctatgacca agacgactcg agggacttcc cacgctcccg   20580 ggaccccccac tacgacgact tcaggtctcg ggagcgccct cctgccgacc ccaggtccca   20640
ccaccaccgt acccgggacc ctcgggacaa cggctccagg tccggggacc tccccctatga  20700 tgggcggcta ctggaggagg ctgtgaggaa gaggggtcg gaggagagga ggagacccca    20760
caaggaggag gaggaagagg cctactaccc gcccgcgccg cccccgtact cggagaccga   20820
ctcgcaggcg tcccgagagc gcaggctcaa gaaggtgagg gccgccctcc ctggcgtcca   20880
gaccgtccct gggcccccag ccggtccccg cggctcatac ccttctttct ttctcccttg   20940
cagaacttgg ccctgagtcg ggaaagttta gtcgtctgat ctgacgtttt ctacgtagct   21000
tttgtatttt tttttttaat ttgaaggaac actgatgaag ccctgccata cccctcccga   21060
gtctaataaa acgtataatc acaagctctg gagagaacca tttgttcggc cgcgcggggc   21120
gggggaccgg ggctgctccc gtatgcgtct gtaaagcgcc gcgtcccggg ggcaccggag   21180
tccggggccg ggaggaagag acccagcctg gcccggcccg cgcccgcgcc gccggccgga   21240
gaacgtgccc cgcgcagccg ccgccgcct cgtgcgcgc cccggccccg cccaggcgtg    21300
cgcatgcgcc ccggccctcc gccttcgcgc accgcaggct ggccgtccgg gacgcgcgcg   21360
cgctcctctc cccttccagc ccatccccc cagccccca ccgacctact ttactgtctc     21420
caaactcggg cagcccacct ggccccgac gaccccagcc cctgcaccgg gtaccccgac    21480
gttccatcca gacccgcgtt tcaccagggc ggcgcgcggc gacctcgcgc ccgcggagc    21540 cccgggctcg cgcgcgcccg cccgcccccg gagacagacc agcgcgcgcg ccccgggccg   21600 cctccccca gcgcgcgtcc gccccgggc tcgcgccgcc gccgccgccg ccgccgcgcg    21660
cgcgcagctc aagtaaagga ggaaaaaaaa aagggggaaa aatagaaagc ggcggcggct   21720
gcagcagcga tccgccgccg gactgggcca agccgggcgg cggccgcgcg agccggcgat   21780
ccagggcact ggcggcggcc agccagggcg ggccgtgttc aaaaaaaaaa gtcgcggcgg   21840
cggcggctgc tcagggaagg aggcctgagg gccgcgtgca gcgggcgggc agctgggtgg   21900 gctggggcg gccgcgcggc gtcccggagc ctcgggccgc ccggagccgg cgggcgggcg   21960
gaggcggagg cggcggcggc tgcagcggct gcaggagcgg cggcggctgc ggcggcggcg   22020
gcggcatctc ctcctcacat gacccactg tttgtccccg tgatcagcgc gagcggctcc    22080
cgtatctcct ccgtcccctc ctgccgcgcg gcgtgagcgc cgggctcggg gccccccgg    22140 ccgcccgccc cctcccctcc ctccctcccc tccctcccc tccccccgg gccccgcgcc    22200 ccccccgccc ccgccccccc catggacatg ctggaccgg gtctggatcc cgctgcctcg   22260
gccaccgctg ctgccgccgc caggtaagat ccccggcccg gccgtgcccc cgcgcccgg   22320 cccccggcccc ggcccgcgg cctgcaggcc ggggccgcca tgatcccgag cggccgcggg    22380
cccggctcaa aatggaggcc gccggcgcgg ggggacctg gcgcctcccg ccccggccc     22440 ccggcctcgg cggcgccccc ggcctcaggc gcggccgggt gggactgggg ccctgcagct   22500
gggcgcgggg gcggggggcg gggcgcgggc cgcgctgacc ctgctccctc ctgtgccct    22560 ggcagccacg acaagggacc cgaggcggag gagggcgtcg agctgcagga aggtgagtgc   22620
```

-continued

```
ttgccgggcc ggccgcgccc ggggagggct ggggcgctc ggcgcggccc tgaccgtgcc      22680
ccgaccctcc tcggccccag gcggggacgg cccaggagcg gaggagcaga cagcggtggc      22740
catcaccagc gtccagcagg cggcgttcgg cgaccacaac atccagtacc agttccgcac      22800
agagacaaat ggaggacagg tgagcggcgg gccgcgaggg cgaacgggcg ggcgggcggg      22860
cgcgccggga aggctcggac ctggcccag cgccggcctc gccgctctgc cgcccctgc       22920 aggtgacata ccgcgtagtc caggtgactg atggtcagct ggacggccag ggcgac         22976
```

<210> SEQ ID NO 20
<211> LENGTH: 30
<212> TYPE: DNA
<213> ORGANISM: Rattus norvegicus

<400> SEQUENCE: 20

```
gttacagaat tcgccgcgat ggcgccggcg                                         30
```

<210> SEQ ID NO 21
<211> LENGTH: 20
<212> TYPE: DNA
<213> ORGANISM: Rattus norvegicus

<400> SEQUENCE: 21

```
gccaggacag tgtacgcact                                                    20
```

<210> SEQ ID NO 22
<211> LENGTH: 20
<212> TYPE: DNA
<213> ORGANISM: Ratus norvegicus

<400> SEQUENCE: 22

```
acctcaggtg tcccgagcat                                                    20
```

<210> SEQ ID NO 23
<211> LENGTH: 20
<212> TYPE: DNA
<213> ORGANISM: Rattus norvegicus

<400> SEQUENCE: 23

```
gaagatgact ggcgatcgag                                                    20
```

<210> SEQ ID NO 24
<211> LENGTH: 20
<212> TYPE: DNA
<213> ORGANISM: Rattus norvegicus

<400> SEQUENCE: 24

```
acctctatga cccggacgat                                                    20
```

<210> SEQ ID NO 25
<211> LENGTH: 20
<212> TYPE: DNA
<213> ORGANISM: Rattus norvegicus

<400> SEQUENCE: 25

```
caccaccctg acagtgcgta                                                    20
```

<210> SEQ ID NO 26
<211> LENGTH: 20
<212> TYPE: DNA
<213> ORGANISM: rattus norvegicus

<400> SEQUENCE: 26

```
ctgggggcat agatgctcgg                                              20

<210> SEQ ID NO 27
<211> LENGTH: 20
<212> TYPE: DNA
<213> ORGANISM: Rattus norvegicus

<400> SEQUENCE: 27
gccctggaag gcctcgatcg                                              20

<210> SEQ ID NO 28
<211> LENGTH: 20
<212> TYPE: DNA
<213> ORGANISM: Rattus norvegicus

<400> SEQUENCE: 28
caagtcccta ggatcgtccg                                              20

<210> SEQ ID NO 29
<211> LENGTH: 20
<212> TYPE: PRT
<213> ORGANISM: Rattus norvegicus
<220> FEATURE:
<221> NAME/KEY: Misc_Feature
<222> LOCATION: 169..188
<223> OTHER INFORMATION: Position in SEQID2

<400> SEQUENCE: 29

Ser Ala Gln Asp Leu Asp Gly Asn Asn Glu Ala Tyr Ala Glu Leu Ile
1               5                   10                  15

Val Leu Gly Arg
            20

<210> SEQ ID NO 30
<211> LENGTH: 15
<212> TYPE: PRT
<213> ORGANISM: Rattus norvegicus
<220> FEATURE:
<221> NAME/KEY: Misc_Feature
<222> LOCATION: 556..570
<223> OTHER INFORMATION: Position in SEQID2

<400> SEQUENCE: 30

Glu Glu Gly Gln Tyr Pro Pro Ala Pro Pro Tyr Ser Glu Thr
1               5                   10                  15

<210> SEQ ID NO 31
<211> LENGTH: 21
<212> TYPE: DNA
<213> ORGANISM: Homo sapiens

<400> SEQUENCE: 31
atgcaacagg acggacttgg a                                            21

<210> SEQ ID NO 32
<211> LENGTH: 28
<212> TYPE: DNA
<213> ORGANISM: Homo sapiens

<400> SEQUENCE: 32
tcagacgact aaactttccc gactcagg                                     28

<210> SEQ ID NO 33
<211> LENGTH: 20
```

<210> SEQ ID NO 33
<211> LENGTH: (not shown)
<212> TYPE: DNA
<213> ORGANISM: Homo sapiens

<400> SEQUENCE: 33
ctacaacccc tacgttgagt                                              20

<210> SEQ ID NO 34
<211> LENGTH: 24
<212> TYPE: DNA
<213> ORGANISM: Homo sapiens

<400> SEQUENCE: 34
tcgtgacctg acctttgacc agac                                         24

<210> SEQ ID NO 35
<211> LENGTH: 24
<212> TYPE: DNA
<213> ORGANISM: Homo sapiens

<400> SEQUENCE: 35
cctgagctac tcctgtcaac gtct                                         24

<210> SEQ ID NO 36
<211> LENGTH: 20
<212> TYPE: DNA
<213> ORGANISM: Homo sapiens

<400> SEQUENCE: 36
aggccgagat cgccagtcgt                                              20

<210> SEQ ID NO 37
<211> LENGTH: 27
<212> TYPE: DNA
<213> ORGANISM: Homo sapiens

<400> SEQUENCE: 37
ctacatggat ccagtcatgc cgaagat                                      27

<210> SEQ ID NO 38
<211> LENGTH: 28
<212> TYPE: DNA
<213> ORGANISM: Homo sapiens

<400> SEQUENCE: 38
cgacaactcg agtcagttgg tatcatgg                                     28

<210> SEQ ID NO 39
<211> LENGTH: 15
<212> TYPE: PRT
<213> ORGANISM: Homo sapiens
<220> FEATURE:
<221> NAME/KEY: Misc_Feature
<222> LOCATION: 1..14
<223> OTHER INFORMATION: Identical to 5 .. 18 in ref swissprot :Q07021

<400> SEQUENCE: 39

Leu Arg Cys Val Pro Arg Val Leu Gly Ser Ser Val Ala Gly Tyr
 1               5                  10                  15

<210> SEQ ID NO 40
<211> LENGTH: 16
<212> TYPE: PRT
<213> ORGANISM: Homo sapiens
<220> FEATURE:
<221> NAME/KEY: Misc_Feature

```
<222> LOCATION: 2..15
<223> OTHER INFORMATION: Identical to 268 .. 282 in ref swissprot
      :Q07021

<400> SEQUENCE: 40

Cys Tyr Ile Thr Phe Leu Glu Asp Leu Lys Ser Phe Val Lys Ser Gln
1               5                   10                  15

<210> SEQ ID NO 41
<211> LENGTH: 21721
<212> TYPE: DNA
<213> ORGANISM: Homo sapiens
<220> FEATURE:
<221> NAME/KEY: exon
<222> LOCATION: 1898..2253
<221> NAME/KEY: exon
<222> LOCATION: 3438..3782
<221> NAME/KEY: exon
<222> LOCATION: 12064..12183
<221> NAME/KEY: exon
<222> LOCATION: 15049..15105
<221> NAME/KEY: exon
<222> LOCATION: 15670..15816
<221> NAME/KEY: exon
<222> LOCATION: 19486..19659
<221> NAME/KEY: exon
<222> LOCATION: 19806..19865
<221> NAME/KEY: exon
<222> LOCATION: 19963..20094
<221> NAME/KEY: exon
<222> LOCATION: 20236..20864
<221> NAME/KEY: exon
<222> LOCATION: 20954..21094
<221> NAME/KEY: Misc_Feature
<222> LOCATION: 715
<223> OTHER INFORMATION: diverging nucleotide, G in ref genbank:AC002128
<221> NAME/KEY: Misc_Feature
<222> LOCATION: 1229
<223> OTHER INFORMATION: diverging insertion, G in ref genbank:AC002128
<221> NAME/KEY: Misc_Feature
<222> LOCATION: 3676
<223> OTHER INFORMATION: diverging nucleotide, T in ref genbank:AC002128
<221> NAME/KEY: Misc_Feature
<222> LOCATION: 5039
<223> OTHER INFORMATION: diverging deletion, G in ref genbank:AD000684
<221> NAME/KEY: Misc_Feature
<222> LOCATION: 5118
<223> OTHER INFORMATION: diverging nucleotide, C in ref genbank:AD000684
<221> NAME/KEY: Misc_Feature
<222> LOCATION: 7337
<223> OTHER INFORMATION: diverging deletion, C in ref genbank:AD000684
<221> NAME/KEY: Misc_Feature
<222> LOCATION: 8294
<223> OTHER INFORMATION: diverging nucleotide, G in ref genebank:
      AD000684
<221> NAME/KEY: Misc_Feature
<222> LOCATION: 8604
<223> OTHER INFORMATION: diverging nucleotide, C in ref genbank:AD000684
<221> NAME/KEY: Misc_Feature
<222> LOCATION: 8928
<223> OTHER INFORMATION: diverging nucleotide, A in ref genbank:AD000684
<221> NAME/KEY: Misc_Feature
<222> LOCATION: 9021
<223> OTHER INFORMATION: diverging nucleotide, G in ref genbank:AD000684
<221> NAME/KEY: Misc_Feature
<222> LOCATION: 9851
<223> OTHER INFORMATION: diverging insertion, GAATGAAA in ref genbank:
      AD000684
<221> NAME/KEY: Misc_Feature
<222> LOCATION: 9878
<223> OTHER INFORMATION: diverging nucleotide, C in ref genbank:AD000684
<221> NAME/KEY: Misc_Feature
<222> LOCATION: 11478
<223> OTHER INFORMATION: diverging mucleotide, T in ref genbank:
      AD000684
<221> NAME/KEY: Misc_Feature
<222> LOCATION: 11577
```

```
<223> OTHER INFORMATION: diverging deletion, C in ref genbank:AD000684
<221> NAME/KEY: Misc_Feature
<222> LOCATION: 11779
<223> OTHER INFORMATION: diverging nucleotide, T in ref genbank:AD000684
<221> NAME/KEY: Misc_Feature
<222> LOCATION: 13411
<223> OTHER INFORMATION: diverging deletion, T in ref genbank:AD000684
<221> NAME/KEY: Misc_Feature
<222> LOCATION: 13538
<223> OTHER INFORMATION: diverging nucleotide, G in ref genbank:AD000684
<221> NAME/KEY: Misc_Feature
<222> LOCATION: 13896
<223> OTHER INFORMATION: diverging nucleotide, G in ref genbank:AD000684
<221> NAME/KEY: Misc_Feature
<222> LOCATION: 14912
<223> OTHER INFORMATION: diverging nucleotide, A in ref genbank:AD000684
<221> NAME/KEY: Misc_Feature
<222> LOCATION: 16732
<223> OTHER INFORMATION: diverging nucleotide, C in ref genbank:AD000684
<221> NAME/KEY: Misc_Feature
<222> LOCATION: 17169
<223> OTHER INFORMATION: diverging nucleotide, G in ref genbank:AD000684
<221> NAME/KEY: Misc_Feature
<222> LOCATION: 18946
<223> OTHER INFORMATION: diverging deletion, G in ref genbank:AD000684
<221> NAME/KEY: Misc_Feature
<222> LOCATION: 19474
<223> OTHER INFORMATION: diverging mucleotide, G in ref genbank:AD000684
<221> NAME/KEY: Misc_Feature
<222> LOCATION: 20500
<223> OTHER INFORMATION: diverging deletion, G in ref genbank:AD000684
<221> NAME/KEY: Misc_Feature
<222> LOCATION: 20501
<223> OTHER INFORMATION: diverging deletion, G in ref genbank:AD000684
<221> NAME/KEY: Misc_Feature
<222> LOCATION: 20502
<223> OTHER INFORMATION: diverging deletion, A in ref genbank:AD000684
<221> NAME/KEY: Misc_Feature
<222> LOCATION: 21270
<223> OTHER INFORMATION: diverging nucleotid, G in ref genbank:AD000684
<221> NAME/KEY: Misc_Feature
<222> LOCATION: 21356
<223> OTHER INFORMATION: diverging insertion, T in ref genbank:AD000684
<221> NAME/KEY: Misc_Feature
<222> LOCATION: 21476
<223> OTHER INFORMATION: diverging nucleotide, A in ref genbank:AD000684
<221> NAME/KEY: Misc_Feature
<222> LOCATION: 21588
<223> OTHER INFORMATION: diverging insertion, C in ref genbank:AD000684
<221> NAME/KEY: Misc_Feature
<222> LOCATION: 21601
<223> OTHER INFORMATION: diverging deletion, T in ref genbank:AD000684
<221> NAME/KEY: Misc_Feature
<222> LOCATION: 21635
<223> OTHER INFORMATION: diverging insertion, G in ref genbank:AD000684
<221> NAME/KEY: Misc_Feature
<222> LOCATION: 19963..19965
<223> OTHER INFORMATION: Potential variant splicing site AAG
<221> NAME/KEY: Misc_Feature
<222> LOCATION: 1..21721
<223> OTHER INFORMATION: n= a,g,c or t

<400> SEQUENCE: 41
aacagtttgg cagttcctca aaaggttaaa aatagaacta ccaagtcacc cagcaattcc      60
attcttaggc atatattcaa agaaatgaa agcagatatt tgtacaccag tgttcacagc     120
tgcactattt acaatagtca aaaggtagaa acaacctagg tccatccaca aatgaatgga    180
taaataaaac gtagcatata catacaatgg tacactagtc cgctgtaaaa agaaattttg    240
atcttactgc atgctacatg gcttcgacat actacaacat ggatggacct tgaaaacatt    300
attctttgtg aaataaaacta gacacaggac aaatgttaga cgattccact tatatgaggc    360
acctagaatg ggcaatttgg taagcaaagt agaatagaaa ttactagggg cacaggtagc    420
agggaatggg gagttactgt ttaatggtca cagagtttat gttggggatg atgaaacagt    480
```

```
ttcggggata aagagtggtg actggtacac gacattgtga atatacttaa tgccactgaa    540
ttttacactt gaagtggtta aagcgataaa tattatagnt ttgcatattt tatcataaaa    600
atatttttt aaacgatgaa gggacgtgaa cgggttgaaa ttttataaaa agtggccagg    660
gaaggtgtca ctgcaatggt gtcctacagg aggaggaaga tcatgtggac atctccggga    720
agggtgttct ggcagaggga gtagcacggg cgatggctct gaggactgtg agaagtatag    780
ttggaaacag cgaggaggcc agggtgtccg aagctgagta agccagagag agtgggagga    840
ggtgagataa gagggggaag gtcagtttct gctgagagtg aggaggagcc acaggagggc    900
tgtgagcagg tggacgtgat ctggcttgag ttttaacagg gccagtagaa caaagcacgc    960
ctgggtaccg aaaccagcca ctggccagtt ggcaacctgg gggagtctaa cgcgaggaag   1020
cgcccagggt tcccccagga tgcgctttcc ctcgccgcca cctggagaca gcagagtcac   1080
gcccagcgct gcgcaggctg atcgccgcgc gcgcccccg cctcggtcg caggtggctc   1140
gttccgggaa ttcctaagcg gaaaccggtc ccaagcccg cgccttcgct cggccccttt    1200
aagagccaga atttccggag ggctgacccg ggctaggga tgcccagggg ccgaaccaca   1260
agttgggaac gggtggggga ggtggcgaaa acttccgaag tggaattcca acttttcctg    1320
gccctgattc cccttgggca tccctgangg ggcagagctt ccccttccggg gactttagag    1380
ggttcctcag gtcatctaac tgggagacac aggaggcccg aagcgccccc cctccacccg    1440
gtccggagga accccagtgg aagtggagaa gtcaggcgcc accaacaagc ctctcccagc    1500
caggactttg cttagactcg ctcctcccgg cagggcgcac ctaggcgggt ccatcgccag    1560
ccggggagag gggtttgggc agggagggaa caggtgcgcg gcgggacccg ccctatctca    1620
acaggtgaat cgctccaagt gggtctcggt tgcatggatc tcggtgcgct tggtttggcc    1680
ggagcagatg ggggccggaa gggacctgtg gtccgcaggc gccctcccag cgggccagtc    1740
acttggttcg ggcctggg gacggagcgc acctgggtca gcccacttcc ggggagggag    1800
gcagaggaac cctccccgc cgctcacccc taagcccagc cctcggctcc cacccttgtg    1860
tacctgggcc gaaccattca ccggagcgcg cagcgggtgg agtgtggctc ggaggaccgc    1920
ggcgggtcaa gcacctttct cccccatatc tgaaagcatg ccctttgtcc acgtcgttta    1980
cgctcattaa aacttccaga atgcaacagg acggacttgg agtagggaca aggaacggaa   2040
gtgggaaggg gaggagcgtg caccctcct ggccttggtg cgcgccgcgc ccctaaggt    2100
actttggaag ggacgcgcgg gccagacgcg cccagacggc cgcgatggcg ctgttggccg    2160
gcgggctctc cagagggctg ggctccacc cggccgccgc aggccgggac gcggtcgtct    2220
tcgtgtggct tctgcttagc acctggtgca caggtacggg gcacggggcc tctgacgctg    2280
cggaacgccg gagggaactg tagaggggga tggatggagt tggaggcggc gggaagcggg    2340
aagcggggt ctcagaggct gggaccttcc gatcccctgg gtcttgggcg atctgttgcg    2400
ncgcggagt gagaggaatt cccatttgt gccggggagc gctccccgcg cccttatctg    2460
gaagatagca ggaagtgaaa ctccctggac ggtgagaccc ggagcggcag ggagaatgga    2520
actctttgtg gggagggagt ggaagaccgc ccgatctctg ggaaaagaaa agccgggatg    2580
ggacttgggc gcacccgggg atttctaagt tttggagtaa cggggagagg gcacgggagg    2640
gctggatcag acgcttccta gagggacaga gacgaaggaa caatgcctag gcctcgggtg    2700
ggtgtgggac tggggactcc ccatcccccg caccccaccc acctcccgcg ggctccggat    2760
tatacgtgcg taagagtctg gtgggatgga tttacggact tgaaaccgac ttctgctggc    2820
```

```
aggcttccac ctggatggga tatttgggtg gtgatgaggt cttcccgag acacttttgg   2880 ttcagtcatt tgaaatgact ttagagtagg gtgaggtggt gggaggctga tggagatatt   2940 gtggggggctt tagtccctcc atggcaaagc agttcaggca aacaactcca tggtttttccc  3000 tccaaattca aaggccccg ggtaacctgg aatccttcgt agtcggtttt gaagtggggc   3060
cttggccgct gggggcatca acatggccat ctgggcttgc ctgcccaggc cacacagagg   3120
ccccttgttg tgggtgaatg gcaaagggaa gagggactg gtgtggttca gaggccacag    3180
gctgggaaga gggatggcgg gcgagtccaa ggaaactggc cgtgtcaccg tgcacctgcc   3240
acttcagccc cacgggtcta taaaatgggc atgattatcg tggctacctc actggtcctg   3300
gcaattaagg aacaatgtgt gccaggcact ctgtaaacca catacttgcg agtgtcaagc   3360
tggtgacagg tggcgttcct gttgaagcac ctccctgagc tcacagcaac ccttgctgtc   3420
tctcctcttg ccctcagctc ctgccagggc catccaggtg accgtgtcca cccctacca   3480 cgtggtgatc ctcttccagc ctgtgaccct gccctgtacc taccagatga cctcgacccc   3540
cacgcaaccc atcgtcatct ggaagtacaa gtctttctgc cgggaccgca tcgccgatgc   3600
cttctccccg gccagcgtcg acaaccagct caatgcccag ctggcagccg ggaacccagg   3660
ctacaacccc tacgtcgagt gccaggacag cgtgcgcacc gtcagggtcg tggccaccaa   3720
gcagggcaac gctgtgaccc tgggagatta ctaccagggc cggaggatta ccatcaccgg   3780
aagtatgttg ggcagggcag ggggatgagg ctgggcttgc ccgggtggtg ggactggcgt   3840
ccttgtgcgg gacctggagt ccccatctga aagctcttga gtgccagtgt ctgaaaggac   3900
cattgaaggg agcaattctt ttttttttt tttttgaaga tggagtcttg ctctggactc   3960
caggctggag tgcagtggtg cgatctcagc tcactgcaac ctccacctcc caggttcaag   4020
caattctctt gcctcagcct cccgagtagc tgggactcca ggtgcgtgcc accacgccca   4080
gttaattttt gtattttag tagagatggg gtttcaccat gttggccagg ctggtctcaa   4140
actcctgacc tcaaatgatc tgcccgcctt ggcctcgcaa agtgctgaga cacatac   4200 ccagcctaaa gggagcgatt ctattctact attcttcctt ctgctaatcc ttccattctt   4260
taatttaata cgaagatt tttgagtacc tgtcatatac caggtgctgt tctgggccct   4320
gggaatacag ctgttaacaa aatcatcaaa ccacttccct cgtggagccc acattgcagt   4380
gagagagaca aacacgacac acactctcaa gtccttgaag ataaagaaaa ctgggtaacg   4440
gagagaagag gccagggttt gttctataat cattaataac acgagcagta agaagtaaaa   4500
tttatctaag taacaactta taagggtct actgtgtgct aagctctcat ccaggttccc   4560
aaggattaac tcagaccaca cagtaattga atagattcta tcattgtcat cttacagagg   4620
cccagagaga gaaagtgact tgcctagtgt catagctggt aacggggctg ggattctaac   4680
tcagccactt tgggtctagt ggccaagctc ctaatccctt tgcttgccta gggtggtccg   4740
cagaggactc acagaggaga tggcaggagt gaactgcagg ggcaagagag cttaatggag   4800
aaagcctgtg acatgccagg aactgcacac atattctccc attgagtcct ctcctctacc   4860
ctcctgacag ctgaggcaca gagaggttac cttgttcaaa tgggtgcata ggaagtcaaa   4920
gtctggagct ggggttttgaa cccaggcagc cctgagaacc ttgttctttt tttttnannc   4980
ggagtctcgc tctgtcgccc aggctggagt gcagtggcgg gatctcggct cactgcaagc   5040
tccgcctccc gggttcacgc cattctcctg cctcagcctc caagtagct gggactacag   5100 gcgcccgcca ctacgcctgg ctaatttttt gtatttttag tagagacggg gtttcaccgt   5160
tttagccggg atggtctcga tctcctgacc tcgtgatccg cccgcctcgg cctcccaaag   5220
```

```
tgctgggatt acaggcgtga gccaccgcgc ccggccccett gttcttaact gtaatgctgc    5280
ctcctgatag gatgtgcctg ttgggactaa gtaaggggca gtcattcatt cattcatttg    5340
gtatttatca agcatcgact atgtgtcgtt ggtgctgggg atagaggtga ttgggatggc    5400
tgaagtttct gtcgtcaagg agatgacatt ctggtggagt nagactggca gtaaatnaag    5460
cagataaaga aagagtatga aatttcaaa gtctgggcac ggtggctcac gtctgtaatc     5520
tcagcacttt gggaggccaa ggtgggtgga tcacctgagg tcaggagttc agaccagcc    5580 tggccaacat ggtgaaaccc cgtctctact aaaaatacaa agattagcca ggcatggtgg    5640
cacatgcctg taatcccagc tactcaggag gctgaggcat gagaatcgct tgaacccagg    5700
aggcagaggt tgcagtgagc tgagatcgca ccactgtact gcagtntggg cgacagagtg    5760
agactctgtc tcaaaaaaaa aaaaaaaaa aaagactccg tcaaggtata agaatgtcag     5820
agagtactaa gtgttgcaaa gaaaataaca ccaggctggg tgcattggct catgcctgta    5880
aatttcagca ctttgggagg ccaaggcagg aggatcactt gagcctagga gtttgagacc    5940
agcctggaca acaaaatgag accccatgtc tacaaaaatt ttaaaatttt aaaaattagc    6000
tgggcatggt ggcatgtgcc tgtggtcccg gctgctcagg aggctgaggt gggaggattg    6060
cttgggcttg agaggtcaag gcttcagtga gtcatgatcg tgccactgca ttccagcctg    6120
ggtgacagag tgagaccctg tcttgaaatg aaaagaaaat aggctgggcg cagtggctca    6180
cacctgtaat cccagcactt tgggaggccg aggtgggtgg atcacctgag gtcaggagat    6240
cgagaccagc ctggccaaca tggtgaaatc ccatctctac taaaaataca aaatttagcc    6300
gggcgtggtg gtgggcgcct gtaatcccag ctactcggga ggctgaggca ggagaatcgc    6360
ttgaacctgg gaggcgaagg ttgcggtgcg ccaagattgc gccactgcac tctagcctgg    6420
gaaacagtga gactccgtct taaaaaaaaa agaaaaaaga aaatagcact gggtgatgtg    6480
ctacatggaa tgacttgggc tgtgaatatg atttgaggag ggcctgggcc tgggccttac    6540
agaacctaga aggcagagag gaaggggagg ggcagggtgc cagggatgaa ggctcacgta    6600
cctcatgtct tagtgtgtgt tcactgtctt aaacaagaat ttaaagttgg gcatgggggca   6660 gagcggggaa gggagcatcc ctttgcagac cccaagaagc caggaactgg agcacattct    6720
gctagaggat cgatgggaag cagggttcca ggggctgagc ctatgtcagt cctgtttcag    6780
aggaggcacc aggcttgctt gccctgaatt tctgtgggca gctcagccat gagcatccta    6840
ctgttattga ggtcacaggg ctgcttaggc cccctcctct ctaacccagg gattgtgcct    6900
gcctggacca ggcgtgactg ctaagcttct gccaggacaa gccaaatact gagggtgctt    6960
cctctgctgg acgcaaaagt ccaggatgac ccccaggct ctgtctcggg aaggggccc      7020 tgcatgctcc aggggcctca caggcctggg tctttcaaac cacccccacc tgggcctgtg    7080
tttgatcaag gccctgagtg taaacatcca ttgtgtgtgt cctttcagga aatcccatag    7140
ccataggagc ttcctctgtt tcagctttga ggatgggaa agtggactc cccgtggtgt      7200 tcctagggtc acccactgtg ctgggttttt tctgttgnnt gttgtttttt ttctgttgcc    7260
caggctggag tgcagtggtg caatctcagc tcactgcaac ctctgcctcg caagttcaag    7320
tgattctccc gcctcagcct cctgagtagc tgggattaca ggtgcacacc accacacctg    7380
gctaattttt gtatcttttt ggtagagatg gatttcgcc atgttggcca ggctggtctc     7440
aaactcctga cctcaggtga tctgcctgcc ttggcctccc aaagttctgg gattacagat    7500
gtgagccacc atgcccggcc tatcctggtt tcaaaagtga aaatagtcct ggataaggta    7560
```

```
gaaggctgtc cactccaggc atccctccgg tccggtggct cattccctgc tttgtccttc   7620
catgctttgg gtgatggacc agcacctgga caggaggccc tgttccacct cctcgggctc   7680
cttggggtcc aagtgccccc acctccagct gcactgcagc agagagccca tgggacctct   7740
gaaatcatga aggtcacctt tgcggtgtat aaagaaggaa ccagaggttg agatgtgga    7800 ggaggcctgc tgctgttcc cactggagac ctggcatctt ctccccgacc taaaacaatg    7860
aaagcagtgc tcagcccgga tgagatcacg gccagcccaa gaccaggaac agggtacgcc   7920
ctgcaggaag aaggtgtgcc agaccttag gatggatcaa agaagccgg aaaactatat     7980 tttttgtgag ttttgaaaat gtcagacagg tcaaacaaaa cacagtgagg tccagcctcg   8040
gcctacaaga tgccagattt caaccccctgg cctatatgat ctgttttgcca tggcaggcgg 8100 ttcctgtcca cctcttttgt ttatagcagg gaccagctct tgagctccag tgttgaagag   8160
gcacggtcag ggtctgatct gaagacactg gtggctcatg cctgtaatcc cagcacttca   8220
ggaggccgag gcaggaggat tgcttgagga caggagctgg agaccagcc tgggcaacac    8280 agtgagaccc agacactaca aaaaaataaa tttagcgggg catgatggca caccctgcta   8340
ctctggagat gggaagattg cttgagccta ggagttcgaa gctgcagtga cccatgatcg   8400
caccactgca ctccagcctg gcgaccaag ctaggccctc tcaaaaaaga tacaggtgga    8460
aaaatgatga acgaagaggg cattgtggca aacctgggga tttaggagaa cctagtttgg   8520
aattctatga ggattcaatg aaagaatgtg tgtagagggg cccagcacat agtaagagct   8580
caataaacgg tgggggctag gggtggtggc tcatgcctgt aatcccagca ctttgggagg   8640
ctgaggcagg tggatcactt gagccctgga gttcaagatc aacctggaca acaaagcaag   8700
atcccatctc aaaattaaaa aacaacacca acaacaaaaa aacagtggct tagatgcctg   8760
atcattaggg taagtcgtgt cctcaacccc ttcacatctg ctctgaaggt caccatatcc   8820
ggaagccttc cctggcctcc ttgtttaaaa tggcacagcc cccactccac gcctggcact   8880
ctctgctgtc cctgattcgt tttctccata cagcttatct ttgtctggta tgtgacatag   8940
ttaacatttt atatttgtct ttctttccta gttagaatct gaactctaga agggcaaggg   9000
caaggattta taactcaaag attccgggct taggcctctt ttatattctt gattttgagg   9060
ttaattaaga gctcaggcct agcgaggtgg ctcatgcctg gaatcccagc actttgggag   9120
gcccaggcgg gcagatcact tgaggtcagg agttccagac ctgcctggcc aacacagtga   9180
aaaacctgtc tctactaaaa atacaaaaat tagccagtta tgttggcagg cgcctataat   9240
cccagctact caagaggctg aggcaggaga atcgcttgaa cccaggaggc agaggctgca   9300
gtgagccaag atcgtgccac tgcactccag cctgggcaac agagcgagac tccatctcaa   9360
aaaaaaaaaa aaaattaaga gctcaaagag tttgttttca taggcagcag aatgagaaaa   9420
gtttacaaaa tagtttaaat gacaataaag tcattataga ttaacataaa taaaatacct   9480
tttatgaaaa aaataatcat tttctgaaat cagacaaaac attgtgaatg agaaggtggc   9540
atggttttat ttttttgcaa gtctccgaag cctggctgga tagaagagcc tggcttctca   9600
gagctgcttc agtctgttgt gatatctatt gtatgtcacg tagcctctgg aaaactccac   9660
agttagtatt gttgggaaaa taactttgac ctcaggatct cctgaaaacg tcttggggaa   9720
ccccagggtc tagaggctgc agtttgagaa ctgttgctgt ggtatcccag tgtctcaaa    9780 tactgcctag aacataggtg gtactcagta attattgttg naaggatgaa tgaatgaatg   9840
aatgaatgaa tgaaagaaag aaatgtgtct ttgaatctag ccatgtgccc agaatgatga   9900
gacagatgac aaaagctaag ggactttagc atgaggagag ggggttcgtt tccttttttt   9960
```

```
                                                        -continued tcttttttt  ttgagatgga  gtctcactct  actgcccagg  ctagagtgca  gtggtgcaat  10020
ctcagctcac  tgcaatctct  gcctcctgag  ttcaagcaat  tctcctgcct  cagcctccag  10080
ggtagctggg  actacaggtg  cgtgccacca  tgcctagcta  attttttaca  tttttggtag  10140
agatggggtt  ttaccatgtt  ggccgggctg  gtctggaact  cctgacctca  agtgatccac  10200
ctgcctcagc  ctcccaaagt  gttaggatta  caggtgtgag  ccaccatgtc  cggccaagag  10260
ggtgttcatt  tctgctcctt  gccaggtatt  gtgtcaggca  ctgggaccc   agcagtggct  10320 gagacagaca  gggctctgcc  tcacggagcc  cacattttca  ccaggcaaag  gatggtcggc  10380
ccctaagctg  ggagataaga  cttcagcagt  tgggtggggg  agccgtggga  gaagcccagc  10440
ccacaggggg  acagtgcaaa  tctagaacca  aggcgatggc  agggggtgagg  ctggcacggt  10500 agctagagac  cacgtcgtgc  caagggcctt  ggggaccatg  ggactatggg  accttaggga  10560
aggcgtctgg  aatgctgtag  ccagacactg  ttgcaaggag  gattttttctg  tagacatgag  10620 gccttcctta  tgaagaaagc  aagggttctt  tcattcctgg  gggtgccagg  tgctgtggac  10680
tgcagcacgc  gtggttgctg  ccgtcacaga  gctgtcatgc  aggagggcag  cgcgtccttg  10740
ggaaggtggc  aggcaggtca  ggctaggagg  aaagaggccg  ggaagctgag  ggcatttcct  10800
gcccgagatg  cccaatgtag  cctacttctg  tccccagtgg  cttaaggcag  agttgcctgg  10860
taggtgccct  ggtcccaccc  tggtgaaagg  ctgaaggtat  ttaattagtg  cctgagaagc  10920
agagaggaaa  caggatgtgc  caaaacactt  tgatggatgg  tagagttaac  aggctccttg  10980
cctgcagctg  cttcagacaa  gagcgtcccc  aagccctggg  cctgacctgg  aatgtgggga  11040 tggaaggggga  ggggagggaa  ccaaggcact  gggagggtaa  gtctctctct  cccacataga  11100
cacacccact  ccttatgggt  gcctgggcat  ctcctggtac  ctagaatctg  gcctgtttat  11160
ctccacaccc  atccctgggg  tctacactag  gccctgtggg  tggcagttca  catcagggga  11220
gttctgactt  tggctctgag  aggtggttca  gagatggctg  taagttgaga  agcacagact  11280
gctgggtgtg  gtggttcacg  cctgtaatcc  cagcactttg  ggaggctgag  gtgggggtgg  11340
atcacctgag  gtctggagtt  caaaaccaac  ttggtcaaca  tggcgaaact  ccatctctac  11400
taaaaatgca  aaaattagcc  aggtgtggtg  gcaggtgcct  ataatcccag  ctacatggga  11460
ggctgaggca  ggagaatcgc  ttgaatctgg  gaggcgaaga  ttgtagtgag  ccgagattag  11520
ttcgcaccat  tgcatgccag  cctgggcaac  aagagtgaaa  ctccgattca  aacaaacaaa  11580
aaaaaaaagc  tgggcatggt  ggagtgcctg  tagtcctaac  tactcaggtg  ggaggattgc  11640
ttgagtccag  gaggttgaag  ttgcagtggg  ctataattac  accactgcac  tccagccagg  11700
gccacagagt  gagaccctgt  ctctaaagaa  agaaaaaaaa  aaacaacctc  aggctccgag  11760
ggcaccatta  ctgctctaca  ctgaagagct  gtgcagcttt  tccagacccg  aaatgtcatc  11820
cacaaaacag  aagtgataat  ggtcctgcct  cacagacttc  ttgcagtagt  ccaggtgttt  11880
agaacggggt  gtaaaaggcc  gtgtgccctt  ggtaggaatc  ttngcatatg  catttgatca  11940
tctgcagcct  gcccagccca  ctgcttgccc  cctcctgggt  gtgctgggaa  ggggtctttg  12000
gccctccagg  ggttaggtgc  cccagcctcc  aagtgccct   cacgccttt   catcccgact  12060 cagatgctga  cctgacctt   gaccagacg   cgtggggggga  cagtggtgtg  tattactgct  12120
ccgtggtctc  agcccaggac  ctccagggga  acaatgaggc  ctacgcagag  ctcatcgtcc  12180
ttggtgagtg  ggcctgggaa  gggggaggca  tggcccttcc  ttttgtccgc  ttctgttctg  12240
tctgccctcc  cctgtgtccg  ccctctgccc  tccagcttac  cctctgggct  ctgtcgcctg  12300
```

```
ctctgctctc cccaggctc tgccagtcac ttaggctccc ctgtgccctg caccccaggc   12360 aggaccact ggcccacagt gcctccaatc acccaagcca aactaagaga agagtggaga   12420
caattggaga ctctgccttt tcaaagtctc attttaaaa aaaatccaga cttgggtcc    12480 gggtgcggta gttcatgcct gtaatcccag cactttggga ggccgaggcg ggtggatcac   12540
ttgaggccag gagttcgaga ctagcctggc caacgtggca aaatcccgtc tctataaaaa   12600
atataaaagc caggcgtggt ggtgcacatg cctgtaatcc cagttactca gaaggctgag   12660
gcatgaggat tgcttgaacc tgggaggcag aggatgcagt aagccaagat caagccactg   12720
cactccagcc tgggcgacag agtgagactc tgtccaaaaa aaaaaaaat ccagacgtgg   12780 tcagagtcca tgggcagtga atgaggacag ttgatggtgt gcaaaatcga cccacctctt   12840
gctacatccc caaggcctca tctcacccga gtccctcgcc aaagcacagc ggttttgccg   12900
tgtgccctgc tgggatggcg ctgcatggca cacacactgt gtaagtttga gtgcagctga   12960
aacgaagccg attccagaca cccaggggca gggcggggtg tccgtgtggc tgggaggcct   13020
ccttgtgtta gggggatgtt gccatcggcc aggtgccctg ctgtaagcca acacatggag   13080
tcttgtatga catgtgctct gcatgagtga tgccgctggg ctgtacactg ccatcttcac   13140
atgtgtgaat gagcacgtga ctggggggta cttgggctgc aagacagagt tcatgtgtgg   13200
gggatggaac acgtgcacca gtgacccagg aacctctgcc tgttcttcgg taaaatgcac   13260
catttgcatc agcagttccc aaaattagtc tccaggtcta tttacactct aaaacattat   13320
cgagggtctc caagagcttt tgtttgtttc tgtgggtttt atgtctatct gttgcttaac   13380
atattaggaa ttaaaatggg gagattttcc tttttttttt ttttttttg agatggagtc   13440 tcgttctgtc gcccaggctg gagtgcagtg gctcgatctc ggctcactgc aagcttcacc   13500
tcctgggttc acgccattct cctgcctcag cctcccaagt agctgggact acaggcaccc   13560
gccaccacac ccggctaatt ttttttgtat tttagtaga ctgggttt caccatgtta    13620 gccaggatgg tctcgatctc ctgacctcgt gatccaccca cctgggcctc ccaaagtgct   13680
gggattacag gcatgagcca ctgcccgcc ttaaatggg gagattttc aagcccaaga    13740 tacacaagga agactgggca acatggcaag accctgactc tacaaaaaat tttaaaatta   13800
accaggcatg gtggcatgca cctgtgagcc cagcttcttg ggaggctgag gcaggagtat   13860
cgcttgcacc caggaggtca aggctgcagt gagccatgac tatgctactg cactctagca   13920
tgagtgacag agaccctggc tcaagaaann canacaaaca cacacacaca cacacacacg   13980
catatagtcc attaggcatc agggcgatga tggcatcagg gagcctggga aactctactg   14040
gacattcatg ggagaacaag tgaaaaaggc aaataacatc ttagtgttat tctaaaattt   14100
cttcttttgg ccttgtggac aggaccacgc tttgagagct gtgactgaca tgcctctgtc   14160
ctgttgcgag ggcctatagt gccaagtgca tgagctctgg ggagggcttc gtgggtgcag   14220
agctgggcct gtggaggccc ctcagacaca acactggtgg ggctcagagc tccagggca    14280 ctcgagggaa gacaagaacc ggctctgaga tgcgtgaatg tgacagtgca tgagtagaga   14340
tggagacctt gtgggtccca gaaccaggac tgcatatgac tttcatatgt gggtattttt   14400
gccttcatgg gtcccttcct gttttaaaaa aaatgtgtga ttatgttgtc acaaagagtt   14460
tattcctgta tattgtgtta atttgtgttc agatttgtaa agtaaaatta aaccatttca   14520
gccaggtgtg gtgacacatg cctgtagccc tagctactta ccccagaggc tgaggtggga   14580
ggatcgcctg agcccacgag gttgaagctg cagtgagcca tgatcacacc cctgcactcc   14640
agactgggcg acagagctga gatcctattt cgtgggccct aggtccctgt gcctgctgga   14700
```

-continued

```
acaggacatc cctatcaccg tggttggagc cctttggggt gctaagacct atgaatgagg    14760
gaaacttagg gtgcccaagc tgaggtagag ccctcagaac ccctgggat ttgtattgga     14820 gccctcgtgg cataacacag gtggattatg caatgggagt ttcttaccta taagcaccca   14880
catgtgggcg ggtggagggt aggagccatg cgctagggct tcagccccca gccccttccc   14940
gcttcagggc acaccttgca cttggccagc ctggagctgg gctttcgggg gtggcacagc   15000
ctgggctggc tctggccagc ataatctgtt tctcttttgt ccctccaggg aggacctcag   15060
gggtggctga gctcttacct ggttttcagg cggggcccat agaaggtacg gggggtggat   15120
cctgagttgg gcttctcggg agctcccata catcacctac tgcttctgac tctagttagt   15180 atcccttcc ccactaaacc ctgctcactg tggacccctc actaacctgg cctgactgtg     15240
gctctgaggc atctagtggt ctggcgctgg gcctaggcta ggctgggctg aggagagcct   15300
ggggtgcagg ccagggctct gtgactggca cctgcggtgc tcttgagggt gtggcgtctg   15360
ggcagctggc tctctctttg gtctgggggc tgcagtctgt ctccctctgt gcaggctgcc   15420
tcgttttctg ccttgtgttt tttgcacctg ggggagggcc gtaactgggg aatgccgggg   15480
atggtagaat ggggagtgtg ctgtgcccag cctctggcac aaaaaatcca gccagggctg   15540
caggttcctt ggtgagcttt gcaaatcgtc cccgacctca gtgctggctc cgcaccatgt   15600
acccctgctg tgccgttagc cctgttccct cccaggcctc cgggctcagg gcctgttgtc   15660
tttctgcaga ctggctcttc gtggttgtgg tatgcctggc tgccttcctc atcttcctcc   15720
tcctgggcat ctgctggtgc cagtgctgcc cgcacacttg ctgctgctac gtcaggtgcc   15780
cctgctgccc agacaagtgc tgctgccccg aggcccgtaa gtgtcccgct catggccacc   15840
ctggtttggg caacatcctg catccaaggg aaggaggtgg ccatccacct gcccccagga   15900
cagtggcgtt ggtctggagg gtgtgaattt agccagtggg gagaaagtag gctgaggagg   15960
gtctgctgtt tagattgtcg tttacttcct ccaacttta gtttatttt atttatgttg     16020 ttcttttctt ttgtaagtat aatccataca catggtaaaa atgtccaaca gtacaagata   16080
ctagtcacat ggaagtaaag ccctctaaaa aaaccaaatc ttggctaggc gcagtgatta   16140
cgcctgtaat cccagcactt tgggaggcca agacgagtgg atcacttgag gtcaggagtt   16200
ccagatcagc ctggccaaca tggtaaaacc cagttctcta ctaaaaatac aaaaattagc   16260
tgggcatggt ggtgatcgcc tgtaatccca gctactcagg agactgaggc atgagaatcg   16320
cttaaaccca agaagtggag gttgcagtga gctgagatca cgccactgca ctccagcctg   16380
ggcgacagag tgagactctg tctcaaaaaa aaagaaaaa aaatgttaa gtgaaaagt      16440 taagaaacca aacaaggttt acaacactac atgatttaag caaaaaaat ttttttgtt      16500 ttagagaaag ggtctcattc tgtcatccag gcagtgcagt gcgatcatag ctctctgcag   16560
cctcaaactc ccgggttcaa gcagtcctcc cgcctcagcc tctggagcag ctgggactgt   16620
aggcacacac caccatgccc agctaatttt ttgatttttg ttttttgtag acgggggtc    16680 tcagtatgtt gcccagcctg atctcaaact cctggcctca ggtgatcctc cgaagtcagc   16740
ctccccaaag tgctgggatt acaggcatgt gccaccatgc tggccaattt ttaaaaattt   16800
tctgtagaga cagggtcttg ctatgttgcc caggctggtc ttgaactctt gacctcaagt   16860
gatcctgcct caggctccca aagtgatggg attacaggca tgaactacca cacctggcct   16920
taaacttaag caaatttttt ttttttttg gagacagttt cactctgtcg cccaggctgg   16980
agtaaagtgg cgtgatctct gctcactgca acctccgccc ccgggttta agctattctc    17040
```

```
ctgcctcagc ctcccgagta gctgggatat aggcgcctgc caccacgcct gactaatttt    17100 tgtatttta gtagagacgg ggttttgcca tgttggccag gctggtctcg aactcctgac     17160
ctcaggcaat ccgctccccc gcacccctac cttggcctcc caaagtgtta ggactacagg    17220
tgtgagccac catgcctggc caaatttaag caaatgtttg aaaacacata cccacaggaa    17280
tgctgcacat tttacccagc tactatgtct agggtcgtat ctagcacacc agcatggcta    17340
ctgtggagag ctgggactgg atgtgagatg agagctaaag gggaagtaag caaaccaagc    17400
aggggaaggt aagagaagac agaagacaga gagagaggga cctaactcta tgagaggagt    17460
cagacatgtg caattgaaaa agacttgctc ctgtctctct tctgtgaatg tttgtgaata    17520
tcccaacggg acactttcac agaggagctg attgacgtgg tcacagccat cagccttggg    17580
acaccagacc acagtgtgta cactaagtgg cactgatgga cacttcagca tccctctagc    17640
tgctgtcccg tttcccctcc tcggggacca cagctgttgc cagtccttgg tttccttcag    17700
gagggtgtct gggtagacca gcctgtgtgc acacagtcca agatacatga acagtgaagt    17760
gccaggcaat ccttgcaagc atgggcaggt ggagagctga ggcctgcttg acaccttcct    17820
gctcagaagc ccagtgagca gtttccctcc ctagggctca gtgtcatccc ctataaaatg    17880
gggcttatgg cagagctcac cacactgggt gcatctgggg atttggcgag ctcatgtgca    17940
caccattgag catgggccc aacctatata aaatattcta cgtctgtcag ctgctgggca    18000
ctgccactat cagcctcagt agtgactgag ggacagggca ccagtcagag ccctggtgca    18060
cacagagtga ccccagagaa gcagccttcc ctctctgagt cctgtttcct tctgttaggt    18120
cctgacttca tggttgttg ttagcattaa ggaagtcgct ggctaatttt atagtcattg     18180
aagtcagtgg tgtgcaacct ggttcctcaa aggatcactt ccctgaaaaa attccactgc    18240
tccctggagg cttatgcagg ccatcccatc ccctccctct tgttgtgttc agctgacagc    18300
tttttgctca gtgagtaagt gttaggtcca tttcacagat gggctgcaac caagtttgca    18360
gtgaacccac taagaccaga gctagggcca ggactaaatg ctggtcccaa tgccacattc    18420
ccctgtcccc acaccacatt tcctccatcc ggagaccctg ttaccccaac ccagggcccc    18480
attaactccc tggcagaggc cctgttacat ctgctgctgc cacagcctcc gcccacccctt   18540 caggaggcag caggtcccac tgctgatgat aaagttgcag gctgcctgag ctaatgaagg    18600
ggcttcctct aggctgtgca cttagtcttc tgcttccaaa ccaaatcaga ggtgaggcac    18660
cctctctggg cccatctctc tcctccattt tcctgttggg gtcccaggga ggaagccact    18720
tgcctagggc ccaggaattt tgcaagcctc ttgccctagg aggaaggaa gggaggagga     18780 tcttaccttg aactgtcaag cctagagcct ggtgggcag gcagaaatgg gtgcagtcca     18840
tgagttagaa acactagagg agacactttg ctgcttggnc cggggcaggc aagnttaatt    18900
cccgaggctc ctgccactgc atctcaatct ggaaggtgac caggtgggc aggacccacg     18960 tctcccagat gactcatttt ttctagaaca ggggcttggc tgccaaagag gatacttgat    19020
ttcggcttgt ggggacagtg gtggacccag catctgggct ttatataaag ggcagctttg    19080
ttgccctgta aacacacaga ccatgggtgg ccacttcttc cagtaagtta gctggggagt    19140
tggaagttta ggtaaaacct tttgattgac aaatgttggc gaattaccat gctgttaaat    19200
gaaacattgt tctgccaccc tggggctgtg ggtgcctgcg tgcaccctct gaaaaatcac    19260
acaggaagtg gggtggggtc tctgtgaagc tggtgtcccc cagcctcagg gatgctgcag    19320
aaatggaatg aggaccaaca gggactcaga tgtccaagga agctctacag cggagaggac    19380
ggcttgggaa ggaggtccag gcccaggtcc ctccggaacc caatgggtat ggggcagcct    19440
```

```
ggctcctgcc tcatcccct  tctcctgttg attatgtcct cacagtgtat gccgccggca  19500
aagcagccac ctcaggtgtt cccagcattt atgcccccag cacctatgcc cacctgtctc  19560
ccgccaagac cccaccccca ccagctatga ttcccatggg ccctgcctac aacgggtacc  19620
ctggaggata ccctgagac  gttgacagga gtagctcagg tgaggccggg ggaagcagga  19680
acagctggtg ggagtgtgct gggcatctgg acactgaggg gcagggctg  gaaggaagag  19740
tgtcttggga gccgaggagg ggctctgctc ctggtgcgcg ccactgaca  gccactctcc  19800
cccagctggt ggccaaggct cctatgtacc cctgcttcgg gacacggaca gcagtgtggc  19860
ctctggtgag aatccatcgt cccgaagttg gatgtgcctg taagggagag gggtgggcca  19920
ggatccatcc tcccaaaccg accaccaccc ccctgtccct agaagtccgc agtggctaca  19980
ggattcaggc cagccagcag gacgactcca tgcgggtcct gtactacatg gagaaggagc  20040
tggccaactt cgacccttct cgacctggcc ccccagtgg  ccgtgtggag cggggtaagc  20100
aggagccttg gggtctgagg gcttttaagg tggggggtg  aaacatgtct ccctgatacc  20160
tgccgcaggg actcttggtg caaaccctgg accccgggct cctccagcag tcagtgacac  20220
cccccttccc tgcagccatg agtgaagtca cctccctcca cgaggacgac tggcgatctc  20280
ggccttcccg gggccctgcc ctcaccccga tccgggatga ggagtggggt ggccactccc  20340
cccggagtcc cagggatgg  gaccaggagc ccgccaggga gcaggcaggc ggggctggc  20400
gggccaggcg gccccgggcc cgctccgtgg acgccctgga cgacctcacc ccgccgagca  20460
ccgccgagtc agggagcagg tctcccacga gtaatggtgg gaggagaagc cgggcctaca  20520
tgccccgcg  gagccgcagc cgggacgacc tctatgacca agacgactcg agggacttcc  20580
cacgctcccg ggaccccccac tacgacgact tcaggtctcg ggagcgccct cctgccgacc  20640
ccaggtccca ccaccaccgt acccgggacc ctcgggacaa cggctccagg tccggggacc  20700
tccctatga  tgggcggcta ctggaggagg ctgtgaggaa gaagggtcg  gaggagagga  20760
ggagacccca caaggaggag gaggaagagg cctactaccc gccgcgccg  cccccgtact  20820
cggagaccga ctcgcaggcg tcccgagagc gcaggctcaa gaaggtgagg gccgccctcc  20880
ctggcgtcca gaccgtccct gggccccag  ccggtccccg cggctcatac ccttctttct  20940
ttctcccttg cagaacttgg ccctgagtcg ggaaagttta gtcgtctgat ctgacgtttt  21000
ctacgtagct tttgtatttt ttttttaat  ttgaaggaac actgatgaag ccctgccata  21060
cccctcccga gtctaataaa acgtataatc acaagctctg gagagaacca tttgttcggc  21120
cgcgcgggc  gggggaccgg ggctgctccc gtatgcgtct gtaaagcgcc gcgtcccggg  21180
ggcaccggag tccgggccg  ggaggaagag acccagcctg gccggcccg  cgcccgcgcc  21240
gccggccgga gaacgtgccc cgcgcagcca ccgcccgcct gcgtgcgcgc cccggccccg  21300
cccaggcgtg cgcatgcgcc ccggccctcc gccttcgcgc accgcaggct ggccgccggg  21360
agcgcgcgcg cgctcctctc cccttccagc ccatcccccc cagcccccca ccgacctact  21420
ttactgtctc caaactcggg cagcccacct ggccccgac  accccagcc  cctgctccgg  21480
gtaccccgac gttccatcca gacccgcgtt tcaccagggc ggcgcgcggc gacctcgcgc  21540
cccgcggagc cccgggctcg cgcgcgcccg cccgccccg  gagacagaca gcgcgcgcgc  21600
tcccgggccg cctcccccca gcgcgcgtcc gccccgggct cgcgccgccg ccgccgccgc  21660
cgccgcgcgc gcgcagctca agtaaaggag gaaaaaaaaa aggggggaaa atagaaagcg  21720
g                                                                 21721
```